(12) United States Patent
Scully et al.

(10) Patent No.: US 10,697,026 B2
(45) Date of Patent: Jun. 30, 2020

(54) COMPOSITIONS AND METHODS FOR CHARACTERIZING A DNA REPAIR VARIANT POLYPEPTIDE

(71) Applicant: BETH ISRAEL DEACONESS MEDICAL CENTER, INC., Boston, MA (US)

(72) Inventors: Ralph Scully, Boston, MA (US); Nicholas A. Willis, Boston, MA (US)

(73) Assignee: BETH ISRAEL DEACONESS MEDICAL CENTER, INC., Boston, MA (US)

( * ) Notice: Subject to any disclaimer, the term of this patent is extended or adjusted under 35 U.S.C. 154(b) by 62 days.

(21) Appl. No.: 16/028,600

(22) Filed: Jul. 6, 2018

(65) Prior Publication Data

US 2019/0002990 A1 Jan. 3, 2019

Related U.S. Application Data

(63) Continuation of application No. 14/941,769, filed on Nov. 16, 2015, now Pat. No. 10,017,825.

(60) Provisional application No. 62/080,875, filed on Nov. 17, 2014.

(51) Int. Cl.
*C12Q 1/6886* (2018.01)
*C12N 15/90* (2006.01)

(52) U.S. Cl.
CPC ......... *C12Q 1/6886* (2013.01); *C12N 15/907* (2013.01); *C12Q 2600/106* (2013.01); *C12Q 2600/156* (2013.01)

(58) Field of Classification Search
CPC ........................... C12Q 1/6886; C12Q 1/6897
See application file for complete search history.

(56) References Cited

U.S. PATENT DOCUMENTS

2016/0160294 A1  6/2016  Scully et al.

OTHER PUBLICATIONS

Willis, Nicholas A., et al., "BRCA1 controls homologous recombination at Tus / Ter-stalled mammalian replication forks," Nature, vol. 510, pp. 556-559 (2014).
Chandramouly, Gurushankar, et al., "BRCA1 and CtIP suppress long-tract gene conversion between sister chromatids," Nature Communications, vol. 4, Article 2404 (2013).

*Primary Examiner* — Antonio Galisteo Gonzalez
(74) *Attorney, Agent, or Firm* — Melissa Hunter-Ensor; Greenberg Traurig, LLP

(57) ABSTRACT

As described below, the present invention provides quantitative homologous recombination assays developed to characterize the pathogenicity DNA repair polypeptides (e.g., BRCA1, BRCA2, Rad51) and provide urgently needed functional information on the significance of DNA repair variants of uncertain significance (VUS) alleles. The invention also provides a method of generating site-specific recombination at a genomic locus or site-specific genome editing by inhibiting replication at the genomic locus, e.g., involving contacting the genomic locus with polypeptides that specifically bind target sequences at the genomic locus.

3 Claims, 39 Drawing Sheets
Specification includes a Sequence Listing.

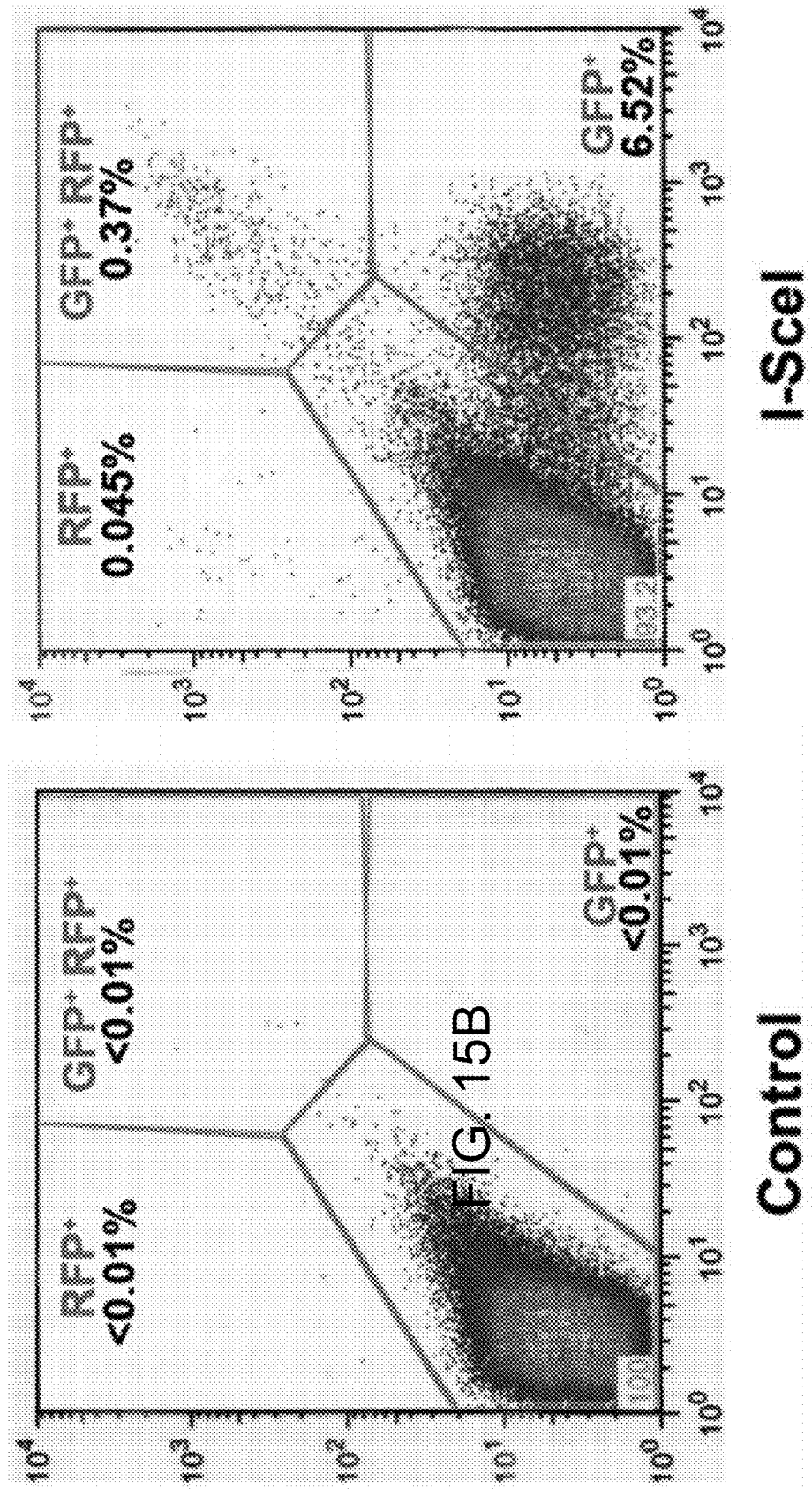

FIG. 18A

LTGC reporter vector-I-SceI

CCCCGCGGCAGGCCCTCCGAGCGTGGTGGAGCCGTTCTGTGAGACAGCCGGGTACG
AGTCGTGACGCTGGAAGGGGCAAGCGGGTGGTGGGCAGGAATGCGGTCCGCCCTGC
AGCAACCGGAGGGGGAGGGAGAAGGGAGCGGAAAAGTCTCCACCGGACGCGGCCA
TGGCTCGGGGGGGGGGGGCAGCGGAGGASCGCTTCCGGCCGACGTCTCGTCGCTG
ATTGGCTTYTTTTCCTCCCGCCGTGTGTGAAAACACAAATGGCGTGTTTTGGTTGGCG
TAAGGCGCCTGTCAGTTAACGGCAGCCGGAGTGCGCAGCCGCCGGCAGCCTCGCTC
TGCCCACTGGGTGGGGCGGGAGGTAGGTGGGGTGAGGCGAGCTGNACGTGCGGGCG
CGGTCGGCCTCTGGCGGGGCGGGGGAGGGGAGGGAGGGTCAGCGAAAGTAGCTCG
CGCGCGAGCGGCCGCCCACCCTCCCCTTCCTCTGGGGGAGTCGTTTTACCCGCCGCC
GGCCGGGCCTCGTCGTCTGATTGGCTCTCGGGGCCCAGAAAACTGGCCCTTGCCATT
GGCTCGTGTTCGTGCAAGTTGAGTCCATCGCCGGCCAGCGGGGGCGGCGAGGAGG
CGCTCCCAGGTTCCGGCCCTCCCCTCGGCCCCGCGCCGCAGAGTCTGGCCGCGCGCC
CCTGCGCAACGTGGCAGGAAGCGCGCGCTGGGGGCGGGGACGGGCAGTAGGGCTG
AGCGGCTGCGGGGCGGGTGCAAGCACGTTCCGACTTGAGTTGCCTCAAGAGGGGC
GTGCTGAGCCAGACCTCCATCGCGCACTCCGGGGAGTGGAGGGAAGGAGCGAGGGC
TCAGTTGGGCTGTTTTGGAGGCAGGAAGCACTTGCTCTCCCAAAGTCGCTCTGAGTT
GTTATCAGTAAGGGAGCTGCAGTGGAGTAGGCGGGGAGAAGGCCGCACCCTTCTCC
GGAGGGGGGAGGGGAGTGTTGCAATACCTTTCTGGGAGTTCTCTGCTGCCTCCTGGC
TTCTGAGGACCGCCCTGGGCCTGGGAGAATCCCTTGCCCCCTCTTCCCTCGTGATCT
GCAACTCCAGTCTTTCTAGCCTTAATTAAGGGATCTGTAGGGCGCAGTAGTCCAGGG
TTTCCTTGATGATGTCATACTTATCCTGTCCCTTTTTTTCCACAGCTCGCGGTTGAGG
ACAAACTCTTCGCGGTCTTTCCAGTGGGGATCGACGGTATCGTAGAGTCGAGGCCGC
TCTAGAACTAGTGGATCTACCATGACCGAGTACAAGCCCACGGTGCGCCTCGCCACC
CGCGACGACGTCCCCGGGCCGTACGCACCCTCGCCGCCGCGTTCGCCGACTACCCC
GCCACGCGCCACACCGTCGACCCGGACCGCCACATCGAGCGGGTCACCGAGCTGCA
AGAACTCTTCCTCACGCGCGTCGGGCTCGACATCGGCAAGGTGTGGGTCGCGGACG
ACGGCGCCGCGGTGGCGGTCTGGACCACGCCGGAGAGCGTCGAAGCGGGGGCGGT
GTTCGCCGAGATCGGCCCGCGCATGGCCGAGTTGAGCGGTTCCCGGCTGGCCGCGC
AGCAACAGATGGAAGGCCTCCTGGCGCCGCACCGGCCCAAGGAGCCCGCGTGGTTC
CTGGCCACCGTCGGCGTCTCGCCCGACCACCAGGGCAAGGGTCTGGGCAGCGCCGT
CGTGCTCCCCGGAGTGGAGGCGGCCGAGCGCGCCGGGGTGCCCGCCTTCCTGGAGA
CCTCCGCGCCCCGCAACCTCCCCTTCTACGAGCGGCTCGGCTTCACCGTCACCGCCG
ACGTCGAGTGCCCGAAGGACCGCGCGACCTGGTGCATGACCCGCAAGCCCGGTGCC
TGACTCGACCCTAGGGGGAGGCTAACTGAAACACGGAAGGAGACAATACCGGAAG
GAACCCGCGCTATGACGGCAATAAAAAGACAGAATAAAACGCACGGTGTTGGGTCG
TTTGTTCATAAACGCGGGGTTCGGTCCCAGGGCTGGCACTCTGTCGATACCCCACCG
AGACCCCATTGGGGCCAATACGCCCGCGTTTCTTCCTTTTCCCCACCCCACCCCCCA
AGTTCGGGTGAAGGCCCAGGGCTCGCAGCCAACGTCGGGGCGGCAGGCCCTGCCAT
AGCCTCAGGTTACTCGGATCTCGACCTCGAGGGGCCCCGCGGGTGGGGAAGATCT
CGGGGTGCCCATCCTGGTCGAGCTGGACGGCGACGTAAACGGCCACAAGTTCAGCG
TGTCCGGCGAGGGCGAGGGCGATGCCACCTACGGCAAGCTGACCCTGAAGTTCATC
TGCACCACCGGCAAGCTGCCCGTGCCCTGGCCCACCCTCGTGACCACCCTGACCTAC
GGCGTGCAGTGCTTCAGCCGCTACCCCGACCACATGAAGCAGCACGACTTCTTCAAG
TCCGCCATGCCCGAAGGCTACGTCCAGGAGCGCACCATCTTCTTCAAGGACGACGG

FIG. 18B

```
CAACTACAAGACCCGCGCCGAGGTGAAGTTCGAGGGCGACACCCTGGTGAACCGCA
TCGAGCTGAAGGGCATCGACTTCAAGGAGGACGGCAACATCCTGGGGCACAAGCTG
GAGTACAACTACAACAGCCACAACGTCTATATCATGGCCGACAAGCAGAAGAACGG
CATCAAGGTGAACTTCAAGATCCGCCACAACATCGAGGACGGCAGCGTGCAGCTCG
CCGACCACTACCAGCAGAACACCCCCATCGGCGACGGCCCCGTGCTGCTGCCCGAC
AACCACTACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCATGGACGA
GCTGTACAAGTAAAGCGGCCGCGACTCTAGATCATAATCAGCCATACCACATTTGTA
GAGGTTTTACTTGCTTTAAAAAACCTCCCACACCTCCCCCTGAACCTGAAACATAAA
ATGAATGCAATTGTTGTTGTTAACTTGTTTATTGCAGCTTATAATGGTTACAAATAAA
GCAATAGCATCACAAATTTCACAAATAAAGCATTTTTTCACTGCATTCTAGTTGTG
GTTTGTCCAAACTCATCAATGTCGGGATCCCGCCAATTGTCTAGATTTCTCTAATCAC
TTTTTTTTCAAGGCAATCAGGGTATATTATATTGTACTTCAGCACAGTTTAGAGAAC
AATTGTTATAATTAAATGATAAGGTAGAATATTTCTGCATATAAATTCTGGCTGGCG
TGGAAATATTCTTATTGGTAGAAACAACTACATCCTGGTCATCATCCTGCCTTTCTCT
TTATGGTTACAATGATATACACTGTTTGAGATGAGGATAAAATACTCTGAGTCCAAA
CCGGGCCCCTCTGCTAACCATGTTCATGCCTTCTTCTTTTCCTACAGGACTCCTCCC
TGCAGGACGGCGAGTTCATCTACAAGGTGAAGCTGCGCGGCACCAACTTCCCCTCC
GACGGCCCCGTAATGCAGAAGAAGACCATGGGCTGGGAGGCCTCCTCCGAGCGGAT
GTACCCCGAGGACGGCGCCCTGAAGGGCGAGATCAAGATGAGGCTGAAGCTGAAG
GACGGTGGCCACTACGACGCCGAGGTCAAGACCACCTACATGGCCAAGAAGCCCGT
GCAGCTGCCCGGCGCCTACAAGACCGACATCAAGCTGGACATCACCTCCCACAACG
AGGACTACACCATCGTGGAACAGTACGAGCGCGCCGAGGGCCGCCACTCCACCGGC
GGTATGGATGAACTCTATAAATAAGCACGGGCCCTATTCTATAGTGTCACCTAAATG
CTAGAGCTCGCTGATCAGCCTCGACTGTGCCTTCTAGTTGCCAGCCATCTGTTGTTTG
CCCCTCCCCCGTGCCTTCCTTGACCCTGGAAGGTGCCACTCCCACTGTCCTTTCCTAA
TAAAATGAGGAAATTGCATCGCATTGTCTGAGTAGGTGTCATTCTATTCTGGGGGGT
GGGGTGGGGCAGGACAGCAAGGGGGAGGATTGGGAAGACAATAGCAGGCATGCTG
GGGAGGATCTGTGTGGAAAGTCCCCAGGCTCCCCAGGCAGGCAGAAGTATGCAAAG
CATGCATCTCAATTAGTCAGCAACCAGGTGTGGAAAGTCCCCAGGCTCCCCAGCAG
GCAGAAGTATGCAAAGCATGCATCTCAATTAGTCAGCAACCATAGTCCCGCCCCTA
ACTCCGCCCATCCCGCCCCTAACTCCGCCCAGTTCCGCCCATTCTCCGCCCCATGGCT
GACTAATTTTTTTTATTTATGCAGAGGCCGAGGCCGCCTCTGCCTCTGAGCTATTCCA
GAAGTAGTGAGGAGGCTTTTTGGAGGCCTAGGCTTTTGCAAAAAGCTCCCGGGAG
CTTGTATATCCATTTTCGGATAAGCTTAACTAAACCATGGTATCAAAAGGTGAAGAA
ACAATATGGCAGTCATCAAGGAGTTCATGCGCTTCAAGGTGCGCATGGAGGGCTC
CGTGAACGGCCACGAGTTCGAGATCGAGGGCGAGGGCGAGGGCCGCCCCTACGAG
GGCACCCAGACCGCCAAGCTGAAGGTGACCGAGGGTGGCCCCCTGCCCTTCGCCTG
GGACATCCTGTCCCCTCAGTTCATGTACGGCTCCAAGGCCTACGTGAAGCACCCCGC
CGACATCCCCGACTACTTGAAGCTGTCCTTCCCCGAGGGCTTCAAGTGGGAGCGCGT
GATGAACTTCGAGGACGGCGGCGTGGTGACCGTGACCCAGGTGAGTTTGGGGACCC
TTGATTGTTCTTTCTTTTTCGCTATTGTAAAATTCATGTTATATGGAGGGGCAAAGT
TTTCAGGGTGTTGTTAGAATGGGAAGATGTCCCTTGTATCACCATGGACCCTCATG
ATAATTTTGTTTCTTTCACTTTCTACTCTGTTGACAACCATTGTCTCCTCTTATTTTCTT
TTCATTTTCTGTAACTTTTTCGTTAAACTTTAGCTTGCATTTGTAACGAATTTTTAAAT
TCACTTTTGTTTATTTGTCAGATTGTAAGTACCGGGACCCGGAATTCTACCGGGTAG
```

FIG. 18C

```
GGGAGGCGCTTTTCCCAAGGCAGTCTGGAGCATGCGCTTTAGCAGCCCCGCTGGCAC
TTGGCGCTACACAAGTGGCCTCTGGCCTCGCACACATTCCACATCCACCGGTAGCGC
CAACCGGCTCCGTTCTTTGGTGGCCCCTTCGCGCCACTTCTACTCCTCCCCTAGTCAG
GAAGTTTCCCCAGCAAGCTCGCGTCGTGCAGGACGTGACAAATGGAAGTAGCACG
TCTCACTAGTCTCGTGCAGATGGACAGCACCGCTGAGCAATGGAAGCGGGTAGGCC
TTTGGGGCAGCGGCCAATAGCAGCTTTGTTCCTTCGCTTTCTGGGCTCAGAGGCTGG
GAAGGGGTGGGTCCGGGGGCGGGCTCAGGGGCGGGCTCAGGGGCGGGCGGGCGCC
CGAAGGTCCTCCCGAGGCCCGGCATTCTGCACGCTTCAAAAGCGCACGTCTGCCGCG
CTGTTCTCCTCTTCCTCATCTCCGGGCCTTTCGACCTGCAGCCCAAGCTCTAGCGCTA
CCGGTCGCCACCATGGTGAGCAAGGGCGAGGAGCTGTTCACCGGGGTGGTGCCCAT
CCTGGTCGAGCTGGACGGCGACGTAAACGGCCACAAGTTCAGCGTGTCCGGCGAGG
GCGAGGGCGATGCCACCTACGGCAAGCTGACCCTGAAGTTCATCTGCACCACCGGC
AAGCTGCCCGTGCCCTGGCCCACCCTCGTGACCACCCTGACCTACGGCGTGCAGTGC
TTCAGCCGCTACCCCGACCACATGAAGCAGCACGACTTCTTCAAGTCCGCCATGCCC
GAAGGCTACGTCCAGGAGCGCACCATCTTCTTCAAGGACGACGGCAACTACAAGAC
CCGCGCCGAGGTGAAGTTCGAGGGCGACACCCTGGTGAACCGCATCGAGCTGAAGG
GCATCGTAGGGATAACAGGGTAATCAAGGAGGACGGCAACATCCTGGGGCACAAGC
TGGAGTACAACTACAACAGCCACAACGTCTATATCATGGCCGACAAGCAGAAGAAC
GGCATCAAGGTGAACTTCAAGATCCGCCACAACATCGAGGACGGCAGCGTGCAGCT
CGCCGACCACTACCAGCAGAACACCCCCATCGGCGACGGCCCCGTGCTGCTGCCCG
ACAACCACTACCTGAGCACCCAGTCCGCCCTGAGCAAAGACCCCAACGAGAAGCGC
GATCACATGGTCCTGCTGGAGTTCGTGACCGCCGCCGGGATCACTCTCGGCATGGAC
GAGCTGTACAAGTAAAGCGGCCGCGACTCTAGATCATAATCAGCCATACCACATTTG
TAGAGGTTTTACTTGCTTTAAAAAACCTCCCACACCTCCCCCTGAACCTGAAACATA
AAATGAATGCAATTGTTGTTGTTAACTTGTTTATTGCAGCTTATAATGGTTACAAATA
AAGCAATAGCATCACAAATTTCACAAATAAAGCATTTTTTCACTGCATTCTAGTTG
TGGTTTGTCCAAACTCATCAATGTCGGATGGCCGCGCTGGGGATGCGGTGGGCTCTA
TGGCTTATGAGGCGGAAAGAACCAGCTGGGGCTCGATCCTCTAGTTGGCGCGCCGG
CTAGAAGATGGGCGGGAGTCTTCTGGGCAGGCTTAAAGGCTAACCTGGTGTGTGGG
CGTTGTCCTGCAGGGGAATTGAACAGGTGTAAAATTGGAGGGACAAGACTTCCCAC
AGATTTTCGGTTTTGTCGGGAAGTTTTTAATAGGGGCAAATAGGAAAATGGAGGAT
AGGAGTCATCTGGGGTTTATGCAGCAAAACTACAGGTATATTGCTTGTATCCGCCTC
GGAGATTTCCATGAGGAGATAAAGACATGTCACCCGAGTTTATACTCTCCTGCTTAG
ATCCTACTACAGTATGAAATACAGTGTYGCGAGGTAGACTATGTAAGCAGATTTAAT
CATTTTAAAGAGCCCAGTACTTCATATCCATTTCTCCCGCTCCTTCTGCAGCCTTATC
AAAAGGTATTTAGAACACTCATTTTAGCCCCATTTTCATTTATTATACTGGCTTATCC
AACCCCTAGACAGAGCATTGGCATTTTCCCTTTCCTGATCTTAGAAGTCTGATGACTC
ATGAAACCAGACAGATTAGTTACATACACCACAAATCGAGGCTGTAGCTGGGGCCT
CAACACTGCAGTTCTTTTATAACTCCTTAGTACACTTTTTGTTGATCCTTTGCCTTGAT
CCTTAATTTTCAGTGTCTATCACCTCTCCCGTCAGGTGGTGTTCCACATTTGGGCCTA
TTCTCAGTCCAGGGAGTTTTACAACAATAGATGTATTGAGAATCCAACCTAAAGCTT
AACTTTCCACTCCCATGAATGCCTCTCCTTTTTCTCCATTATAACTGAGCTATWAC
CATTAATGGTTTCAGGTGGATGTCTCCTCCCCAATATACCTGATGTATCTACATATT
GCCAGGCTGATATTTTAAGACATWAAAGGTATATTTCATTATTGAGCCACATGGTAT
TGATTACTGCTACTAAAATTTTGTCATTGTACACATCTGTAAAAGGTGGTTCCTTTTG
GAATGCAAAGTTCAGGTGTTTGTTGTCTTTCCTGACCTAAGGTCTTGTGAGCTTGTAT
```

FIG. 18D

```
TTTTTCTATTTAAGCAGTGCTTTCTCTTGGACTGGCTTGACTCATGGCATTCTACACG
TTATTGCTGGTCTAAATGTGATTTTGCCAAGCTTCTTCAGGACCTATAATTTTGCTTG
ACTTGTAGCCAAACACAAGTAAAATGATTAAGCAACAAATGTATTTGTGAAGCTTG
GTTTTTAGGTTGTTGTGTTGTGTGTGCTTGTGCTCTATAATAATACTATCCAGGGGCT
GGAGAGGTGGCTCGGAGTTCAAGAGCACAGACTGCTCTTCCAGAAGTCCTGAGTTC
AATTCCCAGCAACCACATGGTGGCTCACAACCATCTGTAATGGGATCTGATGCCCTC
TTCTGGTGTGTCTGAAGACCACAAGTGTATTCACATTAAATAAATAATCCTCCTTCTT
CTTCTTTTTTTTTTTAAAGAGAATWCTGTCTCCAGTAGAATTACTGAAGTAATGAA
ATACTTTGTGTTTGTTCCAATATGGWAGCCAATAATCAAATACTCTTWAGCACTGGA
AATGTACCAAGGAACTATTTTATTTAAGTGWACTGTGGACAGAGGAGCCATAACTG
CAGACTTGTGGGATACAGAAGACCAATGCAGACTTAATGTCTTTTCTCTTACACTAA
GCAATAAAGAAATAAAAATTGAACTTCTAGTATCCTATTTGTTAAACTGCTAGCTTT
ACTAACTTTTGTGCTTCATCTATACAAAGCTGAAAGCTAAGTCTGCAGCCATTACTA
AACATGAAAGCAAGTAATGATAATTTTGGATTTCAAAAATGTAGGGCCAGAGTTTA
GCCAGCCAGTGGTGGTGCTTGCCTTTATGCCTTAATCCCAGCACTCTGGAGGCAGAG
ACAGGCAGATCTCTGAGTTTGAGCCCAGCCTGGTCTACACATCAAGTTCTATCTAGG
ATAGCCAGGAATACACACAGAAACCCTGTTGGGGAGGGGGCTCTGAGATTTCATA
AAATTATAATTGAAGCATTCCCTAATGAGCCACTATGGATGTGGCTAAATCCGTCTA
CCTTTCTGATGAGATTTGGGTATTATTTTTCTGTCTCTGCTGTTGGTTGGGTCTTTTG
ACACTGTGGGCTTTCTTAAAGCCTCCTTCCCTGCCATGTGGTCTCTTGTTTGCTACTA
ACTTCCCATGGCTTAAATGGCATGGCTTTTGCCTTCTAAGGGCAGCTGCTGAGWTT
TGCAGCCTGATTTCCAGGGTGGGGTTGGGAAATCTTTCAAACACTAAAATTGTCCTT
TAATTTTTTTTAAAAAATGGGTTATATAATAAACCTCATAAAATAGTTATGAGGAG
TGAGGTGGACTAATATTAATGAGTCCCTCCCCTATAAAGAGCTATTAAGGCTTTTT
GTCTTATACTAACTTTTTTTTAAATGTGGTATCTTTAGAACCAAGGGTCTTAGAGTT
TTAGTATACAGAAACTGTTGCATCGCTTAATCAGATTTTCTAGTTTCAAATCCAGAG
AATCCAAATTCTTCACAGCCAAAGTCAAATTAAGAATTTCTGACTTTAATGTTATTTG
CTACTGTGAATATAAAATGATAGCTTTTCCTGAGGCAGGGTCTCACTATGTATCTCT
GCCTGATCTGCAACAAGATATGTAGACTAAAGTTCTGCCTGCTTTTGTCTCCTGAAT
ACTAAGGTTAAAATGTAGTAATACTTTTGGAACTTGCAGGTCAGATTCTTTTATAGG
GGACACACTAAGGGAGCTTGGGTGATAGTTGGTAAATGTGTTAAGTGATGAAAAC
TTGAATTATTATCACCGCAACCTACTTTTTAAAAAAAAAAGCCAGGCCTGTTAGAGC
ATGCTAAGGGATCCCTAGGACTTGCTGAGCACACAAGAGTAGTACTTGGCAGGCTC
CTGGTGAGAGCATATTTCAAAAAACAAGGCAGACAACCAAGAAACTACAGTAAGGT
TACCTGTCTTTAACCATCTGCATATACACAGGGATATTAAAATATTCCAAATAATAT
TTCATTCAAGTTTTCCCCCATCAAATTGGGACATGGATTTCTCCGGTGAATAGGCAG
AGTTGGAAACTAAACAAATGTTGGTTTTGTGATTTGTGAAATTGTTTTCAAGTGATA
GTTAAAGCCCATGAGATACAGAACAAAGCTGCTATTTCGAGGTCTCTTGGTTATACT
CAGAAGCACTTCTTTGGGTTTCCCTGCACTATCCTGATCATGTGCTAGGCCTWCCTT
AGGCTGATTGTTGTTCAAATAACTTAAGTTTCCTGTCAGGTGATGTCATATGATTTCA
TATATCAAGGCAAAACATGTTATATATGTTAAACATTTGKACTTAATGTGAAAGTTA
GGTCTTTGTGGGTTTTGATTTTAATTTCAAAACCTGAGCTAAATAAGTCATTTTACAT
GTCTTACATTTGGTGAATTGTATATTGTGGTTTGCAGGCAAGACTCTCTGACCTAGTA
ACCCTCCTATAGAGCACTTTGCTGGGTCACAAGTCTAGGAGTCAAGCATTTCACCTT
GAAGTTGAGACGTTTTGTTAGTGTATACTAGTTATATGTTGGAGGACATGTTTATCC
AGAAGATATTCAGGACTATTTTTGACTGGGCTAAGGAATTGATTCTGATTAGCACTG
```

FIG. 18E

```
TTAGTGAGCATTGAGTGGCCTTTAGGCTTGAATTGGAGTCACTTGTATATCTCAAAT
AATGCTGGCCTTTTTWAAAAGCCCTTGTTCTTTATCACCCTGTTTTCTACATAATTT
TTGTTCAAAGAAATACTTGTTTGGATCTCCTTTTGACAACAATAGCATGTTTTCAAGC
CATATTTTTTTCCTTTTTTTTTTTTTTTGGTTTTCGAGACAGGGTTTCTCTGTATA
GCCCTGGCTGTCCTGGAACTCACTTTGTAGACCAGGCTGGCCTCGAACTCAGAAATC
CGCCTGCCTCTGCCTCCTGAGTGCCGGGATTAAAGGCGTGCACCACCACGCCTGGCT
AAGTTGGATATTTTGTATATAACTATAACCAATACTAACTCCACTGGGTGGATTTTTA
ATTCAGTCAGTAGTCTTAAGTGGTCTTTATTGGCCCTTATTAAAATCTACTGTTCACT
CTAACAGAGGCTGTTGGACTAGTGGSACTAAGCAACTTCCTACGGATATACTAGCAG
ATAAGGGTCAGGGATAGAAACTAGTCTAGCGTTTTGTATACCTACCAGCTTATACTA
CCTTGTTCTGATAGAAATATTTAGGACATCTAGCTTATCGATCCGTCGACGGTATCG
ATAAGCTTGATATCGAATTCTACCGGGTAGGGGAGGCGCTTTTCCAAGGCAGTCTGA
GCATGCGCTTAGCAGCCCCGCTGGCACTTGGCGCTACACAAGTGGCCTYTGGCCTCG
CACACATTCCACATCCACCGGTAGGCGCCAACCGGCTCCGTTCTTTGGTGGCCCCTT
CGCGCCACCTTCTWCCTCCCCTAGTCAGGAAGTTCCCCCCCGCCCCGCAGCTCGC
GTCGTSAGGACGTGACAAATGGAAGTAGCACGTCTCACTAGTCTCGTCAGATGGACA
GCACCGCTGAGCAATGGAAGCGGGTAGGCCTTTGGGGCAGCGGCCAATAGCAGCTT
TGCTCCTTCGCTTTCTGGGCTCAGAGGCTGGGAAGGGGTGGGTCCGGGGCGGGCTC
AGGGGCGGGCTCAGGGGCGGGGCGGGCGCCCGAAGGTCCTCCGGAGGCCCGGCATT
CTGCACGCTTCAAAAGCGCACGTCTGCCGCGCTGTTCTCCTCTTCCTCATCTCCGGGC
CTTTCGACCTGCAGGTCCTCGCCATGGATCCTGATGATGTTGTTATTCTTCTAATCTT
TTGTATGGAAAACTTTTCTTCGTACCACGGGACTAAACCTGGTTATGTAGATTCCATT
CAAAAAGGTATACAAAAGCCAAAATCTGGTACACAAGGAAATTATGACGATGATTG
GAAAGGGTTTTATAGTACCGACAATAAATACGACGCTGCGGGATACTCTGTAGATA
ATGAAAACCCGCTCTCTGGAAAAGCTGGAGGCGTGGTCAAAGTGACGTATCCAGGA
CTGACGAAGGTTCTCGCACTAAAAGTGGATAATGCCGAAACTATTAAGAAAGAGTT
AGGTTTAAGTCTCACTGAACCGTTGATGGAGCAAGTCGGAACGGAAGAGTTTATCA
AAAGGTTCGGTGATGGTGCTTCGCGTGTAGTGCTCAGCCTTCCCTTCGCTGAGGGGA
GTTCTAGCGTTGAATATATTAATAACTGGGAACAGGCGAAAGCGTTAAGCGTAGAA
CTTGAGATTAATTTTGAAACCCGTGGAAAACGTGGCCAAGATGCGATGTATGAGTAT
ATGGCTCAAGCCTGTGCAGGAAATCGTGTCAGGCGATCTCTTTGTGAAGGAACCTTA
CTTCTGTGGTGTGACATAATTGGACAAACTACCTACAGAGATTTAAAGCTCTAAGGT
AAATATAAAATTTTTAAGTGTATAATGTGTTAAACTACTGATTCTAATTGTTTGTGTA
TTTTAGATTCCAACCTATGGAACTGATGAATGGGAGCAGTGGTGGAATGCAGATCCT
AGAGCTCGCTGATCAGCCTCGACTGTGCCTTCTAGTTGCCAGCCATCTGTTGTTTGCC
CCTCCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGG
GGTGGGGCAGGACAGCAAGGGGGAGGATTGGGAAGACAATAGCAGGCATGCTGGG
GATGCGGTGGGCTCTATGGCTTCTGAGGCGGAAAGAACCAGCTGGGGCTCGACCTC
GAGGGGGGGCCCGGTACCCAGCTTTTGTTCCCTTTAGTGAGGGTTAATTGCGCGCTT
GGCGTAATCATGGTCATAGCTGTTTCCTGTGTGAATTGTTATCCGCTCACAATTCCA
CACAACATACGAGCCGGAAGCATAAAGTGTAAAGCCTGGGGTGCCTAATGAGTGAG
CTAACTCACATTAATTGCGTTGCGCTCACTGCCCGCTTTCCAGTCGGGAAACCTGTC
GTGCCAGCTGCATTAATGAATCGGCCAACGCGCGGGGAGAGGCGGTTTGCGTATTG
GGCGCTCTTCCGCTTCCTCGCTCACTGACTCGCTGCGCTCGGTCGTTCGGCTGCGGCG
AGCGGTATCAGCTCACTCAAAGGCGGTAATACGGTTATCCACAGAATCAGGGGATA
```

FIG. 18F

ACGCAGGAAAGAACATGTGAGCAAAAGGCCAGCAAAAGGCCAGGAACCGTAAAAA
GGCCGCGTTGCTGGCGTTTTTCCATAGGCTCCGCCCCCTGACGAGCATCACAAAAA
TCGACGCTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGG
TATCTCAGTTCGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAACCCGGTA
AGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAG
AAGGACAGTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTTTTGTTTG
CAAGCAGCAGATTACGCGCAGAAAAAAAGGATCTCAAGAAGATCCTTTGATCTTTT
CTACGGGGTCTGACGCTCAGTGGAACGAAAACTCACGTTAAGGGATTTTGGTCATGA
GATTATCAAAAGGATCTTCACCTAGATCCTTTTAAATTAAAAATGAAGTTTTAAAT
CAATCTAAAGTATATATGAGTAAACTTGGTCTGACAGTTACCAATGCTTAATCAGTG
AGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGAT
ACCGCGAGACCCACGCTCACCGGCTCCAGATTTATCAGCAATAAACCAGCCAGCCG
GAAGGGCCGAGCGCAGAAGTGGTCCTGCAACTTTATCCGCCTCCATCCAGTCTATTA
ATTGTTGCCGGGAAGCTAGAGTAAGTAGTTCGCCAGTTAATAGTTTGCGCAACGTTG
TTGCCATTGCTACAGGCATCGTGGTGTCACGCTCGTCGTTTGGTATGGCTTCATTCAG
CTCCGGTTCCCAACGATCAAGGCGAGTTACATGATCCCCATGTTGTGCAAAAAAGC
GGTTAGCTCCTTCGGTCCTCCGATCGTTGTCAGAAGTAAGTTGGCCGCAGTGTTATC
ACTCATGGTTATGGCAGCACTGCATAATTCTCTTACTGTCATGCCATCCGTAAGATG
CTTTTCTGTGACTGGTGAGTACTCAACCAAGTCATTCTGAGAATAGTGTATGCGGCG
ACCGAGTTGCTCTTGCCCGGCGTCAATACGGGATAATACCGCGCCACATAGCAGAA
CTTTAAAAGTGCTCATCATTGGAAAACGTTCTTCGGGGCGAAAACTCTCAAGGATCT
TACCGCTGTTGAGATCCAGTTCGATGTAACCCACTCGTGCACCCAACTGATCTTCAG
CATCTTTTACTTTCACCAGCGTTTCTGGGTGAGCAAAAACAGGAAGGCAAAATGCCG
CAAAAAAGGGAATAAGGGCGACACGGAAATGTTGAATACTCATACTCTTCCTTTTTC
AATATTATTGAAGCATTTATCAGGGTTATTGTCTCATGAGCGGATACATATTTGAAT
GTATTTAGAAAAATAAACAAATAGGGGTTCCGCGCACATTTCCCCGAAAAGTGCCA
CCTAAATTGTAAGCGTTAATATTTTGTTAAAATTCGCGTTAAATTTTGTTAAATCAG
CTCATTTTTTAACCAATAGGCCGAAATCGGCAAAATCCCTTATAAATCAAAAGAATA
GACCGAGATAGGGTTGAGTGTTGTTCCAGTTTGGAACAAGAGTCCACTATTAAAGA
ACGTGGACTCCAACGTCAAAGGGCGAAAAACCGTCTATCAGGGCGATGGCCCACTA
CGTGAACCATCACCCTAATCAAGTTTTTTGGGGTCGAGGTGCCGTAAAGCACTAAAT
CGGAACCCTAAAGGGAGCCCCCGATTTAGAGCTTGACGGGGAAAGCCGGCGAACGT
GGCGAGAAAGGAAGGGAAGAAAGCGAAAGGAGCGGGCGCTAGGGCGCTGGCAAGT
GTAGCGGTCACGCTGCGCGTAACCACCACACCCGCCGCGCTTAATGCGCCGCTACA
GGGCGCGTCCCATTCGCCATTCAGGCTGCGCAACTGTTGGGAAGGGCGATCGGTGC
GGGCCTCTTCGCTATTACGCCAGCTGGCGAAAGGGGGATGTGCTGCAAGGCGATTA
AGTTGGGTAACGCCAGGGTTTTCCCAGTCACGACGTTGTAAAACGACGGCCAGTGA
GCGCGCGTAATACGACTCACTATAGGGCGAATTGGAGCT

FIG. 19A

Tus expression vector

GACGGATCGGGAGATCTCCCGATCCCCTATGGTCGACTCTCAGTACAATCTGCTCTG
ATGCCGCATAGTTAAGCCAGTATCTGCTCCCTGCTTGTGTGTTGGAGGTCGCTGAGT
AGTGCGCGAGCAAAATTTAAGCTACAACAAGGCAAGGCTTGACCGACAATTGCATG
AAGAATCTGCTTAGGGTTAGGCGTTTTGCGCTGCTTCGCGATGTACGGGCCAGATAT
ACGCGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCT
GGCTGACCGCCCAACGACCCCGCCCATTGACGTCAATAATGACGTATGTTCCCATA
GTAACGCCAATAGGGACTTTCCATTGACGTCAATGGGTGGACTATTTACGGTAAACT
GCCCACTTGGCAGTACATCAAGTGTATCATATGCCAAGTACGCCCCCTATTGACGTC
AATGACGGTAAATGGCCCGCCTGGCATTATGCCCAGTACATGACCTTATGGGACTTT
CCTACTTGGCAGTACATCTACGTATTAGTCATCGCTATTACCATGGTGATGCGGTTTT
GGCAGTACATCAATGGGCGTGGATAGCGGTTTGACTCACGGGGATTTCCAAGTCTCC
ACCCCATTGACGTCAATGGGAGTTTGTTTTGGCACCAAAATCAACGGGACTTTCCAA
AATGTCGTAACAACTCCGCCCCATTGACGCAAATGGGCGGTAGGCGTGTACGGTGG
GAGGTCTATATAAGCAGAGCTCTCTGGCTAACTAGAGAACCCACTGCTTACTGGCTT
ATCGAAATTAATACGACTCACTATAGGGAGACCCAAGCTAGAGTCGATCCTGAGAA
CTTCAGGGTGAGTTTGGGGACCCTTGATTGTTCTTTCTTTTTCGCTATTGTAAAATTC
ATGTTATATGGAGGGGGCAAAGTTTTCAGGGTGTTGTTTAGAATGGGAAGATGTCCC
TTGTATCACCATGGACCCTCATGATAATTTTGTTTCTTTCACTTTCTACTCTGTTGACA
ACCATTGTCTCCTCTTATTTTCTTTTCATTTTCTGTAACTTTTTCGTTAAACTTTAGCTT
GCATTTGTAACGAATTTTTAAATTCACTTTTGTTTATTTGTCAGATTGTAAGTACTTTC
TCTAATCACTTTTTTTTCAAGGCAATCAGGGTATATTATATTGTACTTCAGCACAGTT
TTAGAGAACAATTGTTATAATTAAATGATAAGGTAGAATATTTCTGCATATAAATTC
TGGCTGGCGTGGAAATATTCTTATTGGTAGAAACAACTACATCCTGGTCATCATCCT
GCCTTTCTCTTTATGGTTACAATGATATACACTGTTTGAGATGAGGATAAAATACTCT
GAGTCCAAACCGGGCCCCTCTGCTAACCATGTTCATGCCTTCTTCTTTTTCCTACAGC
TCCTGGGCAACGTGCTGGTTTGTGCTGTCGACCCCAAGCTGGCCGCTCGAGCCACCA
TGGAACAAAAGCTGATTTCTGAAGAAGACTTGGCTAGCAACAAAAGCTGATTTCT
GAAGAAGACTTGGAACAAAAGCTGATTTCTGAAGAAGACTTGACCGGTATGCCAAA
AAAGAAGAGAAAGGTATTAGGATCCATGGCCAGATACGACCTGGTGGACAGGCTGA
ACACCACCTTCAGGCAGATGGAGCAGGAGCTGGCCATCTTCGCCGCTCACCTGGAG
CAGCACAAGCTGCTGGTGGCCCGGGTGTTCTCCCTGCCTGAGGTGAAGAAGGAGGA
TGAGCACAACCCACTGAATCGCATCGAGGTGAAGCAGCACCTGGGCAACGATGCTC
AGAGCCTGGCTCTGCGCCACTTCAGGCACCTGTTCATCCAGCAGCAGTCCGAGAACC
GCTCTTCCAAGGCCGCTGTGAGGCTGCCAGGAGTGCTGTGCTACCAGGTGGACAAC
CTGTCCCAGGCCGCCTGGTGTCTCACATCCAGCACATCAACAAGCTGAAGACCACA
TTCGAGCACATCGTGACCGTGGAGTCCGAGCTGCCAACCGCGGCCCGGTTCGAGTG
GGTGCACAGACACCTGCCAGGCCTGATCACACTGAACGCTTACAGGACCCTGACCG
TGCTGCACGATCCTGCTACCCTGAGATTTGGATGGGCCAACAAGCACATCATCAAGA
ACCTGCACAGAGACGAGGTGCTGGCCCAGCTGGAGAAGAGCCTGAAGAGCCCCAG
GTCTGTGGCTCCCTGGACCAGGGAGGAGTGGCAGAGAAAGCTGGAGCGCGAGTACC
AGGACATCGCCGCCCTGCCCCAGAACGCCAAGCTGAAGATCAAGAGACCTGTGAAG
GTGCAGCCAATCGCCAGAGTGTGGTACAAGGGCGACCAGAAGCAGGTGCAGCACGC
CTGCCCCACACCACTGATCGCCCTGATCAATCGGGACAACGGCGCCGGAGTGCCAG

FIG. 19B

```
ACGTGGGAGAGCTGCTGAACTACGACGCCGATAATGTGCAGCACCGCTACAAGCCC
CAGGCCCAGCCCCTGCGGCTGATCATCCCACGGCTGCACCTGTACGTGGCTGACTGA
TGAGAATTCTGCAGATATCCATCACACTGGCGGCCCTAGAGGGCCCTATTCTATAGT
GTCACCTAAATGCTAGAGCTCGCTGATCAGCCTCGACTGTGCCTTCTAGTTGCCAGC
CATCTGTTGTTTGCCCCTCCCCGTGCCTTCCTTGACCCTGGAAGGTGCCACTCCCAC
TGTCCTTTCCTAATAAAATGAGGAAATTGCATCGCATTGTCTGAGTAGGTGTCATTCT
ATTCTGGGGGGTGGGGTGGGGCAGGACAGCAAGGGGGAGGATTGGGAAGACAATA
GCAGGCATGCTGGGGATGCGGTGGGCTCTATGGCTTCTGAGGCGGAAAGAACCAGC
TGGGGCTCTAGGGGGTATCCCCACGCGCCCTGTAGCGGCGCATTAAGCGCGGCGGG
TGTGGTGGTTACGCGCAGCGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTAA
ATCGGGGCATCCCTTTAGGGTTCCGATTTAGTGCTTTACGGCACCTCGACCCCAAAA
AACTTGATTAGGGTGATGGTTCACGTAGTGGGCCATCGCCCTGATAGACGGTTTTC
GCCCTTTGACGTTGGAGTCCACGTTCTTTAATAGTGGACTCTTGTTCCAAACTGGAAC
AACACTCAACCCTATCTCGGTCTATTCTTTTGATTTATAAGGGATTTTGGGGATTTCG
GCCTATTGGTTAAAAAATGAGCTGATTTAACAAAAATTTAACGCGAATTAATTCTGT
GGAATGTGTGTCAGTTAGGGTGTGGAAAGTCCCCAGGCTCCCCAGGCAGGCAGAAG
TATGCAAAGCATGCATCTCAATTAGTCAGCAACCAGGTGTGGAAAGTCCCCAGGCTC
CCCAGCAGGCAGAAGTATGCAAAGCATGCATCTCAATTAGTCAGCAACCATAGTCC
CGCCCCTAACTCCGCCCATCCCGCCCCTAACTCCGCCCAGTTCCGCCCATTCTCCGCC
CCATGGCTGACTAATTTTTTTATTTATGCAGAGGCCGAGGCCGCCTCTGCCTCTGAG
CTATTCCAGAAGTAGTGAGGAGGCTTTTTGGAGGCCTAGGCTTTTGCAAAAAGCTC
CCGGGAGCTTGTATATCCATTTTCGGATCTGATCAAGAGACAGGATGAGGATCGTTT
CGCATGATTGAACAAGATGGATTGCACGCAGGTTCTCCGGCCGCTTGGGTGGAGAG
GCTATTCGGCTATGACTGGGCACAACAGACAATCGGCTGCTCTGATGCCGCCGTGTT
CCGGCTGTCAGCGCAGGGGCGCCCGGTTCTTTTGTCAAGACCGACCTGTCCGGTGC
CCTGAATGAACTGCAGGACGAGGCAGCGCGGCTATCGTGGCTGGCCACGACGGGCG
TTCCTTGCGCAGCTGTGCTCGACGTTGTCACTGAAGCGGGAAGGGACTGGCTGCTAT
TGGGCGAAGTGCCGGGGCAGGATCTCCTGTCATCTCACCTTGCTCCTGCCGAGAAAG
TATCCATCATGGCTGATGCAATGCGGCGGCTGCATACGCTTGATCCGGCTACCTGCC
CATTCGACCACCAAGCGAAACATCGCATCGAGCGAGCACGTACTCGGATGGAAGCC
GGTCTTGTCGATCAGGATGATCTGGACGAAGAGCATCAGGGGCTCGCGCCAGCCGA
ACTGTTCGCCAGGCTCAAGGCGCGCATGCCCGACGGCGAGGATCTCGTCGTGACCC
ATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCC
GTGATATTGCTGAAGAGCTTGGCGGCGAATGGGCTGACCGCTTCCTCGTGCTTTACG
GTATCGCCGCTCCCGATTCGCAGCGCATCGCCTTCTATCGCCTTCTTGACGAGTTCTT
CTGAGCGGGACTCTGGGGTTCGAAATGACCGACCAAGCGACGCCCAACCTGCCATC
ACGAGATTTCGATTCCACCGCCGCCTTCTATGAAAGGTTGGGCTTCGGAATCGTTTT
CCGGGACGCCGGCTGGATGATCCTCCAGCGCGGGGATCTCATGCTGGAGTTCTTCGC
CCACCCCAACTTGTTTATTGCAGCTTATAATGGTTACAAATAAAGCAATAGCATCAC
AAATTTCACAAATAAAGCATTTTTTCACTGCATTCTAGTTGTGGTTTGTCCAAACTC
ATCAATGTATCTTATCATGTCTGTATACCGTCGACCTCTAGCTAGAGCTTGGCGTAAT
CATGGTCATAGCTGTTTCCTGTGTGAAATTGTTATCCGCTCACAATTCCACACAACAT
ACGAGCCGGAAGCATAAAGTGTAAAGCCTGGGGTGCCTAATGAGTGAGCTAACTCA
CATTAATTGCGTTGCGCTCACTGCCCGCTTTCCAGTCGGGAAACCTGTCGTGCCAGC
```

FIG. 19C

TGCATTAATGAATCGGCCAACGCGCGGGGAGAGGCGGTTTGCGTATTGGGCGCTCTT
CCGCTTCCTCGCTCACTGACTCGCTGCGCTCGGTCGTTCGGCTGCGGCGAGCGGTAT
CAGCTCACTCAAAGGCGGTAATACGGTTATCCACAGAATCAGGGGATAACGCAGGA
AAGAACATGTGAGCAAAAGGCCAGCAAAAGGCCAGGAACCGTAAAAAGGCCGCGT
TGCTGGCGTTTTTCCATAGGCTCCGCCCCCTGACGAGCATCACAAAAATCGACGCT
CAAGTCAGAGGTGGCGAAACCCGACAGGACTATAAAGATACCAGGCGTTTCCCCCT
GGAAGCTCCCTCGTGCGCTCTCCTGTTCCGACCCTGCCGCTTACCGGATACCTGTCC
GCCTTTCTCCCTTCGGGAAGCGTGGCGCTTTCTCAATGCTCACGCTGTAGGTATCTCA
GTTCGGTGTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGGTAG
CTCTTGATCCGGCAAACAAACCACCGCTGGTAGCGGTGGTTTTTTGTTTGCAAGCA
GCAGATTACGCGCAGAAAAAAGGATCTCAAGAAGATCCTTTGATCTTTTCTACGGG
GTCTGACGCTCAGTGGAACGAAAACTCACGTTAAGGGATTTTGGTCATGAGATTATC
AAAAAGGATCTTCACCTAGATCCTTTTAAATTAAAAATGAAGTTTTAAATCAATCTA
AAGTATATATGAGTAAACTTGGTCTGACAGTTACCAATGCTTAATCAGTGAGGCACC
TATCTCAGCGATCTGTCTATTTCGTTCATCCATAGTTGCCTGACTCCCCGTCGTGTAG
ATAACTACGATACGGGAGGGCTTACCATCTGGCCCCAGTGCTGCAATGATACCGCG
AGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTT
GCCGGGAAGCTAGAGTAAGTAGTTCGCCAGTTAATAGTTTGCGCAACGTTGTTGCCA
TTGCTACAGGCATCGTGGTGTCACGCTCGTCGTTTGGTATGGCTTCATTCAGCTCCGG
TTCCCAACGATCAAGGCGAGTTACATGATCCCCATGTTGTGCAAAAAAGCGGTTAG
CTCCTTCGGTCCTCCGATCGTTGTCAGAAGTAAGTTGGCCGCAGTGTTATCACTCATG
GTTATGGCAGCACTGCATAATTCTCTTACTGTCATGCCATCCGTAAGATGCTTTTCTG
TGACTGGTGAGTACTCAACCAAGTCATTCTGAGAATAGTGTATGCGGCGACCGAGTT
GCTCTTGCCCGGCGTCAATACGGGATAATACCGCGCCACATAGCAGAACTTTAAAA
GTGCTCATCATTGGAAAACGTTCTTCGGGGCGAAAACTCTCAAGGATCTTACCGCTG
TTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAG
GGAATAAGGGCGACACGGAAATGTTGAATACTCATACTCTTCCTTTTTCAATATTAT
TGAAGCATTTATCAGGGTTATTGTCTCATGAGCGGATACATATTTGAATGTATTTAG
AAAAATAAACAAATAGGGGTTCCGCGCACATTTCCCCGAAAGTGCCACCTGACGT
C

FIG. 20A

**6x*Ter* array reporter plasmid**

CCCCGCGGCAGGCCCTCCGAGCGTGGTGGAGCCGTTCTGTGAGACAGCCGGGTACG
AGTCGTGACGCTGGAAGGGGCAAGCGGGTGGTGGGCAGGAATGCGGTCCGCCCTGC
AGCAACCGGAGGGGGAGGGAGAAGGGAGCGGAAAAGTCTCCACCGGACGCGGCCA
TGGCTCGGGGGGGGGGGGCAGCGGAGGASCGCTTCCGGCCGACGTCTCGTCGCTG
ATTGGCTTYTTTTCCTCCCGCCGTGTGTGAAAACACAAATGGCGTGTTTTGGTTGGCG
TAAGGCGCCTGTCAGTTAACGGCAGCCGGAGTGCGCAGCCGCCGGCAGCCTCGCTC
TGCCCACTGGGTGGGGCGGGAGGTAGGTGGGGTGAGGCGAGCTGNACGTGCGGGCG
CGGTCGGCCTCTGGCGGGCGGGGGAGGGGAGGGAGGGTCAGCGAAAGTAGCTCG
CGCGCGAGCGGCCGCCCACCCTCCCCTTCCTCTGGGGGAGTCGTTTTACCCGCCGCC
GGCCGGGCCTCGTCGTCTGATTGGCTCTCGGGGCCCAGAAAACTGGCCCTTGCCATT
GGCTCGTGTTCGTGCAAGTTGAGTCCATCCGCCGGCCAGCGGGGGCGGCGAGGAGG
CGCTCCCAGGTTCCGGCCCTCCCCTCGGCCCCGCGCCGCAGAGTCTGGCCGCGCGCC
CCTGCGCAACGTGGCAGGAAGCGCGCGCTGGGGGCGGGGACGGGCAGTAGGGCTG
AGCGGCTGCGGGCGGGTGCAAGCACGTTTCCGACTTGAGTTGCCTCAAGAGGGGC
GTGCTGAGCCAGACCTCCATCGCGCACTCCGGGGAGTGGAGGGAAGGAGCGAGGGC
TCAGTTGGGCTGTTTTGGAGGCAGGAAGCACTTGCTCTCCCAAAGTCGCTCTGAGTT
GTTATCAGTAAGGGAGCTGCAGTGGAGTAGGCGGGGAGAAGGCCGCACCCTTCTCC
GGAGGGGGGAGGGGAGTGTTGCAATACCTTTCTGGGAGTTCTCTGCTGCCTCCTGGC
TTCTGAGGACCGCCCTGGGCCTGGGAGAATCCCTTGCCCCCTCTTCCCTCGTGATCT
GCAACTCCAGTCTTTCTAGCCTTAATTAAGGGATCTGTAGGGCGCAGTAGTCCAGGG
TTTCCTTGATGATGTCATACTTATCCTGTCCCTTTTTTTCCACAGCTCGCGGTTGAGG
ACAAACTCTTCGCGGTCTTTCCAGTGGGGATCGACGGTATCGTAGAGTCGAGGCCGC
TCTAGAACTAGTGGATCTACCATGACCGAGTACAAGCCCACGGTGCGCCTCGCCACC
CGCGACGACGTCCCCCGGGCCGTACGCACCCTCGCCGCCGCGTTCGCCGACTACCCC
GCCACGCGCCACACCGTCGACCCGGACCGCCACATCGAGCGGGTCACCGAGCTGCA
AGAACTCTTCCTCACGCGCGTCGGGCTCGACATCGGCAAGGTGTGGGTCGCGGACG
ACGGCGCCGCGGTGGCGGTCTGGACCACGCCGGAGAGCGTCGAAGCGGGGCGGT
GTTCGCCGAGATCGGCCCGCGCATGGCCGAGTTGAGCGGTTCCCGGCTGGCCGCGC
AGCAACAGATGGAAGGCCTCCTGGCGCCGCACCGGCCCAAGGAGCCCGCGTGGTTC
CTGGCCACCGTCGGCGTCTCGCCCGACCACCAGGGCAAGGGTCTGGGCAGCGCCGT
CGTGCTCCCCGGAGTGGAGGCGGCCGAGCGCGCCGGGGTGCCCGCCTTCCTGGAGA
CCTCCGCGCCCCGCAACCTCCCCTTCTACGAGCGGCTCGGCTTCACCGTCACCGCCG
ACGTCGAGTGCCCGAAGGACCGCGCGACCTGGTGCATGACCCGCAAGCCCGGTGCC
TGACTCGACCCTAGGGGGAGGCTAACTGAAACACGGAAGGAGACAATACCGGAAG
GAACCCGCGCTATGACGGCAATAAAAGACAGAATAAAACGCACGGTGTTGGGTCG
TTTGTTCATAAACGCGGGGTTCGGTCCCAGGGCTGGCACTCTGTCGATACCCCACCG
AGACCCCATTGGGGCCAATACGCCCGCGTTTCTTCCTTTTCCCCACCCCACCCCCCA
AGTTCGGGTGAAGGCCCAGGGCTCGCAGCCAACGTCGGGGCGGCAGGCCCTGCCAT
AGCCTCAGGTTACTCGGATCTCGACCTCGAGACGCGTGCCCCCACTCCACAATTTCA
AAAAAAGAGTGGCCACTTGTCTTTGTTTATGGGCCCCATTGGCGTGGAGCCCCGTT
TAATTTTCGGGGGTGTTAGAGACAACCAGTGGAGTCCGCTGCTGTCGGCGTCCACTC
TCTTTCCCCTTGTTACAAATAGAGTGTAACAACATGGTTCACCTGTCTTGGTCCCTGC
CTGGGACACATCTTAATAACCCCAGTATCATATTGCACTAGGATTATGTGTTGCCCA
TAGCCATAAATTCGTGTGAGATGGACATCCAGTCTTTACGGCTTGTCCCCACCCCAT
GGATTTCTATTGTTAAAGATATTCAGAATGTTTCATTCCTACACTAGTATTTATTGCC

FIG. 20B

```
CAAGGGGTTTGTGAGGGTTATATTGGTGTCATAGCACAATGCCACCACTGAACCCCC
CGTCCAAATTTTATTCTGGGGGCGTCACCTGAAACCTTGTTTTCGAGCACCTCACATA
CACCTTACTGTTCACAACTCAGCAGTTATTCTATTAGCTAAACGAAGGAGAATGAAG
AAGCAGGCGAAGATTCAGGAGAGTTCACTGCCCGCTCCTTGATCTTCAGCCACTGCC
CTTGTGACTAAAATGGTTCACTACCCTCGTGGAATCCTGACCCCATGTAAATAAAAC
CGTGACAGCTCATGGGGTGGGAGATATCGCTGTTCCTTAGGACCCTTTTACTAACCC
TAATTCGATAGCATATGCTTCCCGTTGGGTAACATATGCTATTGAATTAGGGTTAGT
CTGGATAGTATATACTACTACCCGGGAAGCATATGCTACCCGTTTAGGGTTAACAAG
GGGGCCTTATAAACACTATTGCTAATGCCCTCTTGAGGGTCCGCTTATCGGTAGCTA
CACAGGCCCCTCTGATTGACGTTGGTGTAGCCTCCCGTAGTCTTCCTGGGCCCCTGG
GAGGTACATGTCCCCCAGCATTGGTGTAAGAGCTTCAGCCAAGAGTTACACATAAA
GGTACGTACCAGTCTTCGAAAGATCTCGGGGTGCCCATCCTGGTCGAGCTGGACGGC
GACGTAAACGGCCACAAGTTCAGCGTGTCCGGCGAGGGCGAGGGCGATGCCACCTA
CGGCAAGCTGACCCTGAAGTTCATCTGCACCACCGGCAAGCTGCCCGTGCCCTGGCC
CACCCTCGTGACCACCCTGACCTACGGCGTGCAGTGCTTCAGCCGCTACCCCGACCA
CATGAAGCAGCACGACTTCTTCAAGTCCGCCATGCCCGAAGGCTACGTCCAGGAGC
GCACCATCTTCTTCAAGGACGACGGCAACTACAAGACCCGCGCCGAGGTGAAGTTC
GAGGGCGACACCCTGGTGAACCGCATCGAGCTGAAGGGCATCGACTTCAAGGAGGA
CGGCAACATCCTGGGGCACAAGCTGGAGTACAACTACAACAGCCACAACGTCTATA
TCATGGCCGACAAGCAGAAGAACGGCATCAAGGTGAACTTCAAGATCCGCCACAAC
ATCGAGGACGGCAGCGTGCAGCTCGCCGACCACTACCAGCAGAACACCCCCATCGG
CGACGGCCCCGTGCTGCTGCCCGACAACCACTACCTGAGCACCCAGTCCGCCCTGAG
CAAAGACCCCAACGAGAAGCGCGATCACATGGTCCTGCTGGAGTTCGTGACCGCCG
CCGGGATCACTCTCGGCATGGACGAGCTGTACAAGTAAAGCGGCCGCGACTCTAGA
TCATAATCAGCCATACCACATTTGTAGAGGTTTTACTTGCTTTAAAAAACCTCCCAC
ACCTCCCCCTGAACCTGAAACATAAAATGAATGCAATTGTTGTTGTTAACTTGTTTAT
TGCAGCTTATAATGGTTACAAATAAAGCAATAGCATCACAAATTTCACAAATAAAG
CATTTTTTTCACTGCATTCTAGTTGTGGTTTGTCCAAACTCATCAATGTCGGGATCCC
GCCAATTGTCTAGATTTCTCTAATCACTTTTTTTTCAAGGCAATCAGGGTATATTATA
TTGTACTTCAGCACAGTTTTAGAGAACAATTGTTATAATTAAATGATAAGGTAGAAT
ATTTCTGCATATAAATTCTGGCTGGCGTGGAAATATTCTTATTGGTAGAAACAACTA
CATCCTGGTCATCATCCTGCCTTTCTCTTTATGGTTACAATGATATACACTGTTTGAG
ATGAGGATAAAATACTCTGAGTCCAAACCGGGCCCCTCTGCTAACCATGTTCATGCC
TTCTTCTTTTTCCTACAGGACTCCTCCCTGCAGGACGGCAGTTCATCTACAAGGTGA
AGCTGCGCGGCACCAACTTCCCCTCCGACGGCCCCGTAATGCAGAAGAAGACCATG
GGCTGGGAGGCCTCCTCCGAGCGGATGTACCCCGAGGACGGCGCCCTGAAGGGCGA
GATCAAGATGAGGCTGAAGCTGAAGGACGGTGGCCACTACGACGCCGAGGTCAAGA
CCACCTACATGGCCAAGAAGCCCGTGCAGCTGCCCGGCGCCTACAAGACCGACATC
AAGCTGGACATCACCTCCCACAACGAGGACTACACCATCGTGGAACAGTACGAGCG
CGCCGAGGGCCGCCACTCCACCGGCGGTATGGATGAACTCTATAAATAAGCACGGG
CCCTATTCTATAGTGTCACCTAAATGCTAGAGCTCGCTGATCAGCCTCGACTGTGCCT
TCTAGTTGCCAGCCATCTGTTGTTTGCCCCTCCCCGTGCCTTCCTTGACCCTGGAAG
GTGCCACTCCCACTGTCCTTTCCTAATAAAATGAGGAAATTGCATCGCATTGTCTGA
GTAGGTGTCATTCTATTCTGGGGGGTGGGGTGGGGCAGGACAGCAAGGGGGAGGAT
TGGGAAGACAATAGCAGGCATGCTGGGGAGGATCTGTGTGGAAAGTCCCCAGGCTC
CCCAGGCAGGCAGAAGTATGCAAAGCATGCATCTCAATTAGTCAGCAACCAGGTGT
```

FIG. 20C

```
GGAAAGTCCCCAGGCTCCCCAGCAGGCAGAAGTATGCAAAGCATGCATCTCAATTA
GTCAGCAACCATAGTCCCGCCCCTAACTCCGCCCATCCCGCCCCTAACTCCGCCCAG
TTCCGCCCATTCTCCGCCCCATGGCTGACTAATTTTTTTATTTATGCAGAGGCCGAG
GCCGCCTCTGCCTCTGAGCTATTCCAGAAGTAGTGAGGAGGCTTTTTGGAGGCCTA
GGCTTTTGCAAAAAGCTCCCGGGAGCTTGTATATCCATTTTCGGATAAGCTTAACTA
AACCATGGTATCAAAAGGTGAAGAAAACAATATGGCAGTCATCAAGGAGTTCATGC
GCTTCAAGGTGCGCATGGAGGGCTCCGTGAACGGCCACGAGTTCGAGATCGAGGGC
GAGGGCGAGGGCCGCCCCTACGAGGGCACCCAGACCGCCAAGCTGAAGGTGACCG
AGGGTGGCCCCTGCCCTTCGCCTGGGACATCCTGTCCCTCAGTTCATGTACGGCT
CCAAGGCCTACGTGAAGCACCCCGCCGACATCCCCGACTACTTGAAGCTGTCCTTCC
CCGAGGGCTTCAAGTGGGAGCGCGTGATGAACTTCGAGGACGGCGGCGTGGTGACC
GTGACCCAGGTGAGTTTGGGGACCCTTGATTGTTCTTTCTTTTCGCTATTGTAAAAT
TCATGTTATATGGAGGGGCAAAGTTTTCAGGGTGTTGTTTAGAATGGGAAGATGTC
CCTTGTATCACCATGGACCCTCATGATAATTTTGTTTCTTTCACTTTCTACTCTGTTGA
CAACCATTGTCTCCTCTTATTTTCTTTTCATTTCTGTAACTTTTTCGTTAAACTTTAG
CTTGCATTTGTAACGAATTTTTAAATTCACTTTTGTTTATTTGTCAGATTGTAAGTAC
CGGGACCCGGAATTCTACCGGGTAGGGGAGGCGCTTTTCCCAAGGCAGTCTGGAGC
ATGCGCTTTAGCAGCCCCGCTGGCACTTGGCGCTACACAAGTGGCCTCTGGCCTCGC
ACACATTCCACATCCACCGGTAGCGCCAACCGGCTCCGTTCTTTGGTGGCCCCTTCG
CGCCACTTCTACTCCTCCCCTAGTCAGGAAGTTTCCCCCAGCAAGCTCGCGTCGTGC
AGGACGTGACAAATGGAAGTAGCACGTCTCACTAGTCTCGTGCAGATGGACAGCAC
CGCTGAGCAATGGAAGCGGGTAGGCCTTTGGGGCAGCGGCCAATAGCAGCTTTGTT
CCTTCGCTTTCTGGGCTCAGAGGCTGGGAAGGGGTGGGTCCGGGGCGGGCTCAGG
GGCGGGCTCAGGGGCGGGCGGGCGCCCGAAGGTCCTCCCGAGGCCCGGCATTCTGC
ACGCTTCAAAAGCGCACGTCTGCCGCGCTGTTCTCCTCTTCCTCATCTCCGGGCCTTT
CGACCTGCAGCCCAAGCTCTAGCGCTACCGGTCGCCACCATGGTGAGCAAGGGCGA
GGAGCTGTTCACCGGGGTGGTGCCCATCCTGGTCGAGCTGGACGGCGACGTAAACG
GCCACAAGTTCAGCGTGTCCGGCGAGGGCGAGGGCGATGCCACCTACGGCAAGCTG
ACCCTGAAGTTCATCTGCACCACCGGCAAGCTGCCCGTGCCCTGGCCCACCCTCGTG
ACCACCCTGACCTACGGCGTGCAGTGCTTCAGCCGCTACCCCGACCACATGAAGCA
GCACGACTTCTTCAAGTCCGCCATGCCCGAAGGCTACGTCCAGGAGCGCACCATCTT
CTTCAAGGACGACGGCAACTACAAGACCCGCGCCGAGGTGAAGTTCGAGGGCGACA
CCCTGGTGAACCGCATCGAGCTGAAGGGCATCGTAGGGATAACGCTCATATATCGA
TAATAAGTATGTTGTAACTAAAGTCGTGAAATAAGTATGTTGTAACTAAAGTCTTAC
AATAAGTATGTTGTAACTAAAGTGTATACCTTTCCGGATAGGGATAACGCTCATATA
TCGATAATAAGTATGTTGTAACTAAAGTCGTGAAATAAGTATGTTGTAACTAAAGTC
TTACAATAAGTATGTTGTAACTAAAGTGTATACCTTTCCGGATAGGGATAACAGGGT
AATCAAGGAGGACGGCAACATCCTGGGGCACAAGCTGGAGTACAACTACAACAGCC
ACAACGTCTATATCATGGCCGACAAGCAGAAGAACGGCATCAAGGTGAACTTCAAG
ATCCGCCACAACATCGAGGACGGCAGCGTGCAGCTCGCCGACCACTACCAGCAGAA
CACCCCCATCGGCGACGGCCCCGTGCTGCTGCCCGACAACCACTACCTGAGCACCCA
GTCCGCCCTGAGCAAAGACCCCAACGAGAAGCGCGATCACATGGTCCTGCTGGAGT
TCGTGACCGCCGCCGGGATCACTCTCGGCATGGACGAGCTGTACAAGTAAAGCGGC
CGCGACTCTAGATCATAATCAGCCATACCACATTTGTAGAGGTTTTACTTGCTTTAA
AAAACCTCCCACACCTCCCCCTGAACCTGAAACATAAAATGAATGCAATTGTTGTTG
TTAACTTGTTTATTGCAGCTTATAATGGTTACAAATAAAGCAATAGCATCACAAATT
```

FIG. 20D

```
TCACAAATAAAGCATTTTTTTCACTGCATTCTAGTTGTGGTTTGTCCAAACTCATCAA
TGTCGGATGGCCGCGCTGGGGATGCGGTGGGCTCTATGGCTTATGAGGCGGAAAGA
ACCAGCTGGGGCTCGATCCTCTAGTTGGCGCGCCGGCTAGAAGATGGGCGGGAGTC
TTCTGGGCAGGCTTAAAGGCTAACCTGGTGTGTGGGCGTTGTCCTGCAGGGGAATTG
AACAGGTGTAAAATTGGAGGGACAAGACTTCCCACAGATTTTCGGTTTTGTCGGGAA
GTTTTTTAATAGGGGCAAATAGGAAAATGGAGGATAGGAGTCATCTGGGGTTTATG
CAGCAAAACTACAGGTATATTGCTTGTATCCGCCTCGGAGATTTCCATGAGGAGATA
AAGACATGTCACCCGAGTTTATACTCTCCTGCTTAGATCCTACTACAGTATGAAATA
CAGTGTYGCGAGGTAGACTATGTAAGCAGATTTAATCATTTTAAAGAGCCCAGTACT
TCATATCCATTTCTCCCGCTCCTTCTGCAGCCTTATCAAAAGGTATTTAGAACACTCA
TTTTAGCCCCATTTTCATTTATTATACTGGCTTATCCAACCCCTAGACAGAGCATTGG
CATTTTCCCTTTCCTGATCTTAGAAGTCTGATGACTCATGAAACCAGACAGATTAGTT
ACATACACCACAAATCGAGGCTGTAGCTGGGGCCTCAACACTGCAGTTCTTTTATAA
CTCCTTAGTACACTTTTGTTGATCCTTTGCCTTGATCCTTAATTTTCAGTGTCTATCA
CCTCTCCCGTCAGGTGGTGTTCCACATTTGGGCCTATTCTCAGTCCAGGGAGTTTTAC
AACAATAGATGTATTGAGAATCCAACCTAAAGCTTAACTTTCCACTCCCATGAATGC
CTCTCTCCTTTTCTCCATTATAACTGAGCTATWACCATTAATGGTTTCAGGTGGATG
TCTCCTCCCCAATATACCTGATGTATCTACATATTGCCAGGCTGATATTTTAAGACA
TWAAAGGTATATTTCATTATTGAGCCACATGGTATTGATTACTGCTACTAAAATTTT
GTCATTGTACACATCTGTAAAAGGTGGTTCCTTTTGGAATGCAAAGTTCAGGTGTTT
GTTGTCTTTCCTGACCTAAGGTCTTGTGAGCTTGTATTTTTCTATTTAAGCAGTGCTT
TCTCTTGGACTGGCTTGACTCATGGCATTCTACACGTTATTGCTGGTCTAAATGTGAT
TTTGCCAAGCTTCTTCAGGACCTATAATTTTGCTTGACTTGTAGCCAAACACAAGTA
AAATGATTAAGCAACAAATGTATTTGTGAAGCTTGGTTTTAGGTTGTTGTGTTGTGT
GTGCTTGTGCTCTATAATAATACTATCCAGGGGCTGGAGAGGTGGCTCGGAGTTCAA
GAGCACAGACTGCTCTTCCAGAAGTCCTGAGTTCAATTCCCAGCAACCACATGGTGG
CTCACAACCATCTGTAATGGGATCTGATGCCCTCTTCTGGTGTGTCTGAAGACCACA
AGTGTATTCACATTAAATAAATAATCCTCCTTCTTCTTCTTTTTTTTTTTAAAGAGA
ATWCTGTCTCCAGTAGAATTACTGAAGTAATGAAATACTTTGTGTTTGTTCCAATAT
GGWAGCCAATAATCAAATACTCTTWAGCACTGGAAATGTACCAAGGAACTATTTA
TTTAAGTGWACTGTGGACAGAGGAGCCATAACTGCAGACTTGTGGGATACAGAAGA
CCAATGCAGACTTAATGTCTTTTCTCTTACACTAAGCAATAAAGAAATAAAAATTGA
ACTTCTAGTATCCTATTTGTTAAACTGCTAGCTTTACTAACTTTTGTGCTTCATCTATA
CAAAGCTGAAAGCTAAGTCTGCAGCCATTACTAAACATGAAAGCAAGTAATGATAA
TTTTGGATTTCAAAAATGTAGGGCCAGAGTTTAGCCAGCCAGTGGTGGTGCTTGCCT
TTATGCCTTAATCCCAGCACTCTGGAGGCAGAGACAGGCAGATCTCTGAGTTTGAGC
CCAGCCTGGTCTACACATCAAGTTCTATCTAGGATAGCCAGGAATACACAGAAA
CCCTGTTGGGGAGGGGGGCTCTGAGATTTCATAAAATTATAATTGAAGCATTCCCTA
ATGAGCCACTATGGATGTGGCTAAATCCGTCTACCTTTCTGATGAGATTTGGGTATT
ATTTTTTCTGTCTCTGCTGTTGGTTGGGTCTTTGACACTGTGGGCTTTCTTAAAGCCT
CCTTCCCTGCCATGTGGTCTCTTGTTTGCTACTAACTTCCCATGGCTTAAATGGCATG
GCTTTTTGCCTTCTAAGGGCAGCTGCTGAGWTTTGCAGCCTGATTTCCAGGGTGGGG
TTGGGAAATCTTTCAAACACTAAAATTGTCCTTTAATTTTTTTAAAAAATGGGTTA
TATAATAAACCTCATAAAATAGTTATGAGGAGTGAGGTGGACTAATATTAATGAGTC
CCTCCCCTATAAAGAGCTATTAAGGCTTTTTGTCTTATACTAACTTTTTTTTAAAT
GTGGTATCTTTAGAACCAAGGGTCTTAGAGTTTTAGTATACAGAAACTGTTGCATCG
```

FIG. 20E

```
CTTAATCAGATTTTCTAGTTTCAAATCCAGAGAATCCAAATTCTTCACAGCCAAAGT
CAAATTAAGAATTTCTGACTTTAATGTTATTTGCTACTGTGAATATAAAATGATAGCT
TTTCCTGAGGCAGGGTCTCACTATGTATCTCTGCCTGATCTGCAACAAGATATGTAG
ACTAAAGTTCTGCCTGCTTTGTCTCCTGAATACTAAGGTTAAAATGTAGTAATACTT
TTGGAACTTGCAGGTCAGATTCTTTTATAGGGGACACACTAAGGGAGCTTGGGTGAT
AGTTGGTAAATGTGTTTAAGTGATGAAAACTTGAATTATTATCACCGCAACCTACTT
TTTAAAAAAAAAGCCAGGCCTGTTAGAGCATGCTAAGGGATCCCTAGGACTTGCT
GAGCACACAAGAGTAGTACTTGGCAGGCTCCTGGTGAGAGCATATTTCAAAAAACA
AGGCAGACAACCAAGAAACTACAGTAAGGTTACCTGTCTTTAACCATCTGCATATAC
ACAGGGATATTAAAATATTCCAAATAATATTTCATTCAAGTTTTCCCCCATCAAATT
GGGACATGGATTTCTCCGGTGAATAGGCAGAGTTGGAAACTAAACAAATGTTGGTTT
TGTGATTTGTGAAATTGTTTTCAAGTGATAGTTAAAGCCCATGAGATACAGAACAAA
GCTGCTATTTCGAGGTCTCTTGGTTATACTCAGAAGCACTTCTTTGGGTTTCCCTGCA
CTATCCTGATCATGTGCTAGGCCTWCCTTAGGCTGATTGTTGTTCAAATAACTTAAG
TTTCCTGTCAGGTGATGTCATATGATTTCATATATCAAGGCAAAACATGTTATATATG
TTAAACATTTGKACTTAATGTGAAAGTTAGGTCTTTGTGGGTTTTGATTTTAATTTCA
AAACCTGAGCTAAATAAGTCATTTTACATGTCTTACATTTGGTGAATTGTATATTGTG
GTTTGCAGGCAAGACTCTCTGACCTAGTAACCCTCCTATAGAGCACTTTGCTGGGTC
ACAAGTCTAGGAGTCAAGCATTTCACCTTGAAGTTGAGACGTTTTGTTAGTGTATAC
TAGTTATATGTTGGAGGACATGTTTATCCAGAAGATATTCAGGACTATTTTTGACTG
GGCTAAGGAATTGATTCTGATTAGCACTGTTAGTGAGCATTGAGTGGCCTTTAGGCT
TGAATTGGAGTCACTTGTATATCTCAAATAATGCTGGCCTTTTTTWAAAAGCCCTTG
TTCTTTATCACCCTGTTTTCTACATAATTTTTGTTCAAAGAAATACTTGTTTGGATCTC
CTTTTGACAACAATAGCATGTTTTCAAGCCATATTTTTTTCCTTTTTTTTTTTTTTTT
GGTTTTTCGAGACAGGGTTTCTCTGTATAGCCCTGGCTGTCCTGGAACTCACTTTGTA
GACCAGGCTGGCCTCGAACTCAGAAATCCGCCTGCCTCTGCCTCCTGAGTGCCGGGA
TTAAAGGCGTGCACCACCACGCCTGGCTAAGTTGGATATTTGTATATAACTATAAC
CAATACTAACTCCACTGGGTGGATTTTTAATTCAGTCAGTAGTCTTAAGTGGTCTTTA
TTGGCCCTTATTAAAATCTACTGTTCACTCTAACAGAGGCTGTTGGACTAGTGGSACT
AAGCAACTTCCTACGGATATACTAGCAGATAAGGGTCAGGGATAGAAACTAGTCTA
GCGTTTTGTATACCTACCAGCTTATACTACCTTGTTCTGATAGAAATATTTAGGACAT
CTAGCTTATCGATCCGTCGACGGTATCGATAAGCTTGATATCGAATTCTACCGGGTA
GGGGAGGCGCTTTTCCAAGGCAGTCTGAGCATGCGCTTAGCAGCCCCGCTGGCACTT
GGCGCTACACAAGTGGCCTYTGGCCTCGCACACATTCCACATCCACCGGTAGGCGCC
AACCGGCTCCGTTCTTTGGTGGCCCCTTCGCGCCACCTTCTWTCCTCCCCTAGTCAG
GAAGTTCCCCCCCGCCCCGCAGCTCGCGTCGTSAGGACGTGACAAATGGAAGTAGC
ACGTCTCACTAGTCTCGTCAGATGGACAGCACCGCTGAGCAATGGAAGCGGGTAGG
CCTTTGGGGCAGCGGCCAATAGCAGCTTTGCTCCTTCGCTTTCTGGGCTCAGAGGCT
GGGAAGGGGTGGGTCCGGGGCGGGCTCAGGGCGGGCTCAGGGGCGGGCGGGC
GCCCGAAGGTCCTCCGGAGGCCCGGCATTCTGCACGCTTCAAAAGCGCACGTCTGCC
GCGCTGTTCTCCTCTTCCTCATCTCCGGGCCTTTCGACCTGCAGGTCCTCGCCATGGA
TCCTGATGATGTTGTTATTCTTCAATCTTTTGTATGGAAAACTTTTCTTCGTACCACG
GGACTAAACCTGGTTATGTAGATTCCATTCAAAAAGGGTATACAAAAGCCAAAATCT
GGTACACAAGGAAATTATGACGATGATTGGAAAGGGTTTTATAGTACCGACAATAA
ATACGACGCTGCGGGATACTCTGTAGATAATGAAAACCCGCTCTCTGGAAAAGCTG
GAGGCGTGGTCAAAGTGACGTATCCAGGACTGACGAAGGTTCTCGCACTAAAAGTG
```

FIG. 20F

```
GATAATGCCGAAACTATTAAGAAAGAGTTAGGTTTAAGTCTCACTGAACCGTTGATG
GAGCAAGTCGGAACGGAAGAGTTTATCAAAAGGTTCGGTGATGGTGCTTCGCGTGT
AGTGCTCAGCCTTCCCTTCGCTGAGGGGAGTTCTAGCGTTGAATATATTAATAACTG
GGAACAGGCGAAAGCGTTAAGCGTAGAACTTGAGATTAATTTTGAAACCCGTGGAA
AACGTGGCCAAGATGCGATGTATGAGTATATGGCTCAAGCCTGTGCAGGAAATCGT
GTCAGGCGATCTCTTTGTGAAGGAACCTTACTTCTGTGGTGTGACATAATTGGACAA
ACTACCTACAGAGATTTAAAGCTCTAAGGTAAATATAAAATTTTAAGTGTATAATG
TGTTAAACTACTGATTCTAATTGTTTGTGTATTTTAGATTCCAACCTATGGAACTGAT
GAATGGGAGCAGTGGTGGAATGCAGATCCTAGAGCTCGCTGATCAGCCTCGACTGT
GCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGT
CTGAGTAGGTGTCATTCTATTCTGGGGGGTGGGGTGGGGCAGGACAGCAAGGGGGA
GGATTGGAAGACAATAGCAGGCATGCTGGGGATGCGGTGGGCTCTATGGCTTCTG
AGGCGGAAAGAACCAGCTGGGGCTCGACCTCGAGGGGGGGCCCGGTACCCAGCTTT
TGTTCCCTTTAGTGAGGGTTAATTGCGCGCTTGGCGTAATCATGGTCATAGCTGTTTC
CTGTGTGAAATTGTTATCCGCTCACAATTCCACACAACATACGAGCCGGAAGCATAA
AGTGTAAAGCCTGGGGTGCCTAATGAGTGAGCTAACTCACATTAATTGCGTTGCGCT
CACTGCCCGCTTTCCAGTCGGGAAACCTGTCGTGCCAGCTGCATTAATGAATCGGCC
AACGCGCGGGGAGAGGCGGTTTGCGTATTGGGCGCTCTTCCGCTTCCTCGCTCACTG
ACTCGCTGCGCTCGGTCGTTCGGCTGCGGCGAGCGGTATCAGCTCACTCAAAGGCGG
TAATACGGTTATCCACAGAATCAGGGGATAACGCAGGAAAGAACATGTGAGCAAAA
GGCCAGCAAAAGGCCAGGAACCGTAAAAAGGCCGCGTTGCTGGCGTTTTTCCATAG
GCTCCGCCCCCCTGACGAGCATCACAAAAATCGACGCTCAAGTCAGAGGTGGCGAA
ACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCC
GGTAACTATCGTCTTGAGTCCAACCCGGTAAGACACGACTTATCGCCACTGGCAGCA
GCCACTGGTAACAGGATTAGCAGAGCGAGGTATGTAGGCGGTGCTACAGAGTTCTT
GAAGTGGTGGCCTAACTACGGCTACACTAGAAGGACAGTATTTGGTATCTGCGCTCT
GCTGAAGCCAGTTACCTTCGGAAAAAGAGTTGGTAGCTCTTGATCCGGCAAACAAA
CCACCGCTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGTGGAACG
AAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTAT
TTCGTTCATCCATAGTTGCCTGACTCCCCGTCGTGTAGATAACTACGATACGGGAGG
GCTTACCATCTGGCCCCAGTGCTGCAATGATACCGCGAGACCCACGCTCACCGGCTC
CAGATTTATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAGAGTAAGT
AGTTCGCCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCAAGGCGA
GTTACATGATCCCCCATGTTGTGCAAAAAGCGGTTAGCTCCTTCGGTCCTCCGATC
GTTGTCAGAAGTAAGTTGGCCGCAGTGTTATCACTCATGGTTATGGCAGCACTGCAT
AATTCTCTTACTGTCATGCCATCCGTAAGATGCTTTTCTGTGACTGGTGAGTACTCAA
CCAAGTCATTCTGAGAATAGTGTATGCGGCGACCGAGTTGCTCTTGCCCGGCGTCAA
```

FIG. 20G

```
TACGGGATAATACCGCGCCACATAGCAGAACTTTAAAAGTGCTCATCATTGGAAAA
CGTTCTTCGGGGCGAAAACTCTCAAGGATCTTACCGCTGTTGAGATCCAGTTCGATG
TAACCCACTCGTGCACCCAACTGATCTTCAGCATCTTTTACTTTCACCAGCGTTTCTG
GGTGAGCAAAAACAGGAAGGCAAAATGCCGCAAAAAGGGAATAAGGGCGACACG
GAAATGTTGAATACTCATACTCTTCCTTTTTCAATATTATTGAAGCATTTATCAGGGT
TATTGTCTCATGAGCGGATACATATTTGAATGTATTTAGAAAAATAAACAAATAGGG
GTTCCGCGCACATTTCCCCGAAAAGTGCCACCTAAATTGTAAGCGTTAATATTTTGTT
AAAATTCGCGTTAAATTTTGTTAAATCAGCTCATTTTTTAACCAATAGGCCGAAATC
GGCAAAATCCCTTATAAATCAAAAGAATAGACCGAGATAGGGTTGAGTGTTGTTCC
AGTTTGGAACAAGAGTCCACTATTAAAGAACGTGGACTCCAACGTCAAAGGGCGAA
AAACCGTCTATCAGGGCGATGGCCCACTACGTGAACCATCACCCTAATCAAGTTTTT
TGGGGTCGAGGTGCCGTAAAGCACTAAATCGGAACCCTAAAGGGAGCCCCCGATTT
AGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACC
ACACCCGCCGCGCTTAATGCGCCGCTACAGGGCGCGTCCCATTCGCCATTCAGGCTG
CGCAACTGTTGGGAAGGGCGATCGGTGCGGGCCTCTTCGCTATTACGCCAGCTGGCG
AAAGGGGGATGTGCTGCAAGGCGATTAAGTTGGGTAACGCCAGGGTTTTCCCAGTC
ACGACGTTGTAAAACGACGGCCAGTGAGCGCGCGTAATACGACTCACTATAGGGCG
AATTGGAGCT
```

COMPOSITIONS AND METHODS FOR CHARACTERIZING A DNA REPAIR VARIANT POLYPEPTIDE

CROSS-REFERENCE TO RELATED APPLICATION

This application is a continuation of U.S. Ser. No. 14/941,769, filed on Nov. 16, 2015, now U.S. Pat. No. 10,017,825, which claims priority to and the benefit of U.S. Provisional Patent Application Ser. No. 62/080,875, filed Nov. 17, 2014, the entire contents of which is hereby incorporated by reference herein.

STATEMENT OF RIGHTS TO INVENTIONS MADE UNDER FEDERALLY SPONSORED RESEARCH

This invention was made with U.S. government support under Grant Nos: R01CA095175, R01GM073894 and R21CA144017, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 6, 2018, is named 167688.010202USCON_SL.txt and is 140,703 bytes in size.

BACKGROUND OF THE INVENTION

The major breast/ovarian cancer predisposition genes, BRCA1 and BRCA2, function in double strand break (DSB) repair and sister chromatid recombination (SCR), a potentially error-free pathway of homologous recombination (HR). Some BRCA1 missense mutations (encoding point mutant proteins) are known to be either neutral or pathogenic. However, most missense mutants—termed "variants of uncertain significance" (VUS)—are difficult to classify due to their scarcity in the human population. Therefore, if a woman carries a germ line BRCA1 VUS allele, her cancer risk is unknown. Methods of characterizing the functional significance of such variants are urgently required to distinguish variants that increase the risk of breast cancer from those that are not functionally significant.

SUMMARY OF THE INVENTION

As described below, the present invention provides quantitative homologous recombination assays developed to characterize the pathogenicity DNA repair polypeptides (e.g., BRCA1, BRCA2, Rad51) and provide urgently needed functional information on the significance of DNA repair variants of uncertain significance (VUS) alleles.

In one aspect, the invention provides a vector containing a promoter directing expression in a mammalian cell and a nucleic acid sequence containing one or more Ter sites.

In another aspect, the invention provides a homologous recombination reporter gene conversion vector comprising one or more Ter sites in a nucleic acid sequence encoding a reporter polypeptide or other detectable or selectable marker.

In another aspect, the invention provides a homologous recombination reporter of short and long tract gene conversion vector comprising a 5' truncated GFP encoding nucleic acid sequence positioned upstream of 5' and 3' RFP exons positioned upstream of one to six Ter sites positioned within a GFP encoding nucleic acid sequence.

In another aspect, the invention provides a cell containing the vector of any aspect of the invention.

In another aspect, the invention provides a mammalian cell containing or expressing a Tus polypeptide and a polynucleotide comprising one or more Ter sites (e.g., a vector of the invention, or portion thereof, is integrated as a single copy at a defined genomic locus).

In another aspect, the invention provides a cell containing a single copy of a polynucleotide containing a 5' truncated GFP encoding sequence positioned upstream of 5' and 3' RFP exons positioned upstream of one to six Ter sites positioned within a GFP encoding sequence, where the polynucleotide is integrated into the cell genome; and an expression vector encoding a wild-type Tus polypeptide.

In another aspect, the invention provides a method of characterizing the functional significance of a mutation in a DNA repair polypeptide, involving: expressing in a cell a DNA repair polypeptide having a mutation and a wild-type Tus polypeptide fused to a nuclear localization signal, where the cell contains a single genomic integrated copy of a polynucleotide containing a 5' truncated GFP encoding sequence positioned upstream of 5' and 3' RFP exons positioned upstream of one or more Ter sites positioned within a GFP encoding sequence comprising a rare cutting endonuclease site; and detecting long-tract gene conversion in the cell, where an increase in long tract gene conversion in the cell relative to a reference indicates that the mutation in the DNA repair polypeptide is functionally significant.

In another aspect, the invention provides a method of characterizing the functional significance of a mutation in a BRCA1, BRCA2, or Rad51 polypeptide, involving expressing in a cell one or more of a BRCA1, BRCA2, or Rad51 polypeptide comprising a mutation and a wild-type Tus polypeptide fused to a nuclear localization signal, where the cell contains a single genomic integrated copy of a polynucleotide containing a 5' truncated GFP encoding sequence positioned upstream of 5' and 3' RFP exons positioned upstream of one or more Ter sites positioned within a GFP encoding sequence comprising a rare cutting endonuclease site; and detecting long-tract gene conversion in the cell, where an increase in long tract gene conversion in the cell relative to a cell expressing a wild-type DNA repair polypeptide indicates that the mutation in the DNA repair polypeptide is functionally significant.

In another aspect, the invention provides a method of characterizing the functional significance of a mutation in a DNA repair polypeptide in a biological sample, involving sequencing a DNA repair gene in a biological sample derived from a subject, thereby identifying a mutation in the DNA repair gene; contacting a cell lacking the DNA repair polypeptide with each of an expression vector encoding a DNA repair polypeptide comprising the identified mutation; and an expression vector encoding a wild-type Tus polypeptide fused to a nuclear localization signal, where the cell contains a single genomic integrated copy of a polynucleotide containing a 5' truncated GFP encoding sequence positioned upstream of 5' and 3' RFP exons positioned upstream of one or more Ter sites positioned within a GFP encoding sequence containing a rare cutting endonuclease site; and detecting long-tract gene conversion in the cell, where an increase in long tract gene conversion in the cell relative to a reference cell expressing a wild-type DNA repair polypeptide indicates that the mutation in the DNA repair polypeptide is functionally significant.

In another aspect, the invention provides a method of selecting a treatment for a subject identified as having breast cancer, involving: sequencing a DNA repair gene in a biological sample derived from a patient, thereby identifying a mutation in the DNA repair gene; contacting a cell lacking the DNA repair polypeptide with each of: an expression vector encoding a DNA repair polypeptide comprising the identified mutation; and an expression vector encoding a wild-type Tus polypeptide fused to a nuclear localization signal; where the cell contains a single genomic integrated copy of a polynucleotide containing a 5' truncated GFP encoding sequence positioned upstream of 5' and 3' RFP exons positioned upstream of one or more Ter sites positioned within a GFP encoding sequence containing a rare cutting endonuclease site; and detecting long-tract gene conversion in the cell, where an increase in long tract gene conversion in the cell relative to a reference cell expressing a wild-type DNA repair polypeptide indicates that the mutation in the DNA repair polypeptide is functionally significant, thereby indicating that the patient should receive a PARP inhibitor or cisplatin. In various embodiments, the DNA repair polypeptide is BRCA1, BRCA2, and/or Rad51.

In one aspect, the invention provides a method of site-specific genome editing, involving contacting a genomic locus with two or more polypeptides that specifically bind two or more target nucleic acid sequences in the genomic locus and induce replication fork stalling, thereby producing error-free genome editing.

In another aspect, the invention provides a method of generating site specific recombination at a genomic locus, involving: inhibiting replication at the genomic locus, thereby generating site specific recombination at the genomic locus.

In another aspect, the invention provides a vector containing one or more Ter sites upstream of an origin of replication, which is upstream of a replication block.

In various embodiments of any of the aspects delineated herein, the origin of replication is an Epstein-Barr virus nuclear antigen 1 binding origin of replication and/or Epstein-Barr virus nuclear antigen 1-bound family of repeats. In various embodiments of any of the aspects delineated herein, the vector comprises more than one Ter sites. In particular embodiments, the vector contains one or more Ter sites upstream of an Epstein-Barr virus nuclear antigen 1 binding origin of replication and a replication block that is the Epstein-Barr virus nuclear antigen 1-bound family of repeats.

In a related aspect, the invention provides a cell containing a vector having one or more Ter sites upstream of an origin of replication. In various embodiments of any of the aspects delineated herein, the cell further contains a polynucleotide encoding a wild-type or variant Tus.

In another related aspect, the invention provides a cell containing a vector having one or more Ter sites upstream of an Epstein-Barr virus nuclear antigen 1 binding origin of replication and a replication block that is the Epstein-Barr virus nuclear antigen 1-bound family of repeats.

In another aspect, the invention provides a method of characterizing replication involving: contacting a cell that expresses EBNA1 with a vector comprising one or more Ter sites upstream of an Epstein-Barr virus nuclear antigen 1 binding origin of replication and a replication block that is the Epstein-Barr virus nuclear antigen 1-bound family of repeats and a vector encoding wild-type or variant Tus; and detecting long-tract gene conversion at Tus/Ter-stalled forks.

In various embodiments of any of the aspects delineated herein, the vector contains two, three, four, five, six or more Ter sites. In particular embodiments, the vector contains 6, 9, 12, 15, or 21 Ter sites. In various embodiments of any of the aspects delineated herein, the reporter polypeptide or other detectable or selectable marker is GFP, RFP, CFP, YFP, an antibiotic resistance marker, ampicillin-resistance, or cell surface marker selectable by antibody. In various embodiments of any of the aspects delineated herein, the vector is codon-optimized for mammalian expression. In various embodiments of any of the aspects delineated herein, the vector contains a rare cutting endonuclease site (e.g., targeted by I-SceI, I-PpoI, CRISPR/Cas9, TALEN, and/or Zinc finger nuclease).

In various embodiments of any of the aspects delineated herein, the polynucleotide is randomly integrated or targeted into the cell genome. In various embodiments of any of the aspects delineated herein, the Tus polypeptide is fused to a nuclear localization signal and/or an epitope tag. In various embodiments of any of the aspects delineated herein, the cell is a eukaryotic cell, mammalian cell, vertebrate cell, insect cell, chicken cell, mouse cell, or human cell.

In various embodiments of any of the aspects delineated herein, the reference is a cell expressing a wild-type DNA repair polypeptide. In various embodiments of any of the aspects delineated herein, the the DNA repair polypeptide is selected from one or more genes involved in homologous recombination. In specific embodiments, the the DNA repair polypeptide is one or more of BRCA1, BRCA2, BARD1, PALB2, RAD51, RAD51B, RAD51C, RAD51D, XRCC2, XRCC3, BLM, other RECQ helicases, MRE11, Rad50, NBS1, ATM, ATR, CTIP, Brip, RPA, and/or RPA-like polypeptide.

In various embodiments of any of the aspects delineated herein, long tract gene conversion is detected by detecting an alteration in fluorescence between the cell and the reference cell. In various embodiments, the fluorescence is detected using flow cytometry. In various embodiments of any of the aspects delineated herein, detection involves detecting $GFP^+$ $RFP^-$; $GFP^+$ $RFP^+$; and/or $GFP^-$ $RFP^+$ in the cells.

In various embodiments of any of the aspects delineated herein, the functional significance of a mutation in a DNA repair polypeptide in a biological sample indicates the subject has or has a propensity to develop cancer. In various embodiments of any of the aspects delineated herein, the biological sample is a tumor sample or blood sample.

In various embodiments of any of the aspects delineated herein, replication is inhibited by contacting the genomic locus with a polypeptide or polypeptide complex that specifically binds a target nucleic acid sequence in the genomic locus. In various embodiments of any of the aspects delineated herein, the genomic locus is contacted with a plurality of polypeptides or polypeptide complexes. In various embodiments of any of the aspects delineated herein, the polypeptide or polypeptide complex comprises one or more of Cas9, Cas 9 null, guide nucleic acid, Tus, Zinc finger domain, Zinc finger nuclease, transcription activator-like effector (TALE) domain, and/or TALE nuclease. In various embodiments two or more polypeptides are Cas9, Cas9 null (i.e., catalytically inactive Cas9), Tus, Zinc finger domain, Zinc finger nuclease, transcription activator-like effector (TALE) domain, and/or TALE nucleases. In various embodiments of any of the aspects delineated herein, the genome editing or site specific recombination alters the DNA sequence of a disease gene at the genomic locus.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "biologic sample" is meant any tissue, cell, fluid, or other material derived from an organism.

By "BRCA1 polypeptide" is meant a protein having at least about 85% amino acid sequence identity to the sequence provided at Genbank accession no. AAC37594 or a fragment thereof and having DNA repair activity.

```
GenBank: AAC37594.1 >gi|1698399|gb|AAC37594.1|
BRCA1 [Homo sapiens]
                                               (SEQ ID NO: 1)
MDLSALRVEEVQNVINAMQKILECPICLELIKEPVSTKCDHIFCKFCMLK

LLNQKKGPSQCPLCKNDITKRSLQESTRFSQLVEELLKIICAFQLDTGLE

YANSYNFAKKENNSPEHLKDEVSIIQSMGYRNRAKRLLQSEPENPSLQET

SLSVQLSNLGTVRTLRTKQRIQPQKTSVYIELGSDSSEDTVNKATYCSVG

DQELLQITPQGTRDEISLDSAKKAACEFSETDVTNTEHHQPSNNDLNTTE

KRAAERHPEKYQGSSVSNLHVEPCGTNTHASSLQHENSSLLLTKDRMNVE

KAEFCNKSKQPGLARSQHNRWAGSKETCNDRRTPSTEKKVDLNADPLCER

KEWNKQKLPCSENPRDTEDVPWITLNSSIQKVNEWFSRSDELLGSDDSHD

GESESNAKVADVLDVLNEVDEYSGSSEKIDLLASDPHEALICKSERVHSK

SVESNIEDKIFGKTYRKKASLPNLSHVTENLIIGAFVTEPQIIQERPLTN

KLKRKRRPTSGLHPEDFIKKADLAVQKTPEMINQGTNQTEQNGQVMNITN

SGHENKTKGDSIQNEKNPNPIESLEKESAFKTKAEPISSSISNMELELNI

HNSKAPKKNRLRRKSSTRHIHALELVVSRNLSPPNCTELQIDSCSSSEEI

KKKKYNQMPVRHSRNLQLMEGKEPATGAKKSNKPNEQTSKRHDSDTFPEL

KLTNAPGSFTKCSNTSELKEFVNPSLPREEKEEKLETVKVSNNAEDPKDL

MLSGERVLQTERSVESSSISLVPGTDYGTQESISLLEVSTLGKAKTEPNK

CVSQCAAFENPKGLIHGCSKDNRNDTEGFKYPLGHEVNHSRETSIEMEES

ELDAQYLQNTFKVSKRQSFAPFSNPGNAEEECATFSAHSGSLKKQSPKVT

FECEQKEENQGKNESNIKPVQTVNITAGFPVVGQKDKPVDNAKCSIKGGS

RFCLSSQFRGNETGLITPNKHGLLQNPYRIPPLFPIKSFVKTKCKKNLLE

ENFEEHSMSPEREMGNENIPSTVSTISRNNIRENVFKEASSSNINEVGSS

TNEVGSSINEIGSSDENIQAELGRNRGPKLNAMLRLGVLQPEVYKQSLPG

SNCKHPEIKKQEYEEVVQTVNTDFSPYLISDNLEQPMGSSHASQVCSETP

DDLLDDGEIKEDTSFAENDIKESSAVFSKSVQKGELSRSPSPFTHTHLAQ

GYRRGAKKLESSEENLSSEDEELPCFQHLLFGKVNNIPSQSTRHSTVATE

CLSKNTEENLLSLKNSLNDCSNQVILAKASQEHHLSEETKCSASLFSSQC

SELEDLTANTNTQDPFLIGSSKQMRHQSESQGVGLSDKELVSDDEERGTG

LEENNQEEQSMDSNLGEAASGCESETSVSEDCSGLSSQSDILTTQQRDTM

QHNLIKLQQEMAELEAVLEQHGSQPSNSYPSIISDSSALEDLRNPEQSTS

EKAVLTSQKSSEYPISQNPEGLSADKFEVSADSSTSKNKEPGVERSSPSK

CPSLDDRWYMHSCSGSLQNRNYPSQEELIKVVDVEEQQLEESGPHDLTET

SYLPRQDLEGTPYLESGISLFSDDPESDPSEDRAPESARVGNIPSSTSAL

KVPQLKVAESAQSPAAAHTTDTAGYNAMEESVSREKPELTASTERVNKRM

SMVVSGLTPEEFMLVYKFARKHHITLTNLITEETTHVVMKTDAEFVCERT

LKYFLGIAGGKWVVSYFWVTQSIKERKMLNEHDFEVRGDVVNGRNHQGPK

RARESQDRKIFRGLEICCYGPFTNMPTDQLEWMVQLCGASVVKELSSFTL

GTGVHPIVVVQPDAWTEDNGFHAIGQMCEAPVVTREWVLDSVALYQCQEL

DTYLIPQIPHSHY
```

By "BRCA1 polynucleotide" is meant a nucleic acid molecule encoding a BRCA1 polypeptide. An exemplary polynucleotide sequence is provided at NCBI Ref. No. NM_007294, which is reproduced below:

```
                                              (SEQ ID NO: 2)
  1  gtaccttgat ttcgtattct gagaggctgc tgcttagcgg tagccccttg gtttccgtgg 61  caacggaaaa gcgcgggaat tacagataaa ttaaaactgc gactgcgcgg cgtgagctcg 121  ctgagacttc ctggacgggg gacaggctgt ggggtttctc agataactgg gcccctgcgc 181  tcaggaggcc ttcaccctct gctctgggta aagttcattg gaacagaaag aaatggattt 241  atctgctctt cgcgttgaag aagtacaaaa tgtcattaat gctatgcaga aaatcttaga 301  gtgtcccatc tgtctggagt tgatcaagga acctgtctcc acaaagtgtg accacatatt 361  ttgcaaattt tgcatgctga aacttctcaa ccagaagaaa gggccttcac agtgtccttt 421  atgtaagaat gatataacca aaaggagcct acaagaaagt acgagattta gtcaacttgt 481  tgaagagcta ttgaaaatca tttgtgcttt tcagcttgac acaggtttgg agtatgcaaa 541  cagctataat tttgcaaaaa aggaaaataa ctctcctgaa catctaaaag atgaagtttc 601  tatcatccaa agtatgggct acagaaaccg tgccaaaaga cttctacaga gtgaacccga 661  aaatccttcc ttgcaggaaa ccagtctcag tgtccaactc tctaaccttg gaactgtgag
```

-continued

```
 721   aactctgagg acaaagcagc ggatacaacc tcaaaagacg tctgtctaca ttgaattggg
 781   atctgattct tctgaagata ccgttaataa ggcaacttat tgcagtgtgg gagatcaaga
 841   attgttacaa atcaccccctc aaggaaccag ggatgaaatc agtttggatt ctgcaaaaaa
 901   ggctgcttgt gaattttctg agacggatgt aacaaatact gaacatcatc aacccagtaa
 961   taatgatttg aacaccactg agaagcgtgc agctgagagg catccagaaa agtatcaggg
1021   tagttctgtt tcaaacttgc atgtggagcc atgtggcaca aatactcatg ccagctcatt
1081   acagcatgag aacagcagtt tattactcac taaagacaga atgaatgtag aaaaggctga
1141   attctgtaat aaaagcaaac agcctggctt agcaaggagc caacataaca gatgggctgg
1201   aagtaaggaa acatgtaatg ataggcggac tcccagcaca gaaaaaaagg tagatctgaa
1261   tgctgatccc ctgtgtgaga aaaagaatg gaataagcag aaactgccat gctcagagaa
1321   tcctagagat actgaagatg ttccttggat aacactaaat agcagcattc agaaagttaa
1381   tgagtggttt tccagaagtg atgaactgtt aggttctgat gactcacatg atggggagtc
1441   tgaatcaaat gccaaagtag ctgatgtatt ggacgttcta atgaggtag atgaatattc
1501   tggttcttca gagaaaatag acttactggc cagtgatcct catgaggctt taatatgtaa
1561   aagtgaaaga gttcactcca atcagtagaa gagtaatatt gaagacaaaa tatttgggaa
1621   aacctatcgg aagaaggcaa gcctccccaa cttaagccat gtaactgaaa atctaattat
1681   aggagcattt gttactgagc cacagataat acaagagcgt cccctcacaa ataaattaaa
1741   gcgtaaaagg agacctacat caggccttca tcctgaggat tttatcaaga aagcagattt
1801   ggcagttcaa aagactcctg aaatgataaa tcagggaact aaccaaacgg agcagaatgg
1861   tcaagtgatg aatattacta atagtggtca tgagaataaa acaaaaggtg attctattca
1921   gaatgagaaa atcctaaccc aatagaatc actcgaaaaa gaatctgctt tcaaaacgaa
1981   agctgaacct ataagcagca gtataagcaa tatggaactc gaattaaata tccacaattc
2041   aaaagcaccct aaaaagaata ggctgaggag gaagtcttct accaggcata ttcatgcgct
2101   tgaactagta gtcagtagaa atctaagccc acctaattgt actgaattgc aaattgatag
2161   ttgttctagc agtgaagaga taaagaaaaa aagtacaac caaatgccag tcaggcacag
2221   cagaaaccta caactcatgg aaggtaaaga acctgcaact ggagccaaga agagtaacaa
2281   gccaaatgaa cagacaagta aaagacatga cagcgatact ttcccagagc tgaagttaac
2341   aaatgcacct ggttctttta ctaagtgttc aaataccagt gaacttaaag aatttgtcaa
2401   tcctagccctt ccaagagaag aaaaagaaga gaaactgaaa acagttaaag tgtctaataa
2461   tgctgaagac cccaaagatc tcatgttaag tggagaaagg gttttgcaaa ctgaaagatc
2521   tgtagagagt agcagtattt cattggtacc tggtactgat tatggcactc aggaaagtat
2581   ctcgttactg gaagttagca ctctagggaa ggcaaaaaca gaaccaaata aatgtgtgag
2641   tcagtgtgca gcatttgaaa accccaaggg actaattcat ggttgttcca agataatag
2701   aaatgacaca gaaggcttta agtatccatt gggacatgaa gttaaccaca gtcgggaaac
2761   aagcatgaaa atggaagaaa gtgaacttga tgctcagtat ttgcagaata cattcaaggt
2821   ttcaaagcgc cagtcatttg ctccgttttc aaatccagga aatgcagaag aggaatgtgc
2881   aacattctct gcccactctg ggtccttaaa gaaacaaagt ccaaaagtca cttttgaatg
2941   tgaacaaaag gaagaaaatc aaggaaagaa tgagtctaat atcaagcctg tacagacagt
3001   taatatcact gcaggctttc ctgtggttgg tcagaaagat aagccagttg ataatgccaa
3061   atgtagtatc aaaggaggct ctaggttttg tctatcatct cagttcagag gcaacgaaac
3121   tggactcatt actccaaata aacatggact tttacaaaac ccatatcgta taccaccact
```

-continued

```
3181  ttttcccatc aagtcatttg ttaaaactaa atgtaagaaa atctgctag aggaaaactt
3241  tgaggaacat tcaatgtcac ctgaaagaga atgggaaat gagaacattc caagtacagt
3301  gagcacaatt agccgtaata acattagaga aaatgttttt aaagaagcca gctcaagcaa
3361  tattaatgaa gtaggttcca gtactaatga agtgggctcc agtattaatg aaataggttc
3421  cagtgatgaa acattcaag cagaactagg tagaaacaga gggccaaaat tgaatgctat
3481  gcttagatta ggggttttgc aacctgaggt ctataaacaa agtcttcctg gaagtaattg
3541  taagcatcct gaaataaaaa agcaagaata tgaagaagta gttcagactg ttaatacaga
3601  tttctctcca tatctgattt cagataactt agaacagcct atgggaagta gtcatgcatc
3661  tcaggtttgt tctgagacac ctgatgacct gttagatgat ggtgaaataa aggaagatac
3721  tagttttgct gaaaatgaca ttaaggaaag ttctgctgtt tttagcaaaa gcgtccagaa
3781  aggagagctt agcaggagtc ctagccctttt cacccataca catttggctc agggttaccg
3841  aagaggggcc aagaaattag agtcctcaga agagaactta tctagtgagg atgaagagct
3901  tccctgcttc caacacttgt tatttggtaa agtaaacaat ataccttctc agtctactag
3961  gcatagcacc gttgctaccg agtgtctgtc taagaacaca gaggagaatt tattatcatt
4021  gaagaatagc ttaaatgact gcagtaacca ggtaatattg gcaaaggcat ctcaggaaca
4081  tcaccttagt gaggaaacaa aatgttctgc tagcttgttt tcttcacagt gcagtgaatt
4141  ggaagacttg actgcaaata caaacaccca ggatcctttc ttgattggtt cttccaaaca
4201  aatgaggcat cagtctgaaa gccagggagt tggtctgagt gacaaggaat tggtttcaga
4261  tgatgaagaa agaggaacgg gcttggaaga aaataatcaa gaagagcaaa gcatggattc
4321  aaacttaggt gaagcagcat ctgggtgtga gagtgaaaca agcgtctctg aagactgctc
4381  agggctatcc tctcagagtg acattttaac cactcagcag agggatacca tgcaacataa
4441  cctgataaag ctccagcagg aaatggctga actagaagct gtgttagaac agcatgggag
4501  ccagccttct aacagctacc cttccatcat aagtgactct tctgcccttg aggacctgcg
4561  aaatccgaaa caaagcacat cagaaaaagc agtattaact tcacagaaaa gtagtgaata
4621  ccctataagc cagaatccag aaggcctttc tgctgacaag tttgaggtgt ctgcagatag
4681  ttctaccagt aaaaataaag aaccaggagt ggaaaggtca tccccttcta aatgcccatc
4741  attagatgat aggtggtaca tgcacagttg ctctgggagt cttcagaata gaaactaccc
4801  atctcaagag gagctcatta aggttgttga tgtggaggag caacagctgg aagagtctgg
4861  gccacacgat ttgacggaaa catcttactt gccaaggcaa gatctagagg gaaccccta
4921  cctggaatct ggaatcagcc tcttctctga tgaccctgaa tctgatcctt ctgaagacag
4981  agccccagag tcagctcgtg ttggcaacat accatcttca acctctgcat tgaaagttcc
5041  ccaattgaaa gttgcagaat ctgcccagag tccagctgct gctcatacta ctgatactgc
5101  tgggtataat gcaatggaag aaagtgtgag cagggagaag ccagaattga cagcttcaac
5161  agaaagggtc aacaaagaa tgtccatggt ggtgtctggc ctgacccag aagaatttat
5221  gctcgtgtac aagtttgcca gaaacaccac catcacttta actaatctaa ttactgaaga
5281  gactactcat gttgttatga aaacagatgc tgagtttgtg tgtgaacgga cactgaaata
5341  ttttctagga attgcgggag gaaatggggt agttagctat ttctgggtga cccagtctat
5401  taaagaaaga aaaatgctga atgagcatga ttttgaagtc agaggagatg tggtcaatgg
5461  aagaaccac caaggtccaa agcgagcaag agaatcccag gacagaaaga tcttcagggg
5521  gctagaaatc tgttgctatg ggcccttcac caacatgccc acagatcaac tggaatggat
```

```
5581  ggtacagctg tgtggtgctt ctgtggtgaa ggagctttca tcattcaccc ttggcacagg 5641  tgtccaccca attgtggttg tgcagccaga tgcctggaca gaggacaatg gcttccatgc 5701  aattgggcag atgtgtgagg cacctgtggt gacccgagag tgggtgttgg acagtgtagc 5761  actctaccag tgccaggagc tggacaccta cctgataccc cagatccccc acagccacta 5821  ctgactgcag ccagccacag gtacagagcc acaggacccc aagaatgagc ttacaaagtg 5881  gccttccag gccctgggag ctcctctcac tcttcagtcc ttctactgtc ctggctacta 5941  aatattttat gtacatcagc ctgaaaagga cttctggcta tgcaagggtc ccttaaagat 6001  tttctgcttg aagtctccct tggaaatctg ccatgagcac aaaattatgg taattttca 6061  cctgagaaga ttttaaaacc atttaaacgc caccaattga gcaagatgct gattcattat 6121  ttatcagccc tattctttct attcaggctg ttgttggctt agggctggaa gcacagagtg 6181  gcttggcctc aagagaatag ctggtttccc taagtttact tctctaaaac cctgtgttca 6241  caaaggcaga gagtcagacc cttcaatgga aggagagtgc ttgggatcga ttatgtgact 6301  taaagtcaga atagtccttg ggcagttctc aaatgttgga gtggaacatt ggggaggaaa 6361  ttctgaggca ggtattagaa atgaaaagga aacttgaaac ctgggcatgg tggctcacgc 6421  ctgtaatccc agcactttgg gaggccaagg tgggcagatc actggaggtc aggagttcga 6481  aaccagcctg gccaacatgg tgaaaccccca tctctactaa aatacagaa attagccggt 6541  catggtggtg gacacctgta atcccagcta ctcaggtggc taaggcagga gaatcacttc 6601  agcccgggag gtggaggttg cagtgagcca agatcatacc acggcactcc agcctgggtg 6661  acagtgagac tgtggctcaa aaaaaaaaaa aaaaaagga aatgaaact agaagagatt 6721  tctaaaagtc tgagatatat ttgctagatt tctaaagaat gtgttctaaa acagcagaag 6781  attttcaaga accggtttcc aaagacagtc ttctaattcc tcattagtaa taagtaaaat 6841  gtttattgtt gtagctctgg tatataatcc attcctctta aaatataaga cctctggcat 6901  gaatatttca tatctataaa atgacagatc ccaccaggaa ggaagctgtt gctttctttg 6961  aggtgatttt tttcctttgc tccctgttgc tgaaaccata cagcttcata ataattttg 7021  cttgctgaag gaagaaaaag tgttttttcat aaacccatta tccaggactg tttatagctg 7081  ttggaaggac taggtcttcc ctagccccc cagtgtgcaa gggcagtgaa gacttgattg 7141  tacaaaatac gttttgtaaa tgttgtgctg ttaacactgc aaataaactt ggtagcaaac 7201  acttccaaaa aaaaaaaaaa aaaa
```

By "BRCA2 polypeptide" is meant a protein having at least about 85% amino acid sequence identity to GenBank Accession No: AAB07223 or a fragment thereof having DNA repair activity. The amino acid sequence of an exemplary BRCA2 polypeptide is provided below:

```
GenBank: AAB07223.1
>gi|1161384|gb|AAB07223.1| BRCA2 [Homo sapiens]
                                        (SEQ ID NO: 3)
MPIGSKERPTFFEIFKTRCNKADLGPISLNWFEELSSEAPPYNSEPAEES

EHKNNNYEPNLFKTPQRKPSYNQLASTPIIFKEQGLTLPLYQSPVKELDK

FKLDLGRNVPNSRHKSLRTVKTKMDQADDVSCPLLNSCLSESPVVLQCTH

VTPQRDKSVVCGSLFHTPKFVKGRQTPKHISESLGAEVDPDMSWSSSLAT

PPTLSSTVLIVRNEEASETVEPHDTTANVKSYFSNHDESLKKNDRFIASV

TDSENTNQREAASHGEGKTSGNSFKVNSCKDHIGKSMPNVLEDEVYETVV

DTSEEDSFSLCFSKCRTKNLQKVRTSKTRKKIFHEANADECEKSKNQVKE

KYSFVSEVEPNDTDPLDSNVAHQKPFESGSDKISKEVVPSLACEWSQLTL

SGLNGAQMEKIPLLHISSCDQNISEKDLLDTENKRKKDFLTSENSLPRIS

SLPKSEKPLNEETVVNKRDEEQHLESHTDCILAVKQAISGTSPVASSFQG

IKKSIFRIRESPKETFNASFSGHMTDPNFKKETEASESGLEIHTVCSQKE

DSLCPNLIDNGSWPATTTQNSVALKNAGLISTLKKKTNKFIYAIHDETFY

KGKKIPKDQKSELINCSAQFEANAFEAPLTFAMADSGLLHSSVKRSCSQN

DSEEPTLSLTSSEGTILRKCSRNETCSNNTVISQDLDYKEAKCNKEKLQL

FITPEADSLSCLQEGQCENDPKSKKVSDIKEEVLAAACHPVQHSKVEYSD

TDFQSQKSLLYDHENASTLILTPTSKDVLSNLVMISRGKESYKMSDKLKG

NNYESDVELTKNIPMEKNQDVCALNENYKNVELLPPEKYMRVASPSRKVQ
```

```
FNQNTNLRVIQKNQEETTSISKITVNPDSEELFSDNENNFVFQVANERNN
LALGNTKELHETDLTCVNEPIFKNSTMVLYGDTGDKQATQVSIKKDLVYV
LAEEENKNSVKQHIKMTLGQDLKSDISLNIDKIPEKNNDYMNKWAGLLGPI
SNHSEGGSFRTASNKEIKLSEHNIKKSKMFFKDIEEQYPTSLACVEIVNT
LALDNQKKLSKPQSINTVSAHLQSSVVVSDCKNSHITPQMLFSKQDFNSN
HNLTPSQKAEITELSTILEESGSQFEFTQFRKPSYILQKSTFEVPENQMT
ILKTTSEECRDADLHVIMNAPSIGQVDSSKQFEGTVEIKRKFAGLLKNDC
NKSASGYLTDENEVGFRGFYSAHGTKLNVSTEALQKAVKLFSDIENISEE
TSAEVHPISLSSSKCHDSVVSMFKIENHNDKTVSEKNNKCQLILQNNIEM
TTGTFVEEITENYKRNTENEDNKYTAASRSNHNLEFDGSDSSKNDTVCIH
KDETDLLFTDQHNICLKLSGQFMKEGNTQIKEDLSDLTFLEVAKAQEACH
GNTSNKEQLTATKTEQNIKDFETSDTFFQTASGKNISVAKESFNKIVNFF
DQKPEELHNFSLNSELHSDIRKNKMDILSYEETDIVKHKILKESVPVGTG
NQLVTFQGQPERDEKIKEPTLLGFHTASGKKVKIAKESLDKVKNLFDEKE
QGTSEITSFSHQWAKTLKYREACKDLELACETIEITAAPKCKEMQNSLNN
DKNLVSIETVVPPKLLSDNLCRQTENLKTSKSIFLKVKVHENVEKETAKS
PATCYTNQSPYSVIENSALAFYTSCSRKTSVSQTSLLEAKKWLREGIFDG
QPERINTADYVGNYLYENNSNSTIAENDKNHLSEKQDTYLSNSSMSNSYS
YHSDEVYNDSGYLSKNKLDSGIEPVLKNVEDQKNTSFSKVISNVKDANAY
PQTVNEDICVEELVTSSSPCKNKNAAIKLSISNSNNFEVGPPAFRIASGK
IVCVSHETIKKVKDIFTDSFSKVIKENNENKSKICQTKIMAGCYEALDDS
EDILHNSLDNDECSTHSHKVFADIQSEEILQHNQNMSGLEKVSKISPCDV
SLETSDICKCSIGKLHKSVSSANTCGIFSTASGKSVQVSDASLQNARQVF
SEIEDSTKQVFSKVLFKSNEHSDQLTREENTAIRTPEHLISQKGESYNVV
NSSAFSGESTASGKQVSILESSLHKVKGVLEEFDLIRTEHSLHYSPTSRQ
NVSKILPRVDKRNPEHCVNSEMEKTCSKEFKLSNNLNVEGGSSENNHSIK
VSPYLSQFQQDKQQLVLGTKVSLVENIHVLGKEQASPKNVKMEIGKTETE

SDVPVKTNIEVCSTYSKDSENYFETEAVEIAKAFMEDDELTDSKLPSHAT
HSLFTCPENEEMVLSNSRIGKRRGEPLILVGEPSIKRNLLNEFDRIIENQ
EKSLKASKSTPDGTIKDRRLFMHHVSLEPITCVPFRTTKERQEIQNPNFT
APGQEFLSKSHLYEHLTLEKSSSNLAVSGHPFYQVSATRNEKMRHLITTG
RPTKVFVPPFKTKSHFHRVEQCVRNINLEENRQKQNIDGHGSDDSKNKIN
DNEIHQFNKNNSNQAAAVTFTKCEEEPLDLITSLQNARDIQDMRIKKKQR
QRVFPQPGSLYLAKTSTLPRISLKAAVGGQVPSACSHKQLYTYGVSKHCI
KINSKNAESFQFHTEDYFGKESLWTGKGIQLADGGWLIPSNDGKAGKEEF
YRALCDTPGVDPKLISRIWVYNHYRWIIWKLAAMECAFPKEFANRCLSPE
RVLLQLKYRYDTEIDRSRRSAIKKIMERDDTAAKTLVLCVSDIISLSANI
SETSSNKTSSADTQKVAIIELTDGWYAVKAQLDPPLLAVLKNGRLTVGQK
IILHGAELVGSPDACTPLEAPESLMLKISANSTRPARWYTKLGFFPDPRP
FPLPLSSLFSDGGNVGCVDVIIQRAYPIQWMEKTSSGLYIFRNEREEEKE
AAKYVEAQQKRLEALFTKIQEEFEEHEENTTKPYLPSRALTRQQVRALQD
GAELYEAVKNAADPAYLEGYFSEEQLRALNNHRQMLNDKKQAQIQLEIRK
AMESAEQKEQGLSRDVTTVWKLRIVSYSKKEKDSVILSIWRPSSDLYSLL
TEGKRYRIYHLATSKSKSKSERANIQLAATKKTQYQQLPVSDEILFQIYQ
PREPLHFSKFLDPDFQPSCSEVDLIGFVVSVVKKTGLAPFVYLSDECYNL
LAIKFWIDLNEDIIKPHMLIAASNLQWRPESKSGLLTLFAGDFSVFSASP
KEGHFQETFNKMKNTVENIDILCNEAENKLMHILHANDPKWSTPTKDCTS
GPYTAQIIPGTGNKLLMSSPNCEIYYQSPLSLCMAKRKSVSTPVSAQMTS
KSCKGEKEIDDQKNCKKRRALDFLSRLPLPPPVSPICTFVSPAAQKAFQP
PRSCGTKYETPIKKKELNSPQMTPFKKENEISLLESNSIADEELALINTQ
ALLSGSTGEKQFISVSESTRTAPTSSEDYLRLKRRCTTSLIKEQESSQAS
TEECEKNKQDTITTKKYI
```

By "BRCA2 polynucleotide" is meant a nucleic acid molecule encoding a BRCA2 polypeptide. An exemplary BRCA2 polynucleotide is provided at NM_000059, which is reproduced below:

```
                                              (SEQ ID NO: 4)
  1    gtggcgcgag cttctgaaac taggcggcag aggcggagcc gctgtggcac tgctgcgcct
 61    ctgctgcgcc tcgggtgtct tttgcggcgg tgggtcgccg ccgggagaag cgtgagggga
121    cagatttgtg accggcgcgg ttttgtcag cttactccgg ccaaaaaaga actgcacctc
181    tggagcggac ttatttacca agcattggag gaatatcgta ggtaaaaatg cctattggat
241    ccaaagagag gccaacattt tttgaaattt taagacacg ctgcaacaaa gcagatttag
301    gaccaataag tcttaattgg tttgaagaac tttcttcaga agctccaccc tataattctg
361    aacctgcaga agaatctgaa cataaaaaca acaattacga accaaaccta tttaaaactc
421    cacaaaggaa accatcttat aatcagctgg cttcaactcc aataatattc aaagagcaag
481    ggctgactct gccgctgtac caatctcctg taaagaatt agataaattc aaattagact
541    taggaaggaa tgttcccaat agtagacata aaagtcttcg cacagtgaaa actaaaatgg
601    atcaagcaga tgatgtttcc tgtccacttc taaattcttg tcttagtgaa agtcctgttg
```

-continued

```
 661  ttctacaatg tacacatgta acaccacaaa gagataagtc agtggtatgt gggagtttgt
 721  ttcatacacc aaagtttgtg aagggtcgtc agacaccaaa acatatttct gaaagtctag
 781  gagctgaggt ggatcctgat atgtcttggt caagttcttt agctacacca cccacccctta
 841  gttctactgt gctcatagtc agaaatgaag aagcatctga aactgtattt cctcatgata
 901  ctactgctaa tgtgaaaagc tattttttcca atcatgatga agtctgaag aaaaatgata
 961  gatttatcgc ttctgtgaca gacagtgaaa acacaaatca aagagaagct gcaagtcatg
1021  gatttggaaa aacatcaggg aattcattta aagtaaatag ctgcaaagac cacattggaa
1081  agtcaatgcc aaatgtccta gaagatgaag tatatgaaac agttgtagat acctctgaag
1141  aagatagttt ttcattatgt ttttctaaat gtagaacaaa aaatctacaa aaagtaagaa
1201  ctagcaagac taggaaaaaa attttccatg aagcaaacgc tgatgaatgt gaaaaatcta
1261  aaaccaagt gaaagaaaaa tactcatttg tatctgaagt ggaaccaaat gatactgatc
1321  cattagattc aaatgtagca atcagaagc cctttgagag tggaagtgac aaaatctcca
1381  aggaagttgt accgtctttg gcctgtgaat ggtctcaact aacccttca ggtctaaatg
1441  gagcccagat ggagaaaata cccctattgc atatttcttc atgtgaccaa atatttcag
1501  aaaaagacct attagacaca gagaacaaaa gaaagaaaga ttttcttact tcagagaatt
1561  ctttgccacg tatttctagc ctaccaaaat cagagaagcc attaaatgag gaaacagtgg
1621  taaataagag agatgaagag cagcatcttg aatctcatac agactgcatt cttgcagtaa
1681  agcaggcaat atctggaact tctccagtgg cttcttcatt tcagggtatc aaaaagtcta
1741  tattcagaat aagagaatca cctaaagaga ctttcaatgc aagttttca ggtcatatga
1801  ctgatccaaa ctttaaaaaa gaaactgaag cctctgaaag tggactggaa atacatactg
1861  tttgctcaca gaaggaggac tccttatgtc caaatttaat tgataatgga agctggccag
1921  ccaccaccac acagaattct gtagctttga agaatgcagg tttaatatcc actttgaaaa
1981  agaaaacaaa taagtttatt tatgctatac atgatgaaac atcttataaa ggaaaaaaaa
2041  taccgaaaga ccaaaaatca gaactaatta actgttcagc ccagtttgaa gcaaatgctt
2101  ttgaagcacc acttacattt gcaaatgctg attcaggttt attgcattct tctgtgaaaa
2161  gaagctgttc acagaatgat tctgaagaac caactttgtc cttaactagc tcttttggga
2221  caattctgag gaatgttcct agaaatgaaa catgttctaa taatacagta atctctcagg
2281  atcttgatta taaagaagca aaatgtaata aggaaaaact acagttattt attaccccag
2341  aagctgattc tctgtcatgc ctgcaggaag acagtgtga aaatgatcca aaaagcaaaa
2401  aagtttcaga tataaaagaa gaggtcttgg ctgcagcatg tcacccagta caacattcaa
2461  aagtggaata cagtgatact gactttcaat cccagaaaag tcttttatat gatcatgaaa
2521  atgccagcac tcttatttta actcctactt ccaaggatgt tctgtcaaac ctagtcatga
2581  tttctagagg caaagaatca tacaaaatgt cagacaagct caaaggtaac aattatgaat
2641  ctgatgttga attaaccaaa aatattccca tggaaaagaa tcaagatgta tgtgctttaa
2701  atgaaaatta taaaacgtt gagctgttgc cacctgaaaa atacatgaga gtagcatcac
2761  cttcaagaaa ggtacaattc aaccaaaaca caaatctaag agtaatccaa aaaaatcaag
2821  aagaaactac ttcaatttca aaaataactg tcaatccaga ctctgaagaa cttttctcag
2881  acaatgagaa taattttgtc ttccaagtag ctaatgaaag gaataatctt gctttaggaa
2941  atactaagga acttcatgaa acagacttga cttgtgtaaa cgaacccatt ttcaagaact
3001  ctaccatggt tttatatgga gacacaggtg ataaacaagc aacccaagtc tcaattaaaa
3061  aagatttggt ttatgttctt gcagaggaga acaaaaatag tgtaaagcag catataaaaa
```

-continued

```
3121  tgactctagg tcaagattta aaatcggaca tctccttgaa tatagataaa ataccagaaa
3181  aaaataatga ttacatgaac aaatgggcag gactcttagg tccaatttca atcacagtt
3241  ttggaggtag cttcagaaca gcttcaaata aggaaatcaa gctctctgaa cataacatta
3301  agaagagcaa aatgttcttc aaagatattg aagaacaata tcctactagt ttagcttgtg
3361  ttgaaattgt aaataccttg gcattagata atcaaaagaa actgagcaag cctcagtcaa
3421  ttaatactgt atctgcacat ttacagagta gtgtagttgt ttctgattgt aaaaatagtc
3481  atataacccc tcagatgtta ttttccaagc aggattttaa ttcaaaccat aatttaacac
3541  ctagccaaaa ggcagaaatt acagaacttt ctactatatt agaagaatca ggaagtcagt
3601  ttgaatttac tcagtttaga aaaccaagct acatattgca gaagagtaca tttgaagtgc
3661  ctgaaaacca gatgactatc ttaaagacca cttctgagga atgcagagat gctgatcttc
3721  atgtcataat gaatgcccca tcgattggtc aggtagacag cagcaagcaa tttgaaggta
3781  cagttgaaat taaacggaag tttgctggcc tgttgaaaaa tgactgtaac aaaagtgctt
3841  ctggttattt aacagatgaa aatgaagtgg ggtttagggg cttttattct gctcatggca
3901  caaaactgaa tgtttctact gaagctctgc aaaagctgt gaaactgttt agtgatattg
3961  agaatattag tgaggaaact tctgcagagg tacatccaat aagtttatct tcaagtaaat
4021  gtcatgattc tgttgtttca atgtttaaga tagaaaatca taatgataaa actgtaagtg
4081  aaaaaaataa taaatgccaa ctgatattac aaaataatat tgaaatgact actggcactt
4141  ttgttgaaga aattactgaa aattacaaga gaaatactga aaatgaagat aacaaatata
4201  ctgctgccag tagaaattct cataacttag aatttgatgg cagtgattca agtaaaaatg
4261  atactgtttg tattcataaa gatgaaacgg acttgctatt tactgatcag cacaacatat
4321  gtcttaaatt atctggccag tttatgaagg agggaaacac tcagattaaa gaagatttgt
4381  cagatttaac ttttttggaa gttgcgaaag ctcaagaagc atgtcatggt aatacttcaa
4441  ataaagaaca gttaactgct actaaaacgg agcaaaatat aaaagatttt gagacttctg
4501  atacattttt tcagactgca agtgggaaaa atattagtgt cgccaaagag tcatttaata
4561  aaattgtaaa tttctttgat cagaaaccag aagaattgca taacttttcc ttaaattctg
4621  aattacattc tgacataaga aagaacaaaa tggacattct aagttatgag gaaacagaca
4681  tagttaaaca caaaatactg aaagaaagtg tcccagttgg tactggaaat caactagtga
4741  ccttccaggg acaacccgaa cgtgatgaaa agatcaaaga acctactcta ttgggttttc
4801  atacagctag cgggaaaaaa gttaaaattg caaggaatc tttggacaaa gtgaaaaacc
4861  tttttgatga aaaagagcaa ggtactagtg aaatcaccag ttttagccat caatgggcaa
4921  agaccctaaa gtacagagag gcctgtaaag accttgaatt agcatgtgag accattgaga
4981  tcacagctgc cccaaagtgt aaagaaatgc agaattctct caataatgat aaaaaccttg
5041  tttctattga gactgtggtg ccacctaagc tcttaagtga taatttatgt agacaaactg
5101  aaaatctcaa aacatcaaaa agtatctttt tgaaagttaa agtacatgaa aatgtagaaa
5161  aagaaacagc aaaaagtcct gcaacttgtt acacaaatca gtccccttat tcagtcattg
5221  aaaattcagc cttagctttt tacacaagtt gtagtagaaa aacttctgtg agtcagactt
5281  cattacttga agcaaaaaaa tggcttagag aaggaatatt tgatggtcaa ccagaaagaa
5341  taaatactgc agattatgta ggaaattatt tgtatgaaaa taattcaaac agtactatag
5401  ctgaaaatga caaaaatcat ctctccgaaa aacaagatac ttatttaagt aacagtagca
5461  tgtctaacag ctattcctac cattctgatg aggtatataa tgattcagga tatctctcaa
```

-continued

```
5521  aaaataaact tgattctggt attgagccag tattgaagaa tgttgaagat caaaaaaaca
5581  ctagtttttc caaagtaata tccaatgtaa aagatgcaaa tgcataccca caaactgtaa
5641  atgaagatat ttgcgttgag gaacttgtga ctagctcttc accctgcaaa aataaaaatg
5701  cagccattaa attgtccata tctaatagta ataattttga ggtagggcca cctgcattta
5761  ggatagccag tggtaaaatc gtttgtgttt cacatgaaac aattaaaaaa gtgaaagaca
5821  tatttacaga cagtttcagt aaagtaatta aggaaaacaa cgagaataaa tcaaaaattt
5881  gccaaacgaa aattatggca ggttgttacg aggcattgga tgattcagag gatattcttc
5941  ataactctct agataatgat gaatgtagca cgcattcaca taaggttttt gctgacattc
6001  agagtgaaga aattttacaa cataaccaaa atatgtctgg attggagaaa gtttctaaaa
6061  tatcaccttg tgatgttagt ttggaaactt cagatatatg taaatgtagt atagggaagc
6121  ttcataagtc agtctcatct gcaaatactt gtgggatttt tagcacagca agtggaaaat
6181  ctgtccaggt atcagatgct tcattacaaa acgcaagaca agtgttttct gaaatagaag
6241  atagtaccaa gcaagtcttt tccaaagtat tgtttaaaag taacgaacat tcagaccagc
6301  tcacaagaga agaaaatact gctatacgta ctccagaaca tttaatatcc caaaaaggct
6361  tttcatataa tgtggtaaat tcatctgctt tctctggatt tagtacagca agtggaaagc
6421  aagtttccat tttagaaagt ccttacaca aagttaaggg agtgttagag gaatttgatt
6481  taatcagaac tgagcatagt cttcactatt caccctcgtc tagacaaaat gtatcaaaaa
6541  tacttcctcg tgttgataag agaaacccag agcactgtgt aaactcagaa atggaaaaaa
6601  cctgcagtaa agaatttaaa ttatcaaata acttaaatgt tgaaggtggt tcttcagaaa
6661  ataatcactc tattaaagtt tctccatatc tctctcaatt tcaacaagac aaacaacagt
6721  tggtattagg aaccaaagtg tcacttgttg agaacattca tgttttggga aagaacagg
6781  cttcacctaa aaacgtaaaa atggaaattg gtaaaactga aacttttttct gatgttcctg
6841  tgaaaacaaa tatagaagtt tgttctactt actccaaaga ttcagaaaac tactttgaaa
6901  cagaagcagt agaaattgct aaagctttta tggaagatga tgaactgaca gattctaaac
6961  tgccaagtca tgccacacat tctcttttta catgtcccga aaatgaggaa atggttttgt
7021  caaattcaag aattggaaaa agaagaggag agccccttat cttagtggga gaaccctcaa
7081  tcaaaagaaa cttattaaat gaatttgaca ggataataga aaatcaagaa aaatccttaa
7141  aggcttcaaa aagcactcca gatggcacaa taaagatcg aagattgttt atgcatcatg
7201  tttctttaga gccgattacc tgtgtacccc ttcgcacaac taaggaacgt caagagatac
7261  agaatccaaa ttttaccgca cctggtcaag aatttctgtc taaatctcat ttgtatgaac
7321  atctgacttt ggaaaaatct tcaagcaatt tagcagtttc aggacatcca ttttatcaag
7381  tttctgctac aagaaatgaa aaatgagac acttgattac tacaggcaga ccaaccaaag
7441  tctttgttcc accttttaaa actaaatcac attttcacag agttgaacag tgtgttagga
7501  atattaactt ggaggaaaac agacaaaagc aaaacattga tggacatggc tctgatgata
7561  gtaaaaataa gattaatgac aatgagattc atcagtttaa caaaacaac tccaatcaag
7621  cagcagctgt aacttcaca aagtgtgaag aagaaccttt agatttaatt acaagtcttc
7681  agaatgccag agatatacag gatatgcgaa ttaagaagaa acaaaggcaa cgcgtctttc
7741  cacagccagg cagtctgtat cttgcaaaaa catccactct gcctcgaatc tctctgaaag
7801  cagcagtagg aggccaagtt ccctctgcgt gttctcataa acagctgtat acgtatggcg
7861  tttctaaaca ttgcataaaa attaacagca aaaatgcaga gtcttttcag tttcacactg
7921  aagattattt tggtaaggaa agtttatgga ctggaaaagg aatacagttg gctgatggtg
```

-continued

```
 7981 gatggctcat accctccaat gatggaaagg ctggaaaaga agaattttat agggctctgt
 8041 gtgacactcc aggtgtggat ccaaagctta tttctagaat ttgggtttat aatcactata
 8101 gatggatcat atggaaactg gcagctatgg aatgtgcctt tcctaaggaa tttgctaata
 8161 gatgcctaag cccagaaagg gtgcttcttc aactaaaata cagatatgat acggaaattg
 8221 atagaagcag aagatcggct ataaaaaaga taatggaaag ggatgacaca gctgcaaaaa
 8281 cacttgttct ctgtgtttct gacataattt cattgagcgc aaatatatct gaaacttcta
 8341 gcaataaaac tagtagtgca gatacccaaa aagtggccat tattgaactt acagatgggt
 8401 ggtatgctgt taaggcccag ttagatcctc ccctcttagc tgtcttaaag aatggcagac
 8461 tgacagttgg tcagaagatt attcttcatg gagcagaact ggtgggctct cctgatgcct
 8521 gtacacctct tgaagcccca gaatctctta tgttaaagat ttctgctaac agtactcggc
 8581 ctgctcgctg gtataccaaa cttggattct ttcctgaccc tagacctttt cctctgccct
 8641 tatcatcgct tttcagtgat ggaggaaatg ttggttgtgt tgatgtaatt attcaaagag
 8701 catacccctat acagtggatg gagaagacat catctggatt atacatattt cgcaatgaaa
 8761 gagaggaaga aaaggaagca gcaaaatatg tggaggccca acaaaagaga ctagaagcct
 8821 tattcactaa aattcaggag gaatttgaag aacatgaaga aaacacaaca aaaccatatt
 8881 taccatcacg tgcactaaca agacagcaag ttcgtgcttt gcaagatggt gcagagcttt
 8941 atgaagcagt gaagaatgca gcagacccag cttaccttga gggttatttc agtgaagagc
 9001 agttaagagc cttgaataat cacaggcaaa tgttaatga taagaaacaa gctcagatcc
 9061 agttggaaat taggaaggcc atggaatctg ctgaacaaaa ggaacaaggt ttatcaaggg
 9121 atgtcacaac cgtgtggaag ttgcgtattg taagctattc aaaaaaagaa aaagattcag
 9181 ttatactgag tatttggcgt ccatcatcag atttatattc tctgttaaca gaaggaaaga
 9241 gatacagaat ttatcatctt gcaacttcaa aatctaaaag taaatctgaa agagctaaca
 9301 tacagttagc agcgacaaaa aaaactcagt atcaacaact accggtttca gatgaaattt
 9361 tatttcagat ttaccagcca cgggagcccc ttcacttcag caaatttta gatccagact
 9421 ttcagccatc ttgttctgag gtggacctaa taggatttgt cgtttctgtt gtgaaaaaaa
 9481 caggacttgc ccctttcgtc tatttgtcag acgaatgtta caatttactg gcaataaagt
 9541 tttggataga ccttaatgag gacattatta gcctcatat gttaattgct gcaagcaacc
 9601 tccagtggcg accagaatcc aaatcaggcc ttcttacttt atttgctgga gattttctg
 9661 tgttttctgc tagtccaaaa gagggccact ttcaagagac attcaacaaa atgaaaaata
 9721 ctgttgagaa tattgacata ctttgcaatg aagcagaaaa caagcttatg catatactgc
 9781 atgcaaatga tcccaagtgg tccaccccaa ctaaagactg tacttcaggg ccgtacactg
 9841 ctcaaatcat tcctggtaca ggaaacaagc ttctgatgtc ttctcctaat tgtgagatat
 9901 attatcaaag tccttttatca ctttgtatgg ccaaaaggaa gtctgtttcc acacctgtct
 9961 cagcccagat gacttcaaag tcttgtaaag gggagaaaga gattgatgac caaaagaact
10021 gcaaaagag aagagccttg gatttcttga gtagactgcc tttacctcca cctgttagtc
10081 ccatttgtac atttgtttct ccggctgcac agaaggcatt tcagccacca aggagttgtg
10141 gcaccaaata cgaaacaccc ataaagaaaa aagaactgaa ttctcctcag atgactccat
10201 ttaaaaaatt caatgaaatt tctctttttgg aaagtaattc aatagctgac gaagaacttg
10261 cattgataaa tacccaagct cttttgtctg gttcaacagg agaaaaacaa tttatatctg
10321 tcagtgaatc cactaggact gctcccacca gttcagaaga ttatctcaga ctgaaacgac
```

```
-continued
10381  gttgtactac atctctgatc aaagaacagg agagttccca ggccagtacg gaagaatgtg 10441  agaaaaataa gcaggacaca attacaacta aaaaatatat ctaagcattt gcaaaggcga 10501  caataaatta ttgacgctta acctttccag tttataagac tggaatataa tttcaaacca 10561  cacattagta cttatgttgc acaatgagaa aagaaattag tttcaaattt acctcagcgt 10621  ttgtgtatcg ggcaaaaatc gttttgcccg attccgtatt ggtatacttt tgcttcagtt 10681  gcatatctta aaactaaatg taatttatta actaatcaag aaaaacatct ttggctgagc 10741  tcggtggctc atgcctgtaa tcccaacact ttgagaagct gaggtgggag gagtgcttga 10801  ggccaggagt tcaagaccag cctgggcaac atagggagac ccccatcttt acaaagaaaa 10861  aaaaaagggg aaaagaaaat cttttaaatc tttggatttg atcactacaa gtattatttt 10921  acaagtgaaa taaacatacc attttctttt agattgtgtc attaaatgga atgaggtctc 10981  ttagtacagt tattttgatg cagataattc cttttagttt agctactatt ttaggggatt 11041  tttttagag gtaactcact atgaaatagt tctccttaat gcaaatatgt tggttctgct 11101  atagttccat cctgttcaaa agtcaggatg aatatgaaga gtggtgtttc cttttgagca 11161  attcttcatc cttaagtcag catgattata agaaaaatag aaccctcagt gtaactctaa 11221  ttccttttta ctattccagt gtgatctctg aaattaaatt acttcaacta aaaattcaaa 11281  tactttaaat cagaagattt catagttaat ttatttttt tttcaacaaa atggtcatcc 11341  aaactcaaac ttgagaaaat atcttgcttt caaattggca ctgatt
```

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable or selectable marker" is meant a composition that when linked to a molecule of interest renders the latter detectable, via spectroscopic, photochemical, biochemical, immunochemical, or chemical means or genetically selectable (e.g., when expressed in a cell). For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens. Genetically selectable markers include antibiotic resistance, inducible, cell surface expression, auxotrophic complementation, and the like.

By "diagnostic" is meant any method that identifies the presence of a pathologic condition or characterizes the nature of a pathologic condition (e.g., a neoplasia). Diagnostic methods differ in their sensitivity and specificity. While a particular diagnostic method may not provide a definitive diagnosis of a condition, it suffices if the method provides a positive indication that aids in diagnosis.

By "disease" is meant any condition or disorder that damages or interferes with the normal function of a cell, tissue, or organ. Examples of diseases include cancer, including breast and ovarian cancer associated with defects in a DNA repair polypeptide.

By "increases" is meant a positive alteration of at least 10%, 25%, 50%, 75%, or 100%.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder. Exemplary markers of breast or ovarian cancer include polypeptides that function in DNA repair, including but not limited to, BRCA1, BRCA2, BARD, PALB2, RAD51, RAD51B, RAD51C, RAD51D, XRCC2, XRCC3, BLM, RECQ helicase, MRE11, Rad50, NBS1, ATM, ATR, CTIP, Brip, RPA and RPA-like polypeptide.

By "mutation" is meant a variation in a nucleic acid sequence relative to a wild-type reference sequence. In particular embodiments, a mutation is an insertion, deletion, substitution (e.g., missense mutation), or any other alteration known in the art. A DNA repair variant polypeptide comprises an amino acid sequence that varies from the sequence of a wild-type reference DNA repair polypeptide. Such variations may be functionally significant. DNA repair variant polypeptides are characterized according to the methods of the invention.

By "nuclear localization signal (NLS)" is meant any amino acid sequence sufficient to direct a polypeptide into the nucleus. In various embodiments, an NLS comprises one or more short sequences of positively charged lysines or arginines exposed on the protein surface. Exemplary nuclear localization signals include the C-myc NLS, SV40 Large T-antigen NLS, and nucleoplasmin NLS.

By "Rad51 polypeptide" having at least about 85% identity to NCBI Accession No. NP_001157741. An exemplary Rad51 polypeptide sequence is provided below:

```
                                                              (SEQ ID NO: 5)
  1  mamqmqlean adtsveeesf gpqpisrleq cginandvkk leeagfhtve avayapkkel 61  inikgiseak adkiltesrs varlecnsvi lvyctlrlsg ssdspasasr vvgttggiet 121  gsitemfgef rtgktqicht lavtcqlpid rgggegkamy idtegtfrpe rllavaeryg 181  lsgsdvldnv ayarafntdh qtqllyqasa mmvesryall ivdsatalyr tdysgrgels 241  arqmhlarfl rmllrladef gvavvitnqv vaqvdgaamf aadpkkpigg niiahasttr 301  lylrkgrget rickiydspc lpeaeamfai nadgvgdakd
```

By a "Rad51 polynucleotide" is meant a nucleic acid sequence encoding a Rad51 polypeptide. An exemplary polynucleotide sequence is provided at NCBI Accession No. NM_001164269, which is reproduced below:

```
                                                              (SEQ ID NO: 6)
  1  gaaagccgct ggcggaccgc gcgcagcggc cagagaccga gccctaagga gagtgcggcg 61  cttcccgagg cgtgcagctg ggaactgcaa ctcatctggg ttgtgcgcag aaggctgggg 121  caagcgagta gagaagtgga gctaatggca atgcagatgc agcttgaagc aaatgcagat 181  acttcagtgg aagaagaaag ctttggccca aacccatttc cacggttaga gcagtgtggc 241  ataaatgcca acgatgtgaa gaaattggaa gaagctggat tccatactgt ggaggctgtt 301  gcctatgcgc caaagaagga gctaataaat attaagggaa ttagtgaagc caaagctgat 361  aaaattctga cggagtctcg ctctgttgcc aggctggagt gcaatagcgt gatcttggtc 421  tactgcaccc tccgcctctc aggttcaagt gattctcctg cctcagcctc ccgagtagtt 481  gggactacag gtggaattga gactggatct atcacagaaa tgtttggaga attccgaact 541  gggaagaccc agatctgtca tacgctagct gtcacctgcc agcttcccat tgaccgggt 601  ggaggtgaag gaaaggccat gtacattgac actgagggta cctttaggcc agaacggctg 661  ctggcagtgg ctgagaggta tggtctctct ggcagtgatg tcctggataa tgtagcatat 721  gctcgagcgt tcaacacaga ccaccagacc cagctccttt atcaagcatc agccatgatg 781  gtagaatcta ggtatgcact gcttattgta gacagtgcca ccgcccttta cagaacagac 841  tactcgggtc gaggtgagct ttcagccagg cagatgcact tggccaggtt tctgcggatg 901  cttctgcgac tcgctgatga gtttggtgta gcagtggtaa tcactaatca ggtggtagct
```

-continued

```
 961   caagtggatg gagcagcgat gtttgctgct gatcccaaaa aacctattgg aggaaatatc 1021   atcgcccatg catcaacaac cagattgtat ctgaggaaag gaagagggga aaccagaatc 1081   tgcaaaatct acgactctcc ctgtcttcct gaagctgaag ctatgttcgc cattaatgca 1141   gatggagtgg gagatgccaa agactgaatc attgggtttt tcctctgtta aaaaccttaa 1201   gtgctgcagc ctaatgagag tgcactgctc cctggggttc tctacaggcc tcttcctgtt 1261   gtgactgcca ggataaagct tccgggaaaa cagctattat atcagctttt ctgatggtat 1321   aaacaggaga caggtcagta gtcacaaact gatctaaaat gtttattcct tctgtagtgt 1381   attaatctct gtgtgttttc tttggttttg gaggaggggt atgaagtatc tttgacatgg 1441   tgccttagga atgacttggg tttaacaagc tgtctactgg acaatcttat gtttccaaga 1501   gaactaaagc tggagagacc tgaccctctt ctcacttcta aattaatggt aaaataaaat 1561   gcctcagcta tgtagcaaag ggaatgggtc tgcacagatt cttttttttct gtcagtaaaa 1621   ctctcaagca ggttttttaag ttgtctgtct gaatgatctt gtgtaaggtt ttggttatgg 1681   agtcttgtgc caaacctact aggccattag cccttcacca tctacctgct tggtctttca 1741   ttgctaagac taactcaaga taatcctaga gtcttaaagc atttcaggcc agtgtggtgt 1801   cttgcgcctg tactcccagc actttgggag gccgaggcag gtggatcgct tgagcccagg 1861   agttttaagt ccagcttggc caaggtggtg aaatcccatc tctacaaaaa atgcagaact 1921   taatctggac acactgttac acgtgcctgt agtcccagct actcgatagc ctgaggtggg 1981   agaatcactt aagcctggaa ggtggaagtt gcagtgagtc gagattgcac tgctgcattc 2041   cagccagggt gacagagtga gaccatgttt caaacaagaa acatttcaga gggtaagtaa 2101   acagatttga ttgtgaggct tctaataaag tagttattag tagtgaa
```

By "rare cutting endonuclease" is meant a nuclease that cuts about once or less in a wild-type mammalian genome. I-SceI is an exemplary rare cutting endonuclease that recognizes an 18-base pair nucleic acid sequence TAGGGATAACAGGGTAAT (SEQ ID NO: 7). I-PpoI is an exemplary rare cutting endonuclease that recognizes an 15-base pair nucleic acid sequence CTCTCTTAAGGTAGC (SEQ ID NO: 8).

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous nucleic acid sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous nucleic acid sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

By "Ter site" is meant a nucleic acid sequence having at least about 85% sequence identity to AATTAGTATGTTG-TAACTAAAGT (SEQ ID NO: 9) (TerA), AATAAGTAT-GTTGTAACTAAAGT (SEQ ID NO: 10) (TerB), ATATAG-GATGTTGTAACTAATAT (SEQ ID NO: 11) (TerC) and/or variants thereof capable of binding a Tus polypeptide. In certain embodiments, Ter sequences are 23 base-pairs in length. In specific embodiments, Ter sites have a consensus sequence: GNRNGTTGTAAYKA (SEQ ID NO: 12). Exemplary Ter sequences are provided below:

```
TerH
                                     (SEQ ID NO: 13)
CGATCGTATGTTGTAACTATCTC

TerI
                                     (SEQ ID NO: 14)
AACATGGAAGTTGTAACTAACCG

TerD
                                     (SEQ ID NO: 15)
CATTAGTATGTTGTAACTAAATG

TerA
                                     (SEQ ID NO: 9)
AATTAGTATGTTGTAACTAAAGT

TerC
                                     (SEQ ID NO: 11)
ATATAGGATGTTGTAACTAATAT

TerB
                                     (SEQ ID NO: 10)
AATAAGTATGTTGTAACTAAAGT

TerG
                                     (SEQ ID NO: 16)
GTCAAGGATGTTGTAACTAACCA pTerE
                                     (SEQ ID NO: 17)
TTAAAGTATGTTGTAACTAAGCA pTerK
                                     (SEQ ID NO: 18)
CGATTGAGAGTTGTAATGAAGTC pTerF
                                     (SEQ ID NO: 19)
CCTTCGTATGTTGTAACGACGAT pTerJ
                                     (SEQ ID NO: 20)
ACGCAGTAAGTTGTAACTAATGC pTerY
                                     (SEQ ID NO: 21)
TATGGGTACGTTGTAATTAGGGA pTerL
                                     (SEQ ID NO: 22)
GCACTGGGTGTTGTAATGACGCA pTerZ
                                     (SEQ ID NO: 23)
TACCCGCAGGTTGTAACGAGAGC
```

By "Tus (Terminus utilization substance) polypeptide" is meant a protein having at least about 85% amino acid sequence identity to the sequence provided at Genbank accession no. WP_001310846 or a fragment thereof and having DNA binding activity (e.g., to a Ter site) and/or DNA replication inhibitor activity (e.g., replication fork arrest; replication fork stalling; counter-helicase activity). An exemplary Tus polypeptide sequence is provided below:

```
>sp|P16525|TUS_ECOLI DNA replication terminus
site-binding protein
                                        (SEQ ID NO: 24)
MARYDLVDRLNITFRQMEQELAIFAAHLEQHKLLVARVFSLPEVKKEDEH

NPLNRIEVKQHLGNDAQSLALRHERHLFIQQQSENRSSKAAVRLPGVLCY

QVDNLSQAALVSHIQHINKLKTIFEHIVIVESELPTAARFEWVHRHLPGL

ITLNAYRILTVLHDPATLRFGWANKHIIKNLHRDEVLAQLEKSLKSPRSV

APWIREEWQRKLEREYQDIAALPQNAKLKIKRPVKVQPIARVWYKGDQKQ

VQHACPTPLIALINRDNGAGVPDVGELLNYDADNVQHRYKPQAQPLRLII

PRLHLYVAD
```

By a "Tus polynucleotide" is meant a nucleic acid sequence encoding a Tus polypeptide.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a schematic showing EBNA1-driven plasmid replication. Ori, EBNA1-binding origin of replication. EBNA1-binding FR repeats impeded the anticlockwise fork. Red triangle indicates the 6×Ter array (vertex, non-permissive end). Location of Southern blotting probe shown in black. FIG. 1B has two images depicting plasmid replication intermediates in 293E cells transiently transfected with 6×Ter-containing plasmids or 'no Ter' control, co-transfected with empty vector (EV), TusH144A or Tus. Samples from one experiment of DNA digested with XmnI plus SnaBI and analyzed by two-dimensional gel electrophoresis/Southern blotting. 6×REVTer: clockwise fork encountered permissive end of Ter. Arc A, replication fork. Spot B, Tus/Ter-stalled clockwise fork. Spot C, bidirectional fork arrest (double Y) at Tus/6×Ter, reflecting incomplete replication block at FR20. FIG. 1C is a graph showing stall spot B quantification, n=5 (see FIG. 2A). Error bars represent s.e.m. For Student's t-test 6×Ter wild-type Tus versus any other, P<0.01; 6×REVTer wild-type Tus versus any other, P<0.01. 6×Ter TusH144A versus 6×Ter EV, P<0.03. FIG. 1D is an immunoblot showing upper panel, anti-myc immunoblot of 293E cells expressing empty vector (EV), Tus(WT) or TusH144A (H). Lower panel shows beta-tubulin loading control.

FIG. 2A has two images showing phosphorimager quantification of spot B. One of five independent experiments that contributed to FIG. 2C. Four areas were quantified for each sample using ImageJ 1.48p software, as shown by cartoon. A, area containing a portion of replication fork arc A. B, area containing replication fork stall spot B (same shape/size as A). F, largest area of replication fork arc that was accessible to quantification in every sample. G, same shape as F, used to quantify background signal on membrane. Stall spot B intensity was calculated as: $(B-A)/(F-G) \times 100\%$. Note, this value does not correspond to the probability of stalling at the Tus/Ter block, but is used to illustrate the relatively weaker arrest produced by 6×REVTer. FIG. 2B is a schematic diagram illustrating the same plasmid elements as in FIG. 1A. MluI/XmnI digested plasmid yields a linear fragment of 5.4 kb. Probe for Southern blotting is indicated by the black bar. FIG. 2C shows two images of plasmid replication intermediates extracted from 293E cells transiently transfected with 6×Ter-containing plasmids or no Ter control, co-transfected with empty vector (EV), TusH144A or Tus as shown. All samples are from one experiment. Plasmid DNA extracted from 293E cells was digested with XmnI and MluI and analyzed by neutral/neutral two-dimensional gel-electrophoresis and Southern blotting. Replication intermediates as described in FIG. 2A. FIG. 2D is a schematic showing predicted replication intermediates generated by Tus/Ter-induced replication fork stalling with or without effective FR/EBNA1 replication fork block. Diagrams below plasmid maps show shape of the major Tus/Ter-dependent fork arrest species. Green dotted line shows predicted additional branch of double Y structure formed by stalling of anticlockwise fork at Tus/6×Ter when FR/EBNA1 replication block fails. The length of the additional branch is shown in each diagram. Note that the relationship between spots B and C will vary according to the length of this additional branch. FIG. 2E depicts two images showing plasmid replication intermediates extracted from 293E cells transiently transfected with 6×Ter containing plasmids and co-transfected with empty vector (EV) or wild-type Tus as shown. Restriction digests of extracted plasmids are as shown. All samples are from one experiment. Note: replication fork size and position of stall spot B in relation to replication arc A varied with restriction digest. For example, spot B in KpnI/MluI was close to the 2n linear position, since the Tus/Ter-stall site was only approximately 680 bp from the KpnI site. For the same reason, spots B and C were closely placed in the KpnI/MluI-digested sample. Note: the relatively weak spot C in the KpnI/MluI digest, which was consistent across multiple experiments, might reflect a proportionately large contribution of ssDNA (reflecting processed lagging strand DNA) to the approximately 680 bp lagging strand of the stalled anticlockwise fork.

FIG. 3A is a schematic showing that Tus/Ter-mediated replication stall structures responsible for spots B and C. The relative abundance of the single stall spot B and the double Y stall spot C can be used to calculate the efficiency of the FR/EBNA1 replication fork barrier. FIG. 3B shows four images and one graph depicting phosphorimager analysis of twelve independent Southern blot experiments (method described in FIG. 1B). Areas B, B', C and C' were the same shape and size within each experiment, but varied between experiments. B, stall spot B. B', background gel signal of same area as B. C, stall spot C. C', background gel signal of same area as C. Relative intensity of spot B/(B+C) estimated the stalling efficiency at FR/EBNA1 and was calculated as: (B−B')/(B+C−B'−C')×100%. The stalling efficiency at FR/EBNA1 was therefore 70±0.2% (s.e.m.). Relative intensity of spot C was calculated as: (C−C')/(B+C−B'−C')× 100%. FIG. 3C is a schematic showing the structure of p6×Ter-2Ori plasmid. Stalled replication intermediates depicted different combinations of FR/EBNA1 block/bypass and Tus/6×Ter block/bypass. Spots B and B2 were defined as in the diagram. Spots C and C2 resulted from FR/EBNA1 bypass. Spot C2 required successful arrest at both of the 6×Ter arrays. Spot C results from bypass of one of the two 6×Ter arrays. FIG. 3D shows three images and one graph providing one of three independent experiments performed with p6×Ter-2Ori. Methods as in FIG. 1B. Note presence of four stall spots in p6×Ter-2Ori replicating in presence of Tus. Double Y stall spots C and C2 and background signal C' were quantified. Note that the shape and size of each area was identical within an individual experiment, but varied between experiments. By considering only double Y stall spots (that is, in which FR/EBNA1 bypass had occurred), the relative abundance of the double Y stall spots C and C2 were used to estimate the efficiency of the Tus/6×Ter replication fork barrier. Let a=probability of the 6×Ter array blocking the fork and b=probability of 6×Ter bypass. Then a+b=1. The probability of the two 6×Ter arrays blocking each fork on one p6×Ter-2Ori plasmid (generating spot C2) is $a^2$. The probability of one 6×Ter array being blocked and the second array being bypassed (generating spot C) is 2ab. Relative densitometry of spots C and C2 (each with subtraction of background C') shows that spot C contributed 49.6% and C2 contributed 50.4% (s.e.m. 5.6%). Therefore $0.496a^2=0.504\times 2ab$. Solving this, a=0.67 Therefore the estimated efficiency of the Tus/6×xTer replication fork block within the replicating plasmid is 67%. Note that the efficiency of the Tus/6×Ter replication fork block within the chromosome is unknown.

FIG. 4A is a cartoon showing a 6×Ter-HR reporter and major HR products (assuming two-ended breaks). STGC and short-tract gene conversion; LTGC, long-tract gene conversion. LTGC generated wild-type RFP expression through RNA splicing. Grey boxes, mutant GFP. Green box, wild-type GFP. Circles A and B represent 5' and 3' artificial RFP exons. Tr-GFP, 5' truncated GFP. Red triangle indicates 6×Ter array adjacent to I-SceI site. B, BglII; GFP-hybridizing fragment sizes in kilobases. Bidirectional fork stalling triggered SCR. Green arrow, strand exchange. FIG. 4B shows five graphs depicting FACS data of Brca1$^{fl/BRCT}$ 6×Ter-HR cells transfected with empty vector (EV), I-SceI, Tus or TusH144A. No Ter reporter, Brea 1$^{11/BRCT}$ cells carrying the ROSA26-targeted HR reporter lacking the Ter array. FIG. 4C depicts three graphs showing that I-SceI- and Tus-induced HR (blue diamonds and orange circles, respectively) in three independent Brca1$^{fl/BRCT}$ clones. Mean of triplicate samples, n=3. Error bars represent s.e.m. Student's t-test LTGC/total HR, I-SceI versus Tus: P=0.0186. FIG. 4D shows two blots depicting a Southern blot analysis of Tus- and I-SceI-induced HR in Brca1$^{fl/BRCT}$ 6×Ter-HR cells (GFP probe). P, parental reporter; B, BglII digest; BI, BglII plus I-SceI digest.

FIG. 5A is a schematic showing that bidirectional fork arrest would provide two DNA ends for sister chromatid recombination. Termination by annealing generated STGC products of a fixed size. Recombining GFP elements and HR reporter features other than Tus/Ter are not shown. Black strands represent parental DNA. Grey strands represent newly synthesized DNA. Arrowheads on DNA strands represent DNA synthesis. Blue/grey hexagons, Tus monomers. Red triangles, Ter sites. Green line, invading DNA strand. Green dotted line, nascent strand extension. FIG. 5B is a schematic showing that unidirectional fork arrest would provide only one DNA end for sister chromatid recombination. Following one-ended invasion of the neighboring sister chromatid, any STGC products could not be terminated by annealing, as there was no homologous second end. Termination by non-canonical mechanisms would generate STGCs of unpredictable/variable size. DNA and protein elements labelled as in panel FIG. 5A. LTGC was not considered in this analysis, as the mechanisms of termination of the major LTGC products were not accessible from the current data. Each model invoked a hypothetical DSB intermediate. Tus/Ter-induced HR could be initiated by a template switching mechanism (that is, without the formation of an initiating DSB intermediate). However, the requirement for a homologous second end was not altered by consideration of a template switch model and this second end had to be provided by the processing of a second arrested fork (the right-hand fork in panel a).

FIG. 6A depicts three graphs with primary data from FIG. 4C, showing directly measured frequencies of background HR, Tus-induced HR and I-SceI-induced HR in three independent Brca1$^{fl/BRCT}$ 6×Ter/HR reporter clones. Cells were transfected with empty vector (EV, grey squares), myc-NLS-I-SceI (I-SceI, blue diamonds), or myc-NLS-Tus expression vectors (Tus, orange circles). Each point represents the mean of triplicate samples from three independent experiments (that is, n=3). Error bars represent s.e.m. Student's t-test of Tus versus EV: STGC P<0.0001; LTGC P<0.0001. Student's t-test of I-SceI versus EV: STGC P<0.0001; LTGC P<0.0001. Student's t-test of Tus versus I-SceI: STGC P<0.0001; LTGC P=0.0018; LTGC/Total HR P=0.0186. FIG. 6B shows three graphs of primary data comparing a single ROSA26 targeted Brca1$^{fl/BRCT}$ 6×Ter/HR clone with three independently derived clones, each harboring a single intact 6×Ter/HR reporter randomly integrated at an unknown locus. Filled symbols, ROSA26-targeted clone (as in panel a). Open symbols, data from randomly integrated 6×Ter/HR reporter clones. Each point represents the mean of six independent experiments, triplicate replicates for each experiment (that is, n=6). Error bars represent s.e.m. Student's t-test of pooled random integrants Tus versus EV: STGC P<0.0001; LTGC P<0.0001. Student's t-test of pooled random integrants I-SceI versus EV: STGC P<0.0001; LTGC P<0.0001. Student's t-test of pooled random integrants Tus versus I-SceI: STGC P<0.0001; LTGC P=0 P=0.3620; LTGC/total HR P=0.00012. FIG. 6C depicts a graph showing primary data of STGC products observed in Brca1$^{fl/BRCT}$ 6×Ter/HR cells transfected with empty vector (EV), wild-type Tus, DNA binding defective TusH144A, lock defective TusF140A or I-SceI. All expression vectors are codon-optimized for mammalian expression and encode N-terminal myc epitope and NLS sequences. Each column represents the mean of six independent experiments (that is, n=6). Error bars represent s.e.m. Student's t-test of Tus versus EV: P=0.0002; Tus versus TusH144A: P=0.0004; Tus versus TusF140A: P=0.0042; Tus versus I-SceI: P=0.0139; TusH144A versus EV: P=0.4406; TusF140A versus EV: P<0.0001; TusF140A versus TusH144A: P<0.0001; TusF140A versus I-SceI: P=0.0888. FIG. 6D is a blot showing Myc-tagged protein abundance in transfected Brca1$^{fl/BRCT}$ 6×Ter-HR cells. EV, empty vector. Other lanes as marked. Lower panel, beta-tubulin loading control. FIG. 6E shows six cartoons of the Ter/HR reporter constructs assayed in FIG. 6F. FIG. 6F depicts two graphs showing frequencies of Tus-induced STGC in Brca1$^{fl/BRCT}$ cells carrying single copy ROSA26-targeted Ter/HR reporters shown in panel 6E. Left, HR in 6×Ter, 3×Ter, 2×Ter and 1×Ter HR reporters, as shown. Right, HR in three independently derived clones carrying single copy, ROSA26-targeted 6×REVTer HR reporters. Each column represents the mean of three independent experiments (that is, n=3). Error bars represent s.e.m. Student's t-test of 6×Ter versus 3×Ter #1: P=0.2604; 6×Ter versus 3×Ter #2: P=0.5192; 6×Ter versus 2×Ter #1: P=0.0547; 6×Ter versus 2×Ter #2: P=0.0524; 6×Ter versus 1×Ter #1: P=0.0507; 6×Ter versus 1×Ter #2: P=0.0507; 3×Ter #1 versus 3×Ter #2: P=0.8291; 3×Ter #1 versus 2×Ter #1: P=0.0650; 3×Ter #1 versus 2×Ter #2: P=0.0606; 3×Ter #1 versus 1×Ter #1: P=0.0576; 3×Ter #1 versus 1×Ter #2: P=0.0574; 3×Ter #2 versus 2×Ter #1: P=0.1832; 3×Ter #2 versus 2×Ter #2: P=0.1748; 3×Ter #2 versus 1×Ter #1: P=0.1677; 3×Ter #2 versus 1×Ter #2: P=0.1697. By one-way ANOVA (analysis of variance) test used to compare more than three sets of data, the trend in HR from 6× to 1×, P=0.0012.

FIG. 7A depicts two graphs showing frequencies of STGC in Brca1$^{fl/BRCT}$ 6×Ter-HR cells co-transfected with Tus (orange) or I-SceI (blue) and with either control Luciferase siRNA(siLuc), Slx4 SMARTpool (siSlx4), Slx1 SMARTpool (siSlx1), Slx1 and Slx4 SMARTpools (siSlx1 siSlx4), Eme1 SMARTpool (siEme1), Eme1 and Slx4 SMARTpools (siEme1 siSlx4), Xpf SMARTpool (siXpf), Xpf and Slx4 SMARTpools (siXpf siSlx4). Each column represents the mean of triplicate samples from four independent experiments for each clone (that is, n=4). Error bars represent s.e.m. Tus-induced HR: Student's t-test of siSlx4 versus siLuc: P=0.0219; siSlx4 versus siSlx1: P=0.0012; siSlx4 versus siSlx4+Slx1: P=0.5983; siSlx4 versus siEme1: P=0.0171; siSlx4 versus siSlx4+siEme1: P=0.8721; siSlx4 versus siXpf: P=0.0098; siSlx4 versus siSlx4+siXpf: P=0.4711; siSlx1 versus siLuc: P=0.9332; siEme1 versus siLuc: P=0.4631; siXpf versus siLuc: P=0.7818; siSlx4+siSlx1 versus siLuc: P=0.0155; siSlx4+siEme1 versus siLuc: P=0.0215; siSlx4+siXpf versus siLuc: P=0.0305. I-SceI-induced HR: Student's t-test of siSlx4 versus siLuc: P=0.0907; siSlx4 versus siSlx1: P=0.0195; siSlx4 versus siSlx41siSlx1: P=0.4897; siSlx4 versus siEme1: P=0.0568; siSlx4 versus siSlx4+siEme1: P=0.3411; siSlx4 versus siXpf: P=0.0745; siSlx4 versus siSlx4+siXpf: P=0.2726; siSlx1 versus siLuc: P=0.9198; siEme1 versus siLuc: P=0.3349; siXpf versus siLuc: P=0.9217; siSlx4+siSlx1 versus siLuc: P=0.1521; siSlx4+siEme1 versus siLuc: P=0.2864; siSlx4 1 siXpf versus siLuc: P=0.2063. FIG. 7B depicts four graphs showing a qRT-PCR analysis of mRNA exon boundaries for Slx4, Slx1, Eme1 and Xpf mRNA in siRNA-SMARTpool-treated cells used in panel a.

FIG. 8A depicts two cartoons showing the Brca1 gene in Brca1$^{BRCT}$ ES cells. Brca1$^{BRCT}$ encodes a truncated protein. Cre converted Brca$^{fl}$ to the exon 22-24-deleted Brca1$^{\Delta}$ allele. Grey boxes, Brca1 exons; black triangles, loxP sites; pA, polyadenylation signal; SA, splice acceptor; neo: neomycin resistance gene; pgk, phosphoglycerate kinase promoter. FIG. 8B depicts 6 graphs showing that Tus- and I-SceI-induced HR in Brca1$^{fl/BRCT}$ and Brca1$^{\Delta/BRCT}$ 6×Ter-HR cells (three independent clones each). Mean of triplicate samples, n=4. Error bars represent s.e.m. Student's t-test Brca1$^{fl/BRCT}$ versus Brca1$^{\Delta/BRCT}$ in all 6 panels P<0.05. FIG. 8C shows an immunoblot: upper panel, endogenous Brca1 immunoblot in Brca1$^{fl/BRCT}$ and Brca1$^{\Delta/BRCT}$ ES cells. Asterisk indicates a background band. Lower panel, beta-actin loading control. FIG. 8D is a graph showing a quantitative polymerase chain reaction with reverse transcription (qRT-PCR) for Brca1 mRNA. Exon 22-23 was deleted in Brca1$^{\Delta/BRCT}$ cells.

FIG. 9A is a cartoon showing the structure of the 6×Ter/HR parental reporter, and major STGC or LTGC HR products (assuming two-ended breaks). Elements as shown in FIG. 4A. FIG. 9B depicts five blots showing a Southern blot analysis of Tus-induced and I-SceI induced HR products in Brca1$^{\Delta/BRCT}$ 6×Ter-HR cells. P, un-rearranged reporter; STGC and LTGC as shown. SN, STGC accompanied non-disjunction with retention of parental donor reporter; LN, LTGC accompanied non-disjunction with retention of parental donor reporter. B, BglII digest. BI, BglII1I-SceI digest. Membranes probed with full length GFP cDNA. Panels underneath two SN events and one LN event show that re-cloning did not separate the two reporters, confirming that the cell contained two copies of the reporter (consistent with non-disjunction).

FIG. 10A depicts six graphs showing frequencies of Tus-induced and I-SceI-induced HR in Brca1$^{fl/BRCT}$ and Brca1$^{\Delta/BRCT}$ 6×Ter/HR cells transiently co-transfected with Tus or I-SceI and with either control Luciferase siRNA (siLuc) or Brca1 SMARTpool (siBrca1). Each column represents the mean of triplicate samples for each independent clone from seven independent experiments (that is, n=7). Error bars represent s.e.m. Tus induced HR, Brca1$^{fl/BRCT}$ cells, Student's t-test siBrca1 versus siLuc: STGC: P=0.0013; LTGC: P=0.0206; LTGC/total HR: P=0.0003; Brca1$^{\Delta/BRCT}$ cells, siBrca1 versus siLuc: STGC: P=0.0016; LTGC: P=0.4558; LTGC/total HR: P<0.0001. I-SceI-induced HR, Brca1$^{fl/BRCT}$ cells, Student's t-test siBrca1 versus siLuc: STGC: P<0.0001; LTGC: P=0.0033; LTGC/total HR: P=0.9214; Brca1$^{\Delta/BRCT}$ cells, siBrca1 versus siLuc: STGC: P=0.0013; LTGC: P=0.2348; LTGC/total HR: P=0.0071. FIG. 10B is a blot showing Brca1 protein levels and beta-actin loading control in Brca1$^{fl/BRCT}$ and Brca1$^{\Delta/BRCT}$ in siRNA-treated cells as shown. FIG. 10C is a graph showing a qRT-PCR analysis of Brca1 mRNA in siRNA-treated cells as shown.

FIG. 11A is a cartoon of the Brca1 gene in Brca1$^{fl/Exon11}$ ES cells. The Brca1$^{Exon11}$ encodes the Δexon11 product. Cre converts Brca1$^{fl}$ to exon11-deleted Brca1$^{\Delta}$ allele. Symbols as in FIG. 8. PCR primers a, b and d shown. FIG. 11B depicts 6 graphs showing Tus- and I-SceI-induced HR in Brca1$^{fl/Exon11}$ and Brca1$^{\Delta/Exon11}$ 6×Ter-HR cells (three independent clones each). Mean of triplicate samples, n=4. Error bars represent s.e.m. Student's t-test Brca1$^{fl/Exon11}$ versus Brca1$^{\Delta/Exon11}$ in all 6 panels P<0.005. FIG. 11C is an immunoblot, Upper panel, endogenous Brca1 immunoblot in Brca1$^{fl/Exon11}$ and Brca1$^{\Delta/Exon11}$ ES cells. The asterisk denotes a background band. The lower panel denotes a beta-actin loading control. FIG. 11D depicts two gels showing PCR genotyping of Brca1$^{fl/Exon11}$ and Brca1$^{D/Exon11}$ clones from panel b. P, untargeted Brca1$^{fl/Exon11}$. E, empty (no DNA) control. Brca1$^{fl}$ product, 531 bp; Brca1$^{\Delta}$ product, 621 bp.

FIG. 12A depicts three graphs showing frequencies of Tus-induced and I-SceI-induced HR in Brca1fl/BRCT and Brca1Δ/BRCT 6×Ter/HR cells transiently co-transfected with Tus, or I-SceI and with either control Luciferase siRNA (siLuc) or Brca2 SMARTpool (siBrca2). Each column represents the mean of triplicate samples for each independent clone from five independent experiments (that is, n=5). Error bars represent s.e.m. Tus induced HR, Brca1fl/BRCT cells, Student's t-test siBrca2 versus siLuc: STGC: P=0.0031; LTGC: P=0.0007; LTGC/total HR: P=0.0042; Brca1Δ/BRCT cells, siBrca2 versus siLuc: STGC: P=0.0040; LTGC: P=0.0013; LTGC/total HR: P=0.0006. I-SceI-induced HR, Brca1fl/BRCT cells, Student's t-test siBrca2 versus siLuc: STGC: P=0.0028; LTGC: P=0.0456; LTGC/total HR: P=0.7945; Brca1Δ/BRCT cells, siBrca2 versus siLuc: STGC: P=0.0010; LTGC: P=0.2926; LTGC/total HR: P=0.0316. FIG. 12B shows qRT-PCR analysis of Brca2 mRNA in siRNA-treated cells.

FIG. 13A depicts six graphs showing the frequencies of Tus-induced and I-SceI-induced HR in Brca1$^{fl/BRCT}$ and Brca1$^{\Delta/BRCT}$ 6×Ter/HR cells transiently co-transfected with Tus, or I-SceI and with either control Luciferase siRNA (siLuc) or Rad51 SMARTpool (siRad51). Each column represents the mean of triplicate samples for each independent clone from seven independent experiments for Brca1$^{fl/BRCT}$ (that is, n=7) and four independent experiments for Brca1$^{\Delta/BRCT}$ cells (that is, n=4). Error bars represent s.e.m. Tus-induced HR, Brca1$^{fl/BRCT}$ cells, Student's t-test siRad51 versus siLuc: STGC: P<0.0001; LTGC: P=0.1578; LTGC/total HR: P=0.0002; Brca1$^{\Delta/BRCT}$ cells, siRad51 versus siLuc: STGC: P=0.0010; LTGC: P=0.0676; LTGC/total HR: P<0.0001. I-SceI-induced HR, Brca1$^{fl/BRCT}$ cells, Student's t-test siRad51 versus siLuc: STGC: P=0.0014; LTGC: P=0.0002; LTGC/total HR: P=0.6216; Brca1$^{\Delta/BRCT}$ cells, siRad51 versus siLuc: STGC: P=0.0068; LTGC: P=0.2064; LTGC/total HR: P=0.0186. FIG. 13B depicts an immunoblot of Rad51 protein levels and beta-tubulin loading control in Brca1$^{fl/BRCT}$ and Brca1$^{\Delta/BRCT}$ siRNA treated cells as shown.

FIG. 14A depicts six graphs showing frequencies of Tus-induced and I-SceI induced HR in Brca1$^{fl/BRCT}$ and Brca1$^{\Delta/BRCT}$ 6×Ter/ HR cells transiently co-transfected with Tus or I-SceI expression vectors and with either F53BP1 D1521R fragment (D1521R; non-chromatin-binding negative control for 'dominant-negative' 53BP1 fragment) or 'dominant-negative' F53BP1 wt fragment (F53BP1 wt). Each column represents the mean of triplicate samples for each independent clone from five independent experiments (that is, n=5). Error bars represent s.e.m. Tus-induced HR, Brca1$^{fl/BRCT}$ cells, Student's t-test D1521R versus F53BP1 wt: STGC: P=0.1818; LTGC: P=0.9005; LTGC/total HR: P=0.3570; Brca1$^{D/BRCT}$ cells, Student's t-test D1521R versus F53BP1 wt: STGC: P=0.5008; LTGC: P=0.5375; LTGC/total HR: P=0.4921. I-SceI induced HR, Brca1$^{fl/BRCT}$ cells, Student's t-test D1521R versus F53BP1 wt: STGC: P=0.0442; LTGC: P=0.5739; LTGC/total HR: P=0.2250; Brca1$^{\Delta/BRCT}$ cells, Student's t-test D1521R versus F53BP1 wt: STGC: P=0.0086; LTGC: P=0.6888; LTGC/total HR: P=0.0328. Tus-induced LTGC/total HR, Brca1$^{fl/BRCT}$ versus Brca1$^{\Delta/BRCT}$ cells, Student's t-test F53BP1 wt: 0.0064; Brca1$^{fl/BRCT}$ versus Brca1$^{\Delta/BRCT}$ cells, Student's t-test D1521R: 0.0014; I-SceI-induced LTGC/total HR, Brca1$^{fl/BRCT}$ versus Brca1$^{\Delta/BRCT}$ cells, Student's t-test F53BP1 wt: 0.1556; Brca1$^{fl/BRCT}$ versus Brca1$^{\Delta/BRCT}$ cells, Student's t-test D1521R: 0.0208. FIG. 14B depicts an immunoblot showing abundance of 53BP1 fragments, and beta-tubulin (loading control) in treated Brca1$^{fl/BRCT}$ and Brca1$^{\Delta/BRCT}$ 6×Ter/HR reporter ES cells in FIG. 14A.

FIG. 15 depicts two graphs showing induction of GFP$^{+}$ and RFP$^{+}$ HR products by ISceI. RFP-SCR reporter U2OS cells received control (upper panel) or I-SceI-encoding adenovirus (lower panel). Note ISceI-induced STGC (GFP$^{+}$RFP$^{-}$), LTGC (GFP$^{+}$RFP$^{+}$) and "mutagenic" LTGC (GFP$^{-}$RFP$^{+}$). Probability of HR resolving as LTGC=GFP$^{+}$RFP$^{+}$/total GFP$^{+}$=5.4%. Probability of "mutagenic" LTGC=GFP$^{-}$RFP$^{+}$/total RFP$^{+}$=10.8%.

FIGS. 18A-18F depict the DNA sequence of an LTGC reporter vector comprising an I-SceI restriction enzyme site. FIGS. 19A-19C depict the DNA sequence of Tus expression vector.

FIGS. 20A-20G depict the DNA sequence of a Ter array (6×Ter) reporter plasmid.

FIG. 21A depicts an enzymatically active Cas9 nuclease (red oval) binding to the cognate target of a CRISPR guide RNA (yellow). In addition, all endonucleases used for targeted gene editing generate "off-target" mutagenic effects. Binding also occurs at off-target loci that interact with the same guide RNA (sgRNA). FIG. 21B depicts a model in which an array of enzymatically inactive CRISPR/Cas9 complexes (dark gray ovals) formed at the target locus provokes site-specific replication fork arrest only at the target locus. Without being bound to theory, the results described herein indicate multiplexed copies of CRISPR/Cas9 bound in an array at the target locus are able to stall the replication fork and induce HR-mediated gene editing. Notably, the likelihood of off-target binding of individual CRISPR/Cas9 complexes to form a tandem array of stalling complexes is low or greatly minimized. Additionally, the likehood that a single CRISPR/Cas9 would provoke replication arrest, and unintended repair response would be negligible. Thus, the multiplexed nature of the stalling complex has the potential to address the problem of "off-target" effects.

FIG. 22A depicts a model of sister chromatid recombination induced at a Tus/Ter replication fork block. Replication fork stalling triggers breakage of the stalled fork by endogenous stalled fork processing enzymes. The double strand break (DSBs) produced are repaired by HR using the intact sister chromatid as donor template. FIG. 22B depicts a model of gene targeting involving recombination with an exogenous plasmid at a Tus/Ter replication fork block. A Tus/Ter block is established while a homologous plasmid is present. Without being bound to theory, DSBs produced at the arrested fork are primarily repaired by HR using the exogenous plasmid as the donor template. The excess of donor plasmid should favor its use in the repair process rather than the sister chromatid.

FIG. 23A is a schematic of a recombination assay used to detect repair of an inactive mutant GFP at a Tus/Ter-mediated replication block. A single copy reporter containing one mutant copy of GFP is targeted to the ROSA26 locus of mouse ES cells. The mutant copy of GFP ("6xTer-I-SceI") contains an array of 6xTer sites and a cleavage site for the rare-cutting homing endonuclease I-SceI. Arrows indicate promoter to drive GFP expression at the ROSA26 locus. Red triangle: 6xTer array, with neighboring I-SceI site. Without being bound to theory, replication arrest and fork breakage generates double strand break (DSBs) for recombination. The donor plasmid contains a 5' truncated copy of GFP ("Tr-GFP"), which recombines with the broken chromosomal copy of GFP to generate wt GFP. FIG. 23B depicts representative FACS readouts of gene targeting triggered by Tus or by positive control I-SceI. Green cells represent GFP$^+$ cells, indicating successful gene targeting/gene editing. Note absence of GFP$^+$ products in the negative control that received empty vector in the presence of the donor plasmid. FIG. 23C depicts graphs showing quantitation of gene targeting. Cells received either Tus, I-SceI or empty vector (for background level of GFP$^+$, consistently ~zero), together with donor plasmid containing Tr-GFP at increasing concentrations (0, 50, 100 or 150 ng). Total DNA transfected per sample was normalized as needed with addition of further empty vector. Note titratable induction of GFP$^+$ cells with increasing amount of donor vector.

DETAILED DESCRIPTION OF THE INVENTION

Figure 1A:
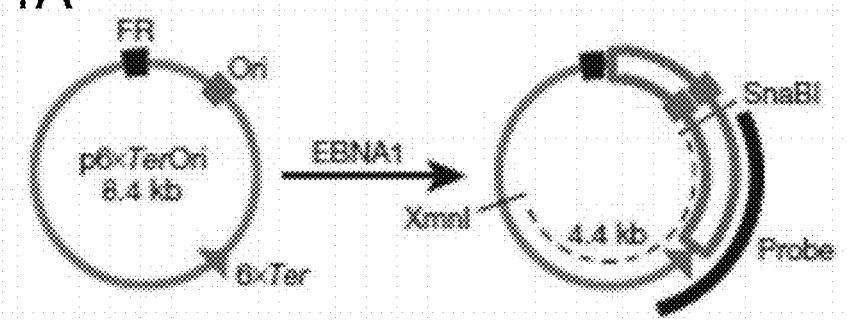
FIGS. 1A-1D show Tus/Ter-induced replication fork stalling in mammalian cells.

As described below, the present invention provides quantitative homologous recombination assays developed to characterize the pathogenicity of DNA repair polypeptides (e.g., BRCA1, BRCA2, Rad51) and provide urgently needed functional information on the significance of DNA repair variants of uncertain significance (VUS) alleles.

The invention is based, at least in part, on the discovery that replication fork stalling can promote genomic instability, predisposing to cancer and other diseases. Stalled replication forks may be processed by sister chromatid recombination (SCR), generating error-free or error-prone homologous recombination (HR) outcomes. In mammalian cells, a long-standing hypothesis proposes that the major hereditary breast/ovarian cancer predisposition gene products, BRCA1 and BRCA2, control HR/SCR at stalled replication forks. Although BRCA1 and BRCA2 affect replication fork processing, direct evidence that BRCA gene products regulate homologous recombination at stalled chromosomal replication forks is lacking, due to a dearth of tools for studying this process. As reported herein below, the *Escherichia coli* Tus/Ter complex can be engineered to induce site-specific replication fork stalling and chromosomal HR/SCR in mouse cells.

Tus/Ter-induced homologous recombination entails processing of bidirectionally arrested forks. As reported herein, the Brca1 carboxy (C)-terminal tandem BRCT repeat and regions of Brca1 encoded by exon 11—two Brca1 elements implicated in tumour suppression—control Tus/Ter-induced homologous recombination. Inactivation of either Brca1 or Brca2 increases the absolute frequency of 'long tract' gene conversions at Tus/Ter-stalled forks, an outcome not observed in response to a site-specific endonuclease-mediated chromosomal double-strand break. Therefore, homologous recombination at stalled forks is regulated differently from homologous recombination at double-strand breaks arising independently of a replication fork. These findings have significance for genome editing, which relies on inducing double stranded breaks to repair or replace deleterious genes. In particular, the invention provides for error-free homologous recombination. Aberrant long-tract homologous recombination at stalled replication forks contributes to genomic instability and breast/ovarian cancer predisposition in BRCA mutant cells.

Accordingly, the invention provides methods for characterizing the functional significance of a DNA repair polypeptide variant, homologous recombination reporter gene conversion vectors, homologous recombination reporter of short and long tract gene conversion vectors, cells comprising such vectors, and methods of characterizing the functional significance of a mutation in a DNA repair polypeptide derived from a biological sample obtained from a patient. Furthermore, the invention provides methods for identifying subjects with a propensity to develop cancer or whose cells have a propensity for genomic instability to occur.

Types of Biological Samples

The present invention provides a method to characterize the functional significance of a mutation in a DNA repair polypeptide (e.g., including but not limited to BRCA1, BRCA2, BARD, PALB2, RAD51, RAD51B, RAD51C, RAD51D, XRCC2, XRCC3, BLM, other RECQ helicases, MRE11, Rad50, NBS1, ATM, ATR, CTIP, Brip, RPA and RPA-like polypeptide). These polynucleotides may be extracted from different types of biologic samples. In one embodiment, the biologic sample is a tissue sample that includes cells of a tissue or organ (e.g., breast or ovarian cancer cells). Breast or ovarian cancer cell tissue is obtained, for example, from a biopsy of the affected organ or a metastasis thereof. In another embodiment, the biologic sample is a biologic fluid sample. Biological fluid samples include blood, blood serum, plasma, urine, or any other biological fluid useful in the methods of the invention.

Detection of Defects in DNA Repair Pathways

Defects in a polynucleotide encoding a DNA repair polypeptide are detected using routine methods known in the art. DNA sequencing remains the "gold standard" for identifying specific nucleotide variations. Such sequencing includes not only traditional sequencing methods (e.g., the Sanger method), but also next-generation sequencing (NGS) technologies capable of sequencing millions of DNA templates in parallel. Methods for characterizing polynucleotides are known in the art and typically focus on allele-specific and sequence-scanning detection methods.

Primer extension (Piggee et al., J Chromatogr A. 1997; 781:367-375), allele-specific amplification (Struewing et al. New Engl J Med. 1997; 336:1401-1408), allele-specific oligonucleotide hybridization (Hacia et al. Nat Genet. 1996; 14:441-447) and oligonucleotide ligation (Iannone et al. Cytometry. 2000; 39:131-140) are specific mutation detection methods that are currently used. The aforementioned publications are incorporated herein by reference for all that they teach relating to these methods.

Other methods for detecting nucleotide variations include heteroduplex analysis (HDA; Gerrard and Dean Single-strand conformation polymorphism and heteroduplex analysis. In: Cotton RGH, Edkins E, Forrest S, editors. Mutation detection—a practical approach. New York: Oxford University Press; 1998. pp. 25-33), single-strand conformation polymorphism (SSCP; Nataraj et al. Electrophoresis. 1999; 20:1177-1185), denaturing gradient gel electrophoresis (DGGE; De Santis and Azzi J Virol Methods. 2000; 85:101-108), temperature gradient gel electrophoresis (TGGE; Toliat et al. Electrophoresis. 2000; 21:541-544), denaturing high-performance liquid chromatography (DHPLC; Nucleic Acids Res. 1998; 26:1396-1400), RNase cleavage (Faudoa et al. Hum Mutat. 2000; 15:474-478), and methods using either DNA repair enzymes or resolvases for the detection of mismatches (Hsu et al. Carcinogenesis. 1994; 15:1657-1662) represent sequence-scanning (or nonspecific) approaches to mutation detection.

Defects in polypeptide biomarkers (e.g., polypeptides that function in DNA repair) can be detected by any suitable method. The methods described herein can be used individually or in combination for a more accurate detection of the biomarkers (e.g., immunoassay, mass spectrometry, and the like).

In particular embodiments, biomarkers of the invention (e.g., DNA repair pathway polypeptides) are measured by immunoassay using an antibody that detects a mutant version of the protein. This invention contemplates traditional immunoassays including, for example, Western blot, sandwich immunoassays including ELISA and other enzyme immunoassays, fluorescence-based immunoassays, chemiluminescence. Nephelometry is an assay done in liquid phase, in which antibodies are in solution. Binding of the antigen to the antibody results in changes in absorbance, which is measured. Other forms of immunoassay include magnetic immunoassay, radioimmunoassay, and real-time immunoquantitative PCR (iqPCR).

Immunoassays can be carried out on solid substrates (e.g., chips, beads, microfluidic platforms, membranes) or on any other forms that supports binding of the antibody to the marker and subsequent detection. A single marker may be detected at a time or a multiplex format may be used. Multiplex immunoanalysis may involve planar microarrays (protein chips) and bead-based microarrays (suspension arrays).

Polynucleotide Vectors of the Invention

The invention provides a number of vectors for characterizing the functional significance of a variation in the sequence of a DNA repair pathway polypeptide. Vectors of the invention encode, for example, a Tus polypeptide (e.g., wild-type). In various embodiments, the Tus polypeptide can have additions and alterations designed to improve function (e.g., addition of an epitope tag, a nuclear localization sequence, codon optimization for use in mammalian cells). In a particular embodiment, the Tus polypeptide is a variant with a point mutation, such as Tus F140A, to increase the affinity of Tus for its binding site Ter. Vectors of the invention encode, for example, a wild-type DNA repair polypeptide, a DNA repair polypeptide comprising a mutation (e.g., a variant DNA repair polypeptide), and one or more detectable proteins (e.g., GFP, RFP). Also, nucleic acid sequences encoding a rare cutting endonuclease may optionally be included in vectors of the invention. Exemplary rare cutting endonucleases include I-SceI. Vectors of the invention also comprise one or more Ter sites (e.g., in an array). In various embodiments, vectors of the invention comprise one, two, three, four, five, six, or more Ter sites. In various specific embodiments, vectors of the invention comprise 6, 9, 12, 15, 21 Ter sites, which are functional for replication fork stalling. Typically, recombinant polypeptides are produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a eukaryotic host (e.g., mammalian cells, e.g., NIH 3T3, HeLa, COS cells). Other cell types that may be used include without limitation vertebrate cells, insect cells, chicken cells, and mouse cells. Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Selection of a Treatment Method

After a subject is diagnosed as having a neoplasia (e.g., breast or ovarian cancer) a method of treatment is selected. In breast or ovarian cancer, for example, a number of standard treatment regimens are available. The presence of a defect in a DNA repair pathway suggests that the subject could be treated, for example, with a PARP inhibitor, cross-linking agents such as cisplatin and other agents that exploit the specific DNA repair defect of the tumor cells. Such a therapy can be combined, for example, with one or more of the following therapies: mastectomy, ovarectomy, radiation therapy (e.g., external beam and brachytherapy), hormone therapy, and chemotherapy. Additionally, prior to the diagnosis of cancer, a patient may opt to have treatments that reduce the risk of cancer based on the characterization of a DNA repair polypeptide. Examples include mastectomy and/or oophrectomy to reduce the risk of breast or ovarian cancer, respectively. The assays proposed might be useful prior to the onset of cancer in certain individuals with high cancer risk.

Kits

The invention also provides kits methods for characterizing the functional significance of a DNA repair pathway mutation to determine whether the patient has or has a propensity to develop breast or ovarian cancer in a biological sample obtained from a subject. The assay currently identifies mutations as high risk and/or distinguishes high risk mutations from those that do not elevate risk. In various embodiments, the kit includes one or more vectors of the invention. Preferably, such vectors include a homologous recombination reporter of short and long tract gene conversion vector comprising one to six Ter sites. In yet other embodiments, the kit comprises a sterile container which contains the primer or probe; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the primers or probes described herein and their use in diagnosing a neoplasia (e.g., breast/ovarian cancer). Preferably, the kit further comprises any one or more of the reagents described in the diagnostic assays described herein. In other embodiments, the instructions include at least one of the following: description of the primer or probe; methods for using the enclosed materials for the diagnosis of a neoplasia; precautions; warnings; indications; clinical or research studies; and/or references. The instructions may be printed directly on the container (when present), or as a label applied to the container, or as a separate sheet, pamphlet, card, or folder supplied in or with the container.

Genome Editing

Therapeutic gene editing is a major focus of biomedical research, embracing the interface between basic and clinical science. A large number of different recessive hereditary human disease syndromes are caused by inheritance of biallelic inactivating point mutations of disease genes. In one embodiment, if it were possible to safely reverse the disease-causing point mutation in cells cultured from the patient and to reconstitute the tissues of the patient's body with these corrected cells, this could lead to a cure for the disease or, at least, significant alleviation of the dysfunction.

Substantial progress towards this goal has been made with the advent of technologies for inducing pluripotency in cells derived from patients and with the remarkable development of novel "gene editing" tools. Broadly, gene editing requires the ability to manipulate the DNA sequence of a cell at a specific chromosomal locus, without introducing mutations at other sites of the genome. This technology effectively enables the researcher to manipulate the genome of the patient's cells in vitro, to effect a reversion of a deleterious genotype and to then reintroduce these cells into the patient. Successful development of gene editing has the potential to impact a large number of patients carrying known, defined genetic mutations and could have additional benefits in other diseases.

In one embodiment, gene editing involves targeting an endonuclease (an enzyme that causes DNA breaks internally within a DNA molecule) to a specific site of the genome and thereby triggering formation of a chromosomal double strand break (DSB) at the chosen site. If, concomitant with the introduction of the chromosome breaks, a donor DNA molecule is introduced (for example, by plasmid or oligonucleotide introduction), interactions between the broken chromosome and the introduced DNA can occur, especially if the two sequences share homology. In this instance, a process termed "gene targeting" can occur, in which the DNA ends of the chromosome invade homologous sequences of the donor DNA by homologous recombination (HR). By using the donor plasmid sequence as a template for HR, a seamless repair of the chromosomal DSB can be accomplished. Importantly, if the donor DNA molecule differs slightly in sequence from the chromosomal sequence, HR-mediated DSB repair will introduce the donor sequence into the chromosome, resulting in gene conversion/gene correction of the chromosomal locus. In the context of therapeutic gene targeting, the altered sequence chosen would be an active or functional fragment (e.g., wild type, normal) of the disease gene of interest. By targeting the nuclease to a genomic site that contains the disease-causing point mutation, the concept is to use DSB formation to stimulate HR and to thereby replace the mutant disease sequence with wild-type sequence (gene correction). The advantage of the HR pathway is that it has the potential to generate seamlessly a wild type copy of the gene in place of the previous mutant allele.

Current genome editing tools use the induction of double strand breaks (DSBs) to enhance gene manipulation of cells. Such methods include zinc finger nucleases (ZFNs; described for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, and U.S. Pat. Publ. Nos. 20030232410 and US2009020314, which are incorporated herein by reference), Transcription Activator-Like Effector Nucleases (TALENs; described for example in U.S. Pat. Nos. 8,440,431, 8,440,432, 8,450,471, 8,586,363, and 8,697,853, and U.S. Pat. Publ. Nos. 20110145940, 20120178131, 20120178169, 20120214228, 20130122581, 20140335592, and 20140335618, which are incorporated herein by reference), and the CRISPR (Clustered Regularly Interspaced Short Palindromic Repeats)/Cas9 system (described for example in U.S. Pat. Nos. 8,697,359, 8,771,945, 8,795,965, 8,871,445, 8,889,356, 8,906,616, 8,932,814, 8,945,839, 8,993,233, and 8,999,641, and U.S. Pat. Publ. Nos. 20140170753, 20140227787, 20140179006, 20140189896, 20140273231, 20140242664, 20140273232, 20150184139, 20150203872, 20150031134, 20150079681, 20150232882, and 20150247150, which are incorporated herein by reference). For example, ZFN DNA sequence recognition capabilities and specificity can be unpredictable. Similarly, TALENs and CRISPR/Cas9 cleave not only at the desired site, but often at other "off-target" sites, as well. These methods have significant issues connected with off-target double-stranded break induction and the potential for deleterious mutations, including indels, genomic rearrangements, and chromosomal rearrangements, associated with these off-target effects. ZFNs and TALENs entail use of modular sequence-specific DNA binding proteins to generate specificity for 18 bp sequences in the genome. The more recently developed, CRISPR/Cas9, adapts an RNA-guided bacterial host defense system and uses engineered RNA-DNA pairing to achieve target specificity. However, all current gene editing methods including CRISPR/Cas9, TALENs and ZFNs are plagued by "off-target" mutagenic effects, related to off-target binding of the gene editing nuclease to additional unintentionally specified sites (shown for CRISPR/Cas9 in FIG. 21A). Unfortunately, off-target effects are commonly observed with all of these methods, registering as "indels"—small insertions or deletions that indicate sites of off-target action of the endonuclease with repair by error-prone mechanisms such as non-homologous end joining (NHEJ). Clearly, if an off-target indel were to disrupt a functional gene in the patient's cell, this could be dangerous. For example, off-target inactivation of one allele of a tumor suppressor gene, such as TP53 or RB, could set the "gene corrected" cells on the path to cancer. Efforts to minimize such off-target effects have included the use of "nickases"—mutants of the endonuclease that inactivate one active site and leave the enzyme capable of inducing "nicks" (single stranded interruption of the sugar-phosphate backbone) in the genomic DNA. By combining two nickases to attack each DNA strand at the target site, the idea is to focus DSBs preferentially at the target locus. Although off-target effects may be reduced by this maneuver, there is no indication that it will abolish off-target indel formation altogether. There are good theoretical reasons why this is the case. Nicked DNA, if encountered during replication, can generate DSBs and, hence, promote indel formation or other types of mutation.

Figure 21A:
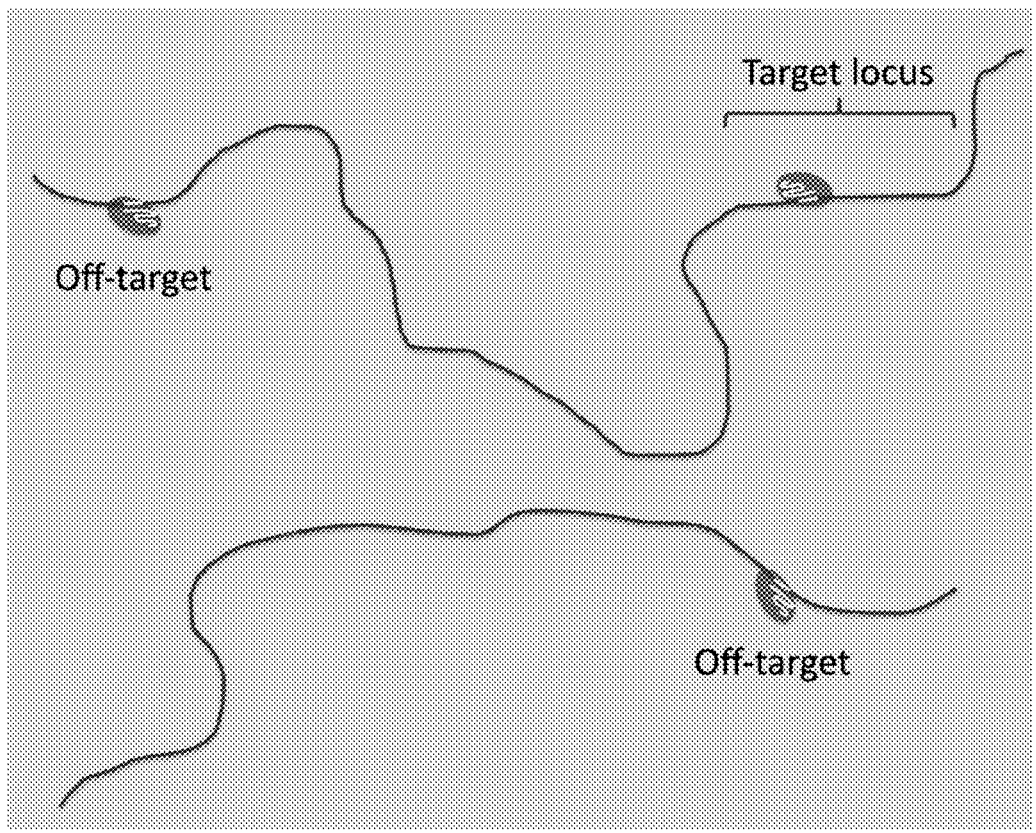
FIGS. 21A and 21B depict a model in which enzymatically inactive CRISPR/Cas9 arrays are used to stall replication in a site-specific manner at a single locus targeted for gene editing.
Figure 21B:
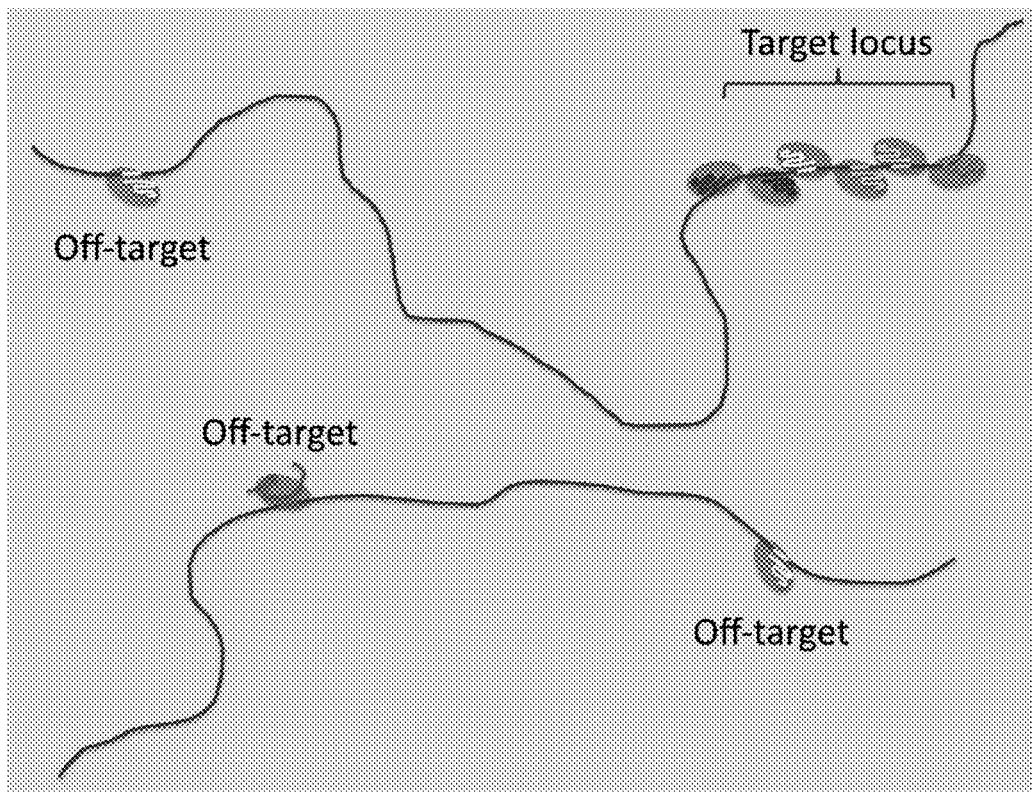

A new adaptation of existing gene editing tools is proposed to address the problem of off-target mutagenesis. This is accomplished by using an array of nuclease dead CRISPR/Cas9 complexes, arrayed in tight succession, side-by-side, at the target locus, to provoke site-specific replication fork stalling and limit gene targeting/gene editing specifically to the target locus (FIG. 21B). Because the stimulus to gene editing (a site-specific replication fork block) will only occur where the editing complexes are clustered/multiplexed in an array at the target locus, off-target binding of individual nuclease dead CRISPR/Cas9 complexes will not provoke replication fork arrest or chromosome breakage. In other words, by making the stimulus to DNA breakage a product of multiplexed CRISPR/Cas9 complex binding, the potential for off-target mutation is reduced to a negligible level. As described herein, experiments with a defined site-specific replication fork arrest tool indicate the potential for this approach to eradicate one of the obstacles to therapeutic gene editing (i.e., off-target mutagenesis) and to accelerate progress towards its safe clinical use. Although this description focuses on CRISPR/Cas9, it is envisioned that this method may be adapted to other gene editing tools (TALENs, ZFNs) in search of the optimal technology.

In one aspect, the invention provides methods of increasing replication fork stalling (e.g., Tus/Ter system), which could be used to induce error free double stranded breaks with fewer off-target effects. In various embodiments, one or more DNA binding proteins can be used to induce replication fork stalling. In one embodiment, the invention provides a GFP cDNA containing an array of Ter sites. A Tus expression vector is co-transfected together with a donor mutant GFP sequence (see e.g., FIGS. 19 and 20), and detection of whether Tus/Ter triggers conversion of the integrated GFP copy to wild type is assayed. Production of GFP+ cells marks those that have undergone successful gene targeting. In this way, the ability of Tus/Ter to stimulate gene targeting is assayed. In other various embodiments, one or more of the following DNA binding proteins is used: Cas9, Cas9 null (i.e., catalytically inactive Cas9), Tus, Zinc finger domain, Zinc finger nuclease, transcription activator-like effector (TALE) domain, and/or TALE nucleases.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 1B:
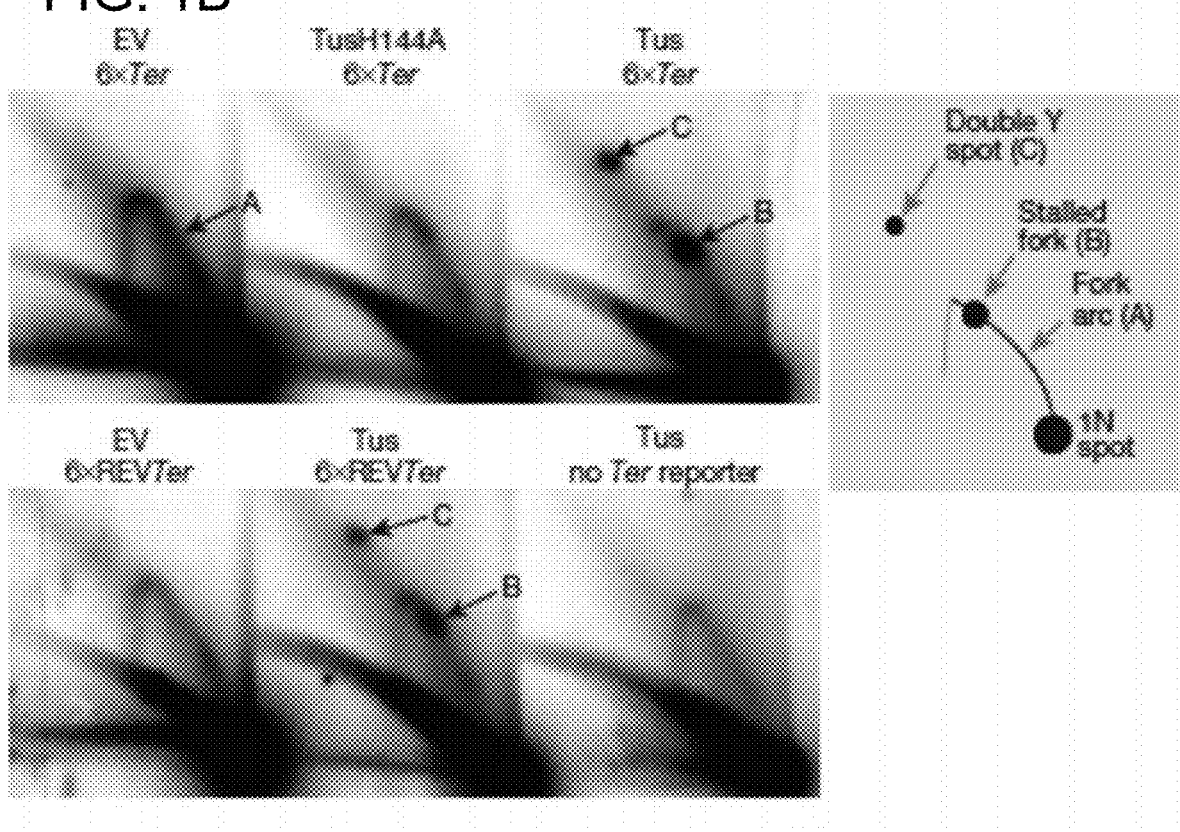
Figure 1C:
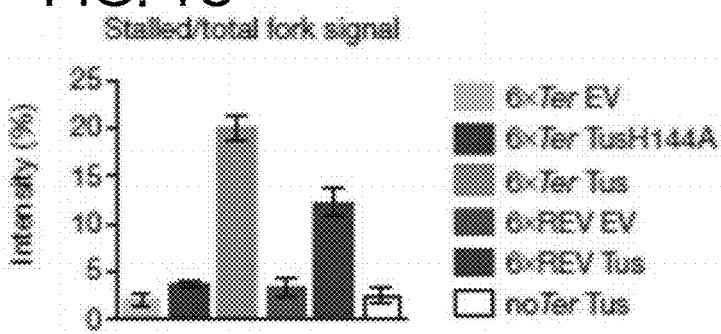
Figure 1D:
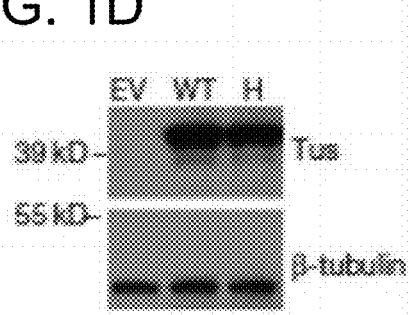
Figure 2A:
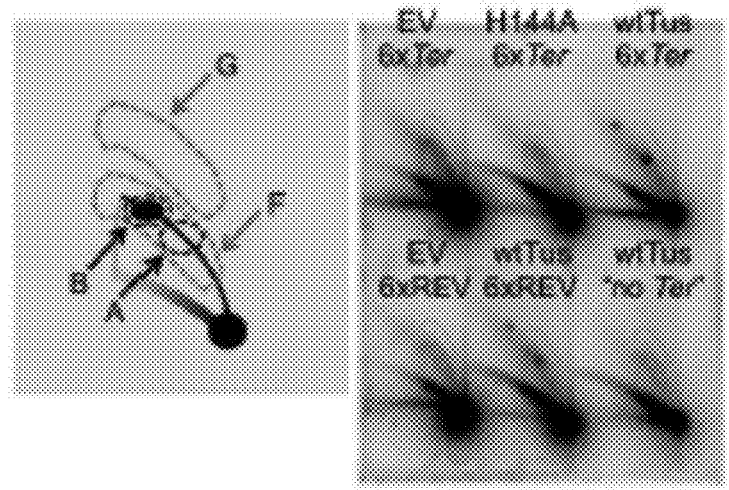
FIGS. 2A-2E show Tus/Ter-induced replication fork stalling visualized by additional restriction digests.
Figure 2B:
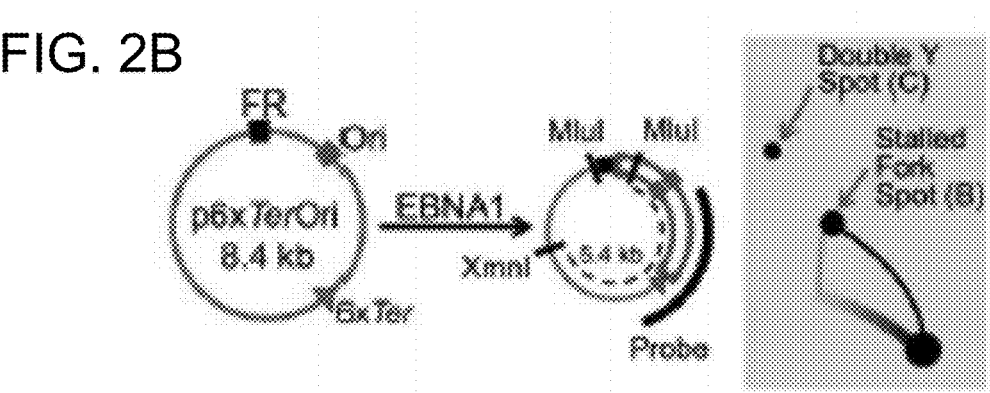
Figure 2C:
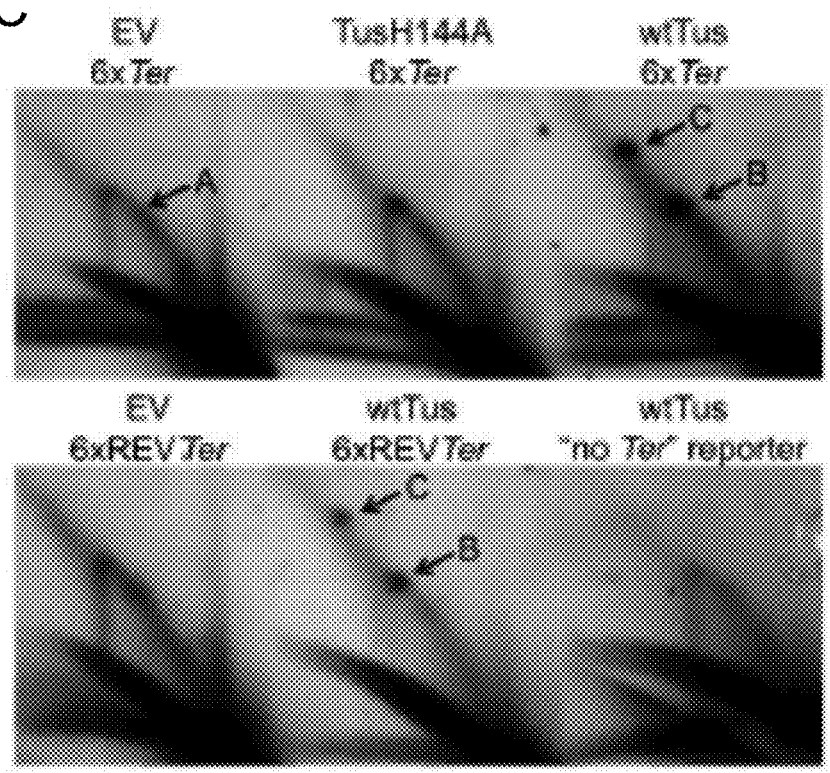
Figure 2D:
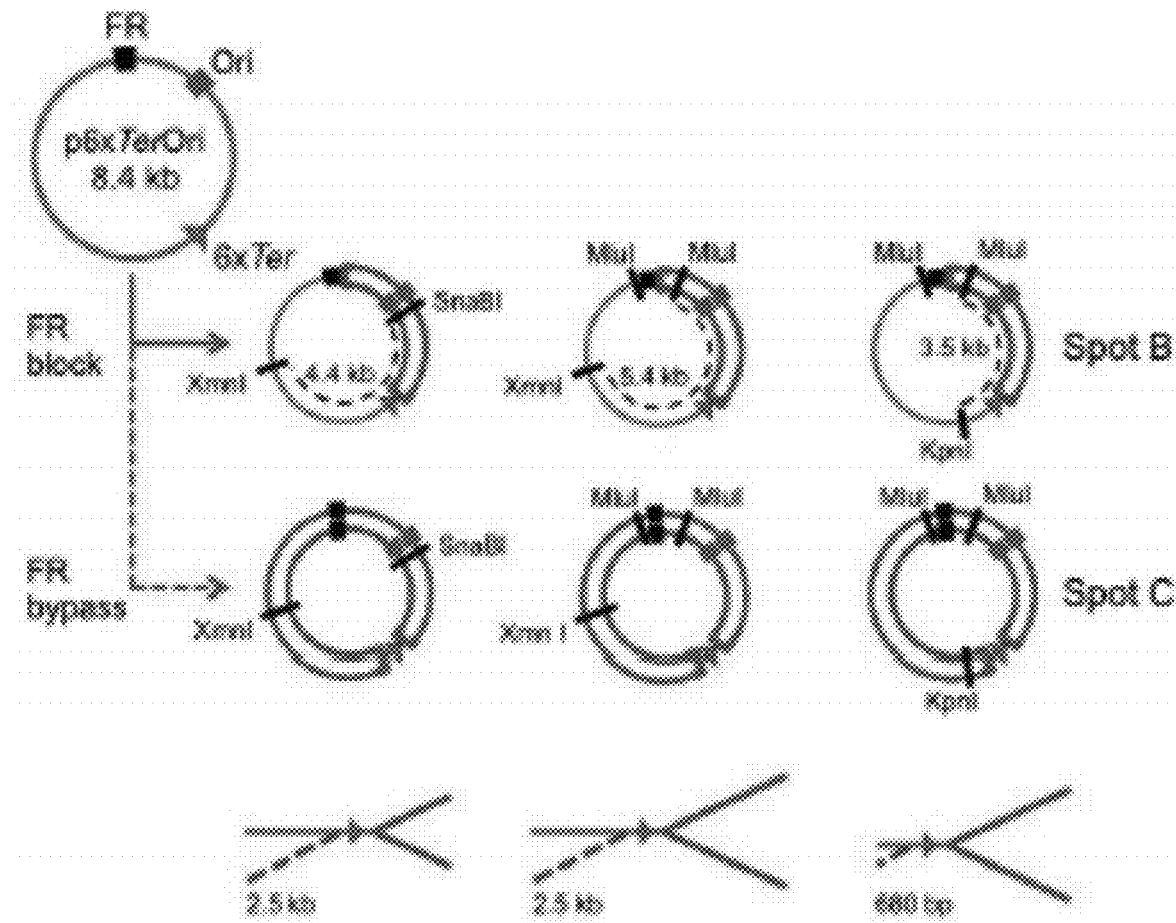
Figure 2E:
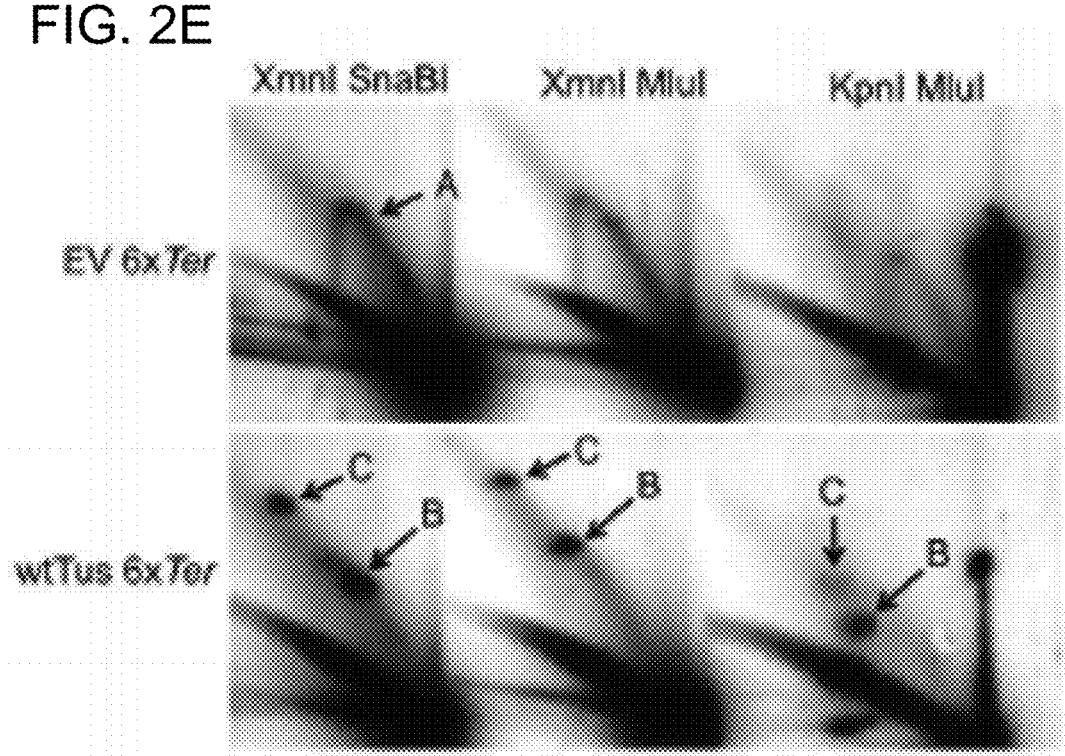
Figure 3A:
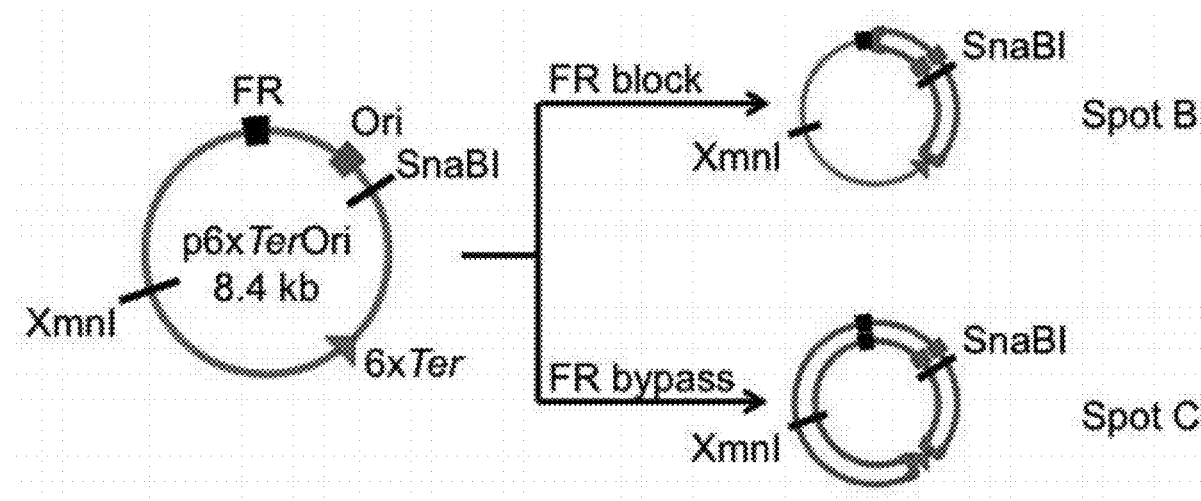
FIGS. 3A-3D show an estimation of efficiencies of the FR/EBNA1 and Tus/6×Ter replication fork barriers.
Figure 3B:
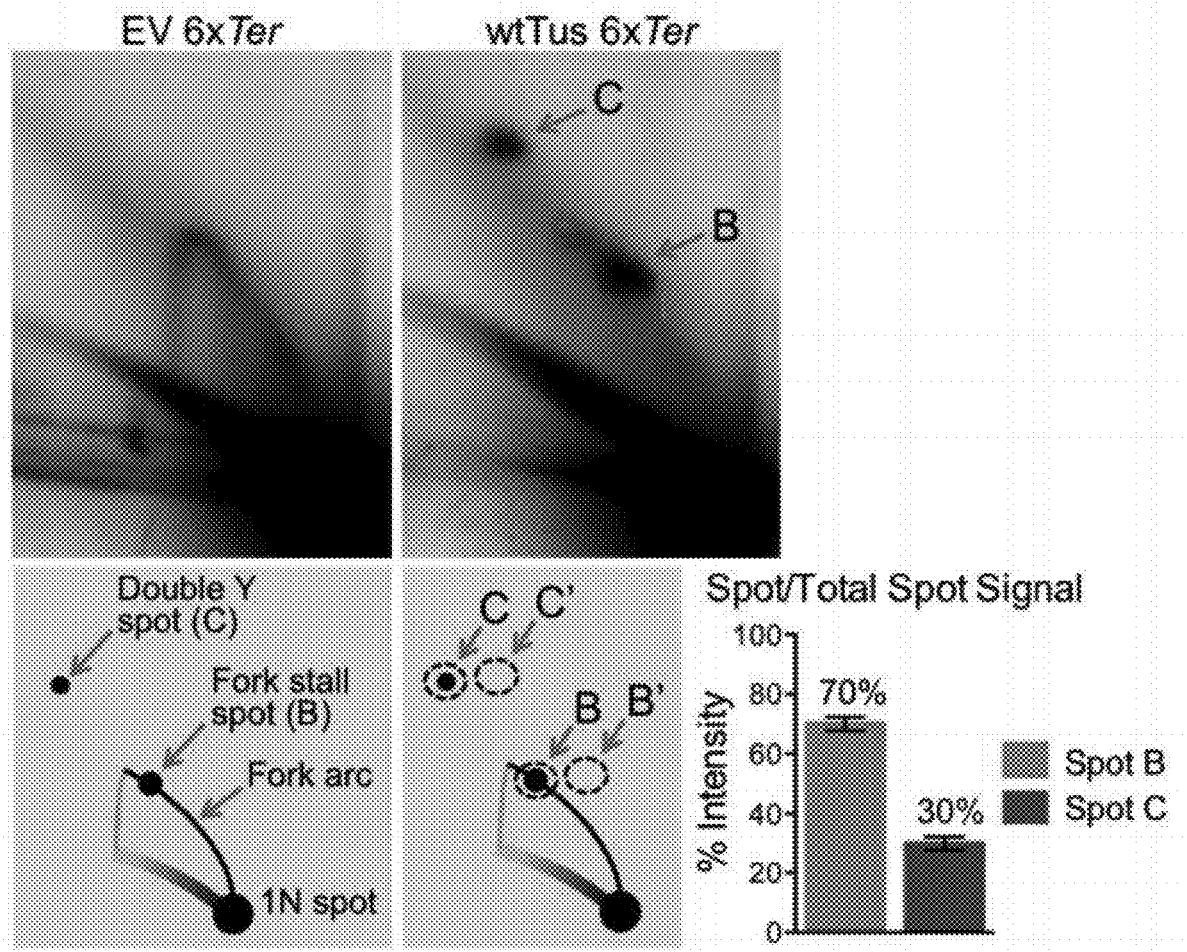
Figure 3C:
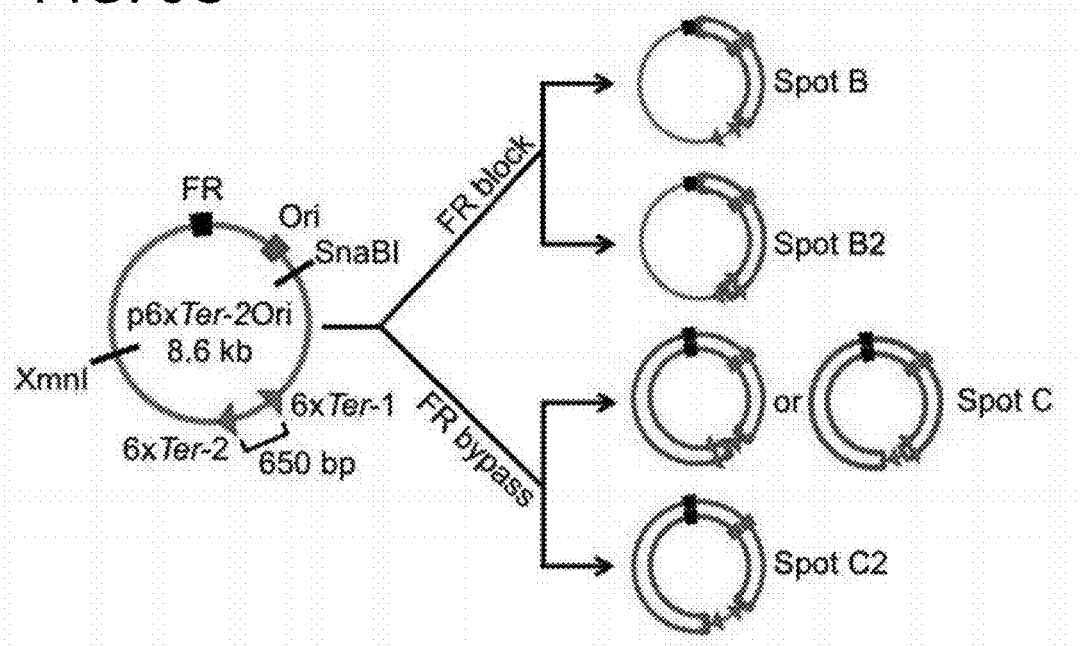
Figure 3D:
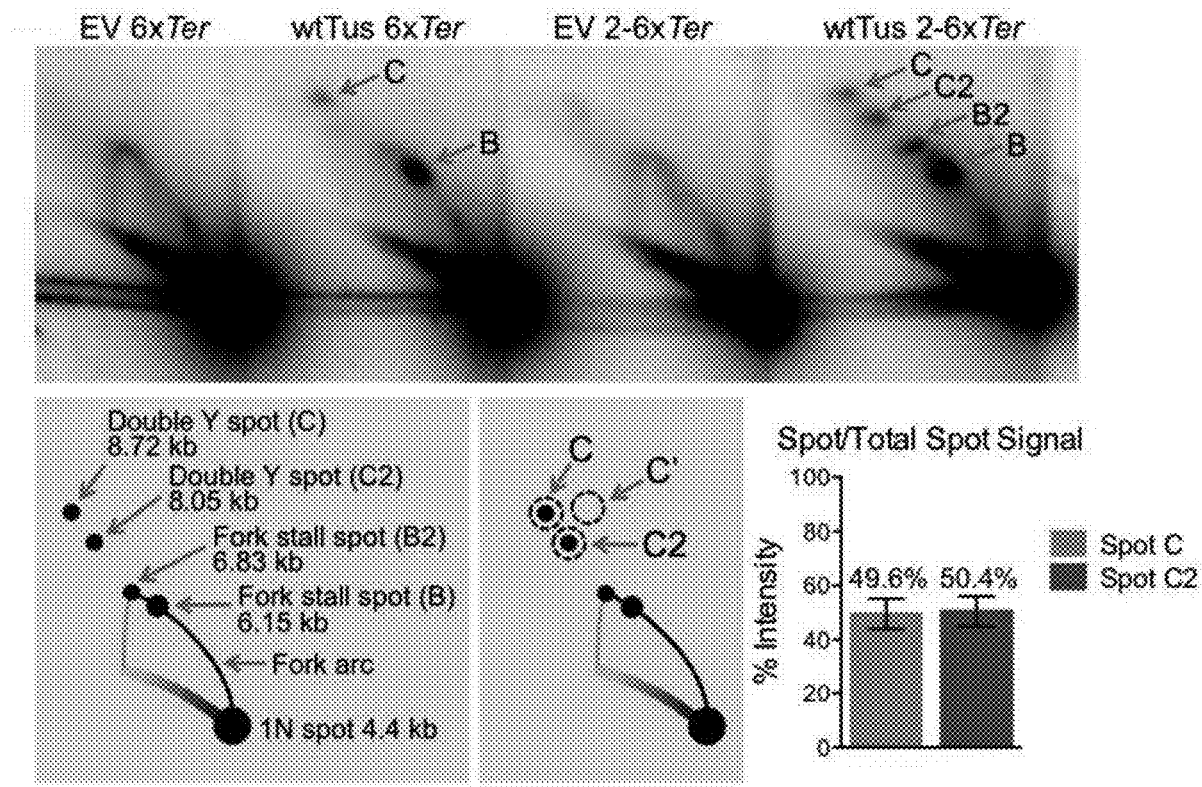

Example 1: Loss of BRCA1/BRCA2/Rad51-Dependent Suppression of LTGC at Stalled Replication Forks Contributes to Breast/Ovarian Cancer Predisposition Tus binds the 23 base pair (bp) Ter site to induce polar replication fork arrest in *E. coli*. To determine whether Tus/Ter can arrest mammalian replisomes, six TerB sites were introduced into a plasmid containing the EpsteinBarr virus nuclear antigen 1 (EBNA1)-binding origin of replication (p6×TerOri, FIG. 1A). EBNA1 recruits mammalian replication factors, mediating predominantly unidirectional plasmid replication, due to a replication block at EBNA1-bound FR (family of repeats). In p6×TerOri, the major clockwise fork approaches the 'non-permissive' (fork-stalling) face of Tus/Ter (FIG. 1A). Two-dimensional DNA gel electrophoresis with Southern blotting was used to visualize replication through Ter. Transfection of 293E cells, which express EBNA1, with p6×TerOri and control empty vector revealed plasmid replication intermediates (arc A, FIG. 1B). Co-transfection of p6×TerOri and myc-tagged Tus revealed site-specific stalling of the clockwise fork (spot B, FIGS. 1B, 1C, 1D and FIGS. 2A-2E). TusH144A, a Ter-binding-impaired mutant, induced minimal fork stalling. Reversal of 6×Ter to the 'permissive' orientation (6×REVTer, FIG. 1B) also supported Tus-dependent stalling of the clockwise fork, albeit less efficiently than non-permissive 6×Ter (FIGS. 1B and 1C). The FR/EBNA1 replication block is incomplete. A weaker Tus/Ter-dependent double-Y spot (C, FIG. 1B and FIGS. 2A-2E) reflects bidirectional fork arrest at 6×Ter. The FR/EBNA1 and Tus/6×Ter replication block efficiencies were estimated as, 70% (FIGS. 3A-3D). Thus, Tus/Ter mediates bidirectional site-specific arrest of mammalian replication forks.

Figure 4A:
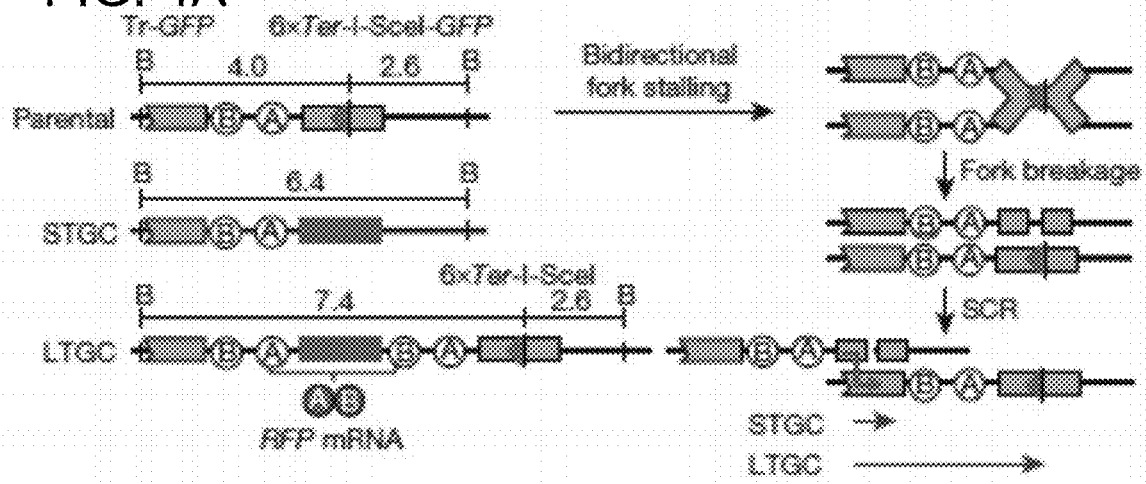
FIGS. 4A-4D show Tus/Ter-induced homologous recombination in mammalian cells.
Figure 4B:
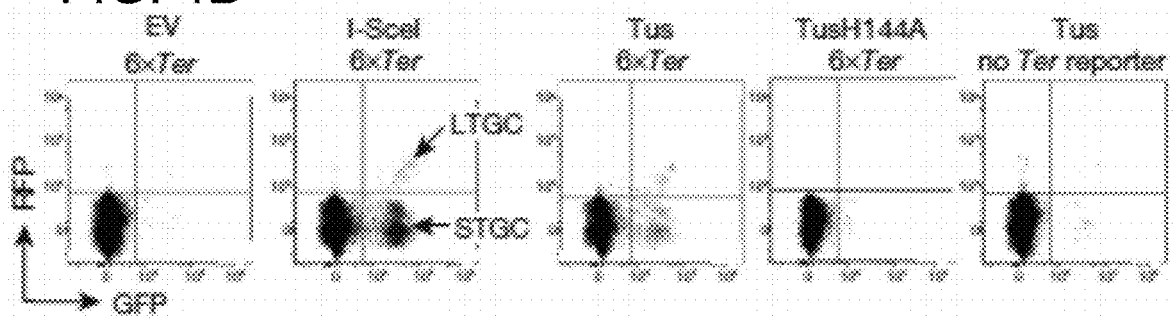
Figure 4C:
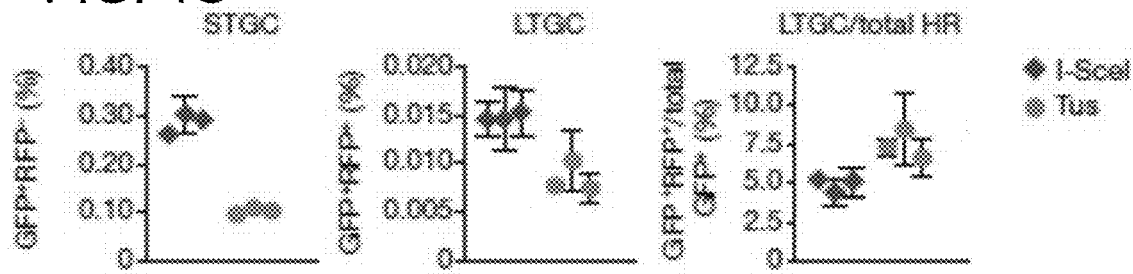
Figure 5A:
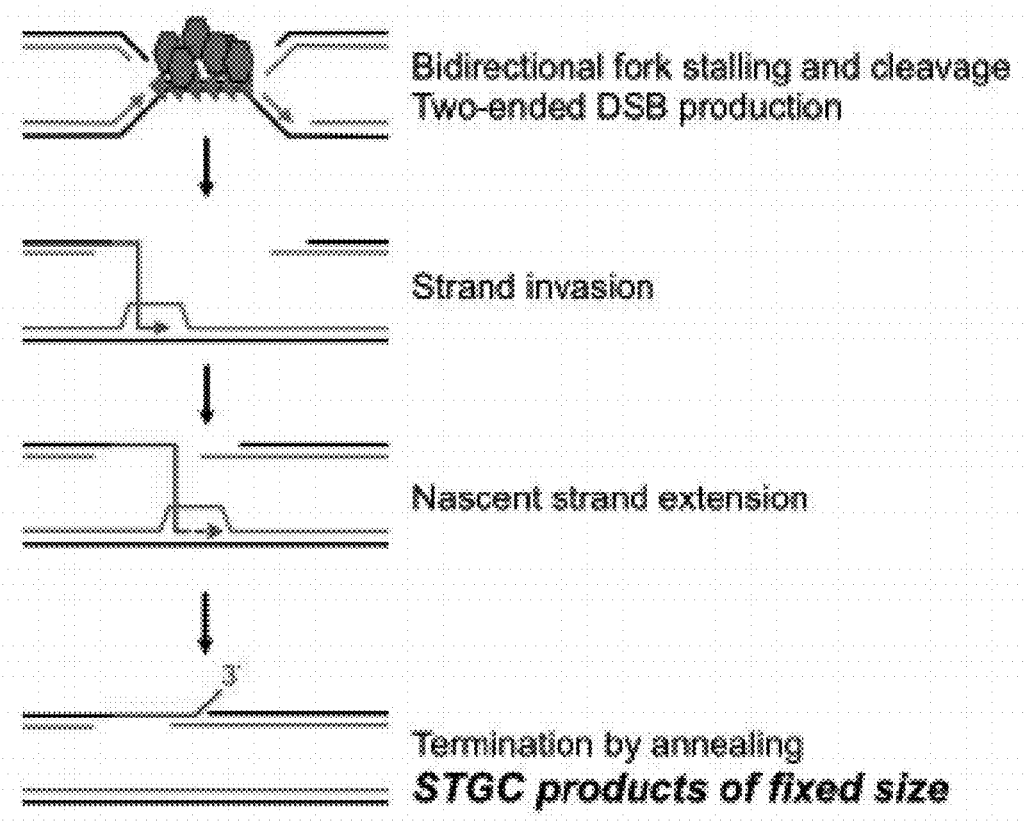
FIGS. 5A and 5B show two-ended versus one-ended break repair models of Tus/Ter-induced homologous recombination.
Figure 5B:
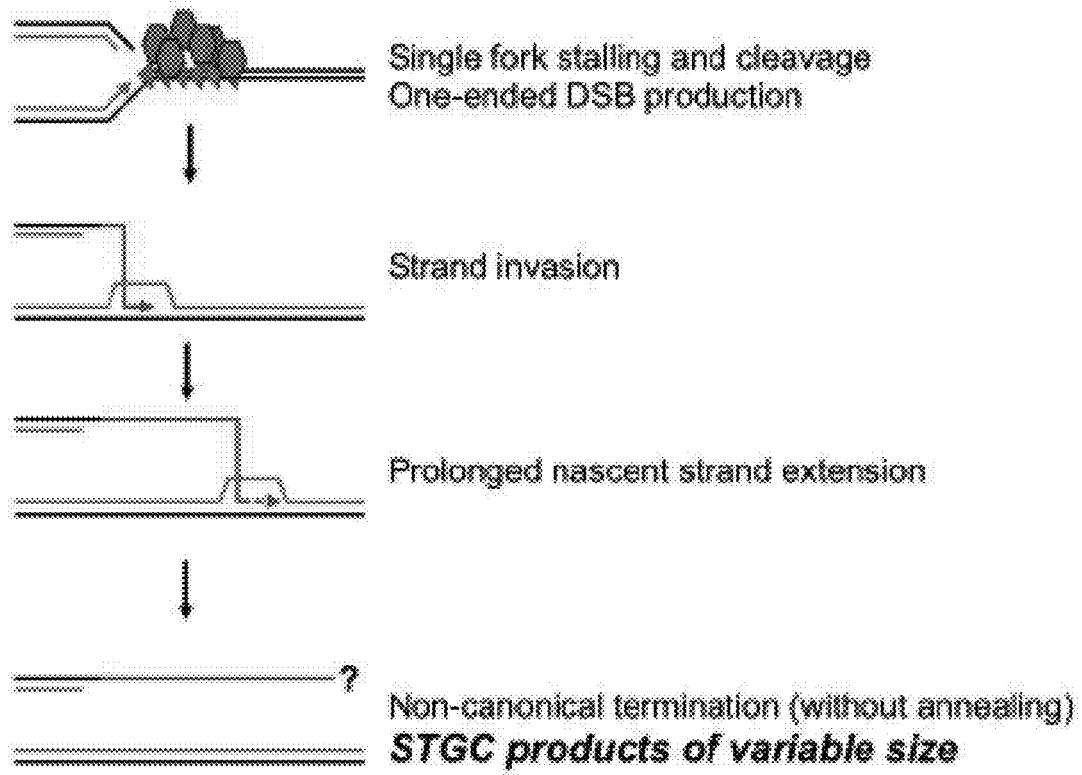
Figure 6A:
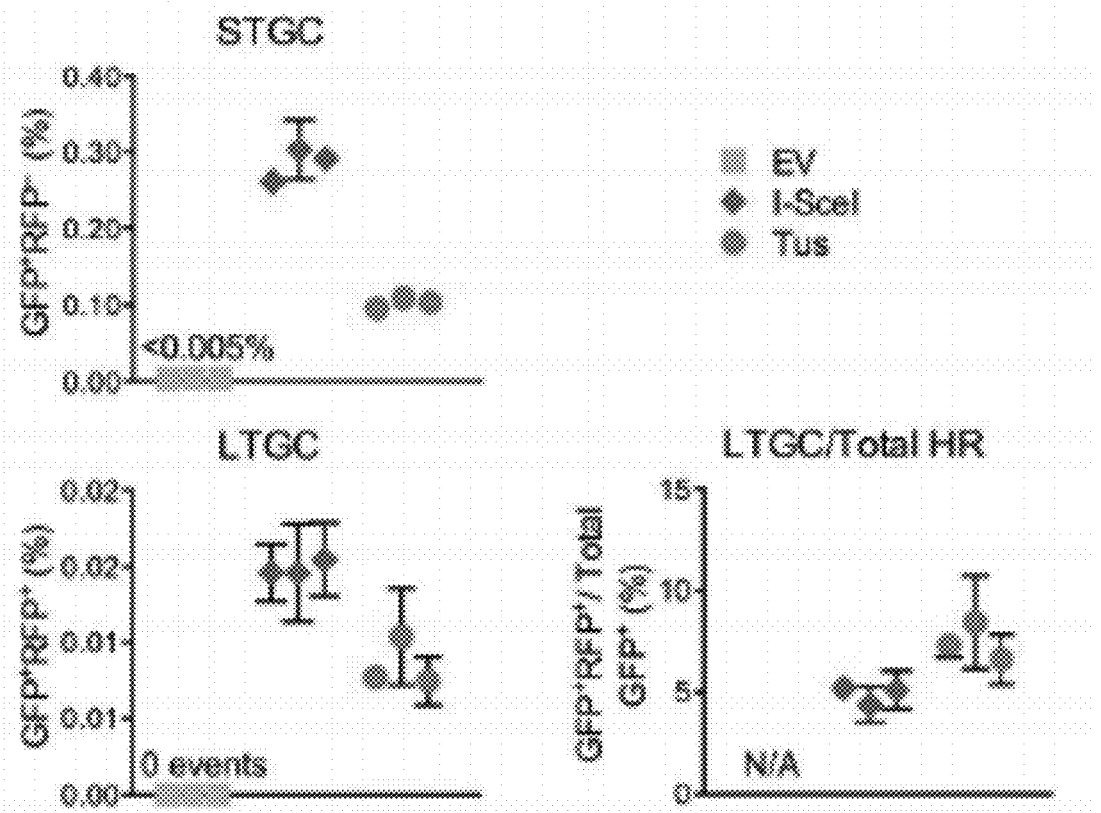
FIGS. 6A-6F show that Tus/Ter-induced homologous recombination in Brca1$^{fl/BRCT}$ 6×Ter/HR cells conformed to an affinity/avidity model.
Figure 6B:
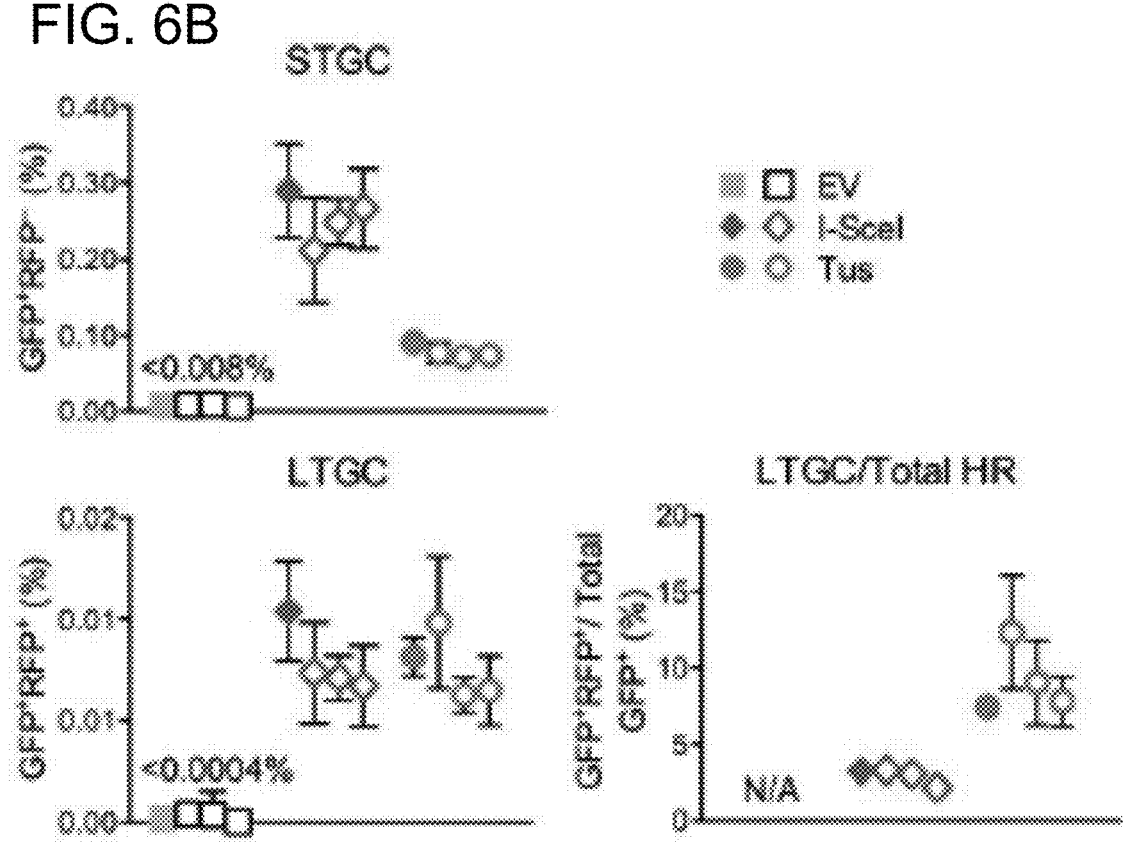

To determine whether Tus/Ter induces HR/SCR at a defined chromosomal locus in mammalian cells, 6×Ter was placed in a homologous recombination reporter of short- and long-tract gene conversion (termed STGC and LTGC, respectively) between sister chromatids. Duplication of a red fluorescent protein (RFP) cassette distinguished LTGC (length≥1252 bp; GFP⁺RFP⁻) from STGC (length<1,252 bp; GFP⁺RFP⁻ FIG. 2A). 6×Ter abuts an I-SceI site, interrupting an enhanced green fluorescent protein gene (6×Ter-I-SceI-GFP, FIG. 4A). Recombination of the stalled left-hand fork (FIG. 4A) with the 59-truncated GFP copy (Tr-GFP) of the sister chromatid generated wild-type GFP. If chromosomal fork arrest were bidirectional, this could produce a two-ended break, generating predominantly STGCs (FIGS. 4A and 5A). In contrast, unidirectional fork arrest with one-ended breaks would favour LTGC, and any STGCs arising from one-ended breaks would necessarily be terminated by non-canonical mechanisms (FIG. 5B). The 6×Ter/HR reporter was targeted as a single copy to the ROSA26 locus of mouse embryonic stem (ES) cell line 11CO/47T (Brca1$^{fl/BRCT}$)Brca1$^{BRCT}$ encodes a C-terminal truncated protein; the BRCT-encoding elements of Brca1$^{fl}$ can be conditionally deleted (generating Brca1$^{\Delta}$). Indeed, Tus, but not TusH144A, induced HR within 63 Ter/HRBrca1$^{fl/BRCT}$ cells, the major HR product being STGC (FIG. 4B). Tus failed to induce HR in Brca1$^{fl/BRCT}$ cells containing a ROSA26-targeted HR reporter lacking the Ter array (FIG. 4B). Thus, Tus/Ter-induced chromosomal HR requires cognate Tus-Ter binding. The ratio LTGC/total HR, a measure of the probability that HR resolves as LTGC, was approximately 7% in three independent Tus-transfected clones (FIGS. 4C and 6A). Three additional independent clones of Brca1$^{fl/BRCT}$ ES cells, each containing a single-copy randomly integrated chromosomal 6×Ter/HR reporter, behaved similarly (FIG. 6B). The predominance of STGC and the consistent results at different loci suggested that Tus/Ter-induced HR entails bidirectional fork arrest (FIG. 5A). This was resolved definitively by Southern blot analysis of Tus/Ter-induced STGCs. Unidirectional fork arrest/breakage (FIG. 5B) could produce a one-ended break, generating STGC products of variable size.

Figure 4D:
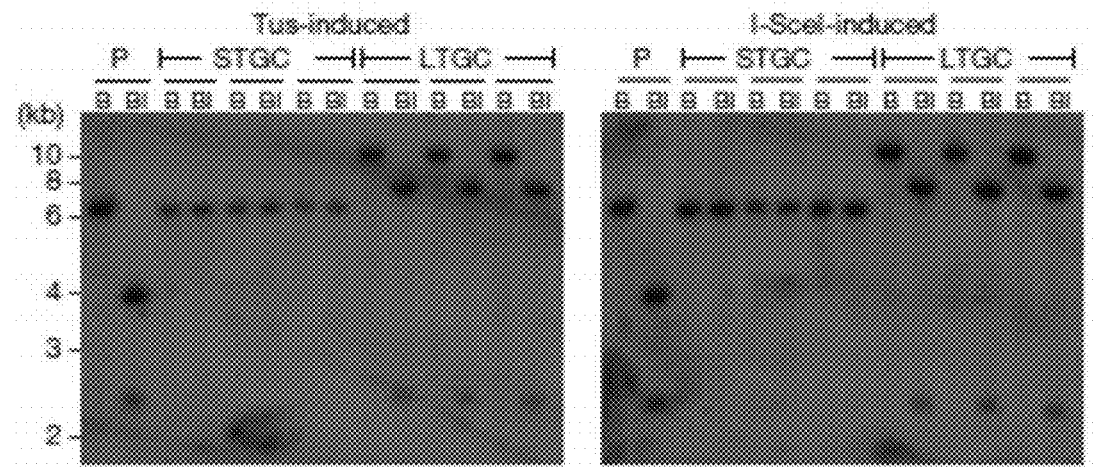
Figure 6C:
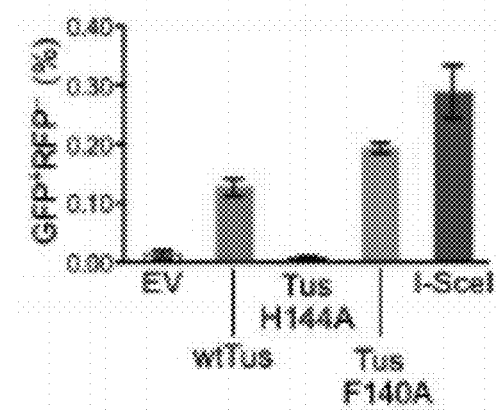
Figure 6D:
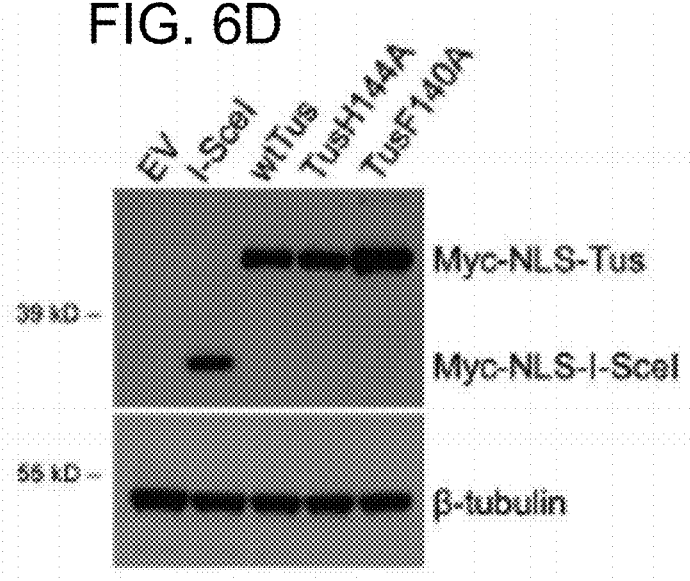
Figure 6E:
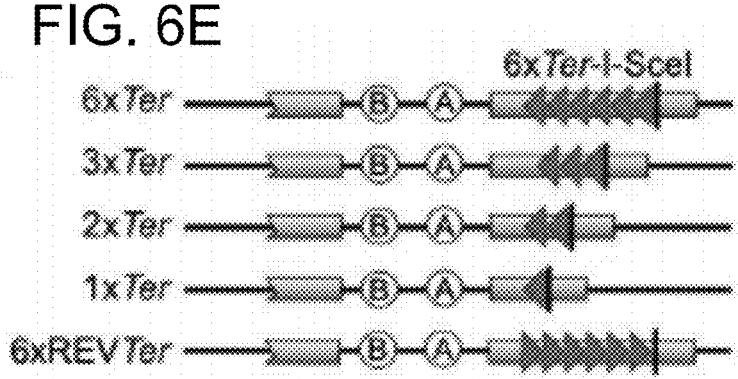
Figure 6F:
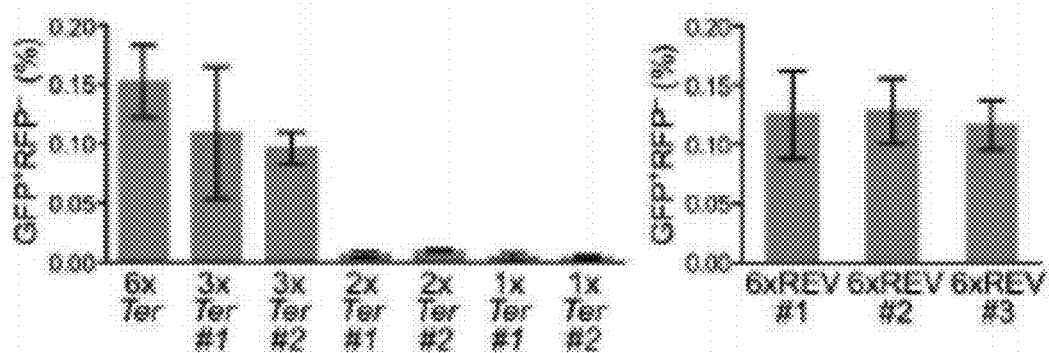

In contrast, bidirectional fork arrest (FIGS. 4A and 5A) could produce a two-ended break, with STGC termination by annealing. This would generate STGC products of fixed size, resembling the parental reporter, but lacking the 6×Ter array or I-SceI site (FIG. 4A). Indeed, 44/44Tus/Ter-induced STGCs in 6×Ter/HR reporter Brca1$^{fl/BRCT}$ cells revealed this latter structure (FIG. 4D). As expected, I-SceI-induced HR behaved similarly (FIG. 4D). A second arrested fork (right-hand fork, FIG. 4A) must provide the homologous second end during Tus/Ter induced STGC. Therefore, Tus/Ter-induced STGC is the product of bidirectional replication fork arrest. Overall, I-SceI-induced HR in Brca1$^{fl/BRCT}$ 6×Ter/HR reporter cells was approximately 20% of that in isogenic ROSA26-targeted Brca1$^{fl/BRCT}$ HR reporter cells, which lack a 6×Ter array. To investigate further the non-polar behaviour of Tus/Ter in mammalian HR, the Tus mutant F140A that binds duplex Ter with higher affinity than Tus, but is defective for the Ter C-6 base-flipping 'locking' mechanism that contributes to polar fork arrest in E. coli was studied. Tus F140A induced higher levels of HR than Tus in 6×Ter/HR Brca1$^{fl/BRCT}$ cells (FIGS. 6C and 6D), showing that the C-6 'lock' is dispensable for Tus/Ter-induced HR in mammalian cells. This might be explained by the different polarities of the E. coli DnaB and vertebrate MCM replicative helicases. Ter C-6 is located on the leading strand of the fork approaching the non-permissive end of Ter. Unlike DnaB, which translocates along the lagging strand, the MCM helicase translocated along the leading strand and might occlude Ter C-6 within its barrel, thereby denying Tus access to the C-6 lock mechanism. To determine the minimal number of Tus/Ter complexes needed for HR induction, reporters containing 3, 2 or 1 Ter sites were generated (FIG. 6E). Each, was targeted in parallel, as a single copy to the ROSA26 locus of Brca1$^{fl/BRCT}$ ES cells and it was found that a minimum of 3 Ter sites was required for robust Tus-induced HR (FIG. 6F). The 6×Ter array orientation was inverted to generate a 6×REVTer/HR reporter. When targeted as a single copy to the ROSA26 locus of Brca1$^{fl/BRCT}$ ES cells, this reporter supported Tus-induced HR as robustly as the 6×Ter/HR reporter (FIG. 6F). These findings do not exclude a polar component to Tus/Ter-induced fork stalling on a mammalian chromosome but this polarity, if present, is relative and not absolute.

In summary, it was discovered that Tus/Ter-induced HR: requires cognate binding of Tus to the Ter array; is independent of Ter site orientation; is dependent on Ter site number (requires at least 3×Ter; optimal is 6×Ter); occurs equally efficiently at different random chromosomal sites; is a product of bidirectional replication fork arrest (shown by Southern blot analysis of HR products); and is regulated differently from HR in response to a "generic" chromosomal DSB induced by the rare-cutting homing endonuclease I-SceI. Furthermore, Tus/Ter-induced HR was observed in human somatic cells, and is therefore not restricted to a specific cell type.

Figure 7A:
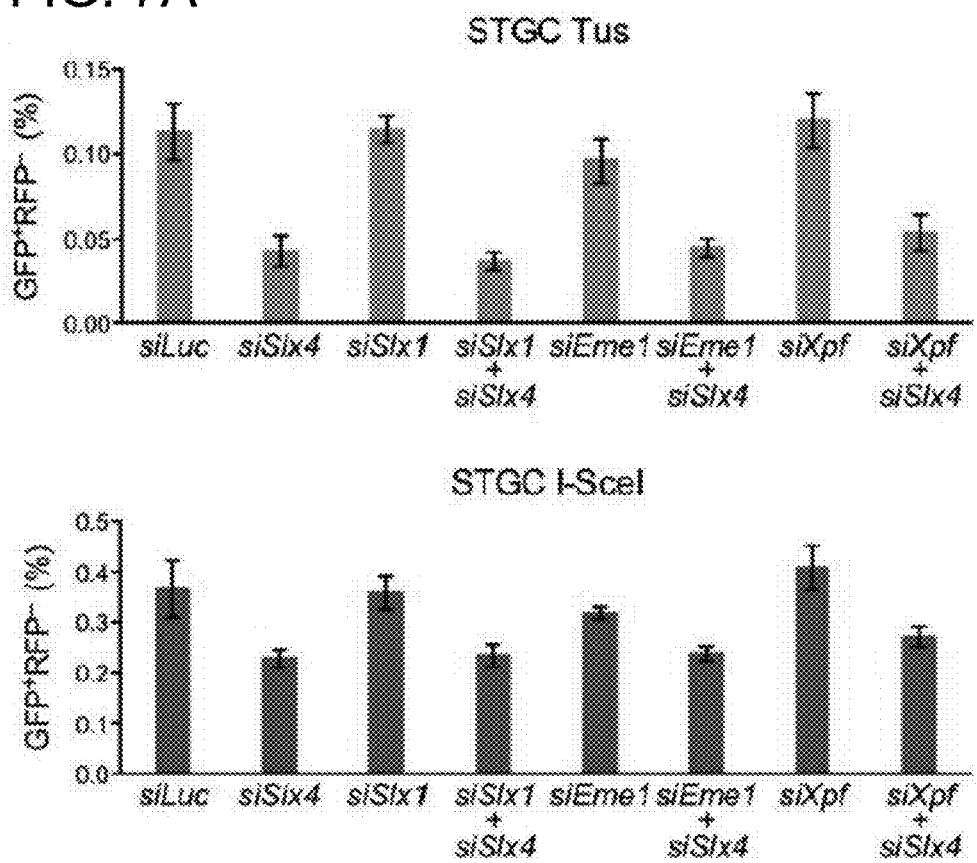
FIGS. 7A and 7B show Slx4/FancP depletion suppressed Tus/Ter induced HR.
Figure 7B:
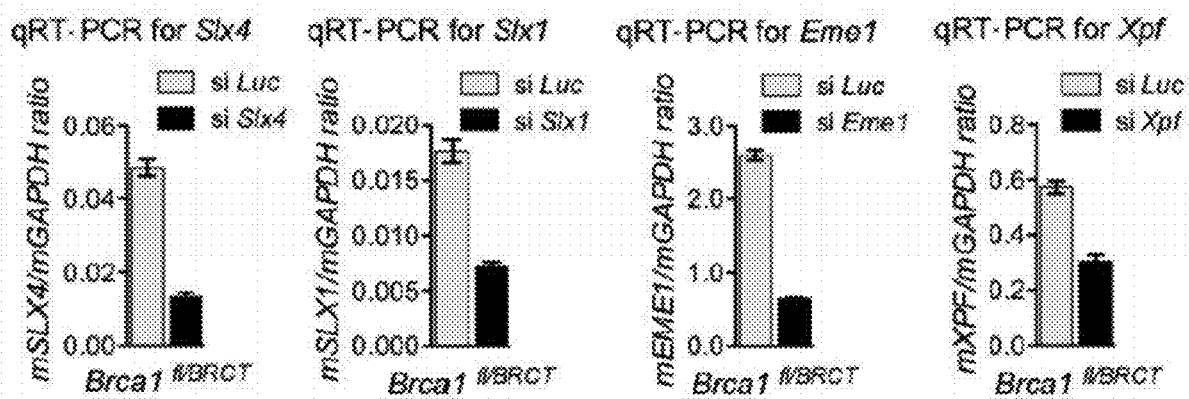

Interstrand DNA crosslink repair of plasmids replicating in Xenopus laevis egg extracts entailed endonucleolytic attack of bidirectionally stalled forks. Interestingly, Tus/Ter-induced HR was suppressed by depletion of the endonuclease scaffold Slx4/FancP to a greater extent than I-SceI-induced HR (FIGS. 7A and 7B), indicating that Slx4 contributes specifically to Tus/Ter-induced HR. However, it was not clear whether Slx4 mediates endonucleolytic attack of stalled forks during Tus/Ter-induced HR. Work in Schizosaccharomyces pombe suggested that alternative mechanisms, such as template switching, could mediate HR at stalled mammalian forks.

Figure 8A:
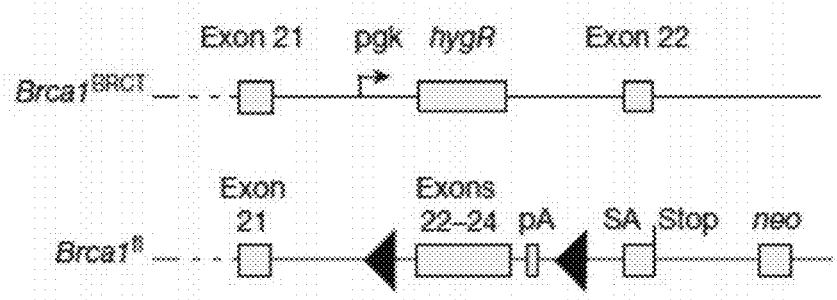
FIGS. 8A-8D show the Brca1 tandem BRCT repeat regulates Tus/Ter-induced homologous recombination.
Figure 8B:
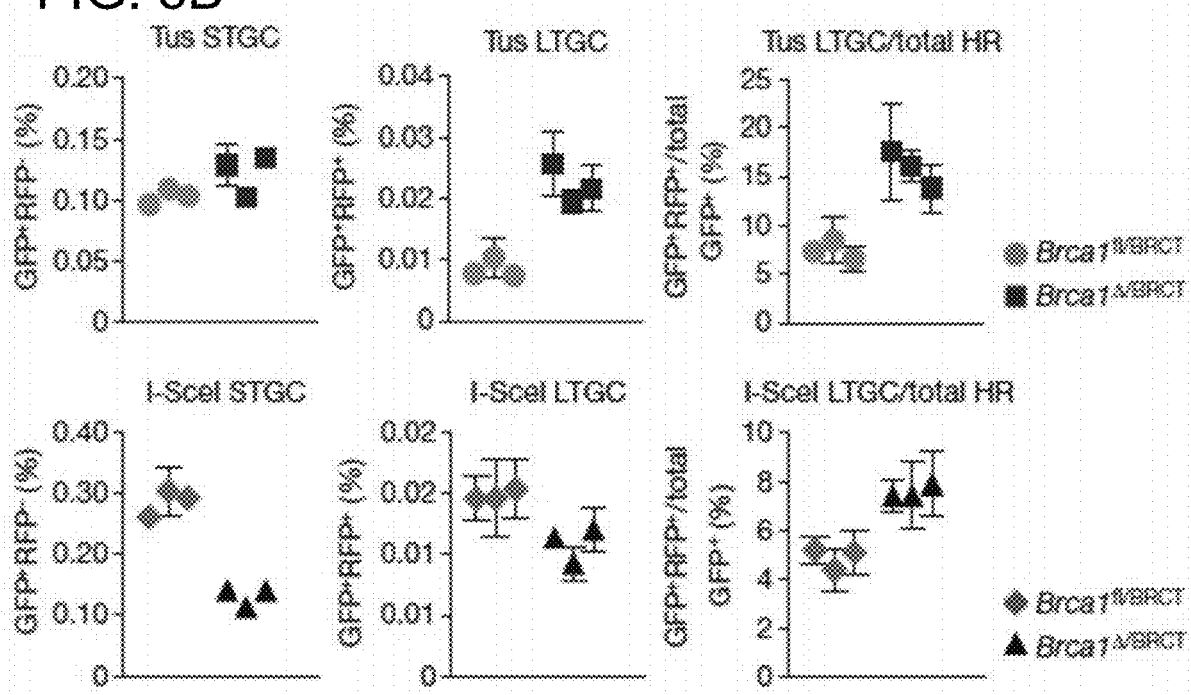
Figure 8C:
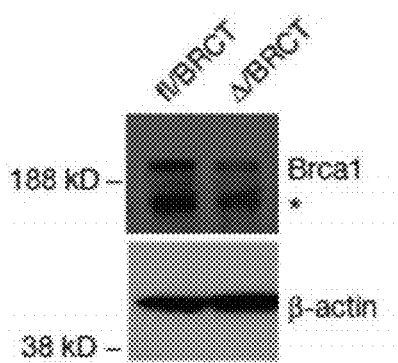
Figure 8D:
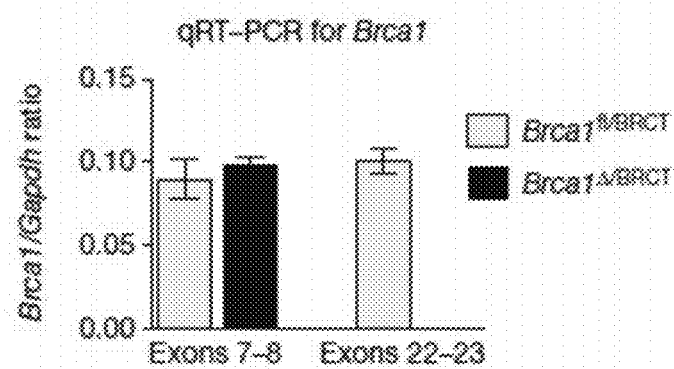
Figure 9A:
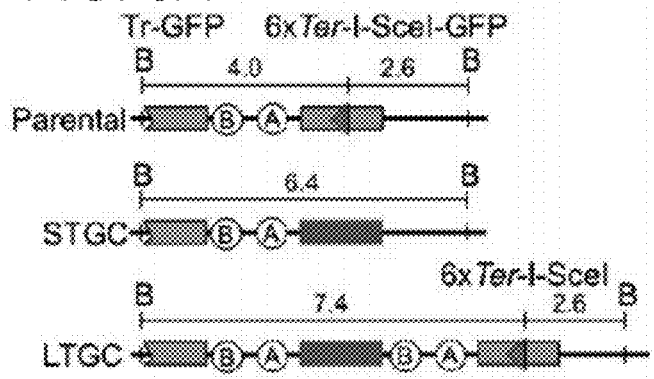
FIGS. 9A and 9B show a Southern blot analysis of Tus/Ter- and I-SceI induced HR products in Brca1$^{\Delta/BRCT}$ 6×Ter/HR cells.
Figure 9B:
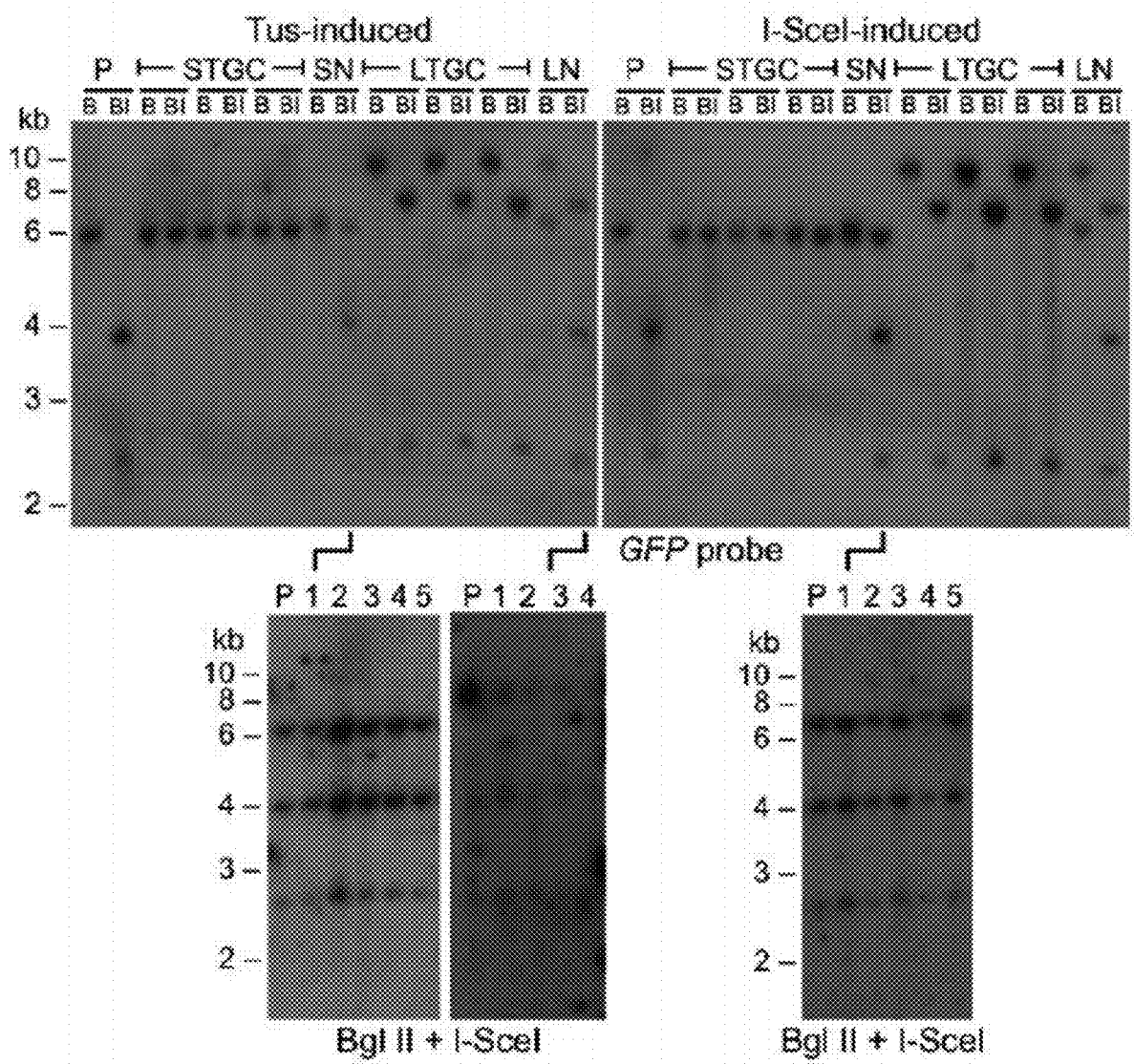

To determine whether BRCA1 regulates HR at stalled replication forks, 6×Ter/HR Brca1$^{fl/BRCT}$ cells were transduced with adeno-Cre and screened for Brca1 loss (FIGS. 8A-8D). The resulting Brca1$^{\Delta/BRCT}$ cells were viable hypomorphs with growth characteristics similar to Brca1$^{fl/BRCT}$ cells 21. Tus-induced HR in three independent Cre-treated clones of each genotype were studied (FIGS. 8A and 8B). Surprisingly, Tus-induced STGC in 6×Ter/HR Brca1$^{\Delta/BRCT}$ cells showed no reduction compared to Brca1$^{fl/BRCT}$ cells, but LTGC was elevated twofold (FIG. 8B). Correspondingly, the probability of engaging LTGC during Tus/Ter-induced HR was doubled to, 15% (FIG. 8B). Consistent with recent findings, I-SceI-induced HR in 6×Ter/HR Brca1$^{D/BRCT}$ cells was diminished and biased in favour of LTGC (FIG. 8B). Southern blot analysis of Tus/Ter-induced STGC and LTGC products in 6×Ter/HR Brca1$^{\Delta/BRCT}$ cells revealed patterns similar to Brca1$^{fl/BRCT}$ cells (FIGS. 9A and 9B). However, in Brca1$^{\Delta/BRCT}$ cells, 6/41 (15%) Tus/Ter-induced STGC and 3/15 (20%) LTGC clones retained an additional copy of the parental reporter (FIGS. 9A and 9B). This was not separable by recloning, suggesting that it was retained by non-disjunction. A total of 4/41 (9.8%) I-SceI-induced STGC Brca1$^{D/BRCT}$ clones revealed non-disjunction; thus, non-disjunction is not specific to Tus/Ter-induced HR. The fact that the donor sister was unaltered during LTGC excludes crossing-over as a cause of the LTGC outcome in these clones.

Figure 10A:
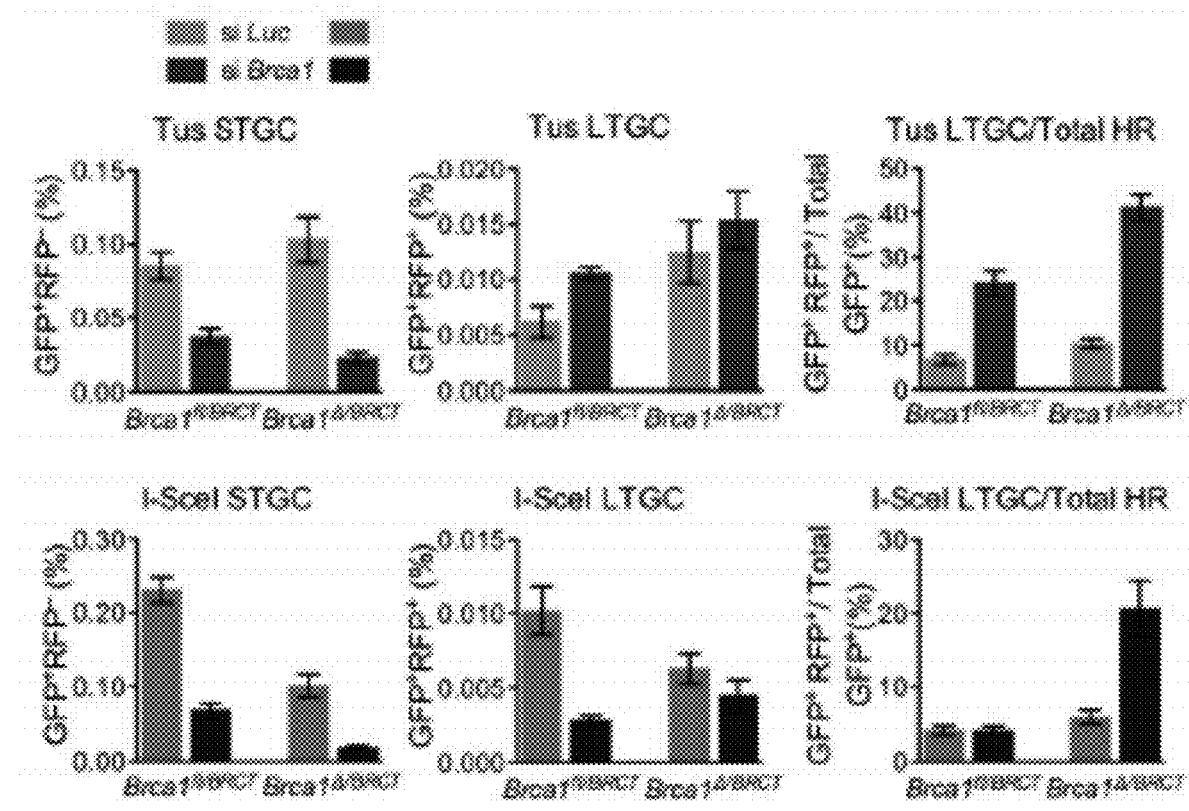
FIGS. 10A-10C show that Brca1 contributed quantitatively and qualitatively to homologous recombination at stalled replication forks.
Figure 10B:
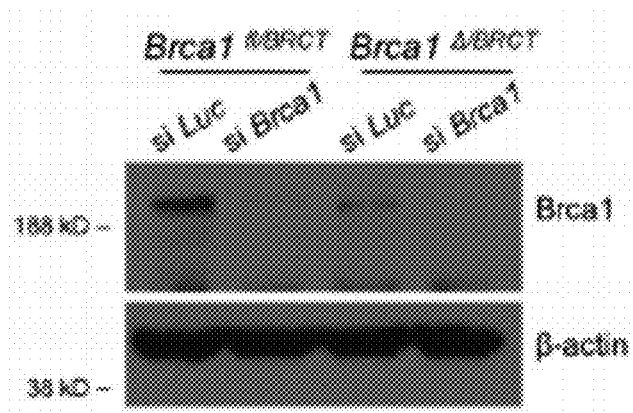
Figure 10C:
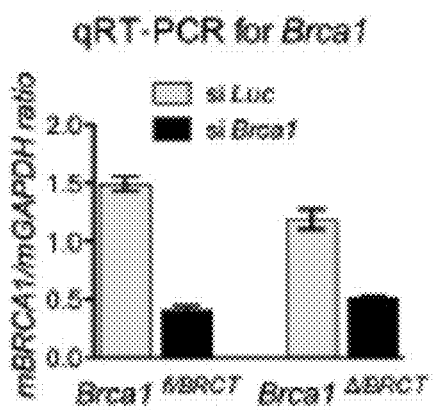

Next it was studied whether Brca1 domains additional to the BRCT repeat regulate Tus/Ter-induced HR. Indeed, short interfering (siRNA)-mediated Brca1 depletion suppressed STGC, but increased LTGC in both $Brca1^{fl/BRCT}$ and $Brca1^{\Delta/BRCT}$ cells (FIGS. 10A-10C). In Brca1-depleted $Brca1^{\Delta/BRCT}$ cells, 40% of all HR products were LTGCs. More than half of the BRCA1 polypeptide is encoded by exon 11, which is a target of inactivating germline mutations in hereditary breast/ovarian cancer; exon 11 is also alternatively spliced, generating an in-frame nuclear Δexon11 gene product that retains an N-terminal RING domain and C-terminal BRCT functions.

Figure 11A:
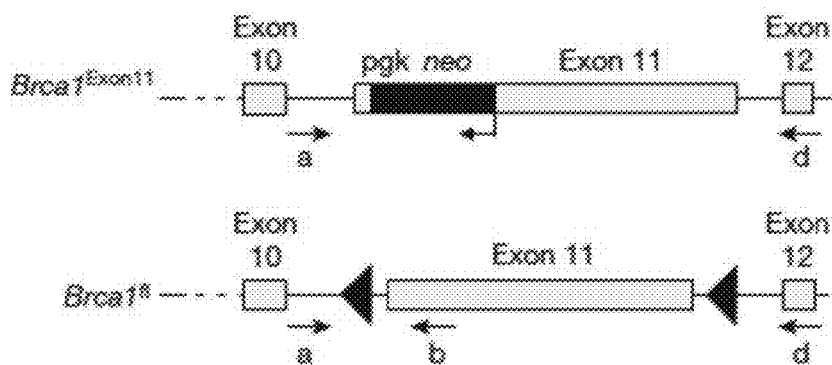
FIGS. 11A-11D show that Brca1 Exon11 regulates Tus/Ter-induced homologous recombination.
Figure 11B:
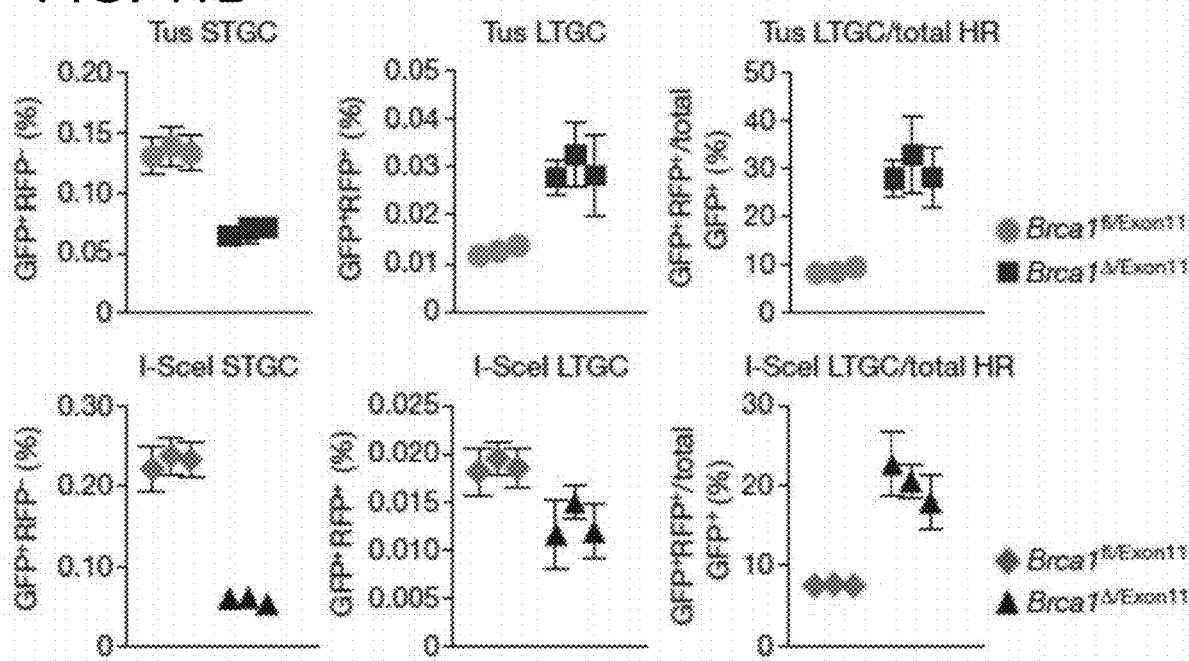
Figure 11C:
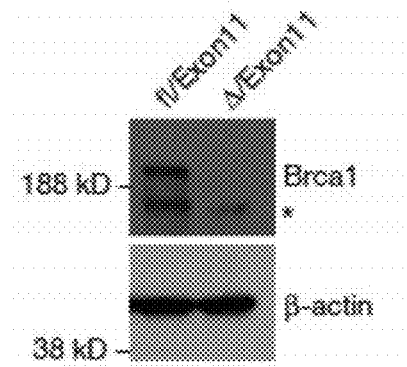
Figure 11D:
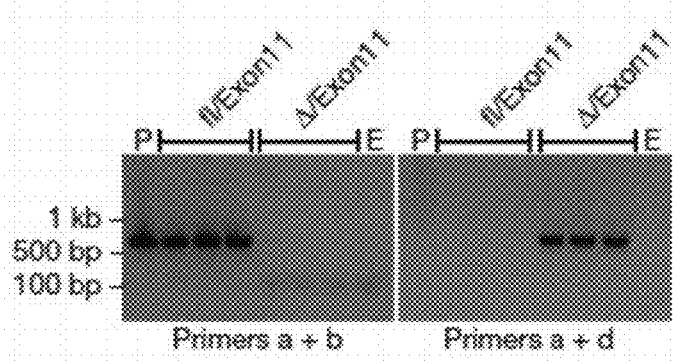
Figure 12A:
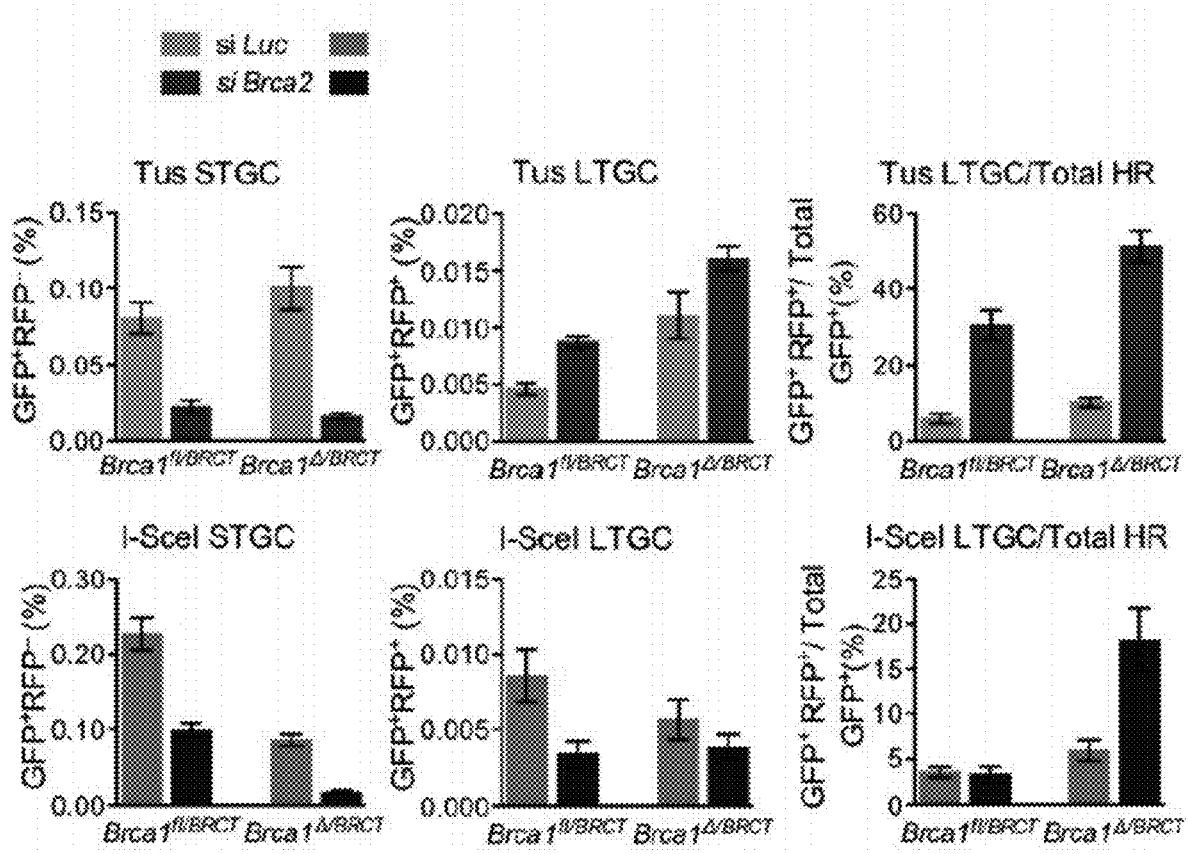
FIGS. 12A and 12B show that Brca2 contributed quantitatively and qualitatively to homologous recombination at stalled replication forks.
Figure 12B:
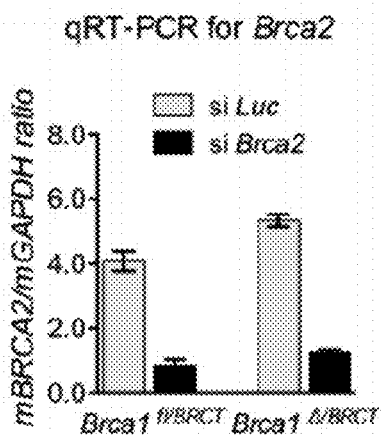
Figure 13A:
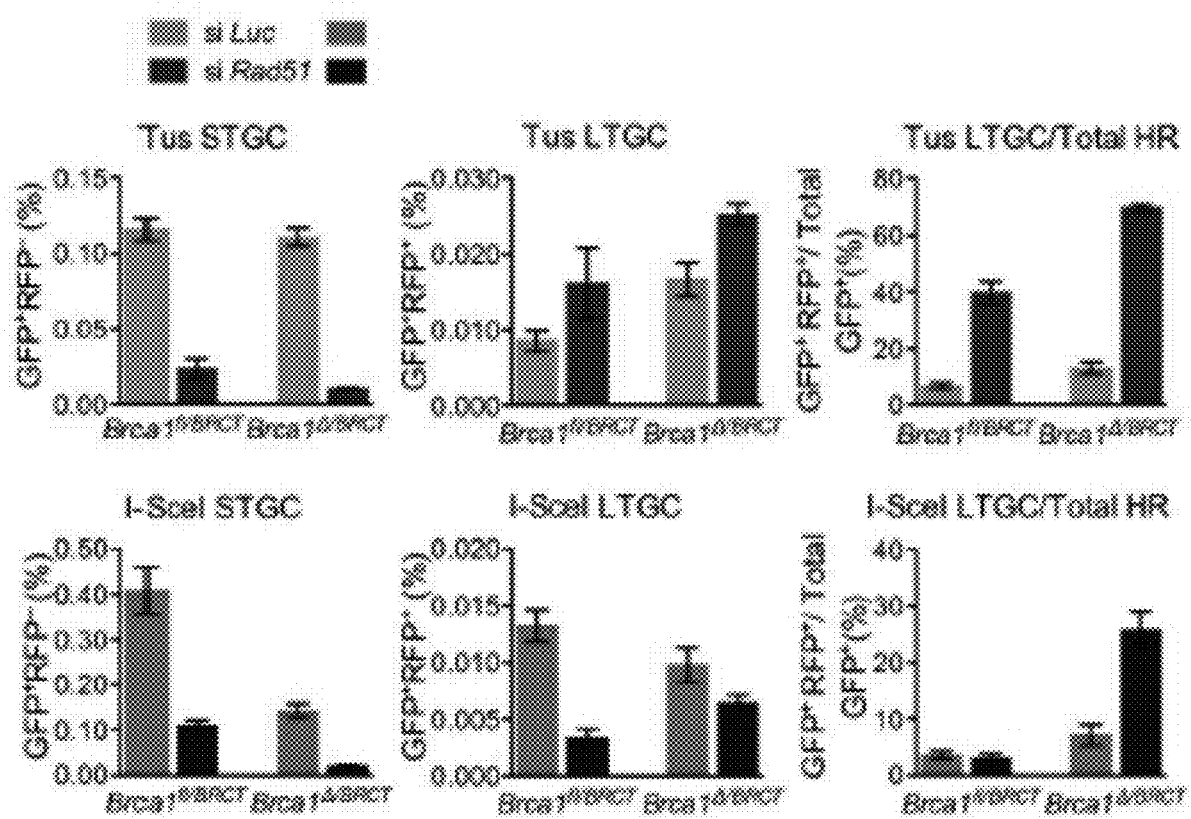
FIGS. 13A and 13B show that Rad51 contributes quantitatively and qualitatively to homologous recombination at stalled replication forks.
Figure 13B:
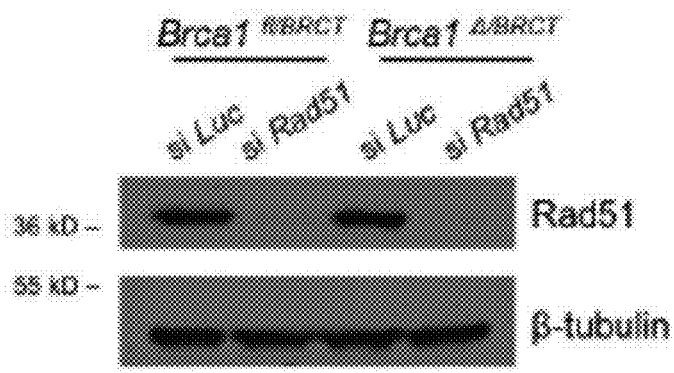
Figure 14A:
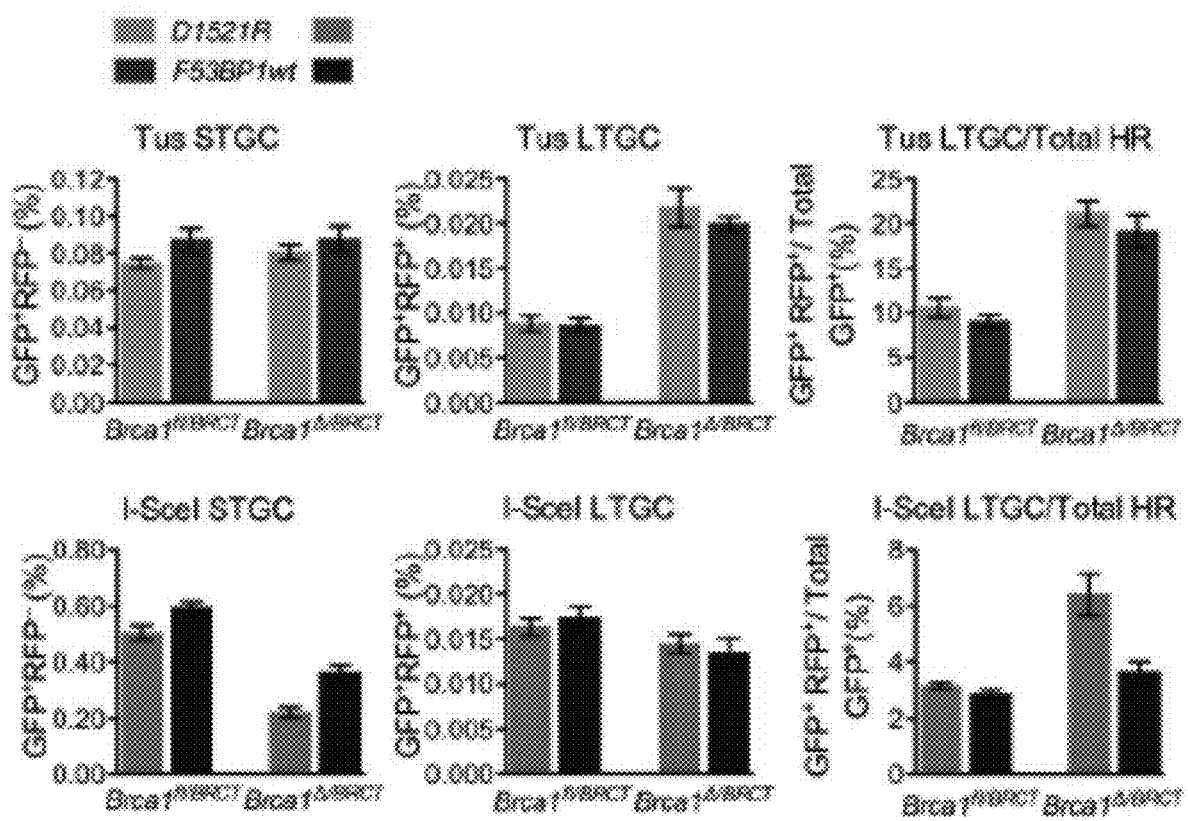
FIGS. 14A and 14B show the effect of 53BP1 inhibition on Tus/Ter-induced homologous recombination.
Figure 14B:

To test whether Brca1 exon 11 regulates Tus/Ter-induced HR, a single copy of the 6×Ter/HR reporter was targeted to the ROSA26 locus of mouse $Brca1^{fl/Exon11}$ ES cells (FIG. 11A-11D). The $Brca1^{Exon11}$ allele lacks exon 11; exon 11 of $Brca1^{fl}$ can be conditionally deleted to generate $Brca1^{\Delta}$ (FIG. 11A). Note that $Brca1^{fl}$ and $Brca1^{\Delta}$ denote distinct Brca1 alleles in the two Brca1 conditional systems described here. Following adeno-Cre treatment, 6×Ter/HR $Brca1^{fl/Exon11}$ and 6×Ter/HR $Brca1^{\Delta/Exon11}$ clones were retrieved. Each of three independent 6×Ter/HR $Brca1^{\Delta/Exon11}$ clones revealed reduced Tus/Ter-induced STGC but increased absolute frequencies of LTGC in comparison with three independent 6×Ter/HR $Brca1^{fl/Exon11}$ clones (FIG. 11B). Deletion of Brca1 exon 11 increased the probability of engaging Tus/Ter-induced LTGC approximately 4-fold to approximately 30% (FIGS. 11B-11D). In contrast, the absolute frequency of I-SceI-induced LTGC was reduced in $Brca1^{\Delta/Exon11}$ cells and approximately 20% of HR products were LTGCs (FIG. 11B). Thus, Brca1 exon 11 contributes to Tus/Ter-induced HR both quantitatively and qualitatively. To determine whether BRCA2/Rad51 regulates Tus/Ter-induced HR, siRNA to deplete Brca2 or Rad51 during HR induction was used. Depletion of Brca2 suppressed Tus/Ter-induced STGC but elevated LTGC frequencies in both $Brca1^{fl/BRCT}$ and $Brca1^{\Delta/BRCT}$ cells (FIGS. 12A and 12B). In $Brca1^{fl/BRCT}$ and $Brca1^{\Delta/BRCT}$ cells depleted of Brca2, approximately 30% and approximately 50% respectively of all Tus/Ter-induced HR products were LTGCs, whereas the equivalent probabilities for Rad51-depleted cells were approximately 40% and approximately 70% (FIGS. 13A and 13B). Thus, suppression of LTGC at stalled forks is a shared function of BRCA1, BRCA2 and Rad51. Inhibition of 53BP1 partially reversed defective I-SceI-induced HR in $Brca1^{\Delta/BRCT}$ cells, as expected, but did not affect Tus/Ter-induced HR in either $Brca1^{fl/BRCT}$ or $Brca1^{\Delta/BRCT}$ cells (FIGS. 14A and 14B). This suggests that BRCA1's functions in Tus/Ter-induced and SceI-induced HR are, in part, distinct. LTGC at stalled forks may include pathological responses analogous to break-induced replication in yeast. The present results identified loss of BRCA1/BRCA2/Rad51-dependent suppression of LTGC at stalled replication forks as contributing to breast/ovarian cancer predisposition.

Example 2: Assay for Analysis of Large Numbers of BRCA1 Variants

BRCA1 mediates error-free STGC and suppresses LTGC. The invention provides a reporter for quantifying short tract gene conversion (STGC) vs. long tract gene conversion (LTGC) in response to a DSB induced by the rare-cutting meganuclease, I-SceI. A new "RFP-SCR" reporter was developed in which STGC (an error-free HR pathway) was scored by conversion of mutant enhanced green fluorescent protein (GFP) allele to wild type and LTGC (an error-prone pathway) by production of red fluorescent protein (RFP) (see e.g., the vector in FIG. 18, which contains the target I-SceI site and into which a Ter array can be inserted, designed to be targeted to the ROSA26 locus of the mouse genome). STGC (GFP⁺RFP⁻) and LTGC (GFP⁺RFP⁺) were scored rapidly and simultaneously by flow cytometry (FACS) (FIG. 15). The ratio of I-SceI induced GFP⁺RFP⁺: Total GFP⁺ estimated the probability that an HR event will resolve as LTGC. A single copy of the RFP-SCR reporter was targeted to the ROSA26 locus of mouse embryonic stem (ES) cells that contain one hypomorphic mutant allele of Brca1 ("$Brca1^{BRCT}$" encoding a gene product lacking functional BRCT repeats) and one "floxed" conditional Brca1 allele ("$Brca1^{fl}$", deletable by Cre-mediated recombination to "$Brca1^{\Delta}$").

$Brca1^{\Delta/BRCT}$ ES cells have growth characteristics similar to $Brca1^{fl/BRCT}$ ES cells. Deletion of wt Brca1 reduced overall HR as expected. However, $Brca1^{\Delta/BRCT}$ cells also revealed a bias towards LTGC—revealed as an increased ratio of LTGC: total HR. siRNA-mediated depletion of BRCA1 in human osteosarcoma U2OS cells also skewed HR towards LTGC. Identical observations were made in mouse ES RFP-SCR cells lacking Brca1 exon 11. Thus, "LTGC suppression" is a general function of BRCA1. Potential relationship of "LTGC suppression" to BRCA1 tumor suppression: Expression of wild type (wt) human (h)BRCA1 in $Brca1^{\Delta/BRCT}$ cells restored overall HR and suppressed the LTGC bias. In contrast, four pathogenic BRCA1 missense alleles that disable either the BRCT or RING domains failed to restore overall HR or to suppress the LTGC bias. This survey of a small number of BRCA1 variants suggested that BRCA1 might perform a tumor suppressor function in "LTGC suppression".

Figure 16:
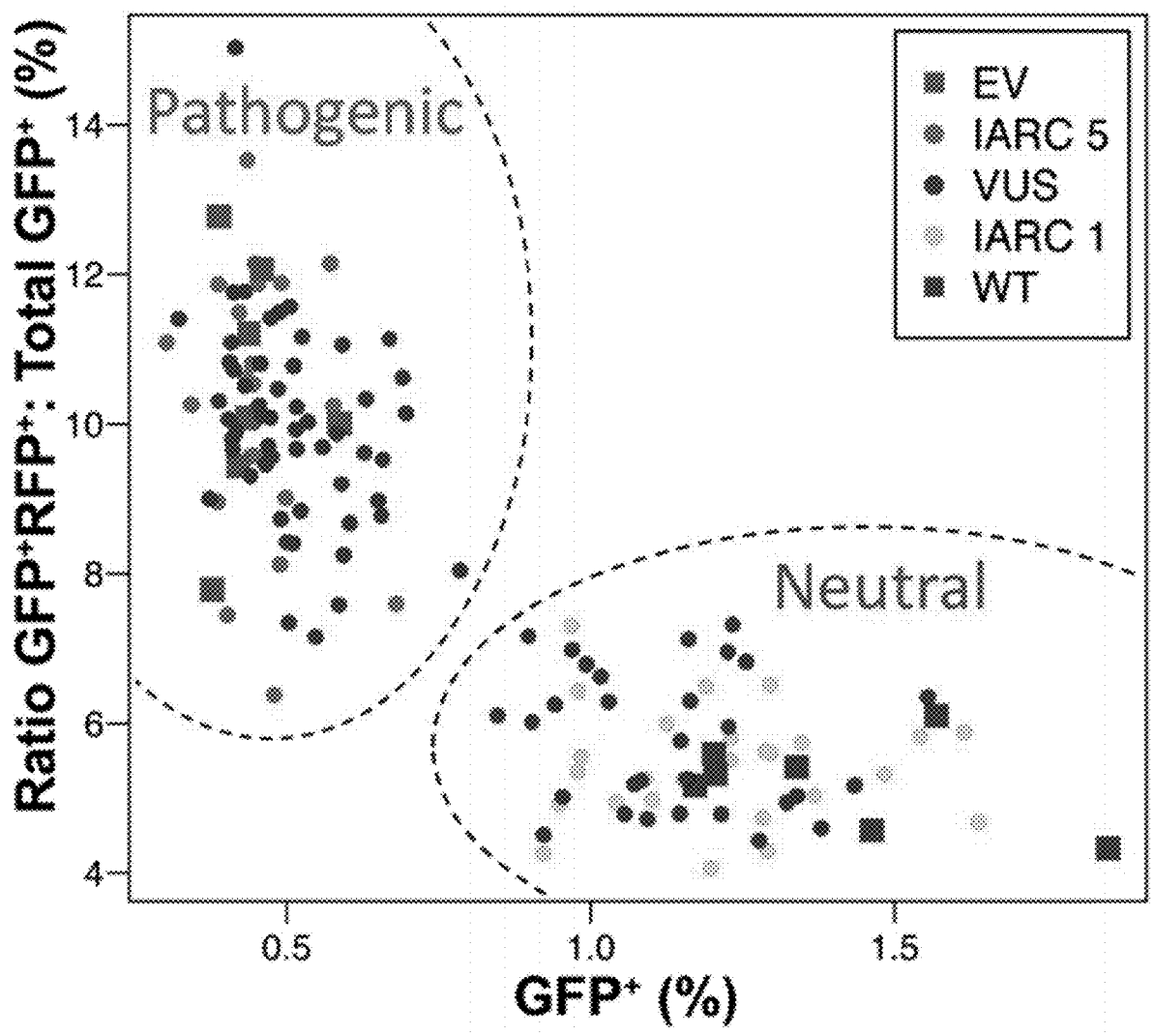
FIG. 16 is a graph showing raw data on 28 BRCA1 variants in HR. Each data point represents the mean value for one variant in one of 7 experiments. No batch correction. EV: empty vector. WT: wt BRCA1. Note apparent segregation into two populations. Neutral (IARC 1) and Pathogenic (IARC 5) variants are mutually exclusive.

A rapid assay of full-length BRCA1 tumor suppressor function in HR and LTGC suppression. The RFP-SCR reporter to the ROSA26 locus of $Brca1^{fl/Exon11}$ ES cells was targeted and Cre-deleted $Brca1^{\Delta/Exon11}$ cells were generated (i.e., deleted for exon 11. Note: "fl" and "Δ" denote distinct Brca1 alleles in the two genetic systems described). As noted above, Brca1 exon 11 deletion reduced overall HR (I-SceI-induced GFP⁺) but elevated the probability of LTGC (ratio of GFP⁺RFP⁺:Total GFP⁺). A rapid assay of full-length BRCA1 function in HR and LTGC suppression was developed. This entailed receipt of plasmids from Dr. Jonkers for expression of BRCA1. $Brca1^{\Delta/Exon11}$ ES RFP-SCR cells with BRCA1 variants (Bowman et al., Cancer Discovery 3(10):1142-1155, 2013) and I-SceI nuclease were transiently co-transfected. In seven experiments, overall HR (GFP⁺) and probability of LTGC (ratio of GFP⁺RFP⁺:Total GFP⁺) of 28 hBRCA1 variants was assayed. The variants included 5 known neutral variants (i.e., IARC class 1; missense amino acid substitution given)—Y105C, T826K, Y856H, R866C and G1706A; 5 known pathogenic variants (i.e., IARC class 5)—C61G, R1699W, A1708E and the common pathogenic frame-shift alleles 185delAG and 5382insC. 18 BRCA1 VUS alleles (each missense mutations) were studied: S4F, R841Q, M1400V, L1407P, M1411T, R1699Q, T1691I, E1735K, H1746Q, R1753T, V1736A, 51651P, 51651F, G1706E, S1655F, L1746P and G1770V, as well as BRCA1 exon 11 del (strictly a VUS allele). Consistent with results reported herein above, each variant appeared to segregate into one of two classes, suggesting a two component model (FIG. 16):

| Neutral (N) | IARC 1 | high GFP⁺; low ratio |
| Pathogenic (P) | IARC 5 | low GFP⁺, high ratio |

Figure 17:
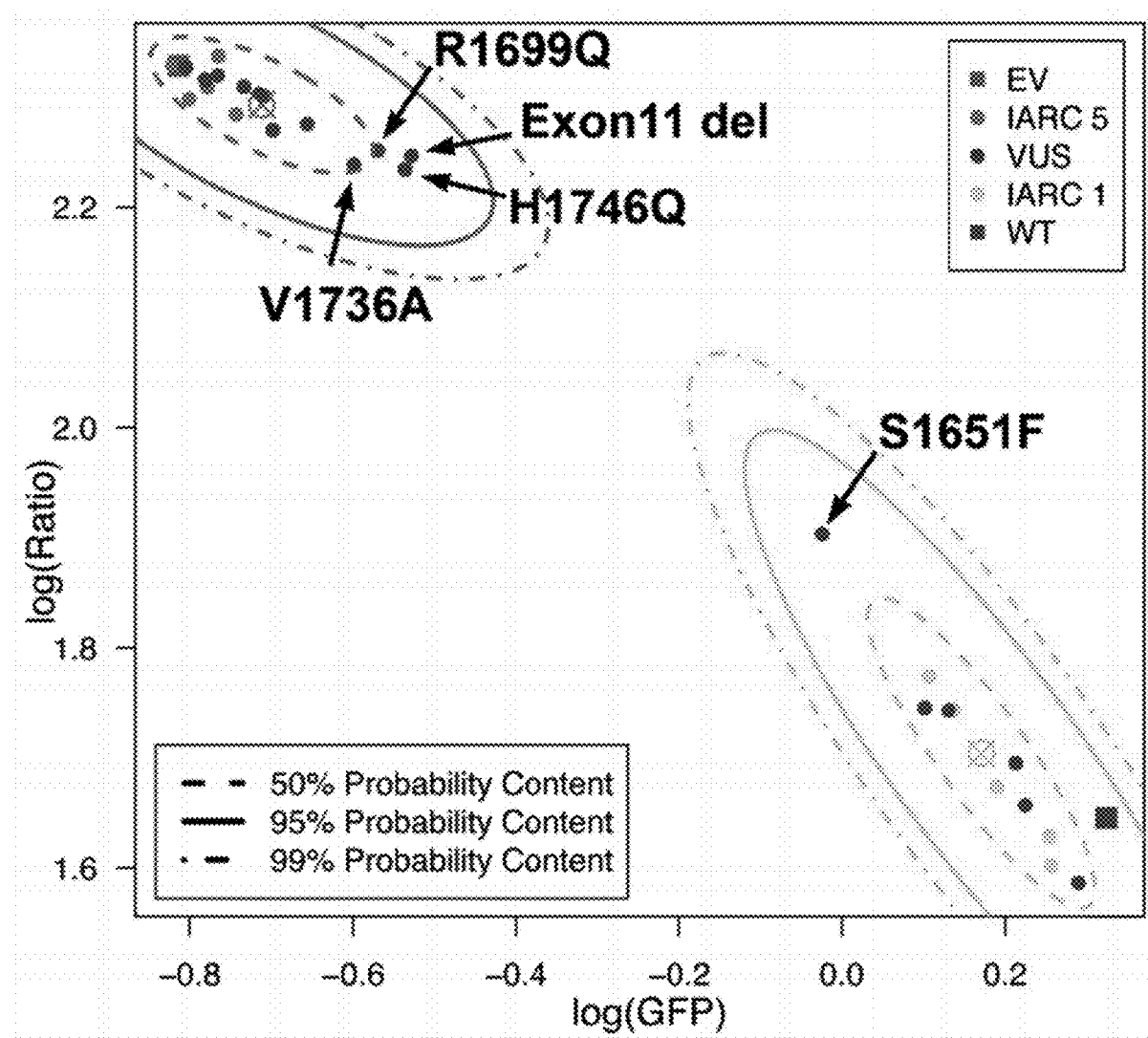
FIG. 17 is a graph providing analysis results of 28 BRCA1 variants. Results of Bayesian bivariate analysis of seven experiments, with 50%, 95% and 99% confidence intervals shown. Neutral (N): green ellipses. Pathogenic (P): red ellipses. 5/5 IARC 1 variants and 6/18 VUS alleles segregate with wtBRCA1 (WT) as N. 5/5 IARC 5 variants and 12/18 VUS alleles segregate with empty vector (EV) as P. Potential "outlier" VUS alleles are indicated.

Importantly, the raw data (FIG. 16) segregated known IARC 1 (N) or IARC 5 (P) alleles in 100% concordance with their IARC classification. These conclusions concur with other functional analyses of some of these VUS alleles. FIG. 17 shows 100% concordance with known IARC classifications. Thus, the present data fully validates this novel, rapid assay of full-length BRCA1 in HR and LTGC suppression. Test results from this assay provides a means to distinguish neutral and pathogenic or potentially pathogenic DNA repair polypeptide variant alleles, thus informing patient monitoring and treatment selection.

A number of hereditary breast/ovarian cancer predisposition genes are known to play important roles in homologous recombination. For example, if a woman inherits one defective copy of either BRCA1 or BRCA2, she will have a greatly elevated risk of breast or ovarian cancer across her lifetime. Full sequencing of the BRCA1 or BRCA2 genes is now used routinely to screen individuals for cancer-predisposing variants of the genes. In many cases, BRCA gene sequencing reveals two wild type copies of the relevant gene, indicating no increase in cancer risk attributable to the BRCA gene in question. However, if sequencing reveals that a woman carries a defective ("pathogenic") variant of the BRCA gene, this indicates that her risk of breast/ovarian cancer is elevated ~10-fold. In this circumstance, a physician might recommend that the woman consider bilateral mastectomy and/or oophorectomy, so as to definitively reduce her risk of breast/ovarian cancer. A third possibility is that gene sequencing reveals a variation in the BRCA gene that alters the encoded protein (for example, a single amino acid substitution), but this specific alteration is too infrequent in the human population for there to be statistical clarity about its associated disease risk. These "variants of uncertain significance" (VUS) are individually rare in the human population, but the number of such alleles is large. Estimates of the frequency of BRCA VUS alleles in the human population vary, but in some estimates ~1% of the population might carry a VUS allele. Currently, if a woman carries a BRCA VUS allele in her germ line, the physician cannot accurately advise the women about whether mastectomy and/or oophorectomy might help her to live a longer, healthier life. Thus, VUS alleles pose a significant burden on the human population.

In an effort to provide information about disease risk associated with specific VUS alleles, the invention provides a rapid test for the homologous recombination functions of individual BRCA1 alleles that is able to differentiate between functionally wild type alleles ("neutral" variants) and "pathogenic" (cancer predisposing) variants. This assay therefore provides a way to predict disease risk attributable to specific BRCA1 missense mutations. This assay could be modified so as to assess disease risk of VUS alleles of other homologous recombination genes implicated in hereditary cancer predisposition. Accordingly, the invention provides for the analysis of large numbers of BRCA1 variants.

Example 3: Tus/Ter-Mediated Replication Fork Stalling was Used to Stimulate Gene Targeting at the Site of Replication Arrest One major obstacle to the use of gene editing in human disease is the existence of "off-target" loci that are cleaved by the endonuclease (FIG. 21A). Systematic studies have shown that no currently existing nuclease-mediated gene editing method has yet avoided the problem of off-target indel formation. This represents a formidable barrier to clinical application of therapeutic gene editing.

The present invention addresses this problem by the use of a fundamentally different mechanism for achieving site-specific gene targeting—a site-specific replication block. The invention is based at least in part from discoveries relating to the development of novel tools for provoking site-specific replication fork arrest on a mammalian chromosome which involved adapting a natural replication terminator complex from *Escherichia coli* called Tus/Ter for use in mammalian cells. In mammalian cells, Tus/Ter is able to block mammalian replication forks' progression and to induce chromosomal homologous recombination (HR). Mechanistic analysis shows that the competence of the Tus/Ter complex to arrest a mammalian replisome is a simple function of affinity/avidity interactions between Tus and Ter. This raises the possibility that other DNA-protein complexes, if present in high enough affinity and in arrays containing multiple copies of the DNA-protein complex, might also mediate site-specific replisome arrest and HR within the chromosome.

Figure 22A:
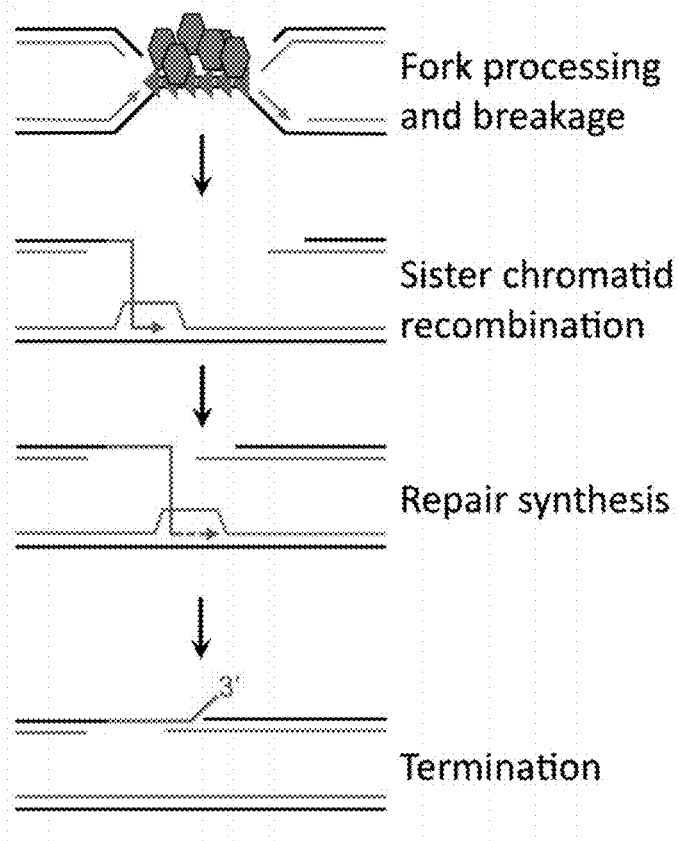
FIGS. 22A and 22B depict models of homologous recombination (HR) induced at a Tus/Ter replication fork block. Red triangles: Ter array. Blue hexagons: Tus protein monomers.
Figure 22B:
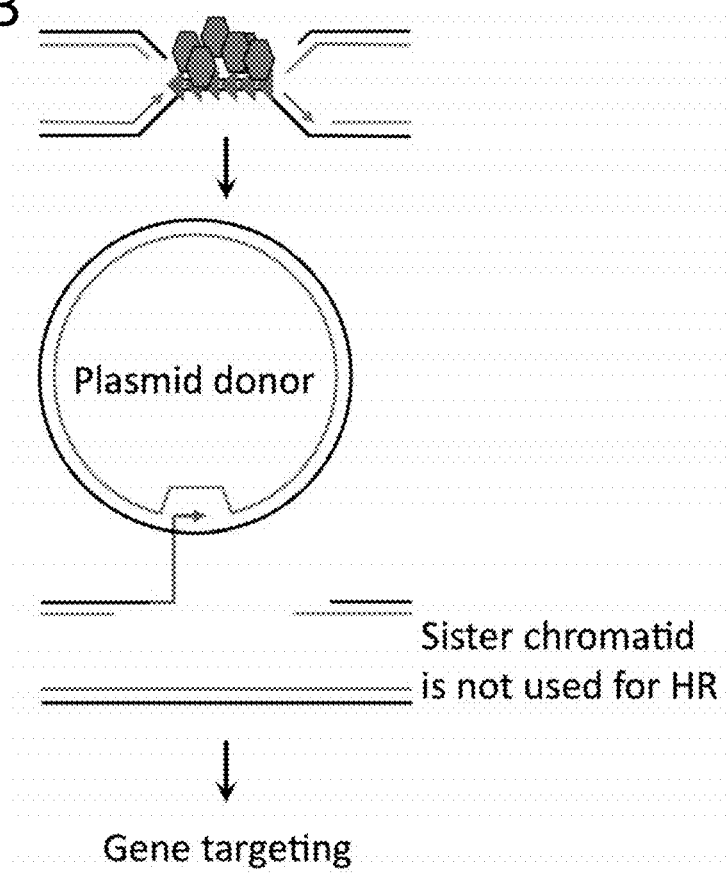
Figure 23A:
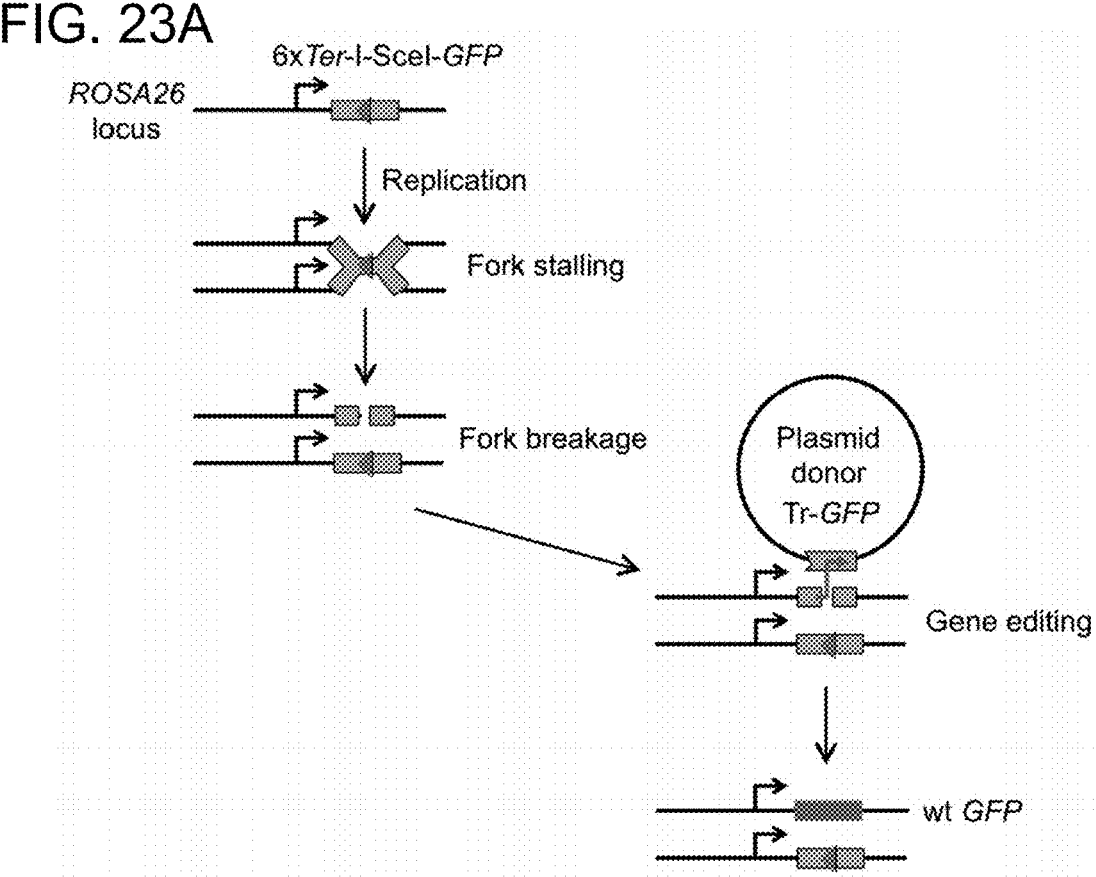
FIGS. 23A-23C depict gene editing involving a Tus/Ter-mediated replication block.
Figure 23B:
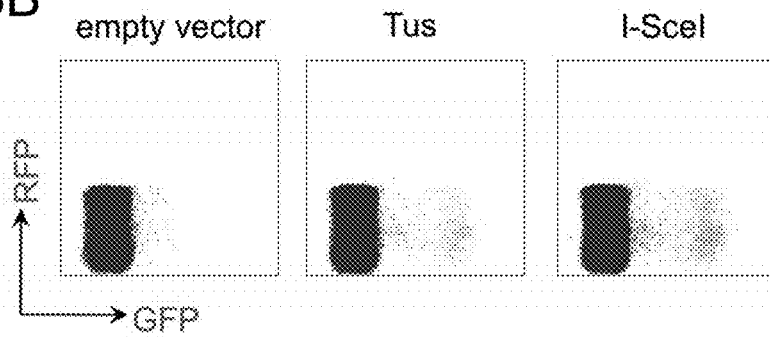
Figure 23C:
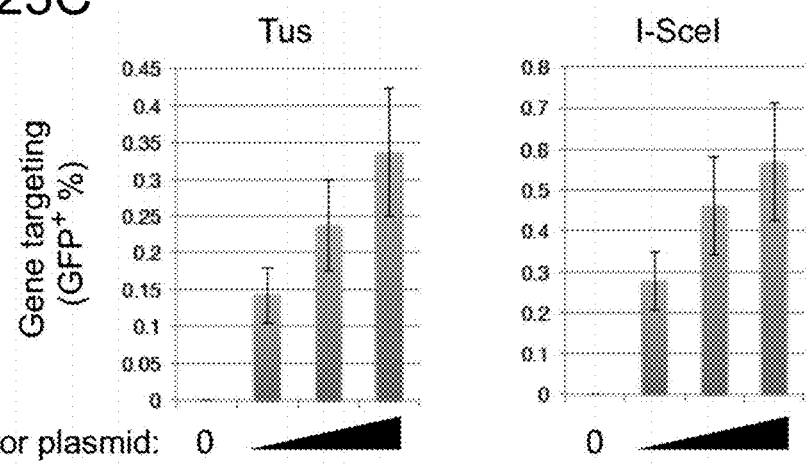

Without being bound to theory, Tus/Ter stimulates HR at the site of replication fork stalling and double strand break (DSBs) are formed at the site of Tus/Ter-induced replication arrest—for example as a result of endogenous nucleases acting at the stalled fork (FIG. 22A). Consistent with this model, homologous recombination might not be limited to the neighboring sister chromatid, but might also engage an exogenous DNA sequence for gene targeting (FIG. 22B). This was tested by targeting a simplified reporter to the ROSA26 locus of mouse ES cells (FIGS. 23A-23C). Briefly, this reporter contains only one copy of the cDNA encoding the enhanced green fluorescent protein ("GFP"), disrupted by an array of 6×Ter sites and a cleavage site for the rare-cutting homing endonuclease I-SceI. I-SceI provides a positive control for nuclease-induced HR. There is no opportunity to generate wt GFP by recombination with chromosomal elements. Donor sequences needed for GFP gene correction were supplied on a co-transfected plasmid, which contained a nonfunctional, 5' truncated copy of GFP ("Tr-GFP", FIG. 23A). This truncation guarantees that the donor plasmid alone also cannot generate wt GFP. If the Tus/Ter-stalled fork were to recombine with the donor plasmid, this would correct the endogenous copy of GFP to wild type and convert the cell to GFP$^+$. Indeed, it was found that Tus induces gene targeting/gene correction to wt GFP almost as efficiently as the I-SceI control (FIGS. 23B and 23C). This establishes that a replication fork blocking complex (e.g., Tus/Ter) that has no innate nuclease function, can guide site-specific gene editing in mammalian cells.

These results indicate that site-specific replication arrest can be used to stimulate gene targeting/gene editing in mammalian cells. This system may offer advantages over current methods of gene editing, by reducing unwanted and potentially hazardous off-target mutations.

The results set forth in Example 1 were obtained using the following methods and materials.

Molecular Biology, siRNAs and Antibodies.

The vector for mammalian expression of myc epitope-tagged, nuclear localized, codon-optimized wild-type Tus (pCMVbeta myc-NLS-Tus), vectors p6×TerOri and p6×REVTerOri and the Ter HR reporters were constructed by conventional cloning methods using a previously described RFP-SCR reporter (Chandramouly et al., Nature Communications. 4, 2404, 2013). Ter-containing plasmids were cultivated in JJC33 (Tus2) strains of *E. coli*. siRNA SMART pools were purchased from Dharmacon. Cells were lysed in RIPA buffer (50 mM Tris-HCl, pH 8.0, 250 mM NaCl, 0.1% sodium dodecyl sulphate, 1% NP-40 containing protease and phosphatase inhibitors PMSF and Roche complete protease inhibitor tablet). Extracted protein was resolved by 4-12% bis-Tris SDS-PAGE (Invitrogen) and analysed by immunoblotting using the following antibodies; Brca1 (a gift of the Baer laboratory, 1:100), beta-tubulin (Abcam ab6046, 1:4,000), beta-actin (Abcam ab8226, 1:10, 000), Myc (Abcam ab9106, 1:10,000), hRad51 (aliquot B32, 1:500), and HA (Santa Cruz sc-805, 1:200).

Cell Lines and Cell Culture.

Mouse embryonic stem (ES) cells were grown in ES medium on either MEF feeders or gelatinized plates as described previously (Chandramouly et al., Nature Communications. 4, 2404, 2013, Xie. et al., Molecular Cell 28, 1045-1057, 2007, Xie et al., Molecular. Cell 16, 1017-1025, 2004).). A total of 10 mg of the 6×Ter HR reporter ROSA26 targeting plasmid was linearized by KpnI digest and introduced by electroporation to $1\times10^7$ to $2\times10^7$ cells and subsequently seeded on 6-cm plates with puromycin-resistant feeders. Plates were supplemented with puromycin (4 µg $ml^{-1}$) 24 hr later and colonies were picked 5-10 days later. ROSA26 targeted lines were screened for by PCR and verified by Southern blotting (Chandramouly et al., Nature Communications. 4, 2404, 2013). Multiple Brca1-deficient ES clones were generated by transient adenovirus-mediated Cre expression. ROSA26 genotyping primers: ROSA26-sense: CA TCAAGGAAACCCTGGACTACTG (SEQ ID NO: 25); TerB36 HR reporter antisense: CCTCGG CTAG-GTAGGGATC (SEQ ID NO: 26). The Brca1 exon11 status was determined by PCR. Brca1 5' sense: CTGGG-TAGTTTGTAAGCATCC (SEQ ID NO: 27); Brca1 exon11 antisense: CAATAA ACTGCTGGTCTCAGGC (SEQ ID NO: 28); Brca1 exon11 sense: GGAAATGGCAACTT-GCCT AG (SEQ ID NO: 29); Brca1 3' antisense: CTGC-GAGCAGTCTTCAGAAAG (SEQ ID NO: 30).

Recombination Assays.

A total of $1.6\times10^5$ cells were transfected in suspension with 0.5 µg pcDNA3beta-myc NLS-I-SceI (Puget et al., DNA Repair 4, 149-161, 2005), pcDNA3beta-mycNLS-Tus, pcDNA3beta-myc NLS-TusH144A, pcDNA3beta-myc NLS-TusF140A, or control vector using Lipofectamine 2000 (Invitrogen). $GFP^+$ and $GFP^+ RFP^+$ frequencies were scored 3 days after transfection by flow cytometry using a Becton Dickinson 5 Laser LSRII in triplicate and values presented corrected for background events and transfection efficiency. Transfection efficiency was measured by parallel transfection with 0.05 µg of wild-type GFP expression vector and 0.45 µg control vector. Typically $6\times10^5$ total events were scored per sample. Tus or I-SceI expression vector transfection efficiencies were typically between 50% and 75%, and background levels of HR products typically less than 0.005% for $GFP^+ RFP^-$ and less than 0.001% for $GFP^+ RFP^+$ (for example, FIGS. 6A and 6B).

Statistical Methods.

Each figure legend reports the sample size in terms of number of replicates per experiment and number of experiments that were analysed to generate the data shown. For statistical analysis of HR values, the arithmetic mean of triplicate samples was calculated for each independent experiment (that is, experiments performed on different days) and these single data points for each experiment were used to calculate the mean and standard deviation between experiments. The standard error of the mean (s.e.m.) was calculated as standard deviation/$\sqrt{n}$, where n=number of experiments (not number of replicates). For example, if triplicate samples in four different independent experiments were measured, then n=4. Differences between groups were analysed by Student's two-tailed unpaired t-test, assuming unknown variance, using GraphPad Prism v5.0d software. P values are given in the figure legends. Densitometry of two-dimensional gel data was also analysed by calculation of arithmetic mean and s.e.m. and analysis by Student's t-test. Analysis of trend in FIG. 6F was performed by ANOVA using GraphPad Prism v5.0d software, in addition to the t-test as described above.

qRT-PCR Analysis.

RNA from transfected ES cells was extracted by Qiagen RNeasy Mini Kit (Qiagen Sciences) 2 days post-transfection. First-strand cDNA analysis was performed on an ABI 7300 Real time PCR System using Power SYBR Green RNA- to CT 1-Step Kit (Applied Biosystems). TaqMan probe and primer sets to genotype for Brca1 were: Brca1 Exon 22-23 sense: TTCCGTGGTGAAGGAGCTT (SEQ ID NO: 31); Brca1 Exon 22-23 antisense: TGGCTGCAC-GATCACAAC (SEQ ID NO: 32); Brca1 Exon 23-24 sense: GCCTGGACAGAAGACAGCA (SEQ ID NO: 33); Brca1 Exon 23-24 antisense: CAGTCCCACA TCACAAGACG (SEQ ID NO: 34); Brca1 Exon 22-23 TaqMan probe FAM-CGCTCACCCATGA CACAGGTGC-BHQ (SEQ ID NO: 35); Brca1 Exon 23-24 TaqMan probe-FAM-TGCACAGCT GCCCAATATCTGGG-BHQ (SEQ ID NO: 36)). Conventional SYBR green qRT-PCR assays of Gapdh and siRNA-targeted gene was performed. The NIH NCI Nucleotide utility to Primer 3 software (Whitehead Institute, MIT) was used to generate gene-specific primer sequences for mouse Brca1 and Gapdh. The NIH NCI Nucleotide utility was used to generate gene-specific primer sequences for mouse Slx4, Slx1, Eme1 and Xpf (also known as Ercc4). Primers for RTPCR were Brca1-exon 21-22 sense: ATG AGCTGGA-GAGGATGCTG (SEQ ID NO: 37); Brca1 exon 21-22 antisense: CTGGGCAGTTGCTGTCTTCT (SEQ ID NO: 38); Brca1 exon 22-23 sense: GGTGCTCATCTAGTTGT-GATCG (SEQ ID NO: 39); Brca1 exon 22-23 antisense: CTGTACCAGGTAGGCATCCA (SEQ ID NO: 40); Brca1 exon 7-8 sense: AGCCTAGGTGTCCAGCTGTC (SEQ ID NO: 41); Brca1 exon 7-8-antisense: CTGCAATCACC TGGCTTAGTT (SEQ ID NO: 42); Brca2 sense: TCTGC-CACTGTGAAAAATGC (SEQ ID NO: 43); Brca2 antisense: TCAAGCTGGGCTGAAGATT (SEQ ID NO: 44); Slx4 sense: GTGGGACGACTGGAATGAGG (SEQ ID NO: 45); Slx4 antisense: GCACCTTTTGGTGTCTCTGG (SEQ ID NO: 46); Slx1 sense: GGATGGACCAT GCAG-CAAGA (SEQ ID NO: 47); Slx1 antisense: CCAT-TCAAACCGAAGGGCG (SEQ ID NO: 48); Eme1 sense: AG GCCAGAGGAATGCCTGAA (SEQ ID NO: 49); Eme1 antisense: CCAGTCATCTCCATCCTCT ACC (SEQ ID NO: 50); Xpf sense: TGGTCAGAATTCAGGTTGGC (SEQ ID NO: 51); Xpf antisense: TTTCAGGAC GTCA-GTCAGCG (SEQ ID NO: 52). The mRNA was measured in triplicates with a standard curve generated for each gene using cDNA obtained from each sample. The expression level of target genes was normalized to internal Gapdh.

293 Cell Transfection and Episome Two-Dimensional Gel Electrophoresis.

A total of $12\times10^6$ 293E (ATCCCRL-10852) cells were plated per 15-cm dish 1 day before transfection. Cells were transfected with 4.5 µg pOri plasmids and 1 µg of control empty vector or pcDNA3beta-mycNLS-Tus in antibiotic free media using Lipofectamine2000 reagent, and media changed 24 hr after transfection. Then 40 hr after transfection, plates were rinsed with 1×PBS and cells washed off the plate with ice-cold PBS, washed again with ice-cold PBS and HIRT extracted as described below. Purified DNA was restriction digested 8-16 hr and run on a 14×16 cm 0.4% agar 0.1 µg $ml^{-1}$ ethidium bromide 0.53TBE gel 13 hr in the dark at 40 V. First dimension gel slabs were cut out and embedded in the second dimension slab gel (20×25 cm 1% agar, 0.5×TBE, 1 µg ml⁻¹ ethidium bromide) and run at 160 V for 7.5 hr in the cold room at 4° C.

HIRT Episome Extraction from 293 Cells.

The plasmid was extracted as published (Follonier et al., Methods Molecular. Biology 1094, 209-219, 2014). Briefly, PBS-washed 293HEK or 293E cells were lysed in 2.25 ml 0.6% sodium dodecyl sulphate 33 mM Tris-HCl, 6 mM EDTA, 66 µg ml⁻¹ RNase followed by digestion with 0.5 µg proteinase K for 90 min at 37° C. Samples were subject to brief, 20 s, base extraction with 0.75 ml 0.1M NaOH and proteins precipitated by addition of 1 ml 4.2M Gu-HCl, 0.9M potassium acetate pH 4.8. Cell debris was pelleted at 39,000 g and supernatant loaded onto a Qiagen Miniprep spin column (Qiagen Sciences, Maryland). Columns were washed with 0.5 ml Qiagen Buffer PB (5M Gu-HCl, 30% ethanol, adding 10 mM Tris-HCl pH 6.6) and 0.75 ml Qiagen Buffer PE (10 mM Tris-HCl pH 7.5, 80% ethanol) and plasmid DNA eluted using two volumes of 40 µl Qiagen EB buffer.

Southern Blotting.

Southern blotting of genomic DNA was performed using GFP cDNA or ROSA26 5' probes as described previously (Xie. et al., Molecular. Cell 16, 1017-1025, 2004, Puget et al., DNA Repair 4, 149-161, 2005). For all experiments, including mouse ES cells containing a randomly integrated reporter not at ROSA26, clones containing only one intact copy of the reporter were used. Genomic DNA was extracted from confluent ES cells on 6-well plates (approximately 5×10⁶ to 10×10⁶ cells) using a Puregene DNA Isolation Kit (Gentra Systems). Episomal plasmid DNA was extracted by HIRT extraction described above and Southern blotting performed using random labelled probe produced from the KpnI/HindIII restriction fragment of p6×TerOri.

Statistical Methods
i) Bayesian two component model: each BRCA1 variant (including VUS alleles) is assumed to be truly either N or P.
ii) Bivariate model uses log-transformed data of two variables: overall HR (GFP⁺) and ratio of LTGC: Total HR.
iii) Batch corrections are incorporated into the analysis.
iv) Assumed prior probabilities of pathogenicity (i.e., the starting assumptions of the computer model) are:
IARC 1: known to be N p=0.0
IARC 5 known to be P p=1.0
VUS alleles: unknown p=0.5
(arbitrarily chosen)

The VarCall program uses an iterative procedure to calculate the best fit for each VUS allele. It generated these posterior probabilities of pathogenicity:

p<0.002: predicted neutral variants: S4F, R841Q, M1400V, L1407P, M1411T, S1651F.

p>0.998: predicted pathogenic variants: R1699Q, T1691I, E1735K, H1746Q, R1753T, V1736A, 51651P, G1706E, S1655F, L1746P, G1770V, and Exon 11 del.

These conclusions concur with other functional analyses of some of these VUS alleles. FIG. 17 shows 100% concordance with known IARC classifications. Thus, the present data fully validates this novel, rapid assay of full-length BRCA1 in HR and LTGC suppression.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

---

What is claimed is:

1. A method of treating breast cancer in a selected patient the method comprising administering a PARP inhibitor or cisplatin to the patient, wherein the patient is selected by a method comprising:
   (a) sequencing a DNA repair gene in a biological sample derived from the patient, thereby identifying a mutation in the DNA repair gene;
   (b) contacting a mammalian cell that lacks a DNA repair polypeptide with each of: a vector encoding a DNA repair polypeptide comprising the identified mutation and a vector encoding a wild-type Tus polypeptide fused to a nuclear localization signal, wherein the mammalian cell comprises
      (i) a single copy of a polynucleotide comprising a 5' truncated GFP encoding sequence positioned upstream of 5' and 3' RFP exons positioned upstream of one to six Ter sites positioned within a GFP encoding sequence comprising a rare cutting endonuclease site, wherein the polynucleotide is integrated into the cell genome; and
      (ii) an expression vector encoding a wild-type Tus polypeptide: and
   (c) detecting long-tract gene conversion in the cell, wherein an increase in long tract gene conversion in the cell relative to a reference cell expressing a wild-type DNA repair polypeptide indicates that the mutation in the DNA repair polypeptide is functionally significant; and
   (d) selecting the patient having a functionally significant mutation in the DNA repair polypeptide.

2. The method of claim 1, wherein the DNA repair polypeptide is one or more of BRCA1, BRCA2, and Rad5.1.

3. A method of treating breast cancer in a selected patient, the method comprising administering a PARP inhibitor or cisplatin to the patient, wherein the patient is selected by a method comprising:
   (a) sequencing a DNA repair gene in a biological sample derived from the patient, thereby identifying a mutation in the DNA repair gene;
   (b) contacting a mammalian cell that lacks a DNA repair polypeptide with each of: a vector encoding a DNA repair polypeptide comprising the identified mutation and a vector encoding a wild-type Tus polypeptide fused to a nuclear localization signal, wherein the mammalian cell comprises
      (i) a single copy of a polynucleotide comprising a 5' sequence encoding a truncated first reporter polypeptide positioned upstream of 5' and 3' exons encoding a second reporter polypeptide positioned upstream of one to six Ter sites positioned within polynucleotide is integrated into the cell genome; and
      (ii) an expression vector encoding a wild-type Tus polypeptide; and (c) detecting long-tract gene conversion in the cell, wherein an increase in long tract gene conversion in the cell relative to a reference cell expressing a wild-type DNA repair polypeptide indicates that the mutation in the DNA repair polypeptide is functionally significant; and
   (d) selecting the patient having a functionally significant mutation in the DNA repair polypeptide.

* * * * *

SEQUENCE LISTING

```
<160> NUMBER OF SEQ ID NOS: 55

<210> SEQ ID NO 1
<211> LENGTH: 1863
<212> TYPE: PRT
<213> ORGANISM: Homo sapiens

<400> SEQUENCE: 1

Met Asp Leu Ser Ala Leu Arg Val Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
```

-continued

```
                100                 105                 110
Asn Ser Pro Glu His Leu Lys Asp Glu Val Ser Ile Ile Gln Ser Met
        115                 120                 125
Gly Tyr Arg Asn Arg Ala Lys Arg Leu Leu Gln Ser Glu Pro Glu Asn
    130                 135                 140
Pro Ser Leu Gln Glu Thr Ser Leu Ser Val Gln Leu Ser Asn Leu Gly
145                 150                 155                 160
Thr Val Arg Thr Leu Arg Thr Lys Gln Arg Ile Gln Pro Gln Lys Thr
                165                 170                 175
Ser Val Tyr Ile Glu Leu Gly Ser Asp Ser Ser Glu Asp Thr Val Asn
            180                 185                 190
Lys Ala Thr Tyr Cys Ser Val Gly Asp Gln Glu Leu Leu Gln Ile Thr
        195                 200                 205
Pro Gln Gly Thr Arg Asp Glu Ile Ser Leu Asp Ser Ala Lys Lys Ala
    210                 215                 220
Ala Cys Glu Phe Ser Glu Thr Asp Val Thr Asn Thr Glu His His Gln
225                 230                 235                 240
Pro Ser Asn Asn Asp Leu Asn Thr Thr Glu Lys Arg Ala Ala Glu Arg
                245                 250                 255
His Pro Glu Lys Tyr Gln Gly Ser Ser Val Ser Asn Leu His Val Glu
            260                 265                 270
Pro Cys Gly Thr Asn Thr His Ala Ser Ser Leu Gln His Glu Asn Ser
        275                 280                 285
Ser Leu Leu Leu Thr Lys Asp Arg Met Asn Val Glu Lys Ala Glu Phe
    290                 295                 300
Cys Asn Lys Ser Lys Gln Pro Gly Leu Ala Arg Ser Gln His Asn Arg
305                 310                 315                 320
Trp Ala Gly Ser Lys Glu Thr Cys Asn Asp Arg Arg Thr Pro Ser Thr
                325                 330                 335
Glu Lys Lys Val Asp Leu Asn Ala Asp Pro Leu Cys Glu Arg Lys Glu
            340                 345                 350
Trp Asn Lys Gln Lys Leu Pro Cys Ser Glu Asn Pro Arg Asp Thr Glu
        355                 360                 365
Asp Val Pro Trp Ile Thr Leu Asn Ser Ser Ile Gln Lys Val Asn Glu
    370                 375                 380
Trp Phe Ser Arg Ser Asp Glu Leu Leu Gly Ser Asp Asp Ser His Asp
385                 390                 395                 400
Gly Glu Ser Glu Ser Asn Ala Lys Val Ala Asp Val Leu Asp Val Leu
                405                 410                 415
Asn Glu Val Asp Glu Tyr Ser Gly Ser Ser Glu Lys Ile Asp Leu Leu
            420                 425                 430
Ala Ser Asp Pro His Glu Ala Leu Ile Cys Lys Ser Glu Arg Val His
        435                 440                 445
Ser Lys Ser Val Glu Ser Asn Ile Glu Asp Lys Ile Phe Gly Lys Thr
    450                 455                 460
Tyr Arg Lys Lys Ala Ser Leu Pro Asn Leu Ser His Val Thr Glu Asn
465                 470                 475                 480
Leu Ile Ile Gly Ala Phe Val Thr Glu Pro Gln Ile Ile Gln Glu Arg
                485                 490                 495
Pro Leu Thr Asn Lys Leu Lys Arg Lys Arg Arg Pro Thr Ser Gly Leu
            500                 505                 510
His Pro Glu Asp Phe Ile Lys Lys Ala Asp Leu Ala Val Gln Lys Thr
        515                 520                 525
```

Pro Glu Met Ile Asn Gln Gly Thr Asn Gln Thr Gln Asn Gly Gln
    530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
    610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
        675                 680                 685

Ser Lys Arg His Asp Ser Asp Thr Phe Pro Glu Leu Lys Leu Thr Asn
    690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
    770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
    930                 935                 940

-continued

```
Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val
    1010                1015                1020

Ser Thr Ile Ser Arg Asn Asn Ile Arg Glu Asn Val Phe Lys Glu
    1025                1030                1035

Ala Ser Ser Ser Asn Ile Asn Glu Val Gly Ser Ser Thr Asn Glu
    1040                1045                1050

Val Gly Ser Ser Ile Asn Glu Ile Gly Ser Ser Asp Glu Asn Ile
    1055                1060                1065

Gln Ala Glu Leu Gly Arg Asn Arg Gly Pro Lys Leu Asn Ala Met
    1070                1075                1080

Leu Arg Leu Gly Val Leu Gln Pro Glu Val Tyr Lys Gln Ser Leu
    1085                1090                1095

Pro Gly Ser Asn Cys Lys His Pro Glu Ile Lys Lys Gln Glu Tyr
    1100                1105                1110

Glu Glu Val Val Gln Thr Val Asn Thr Asp Phe Ser Pro Tyr Leu
    1115                1120                1125

Ile Ser Asp Asn Leu Glu Gln Pro Met Gly Ser Ser His Ala Ser
    1130                1135                1140

Gln Val Cys Ser Glu Thr Pro Asp Asp Leu Leu Asp Asp Gly Glu
    1145                1150                1155

Ile Lys Glu Asp Thr Ser Phe Ala Glu Asn Asp Ile Lys Glu Ser
    1160                1165                1170

Ser Ala Val Phe Ser Lys Ser Val Gln Lys Gly Glu Leu Ser Arg
    1175                1180                1185

Ser Pro Ser Pro Phe Thr His Thr His Leu Ala Gln Gly Tyr Arg
    1190                1195                1200

Arg Gly Ala Lys Lys Leu Glu Ser Ser Glu Glu Asn Leu Ser Ser
    1205                1210                1215

Glu Asp Glu Glu Leu Pro Cys Phe Gln His Leu Leu Phe Gly Lys
    1220                1225                1230

Val Asn Asn Ile Pro Ser Gln Ser Thr Arg His Ser Thr Val Ala
    1235                1240                1245

Thr Glu Cys Leu Ser Lys Asn Thr Glu Glu Asn Leu Leu Ser Leu
    1250                1255                1260

Lys Asn Ser Leu Asn Asp Cys Ser Asn Gln Val Ile Leu Ala Lys
    1265                1270                1275

Ala Ser Gln Glu His His Leu Ser Glu Glu Thr Lys Cys Ser Ala
    1280                1285                1290

Ser Leu Phe Ser Ser Gln Cys Ser Glu Leu Glu Asp Leu Thr Ala
    1295                1300                1305

Asn Thr Asn Thr Gln Asp Pro Phe Leu Ile Gly Ser Ser Lys Gln
    1310                1315                1320

Met Arg His Gln Ser Glu Ser Gln Gly Val Gly Leu Ser Asp Lys
    1325                1330                1335

Glu Leu Val Ser Asp Asp Glu Glu Arg Gly Thr Gly Leu Glu Glu
```

-continued

```
            1340                1345                1350
Asn Asn Gln Glu Glu Gln Ser Met Asp Ser Asn Leu Gly Glu Ala
        1355                1360                1365
Ala Ser Gly Cys Glu Ser Glu Thr Ser Val Ser Glu Asp Cys Ser
        1370                1375                1380
Gly Leu Ser Ser Gln Ser Asp Ile Leu Thr Thr Gln Gln Arg Asp
        1385                1390                1395
Thr Met Gln His Asn Leu Ile Lys Leu Gln Gln Glu Met Ala Glu
        1400                1405                1410
Leu Glu Ala Val Leu Glu Gln His Gly Ser Gln Pro Ser Asn Ser
        1415                1420                1425
Tyr Pro Ser Ile Ile Ser Asp Ser Ser Ala Leu Glu Asp Leu Arg
        1430                1435                1440
Asn Pro Glu Gln Ser Thr Ser Glu Lys Ala Val Leu Thr Ser Gln
        1445                1450                1455
Lys Ser Ser Glu Tyr Pro Ile Ser Gln Asn Pro Glu Gly Leu Ser
        1460                1465                1470
Ala Asp Lys Phe Glu Val Ser Ala Asp Ser Ser Thr Ser Lys Asn
        1475                1480                1485
Lys Glu Pro Gly Val Glu Arg Ser Ser Pro Ser Lys Cys Pro Ser
        1490                1495                1500
Leu Asp Asp Arg Trp Tyr Met His Ser Cys Ser Gly Ser Leu Gln
        1505                1510                1515
Asn Arg Asn Tyr Pro Ser Gln Glu Glu Leu Ile Lys Val Val Asp
        1520                1525                1530
Val Glu Glu Gln Gln Leu Glu Glu Ser Gly Pro His Asp Leu Thr
        1535                1540                1545
Glu Thr Ser Tyr Leu Pro Arg Gln Asp Leu Glu Gly Thr Pro Tyr
        1550                1555                1560
Leu Glu Ser Gly Ile Ser Leu Phe Ser Asp Asp Pro Glu Ser Asp
        1565                1570                1575
Pro Ser Glu Asp Arg Ala Pro Glu Ser Ala Arg Val Gly Asn Ile
        1580                1585                1590
Pro Ser Ser Thr Ser Ala Leu Lys Val Pro Gln Leu Lys Val Ala
        1595                1600                1605
Glu Ser Ala Gln Ser Pro Ala Ala Ala His Thr Thr Asp Thr Ala
        1610                1615                1620
Gly Tyr Asn Ala Met Glu Glu Ser Val Ser Arg Glu Lys Pro Glu
        1625                1630                1635
Leu Thr Ala Ser Thr Glu Arg Val Asn Lys Arg Met Ser Met Val
        1640                1645                1650
Val Ser Gly Leu Thr Pro Glu Glu Phe Met Leu Val Tyr Lys Phe
        1655                1660                1665
Ala Arg Lys His His Ile Thr Leu Thr Asn Leu Ile Thr Glu Glu
        1670                1675                1680
Thr Thr His Val Val Met Lys Thr Asp Ala Glu Phe Val Cys Glu
        1685                1690                1695
Arg Thr Leu Lys Tyr Phe Leu Gly Ile Ala Gly Gly Lys Trp Val
        1700                1705                1710
Val Ser Tyr Phe Trp Val Thr Gln Ser Ile Lys Glu Arg Lys Met
        1715                1720                1725
Leu Asn Glu His Asp Phe Glu Val Arg Gly Asp Val Val Asn Gly
        1730                1735                1740
```

| | | | | | | | | | | |
|---|---|---|---|---|---|---|---|---|---|---|
| Arg | Asn | His | Gln | Gly | Pro | Lys | Arg | Ala | Arg | Glu | Ser | Gln | Asp | Arg |
| | 1745 | | | | 1750 | | | | 1755 | |

Arg Asn His Gln Gly Pro Lys Arg Ala Arg Glu Ser Gln Asp Arg
    1745                1750                1755

Lys Ile Phe Arg Gly Leu Glu Ile Cys Cys Tyr Gly Pro Phe Thr
    1760                1765                1770

Asn Met Pro Thr Asp Gln Leu Glu Trp Met Val Gln Leu Cys Gly
    1775                1780                1785

Ala Ser Val Val Lys Glu Leu Ser Ser Phe Thr Leu Gly Thr Gly
    1790                1795                1800

Val His Pro Ile Val Val Val Gln Pro Asp Ala Trp Thr Glu Asp
    1805                1810                1815

Asn Gly Phe His Ala Ile Gly Gln Met Cys Glu Ala Pro Val Val
    1820                1825                1830

Thr Arg Glu Trp Val Leu Asp Ser Val Ala Leu Tyr Gln Cys Gln
    1835                1840                1845

Glu Leu Asp Thr Tyr Leu Ile Pro Gln Ile Pro His Ser His Tyr
    1850                1855                1860

<210> SEQ ID NO 2
<211> LENGTH: 7224
<212> TYPE: DNA
<213> ORGANISM: Homo sapiens

<400> SEQUENCE: 2

| | |
|---|---|
| gtaccttgat ttcgtattct gagaggctgc tgcttagcgg tagccccttg gtttccgtgg | 60 |
| caacggaaaa gcgcgggaat tacagataaa ttaaaactgc gactgcgcgg cgtgagctcg | 120 |
| ctgagacttc ctggacgggg acaggctgt ggggtttctc agataactgg gccctgcgc | 180 |
| tcaggaggcc ttcaccctct gctctgggta aagttcattg aacagaaag aaatggattt | 240 |
| atctgctctt cgcgttgaag aagtacaaaa tgtcattaat gctatgcaga aaatcttaga | 300 |
| gtgtcccatc tgtctggagt tgatcaagga acctgtctcc acaaagtgtg accacatatt | 360 |
| ttgcaaattt tgcatgctga aacttctcaa ccagaagaaa gggccttcac agtgtccttt | 420 |
| atgtaagaat gatataacca aaaggagcct acaagaaagt acgagattta gtcaacttgt | 480 |
| tgaagagcta ttgaaaatca tttgtgcttt tcagcttgac acaggtttgg agtatgcaaa | 540 |
| cagctataat tttgcaaaaa aggaaaataa ctctcctgaa catctaaaag atgaagtttc | 600 |
| tatcatccaa agtatgggct acagaaaccg tgccaaaaga cttctacaga gtgaacccga | 660 |
| aaatccttcc ttgcaggaaa ccagtctcag tgtccaactc tctaaccttg aactgtgag | 720 |
| aactctgagg acaaagcagc ggatacaacc tcaaaagacg tctgtctaca ttgaattggg | 780 |
| atctgattct tctgaagata ccgttaataa ggcaacttat tgcagtgtgg gagatcaaga | 840 |
| attgttacaa atcaccccctc aaggaaccag ggatgaaatc agtttggatt ctgcaaaaaa | 900 |
| ggctgcttgt gaattttctg agacggatgt aacaaatact gaacatcatc aacccagtaa | 960 |
| taatgatttg aacaccactg agaagcgtgc agctgagagg catccagaaa agtatcaggg | 1020 |
| tagttctgtt tcaaacttgc atgtggagcc atgtggcaca atactcatg ccagctcatt | 1080 |
| acagcatgag aacagcagtt tattactcac taaagacaga atgaatgtag aaaggctga | 1140 |
| attctgtaat aaaagcaaac agcctggctt agcaaggagc caacataaca atgggctgg | 1200 |
| aagtaaggaa acatgtaatg ataggcggac tcccagcaca gaaaaaaagg tagatctgaa | 1260 |
| tgctgatccc ctgtgtgaga gaaaagaatg gaataagcag aaactgccat gctcagaaaa | 1320 |
| tcctagagat actgaagatg ttccttggat aacactaaat agcagcattc agaaagttaa | 1380 |

```
tgagtggttt tccagaagtg atgaactgtt aggttctgat gactcacatg atggggagtc    1440
tgaatcaaat gccaaagtag ctgatgtatt ggacgttcta aatgaggtag atgaatattc    1500
tggttcttca gagaaaatag acttactggc cagtgatcct catgaggctt taatatgtaa    1560
aagtgaaaga gttcactcca aatcagtaga gagtaatatt gaagacaaaa tatttgggaa    1620
aacctatcgg aagaaggcaa gcctccccaa cttaagccat gtaactgaaa atctaattat    1680
aggagcattt gttactgagc cacagataat acaagagcgt cccctcacaa ataaattaaa    1740
gcgtaaaagg agacctacat caggccttca tcctgaggat tttatcaaga aagcagattt    1800
ggcagttcaa aagactcctg aaatgataaa tcagggaact aaccaaacgg agcagaatgg    1860
tcaagtgatg aatattacta atagtggtca tgagaataaa acaaaaggtg attctattca    1920
gaatgagaaa aatcctaacc caatagaatc actcgaaaaa gaatctgctt caaaacgaa     1980 agctgaacct ataagcagca gtataagcaa tatggaactc gaattaaata tccacaattc    2040
aaaagcacct aaaaagaata ggctgaggag gaagtcttct accaggcata ttcatgcgct    2100
tgaactagta gtcagtagaa atctaagccc acctaattgt actgaattgc aaattgatag    2160
ttgttctagc agtgaagaga taaagaaaaa aagtacaac caaatgccag tcaggcacag     2220
cagaaaccta caactcatgg aaggtaaaga acctgcaact ggagccaaga gagtaacaa     2280 gccaaatgaa cagacaagta aaagacatga cagcgatact ttcccagagc tgaagttaac    2340
aaatgcacct ggttctttta ctaagtgttc aaataccagt gaacttaaag aatttgtcaa    2400
tcctagcctt ccaagagaag aaaaagaaga gaaactagaa acagttaaag tgtctaataa    2460
tgctgaagac cccaaagatc tcatgttaag tggagaaagg gttttgcaaa ctgaaagatc    2520
tgtagagagt agcagtattt cattggtacc tggtactgat tatggcactc aggaaagtat    2580
ctcgttactg gaagttagca ctctagggaa ggcaaaaaca gaaccaaata aatgtgtgag    2640
tcagtgtgca gcatttgaaa accccaaggg actaattcat ggttgttcca agataatag     2700 aaatgacaca gaaggcttta gtatccatt gggacatgaa gttaaccaca gtcgggaaac     2760
aagcatagaa atggaagaaa gtgaacttga tgctcagtat ttgcagaata cattcaaggt    2820
ttcaaagcgc cagtcatttg ctccgttttc aaatccagga aatgcagaag aggaatgtgc    2880
aacattctct gcccactctg ggtccttaaa gaaacaaagt ccaaaagtca cttttgaatg    2940
tgaacaaaag gaagaaaatc aaggaaagaa tgagtctaat atcaagcctg tacagacagt    3000
taatatcact gcaggctttc ctgtggttgg tcagaaagat aagccagttg ataatgccaa    3060
atgtagtatc aaaggaggct ctaggttttg tctatcatct cagttcagag gcaacgaaac    3120
tggactcatt actccaaata acatggact tttacaaaac ccatatcgta taccaccact     3180 tttcccatc aagtcatttg ttaaaactaa atgtaagaaa aatctgctag gaaaaactt      3240 tgaggaacat tcaatgtcac ctgaaagaga aatgggaaat gagaacattc caagtacagt    3300
gagcacaatt agccgtaata acattagaga aaatgttttt aaagaagcca gctcaagcaa    3360
tattaatgaa gtaggttcca gtactaatga agtgggctcc agtattaatg aaataggttc    3420
cagtgatgaa acattcaag cagaactagg tagaaacaga gggccaaaat tgaatgctat     3480
gcttagatta ggggttttgc aacctgaggt ctataaacaa agtcttcctg gaagtaattg    3540
taagcatcct gaaataaaaa agcaagaata tgaagaagta gttcagactg ttaatacaga    3600
tttctctcca tatctgattt cagataactt agaacagcct atgggaagta gtcatgcatc    3660
tcaggtttgt tctgagacac ctgatgacct gttagatgat ggtgaaataa aggaagatac    3720
tagttttgct gaaaatgaca ttaaggaaag ttctgctgtt tttagcaaaa gcgtccagaa    3780
```

```
aggagagctt agcaggagtc ctagcccttt cacccataca catttggctc agggttaccg    3840 aagagggggcc aagaaattag agtcctcaga agagaactta tctagtgagg atgaagagct    3900
tccctgcttc caacacttgt tatttggtaa agtaaacaat ataccttctc agtctactag    3960
gcatagcacc gttgctaccg agtgtctgtc taagaacaca gaggagaatt tattatcatt    4020
gaagaatagc ttaaatgact gcagtaacca ggtaatattg gcaaaggcat ctcaggaaca    4080
tcaccttagt gaggaaacaa aatgttctgc tagcttgttt tcttcacagt gcagtgaatt    4140
ggaagacttg actgcaaata caaacaccca ggatccttc ttgattggtt cttccaaaca    4200
aatgaggcat cagtctgaaa gccagggagt tggtctgagt gacaaggaat tggtttcaga    4260
tgatgaagaa agaggaacgg gcttggaaga aaataatcaa gaagagcaaa gcatggattc    4320
aaacttaggt gaagcagcat ctgggtgtga gagtgaaaca agcgtctctg aagactgctc    4380
agggctatcc tctcagagtg acattttaac cactcagcag agggatacca tgcaacataa    4440
cctgataaag ctccagcagg aaatggctga actagaagct gtgttagaac agcatgggag    4500
ccagccttct aacagctacc cttccatcat aagtgactct tctgcccttg aggacctgcg    4560
aaatccagaa caaagcacat cagaaaaagc agtattaact tcacagaaaa gtagtgaata    4620
ccctataagc cagaatccag aaggcctttc tgctgacaag tttgaggtgt ctgcagatag    4680
ttctaccagt aaaaataaag aaccaggagt ggaaaggtca tccccttcta aatgcccatc    4740
attagatgat aggtggtaca tgcacagttg ctctgggagt cttcagaata gaaactaccc    4800
atctcaagag gagctcatta aggttgttga tgtggaggag caacagctgg aagagtctgg    4860
gccacacgat ttgacggaaa catcttactt gccaaggcaa gatctagagg gaaccccta    4920 cctggaatct ggaatcagcc tcttctctga tgaccctgaa tctgatcctt ctgaagacag    4980
agccccagag tcagctcgtg ttggcaacat accatcttca acctctgcat tgaaagttcc    5040
ccaattgaaa gttgcagaat ctgcccagag tccagctgct gctcatacta ctgatactgc    5100
tgggtataat gcaatggaag aaagtgtgag cagggagaag ccagaattga cagcttcaac    5160
agaaagggtc aacaaaagaa tgtccatggt ggtgtctggc ctgacccag aagaatttat    5220 gctcgtgtac aagtttgcca gaaaacacca catcacttta actaatctaa ttactgaaga    5280
gactactcat gttgttatga aaacagatgc tgagtttgtg tgtgaacgga cactgaaata    5340
ttttctagga attgcgggag gaaatgggt agttagctat ttctgggtga cccagtctat    5400
taaagaaaga aaaatgctga atgagcatga ttttgaagtc agaggagatg tggtcaatgg    5460
aagaaaccac caaggtccaa agcgagcaag agaatcccag gacagaaaga tcttcagggg    5520
gctagaaatc tgttgctatg ggcccttcac caacatgccc acagatcaac tggaatggat    5580
ggtacagctg tgtggtgctt ctgtggtgaa ggagctttca tcattcaccc ttggcacagg    5640
tgtccaccca attgtggttg tgcagccaga tgcctggaca gaggacaatg cttccatgc    5700 aattgggcag atgtgtgagg cacctgtggt gacccgagag tgggtgttgg acagtgtagc    5760
actctaccag tgccaggagc tggacaccta cctgataccc cagatccccc acagccacta    5820
ctgactgcag ccagccacag gtacagagcc acaggacccc aagaatgagc ttacaaagtg    5880 gccttccag gccctgggag ctcctctcac tcttcagtcc ttctactgtc ctggctacta    5940
aatattttat gtacatcagc ctgaaaagga cttctggcta tgcaagggtc ccttaaagat    6000
tttctgcttg aagtctccct tggaaatctg ccatgacaac aaaattatgg taattttca    6060 cctgagaaga ttttaaaacc atttaaacgc caccaattga gcaagatgct gattcattat    6120
```

-continued

```
ttatcagccc tattctttct attcaggctg ttgttggctt agggctggaa gcacagagtg    6180
gcttggcctc aagagaatag ctggtttccc taagtttact tctctaaaac cctgtgttca    6240
caaaggcaga gagtcagacc cttcaatgga aggagagtgc ttgggatcga ttatgtgact    6300
taaagtcaga atagtccttg ggcagttctc aaatgttgga gtggaacatt ggggaggaaa    6360
ttctgaggca ggtattagaa atgaaaagga aacttgaaac ctgggcatgg tggctcacgc    6420
ctgtaatccc agcactttgg gaggccaagg tgggcagatc actggaggtc aggagttcga    6480
aaccagcctg gccaacatgg tgaaacccca tctctactaa aaatacagaa attagccggt    6540
catggtggtg gacacctgta atcccagcta ctcaggtggc taaggcagga gaatcacttc    6600
agcccgggag gtggaggttg cagtgagcca agatcatacc acggcactcc agcctgggtg    6660
acagtgagac tgtggctcaa aaaaaaaaaa aaaaaaagga aaatgaaact agaagagatt    6720
tctaaaagtc tgagatatat ttgctagatt tctaaagaat gtgttctaaa acagcagaag    6780
atttttcaaga accggtttcc aaagacagtc ttctaattcc tcattagtaa taagtaaaat    6840
gtttattgtt gtagctctgg tatataatcc attcctctta aaatataaga cctctggcat    6900
gaatatttca tatctataaa atgacagatc ccaccaggaa ggaagctgtt gctttctttg    6960
aggtgatttt tttcctttgc tccctgttgc tgaaaccata cagcttcata ataattttg    7020
cttgctgaag gaagaaaaag tgttttcat aaacccatta tccaggactg tttatagctg    7080
ttggaaggac taggtcttcc ctagcccccc cagtgtgcaa gggcagtgaa gacttgattg    7140
tacaaaatac gttttgtaaa tgttgtgctg ttaacactgc aaataaactt ggtagcaaac    7200
acttccaaaa aaaaaaaaaa aaaa                                           7224
```

<210> SEQ ID NO 3
<211> LENGTH: 3418
<212> TYPE: PRT
<213> ORGANISM: Homo sapiens

<400> SEQUENCE: 3

```
Met Pro Ile Gly Ser Lys Glu Arg Pro Thr Phe Phe Glu Ile Phe Lys
1               5                   10                  15

Thr Arg Cys Asn Lys Ala Asp Leu Gly Pro Ile Ser Leu Asn Trp Phe
            20                  25                  30

Glu Glu Leu Ser Ser Glu Ala Pro Pro Tyr Asn Ser Glu Pro Ala Glu
        35                  40                  45

Glu Ser Glu His Lys Asn Asn Asn Tyr Glu Pro Asn Leu Phe Lys Thr
    50                  55                  60

Pro Gln Arg Lys Pro Ser Tyr Asn Gln Leu Ala Ser Thr Pro Ile Ile
65                  70                  75                  80

Phe Lys Glu Gln Gly Leu Thr Leu Pro Leu Tyr Gln Ser Pro Val Lys
                85                  90                  95

Glu Leu Asp Lys Phe Lys Leu Asp Leu Gly Arg Asn Val Pro Asn Ser
            100                 105                 110

Arg His Lys Ser Leu Arg Thr Val Lys Thr Lys Met Asp Gln Ala Asp
        115                 120                 125

Asp Val Ser Cys Pro Leu Leu Asn Ser Cys Leu Ser Glu Ser Pro Val
    130                 135                 140

Val Leu Gln Cys Thr His Val Thr Pro Gln Arg Asp Lys Ser Val Val
145                 150                 155                 160

Cys Gly Ser Leu Phe His Thr Pro Lys Phe Val Lys Gly Arg Gln Thr
                165                 170                 175
```

```
Pro Lys His Ile Ser Glu Ser Leu Gly Ala Glu Val Asp Pro Asp Met
            180                 185                 190

Ser Trp Ser Ser Ser Leu Ala Thr Pro Pro Thr Leu Ser Ser Thr Val
        195                 200                 205

Leu Ile Val Arg Asn Glu Glu Ala Ser Glu Thr Val Phe Pro His Asp
        210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                245                 250                 255

Asn Gln Arg Glu Ala Ala Ser His Gly Phe Gly Lys Thr Ser Gly Asn
            260                 265                 270

Ser Phe Lys Val Asn Ser Cys Lys Asp His Ile Gly Lys Ser Met Pro
        275                 280                 285

Asn Val Leu Glu Asp Glu Val Tyr Glu Thr Val Val Asp Thr Ser Glu
        290                 295                 300

Glu Asp Ser Phe Ser Leu Cys Phe Ser Lys Cys Arg Thr Lys Asn Leu
305                 310                 315                 320

Gln Lys Val Arg Thr Ser Lys Thr Arg Lys Lys Ile Phe His Glu Ala
                325                 330                 335

Asn Ala Asp Glu Cys Glu Lys Ser Lys Asn Gln Val Lys Glu Lys Tyr
            340                 345                 350

Ser Phe Val Ser Glu Val Glu Pro Asn Asp Thr Asp Pro Leu Asp Ser
        355                 360                 365

Asn Val Ala His Gln Lys Pro Phe Glu Ser Gly Ser Asp Lys Ile Ser
        370                 375                 380

Lys Glu Val Val Pro Ser Leu Ala Cys Glu Trp Ser Gln Leu Thr Leu
385                 390                 395                 400

Ser Gly Leu Asn Gly Ala Gln Met Glu Lys Ile Pro Leu Leu His Ile
                405                 410                 415

Ser Ser Cys Asp Gln Asn Ile Ser Glu Lys Asp Leu Leu Asp Thr Glu
            420                 425                 430

Asn Lys Arg Lys Lys Asp Phe Leu Thr Ser Glu Asn Ser Leu Pro Arg
        435                 440                 445

Ile Ser Ser Leu Pro Lys Ser Glu Lys Pro Leu Asn Glu Glu Thr Val
        450                 455                 460

Val Asn Lys Arg Asp Glu Glu Gln His Leu Glu Ser His Thr Asp Cys
465                 470                 475                 480

Ile Leu Ala Val Lys Gln Ala Ile Ser Gly Thr Ser Pro Val Ala Ser
                485                 490                 495

Ser Phe Gln Gly Ile Lys Lys Ser Ile Phe Arg Ile Arg Glu Ser Pro
            500                 505                 510

Lys Glu Thr Phe Asn Ala Ser Phe Ser Gly His Met Thr Asp Pro Asn
        515                 520                 525

Phe Lys Lys Glu Thr Glu Ala Ser Glu Ser Gly Leu Glu Ile His Thr
        530                 535                 540

Val Cys Ser Gln Lys Glu Asp Ser Leu Cys Pro Asn Leu Ile Asp Asn
545                 550                 555                 560

Gly Ser Trp Pro Ala Thr Thr Gln Asn Ser Val Ala Leu Lys Asn
                565                 570                 575

Ala Gly Leu Ile Ser Thr Leu Lys Lys Lys Thr Asn Lys Phe Ile Tyr
        580                 585                 590

Ala Ile His Asp Glu Thr Phe Tyr Lys Gly Lys Lys Ile Pro Lys Asp
```

```
                595             600             605
Gln Lys Ser Glu Leu Ile Asn Cys Ser Ala Gln Phe Glu Ala Asn Ala
        610             615             620
Phe Glu Ala Pro Leu Thr Phe Ala Asn Ala Asp Ser Gly Leu Leu His
625             630             635             640
Ser Ser Val Lys Arg Ser Cys Ser Gln Asn Asp Ser Glu Glu Pro Thr
                645             650             655
Leu Ser Leu Thr Ser Ser Phe Gly Thr Ile Leu Arg Lys Cys Ser Arg
            660             665             670
Asn Glu Thr Cys Ser Asn Asn Thr Val Ile Ser Gln Asp Leu Asp Tyr
        675             680             685
Lys Glu Ala Lys Cys Asn Lys Glu Lys Leu Gln Leu Phe Ile Thr Pro
    690             695             700
Glu Ala Asp Ser Leu Ser Cys Leu Gln Glu Gly Gln Cys Glu Asn Asp
705             710             715             720
Pro Lys Ser Lys Val Ser Asp Ile Lys Glu Glu Val Leu Ala Ala
                725             730             735
Ala Cys His Pro Val Gln His Ser Lys Val Glu Tyr Ser Asp Thr Asp
            740             745             750
Phe Gln Ser Gln Lys Ser Leu Leu Tyr Asp His Glu Asn Ala Ser Thr
        755             760             765
Leu Ile Leu Thr Pro Thr Ser Lys Asp Val Leu Ser Asn Leu Val Met
    770             775             780
Ile Ser Arg Gly Lys Glu Ser Tyr Lys Met Ser Asp Lys Leu Lys Gly
785             790             795             800
Asn Asn Tyr Glu Ser Asp Val Glu Leu Thr Lys Asn Ile Pro Met Glu
                805             810             815
Lys Asn Gln Asp Val Cys Ala Leu Asn Glu Asn Tyr Lys Asn Val Glu
            820             825             830
Leu Leu Pro Pro Glu Lys Tyr Met Arg Val Ala Ser Pro Ser Arg Lys
        835             840             845
Val Gln Phe Asn Gln Asn Thr Asn Leu Arg Val Ile Gln Lys Asn Gln
    850             855             860
Glu Glu Thr Thr Ser Ile Ser Lys Ile Thr Val Asn Pro Asp Ser Glu
865             870             875             880
Glu Leu Phe Ser Asp Asn Glu Asn Asn Phe Val Phe Gln Val Ala Asn
                885             890             895
Glu Arg Asn Asn Leu Ala Leu Gly Asn Thr Lys Glu Leu His Glu Thr
            900             905             910
Asp Leu Thr Cys Val Asn Glu Pro Ile Phe Lys Asn Ser Thr Met Val
        915             920             925
Leu Tyr Gly Asp Thr Gly Asp Lys Gln Ala Thr Gln Val Ser Ile Lys
    930             935             940
Lys Asp Leu Val Tyr Val Leu Ala Glu Glu Asn Lys Asn Ser Val Lys
945             950             955             960
Gln His Ile Lys Met Thr Leu Gly Gln Asp Leu Lys Ser Asp Ile Ser
                965             970             975
Leu Asn Ile Asp Lys Ile Pro Glu Lys Asn Asn Asp Tyr Met Asn Lys
            980             985             990
Trp Ala Gly Leu Leu Gly Pro Ile  Ser Asn His Ser Phe Gly Gly Ser
            995             1000            1005
Phe Arg Thr Ala Ser Asn Lys  Glu Ile Lys Leu Ser  Glu His Asn
    1010            1015            1020
```

-continued

Ile Lys Lys Ser Lys Met Phe Phe Lys Asp Ile Glu Glu Gln Tyr
1025            1030            1035

Pro Thr Ser Leu Ala Cys Val Glu Ile Val Asn Thr Leu Ala Leu
1040            1045            1050

Asp Asn Gln Lys Lys Leu Ser Lys Pro Gln Ser Ile Asn Thr Val
1055            1060            1065

Ser Ala His Leu Gln Ser Ser Val Val Val Ser Asp Cys Lys Asn
1070            1075            1080

Ser His Ile Thr Pro Gln Met Leu Phe Ser Lys Gln Asp Phe Asn
1085            1090            1095

Ser Asn His Asn Leu Thr Pro Ser Gln Lys Ala Glu Ile Thr Glu
1100            1105            1110

Leu Ser Thr Ile Leu Glu Glu Ser Gly Ser Gln Phe Glu Phe Thr
1115            1120            1125

Gln Phe Arg Lys Pro Ser Tyr Ile Leu Gln Lys Ser Thr Phe Glu
1130            1135            1140

Val Pro Glu Asn Gln Met Thr Ile Leu Lys Thr Thr Ser Glu Glu
1145            1150            1155

Cys Arg Asp Ala Asp Leu His Val Ile Met Asn Ala Pro Ser Ile
1160            1165            1170

Gly Gln Val Asp Ser Ser Lys Gln Phe Glu Gly Thr Val Glu Ile
1175            1180            1185

Lys Arg Lys Phe Ala Gly Leu Leu Lys Asn Asp Cys Asn Lys Ser
1190            1195            1200

Ala Ser Gly Tyr Leu Thr Asp Glu Asn Glu Val Gly Phe Arg Gly
1205            1210            1215

Phe Tyr Ser Ala His Gly Thr Lys Leu Asn Val Ser Thr Glu Ala
1220            1225            1230

Leu Gln Lys Ala Val Lys Leu Phe Ser Asp Ile Glu Asn Ile Ser
1235            1240            1245

Glu Glu Thr Ser Ala Glu Val His Pro Ile Ser Leu Ser Ser Ser
1250            1255            1260

Lys Cys His Asp Ser Val Val Ser Met Phe Lys Ile Glu Asn His
1265            1270            1275

Asn Asp Lys Thr Val Ser Glu Lys Asn Asn Lys Cys Gln Leu Ile
1280            1285            1290

Leu Gln Asn Asn Ile Glu Met Thr Thr Gly Thr Phe Val Glu Glu
1295            1300            1305

Ile Thr Glu Asn Tyr Lys Arg Asn Thr Glu Asn Glu Asp Asn Lys
1310            1315            1320

Tyr Thr Ala Ala Ser Arg Asn Ser His Asn Leu Glu Phe Asp Gly
1325            1330            1335

Ser Asp Ser Ser Lys Asn Asp Thr Val Cys Ile His Lys Asp Glu
1340            1345            1350

Thr Asp Leu Leu Phe Thr Asp Gln His Asn Ile Cys Leu Lys Leu
1355            1360            1365

Ser Gly Gln Phe Met Lys Glu Gly Asn Thr Gln Ile Lys Glu Asp
1370            1375            1380

Leu Ser Asp Leu Thr Phe Leu Glu Val Ala Lys Ala Gln Glu Ala
1385            1390            1395

Cys His Gly Asn Thr Ser Asn Lys Glu Gln Leu Thr Ala Thr Lys
1400            1405            1410

-continued

```
Thr Glu Gln Asn Ile Lys Asp Phe Glu Thr Ser Asp Thr Phe Phe
1415                1420                1425

Gln Thr Ala Ser Gly Lys Asn Ile Ser Val Ala Lys Glu Ser Phe
1430                1435                1440

Asn Lys Ile Val Asn Phe Phe Asp Gln Lys Pro Glu Glu Leu His
1445                1450                1455

Asn Phe Ser Leu Asn Ser Glu Leu His Ser Asp Ile Arg Lys Asn
1460                1465                1470

Lys Met Asp Ile Leu Ser Tyr Glu Glu Thr Asp Ile Val Lys His
1475                1480                1485

Lys Ile Leu Lys Glu Ser Val Pro Val Gly Thr Gly Asn Gln Leu
1490                1495                1500

Val Thr Phe Gln Gly Gln Pro Glu Arg Asp Glu Lys Ile Lys Glu
1505                1510                1515

Pro Thr Leu Leu Gly Phe His Thr Ala Ser Gly Lys Lys Val Lys
1520                1525                1530

Ile Ala Lys Glu Ser Leu Asp Lys Val Lys Asn Leu Phe Asp Glu
1535                1540                1545

Lys Glu Gln Gly Thr Ser Glu Ile Thr Ser Phe Ser His Gln Trp
1550                1555                1560

Ala Lys Thr Leu Lys Tyr Arg Glu Ala Cys Lys Asp Leu Glu Leu
1565                1570                1575

Ala Cys Glu Thr Ile Glu Ile Thr Ala Ala Pro Lys Cys Lys Glu
1580                1585                1590

Met Gln Asn Ser Leu Asn Asn Asp Lys Asn Leu Val Ser Ile Glu
1595                1600                1605

Thr Val Val Pro Pro Lys Leu Leu Ser Asp Asn Leu Cys Arg Gln
1610                1615                1620

Thr Glu Asn Leu Lys Thr Ser Lys Ser Ile Phe Leu Lys Val Lys
1625                1630                1635

Val His Glu Asn Val Glu Lys Glu Thr Ala Lys Ser Pro Ala Thr
1640                1645                1650

Cys Tyr Thr Asn Gln Ser Pro Tyr Ser Val Ile Glu Asn Ser Ala
1655                1660                1665

Leu Ala Phe Tyr Thr Ser Cys Ser Arg Lys Thr Ser Val Ser Gln
1670                1675                1680

Thr Ser Leu Leu Glu Ala Lys Lys Trp Leu Arg Glu Gly Ile Phe
1685                1690                1695

Asp Gly Gln Pro Glu Arg Ile Asn Thr Ala Asp Tyr Val Gly Asn
1700                1705                1710

Tyr Leu Tyr Glu Asn Asn Ser Asn Ser Thr Ile Ala Glu Asn Asp
1715                1720                1725

Lys Asn His Leu Ser Glu Lys Gln Asp Thr Tyr Leu Ser Asn Ser
1730                1735                1740

Ser Met Ser Asn Ser Tyr Ser Tyr His Ser Asp Glu Val Tyr Asn
1745                1750                1755

Asp Ser Gly Tyr Leu Ser Lys Asn Lys Leu Asp Ser Gly Ile Glu
1760                1765                1770

Pro Val Leu Lys Asn Val Glu Asp Gln Lys Asn Thr Ser Phe Ser
1775                1780                1785

Lys Val Ile Ser Asn Val Lys Asp Ala Asn Ala Tyr Pro Gln Thr
1790                1795                1800

Val Asn Glu Asp Ile Cys Val Glu Glu Leu Val Thr Ser Ser Ser
```

-continued

```
                1805                1810                1815
Pro Cys Lys Asn Lys Asn Ala Ala Ile Lys Leu Ser Ile Ser Asn
                1820                1825                1830

Ser Asn Asn Phe Glu Val Gly Pro Pro Ala Phe Arg Ile Ala Ser
                1835                1840                1845

Gly Lys Ile Val Cys Val Ser His Glu Thr Ile Lys Lys Val Lys
                1850                1855                1860

Asp Ile Phe Thr Asp Ser Phe Ser Lys Val Ile Lys Glu Asn Asn
                1865                1870                1875

Glu Asn Lys Ser Lys Ile Cys Gln Thr Lys Ile Met Ala Gly Cys
                1880                1885                1890

Tyr Glu Ala Leu Asp Asp Ser Glu Asp Ile Leu His Asn Ser Leu
                1895                1900                1905

Asp Asn Asp Glu Cys Ser Thr His Ser His Lys Val Phe Ala Asp
                1910                1915                1920

Ile Gln Ser Glu Glu Ile Leu Gln His Asn Gln Asn Met Ser Gly
                1925                1930                1935

Leu Glu Lys Val Ser Lys Ile Ser Pro Cys Asp Val Ser Leu Glu
                1940                1945                1950

Thr Ser Asp Ile Cys Lys Cys Ser Ile Gly Lys Leu His Lys Ser
                1955                1960                1965

Val Ser Ser Ala Asn Thr Cys Gly Ile Phe Ser Thr Ala Ser Gly
                1970                1975                1980

Lys Ser Val Gln Val Ser Asp Ala Ser Leu Gln Asn Ala Arg Gln
                1985                1990                1995

Val Phe Ser Glu Ile Glu Asp Ser Thr Lys Gln Val Phe Ser Lys
                2000                2005                2010

Val Leu Phe Lys Ser Asn Glu His Ser Asp Gln Leu Thr Arg Glu
                2015                2020                2025

Glu Asn Thr Ala Ile Arg Thr Pro Glu His Leu Ile Ser Gln Lys
                2030                2035                2040

Gly Phe Ser Tyr Asn Val Val Asn Ser Ser Ala Phe Ser Gly Phe
                2045                2050                2055

Ser Thr Ala Ser Gly Lys Gln Val Ser Ile Leu Glu Ser Ser Leu
                2060                2065                2070

His Lys Val Lys Gly Val Leu Glu Glu Phe Asp Leu Ile Arg Thr
                2075                2080                2085

Glu His Ser Leu His Tyr Ser Pro Thr Ser Arg Gln Asn Val Ser
                2090                2095                2100

Lys Ile Leu Pro Arg Val Asp Lys Arg Asn Pro Glu His Cys Val
                2105                2110                2115

Asn Ser Glu Met Glu Lys Thr Cys Ser Lys Glu Phe Lys Leu Ser
                2120                2125                2130

Asn Asn Leu Asn Val Glu Gly Gly Ser Ser Glu Asn Asn His Ser
                2135                2140                2145

Ile Lys Val Ser Pro Tyr Leu Ser Gln Phe Gln Gln Asp Lys Gln
                2150                2155                2160

Gln Leu Val Leu Gly Thr Lys Val Ser Leu Val Glu Asn Ile His
                2165                2170                2175

Val Leu Gly Lys Glu Gln Ala Ser Pro Lys Asn Val Lys Met Glu
                2180                2185                2190

Ile Gly Lys Thr Glu Thr Phe Ser Asp Val Pro Val Lys Thr Asn
                2195                2200                2205
```

```
Ile Glu Val Cys Ser Thr Tyr Ser Lys Asp Ser Glu Asn Tyr Phe
    2210            2215            2220

Glu Thr Glu Ala Val Glu Ile Ala Lys Ala Phe Met Glu Asp Asp
    2225            2230            2235

Glu Leu Thr Asp Ser Lys Leu Pro Ser His Ala Thr His Ser Leu
    2240            2245            2250

Phe Thr Cys Pro Glu Asn Glu Glu Met Val Leu Ser Asn Ser Arg
    2255            2260            2265

Ile Gly Lys Arg Arg Gly Glu Pro Leu Ile Leu Val Gly Glu Pro
    2270            2275            2280

Ser Ile Lys Arg Asn Leu Leu Asn Glu Phe Asp Arg Ile Ile Glu
    2285            2290            2295

Asn Gln Glu Lys Ser Leu Lys Ala Ser Lys Ser Thr Pro Asp Gly
    2300            2305            2310

Thr Ile Lys Asp Arg Arg Leu Phe Met His His Val Ser Leu Glu
    2315            2320            2325

Pro Ile Thr Cys Val Pro Phe Arg Thr Thr Lys Glu Arg Gln Glu
    2330            2335            2340

Ile Gln Asn Pro Asn Phe Thr Ala Pro Gly Gln Glu Phe Leu Ser
    2345            2350            2355

Lys Ser His Leu Tyr Glu His Leu Thr Leu Glu Lys Ser Ser Ser
    2360            2365            2370

Asn Leu Ala Val Ser Gly His Pro Phe Tyr Gln Val Ser Ala Thr
    2375            2380            2385

Arg Asn Glu Lys Met Arg His Leu Ile Thr Thr Gly Arg Pro Thr
    2390            2395            2400

Lys Val Phe Val Pro Pro Phe Lys Thr Lys Ser His Phe His Arg
    2405            2410            2415

Val Glu Gln Cys Val Arg Asn Ile Asn Leu Glu Glu Asn Arg Gln
    2420            2425            2430

Lys Gln Asn Ile Asp Gly His Gly Ser Asp Asp Ser Lys Asn Lys
    2435            2440            2445

Ile Asn Asp Asn Glu Ile His Gln Phe Asn Lys Asn Asn Ser Asn
    2450            2455            2460

Gln Ala Ala Ala Val Thr Phe Thr Lys Cys Glu Glu Glu Pro Leu
    2465            2470            2475

Asp Leu Ile Thr Ser Leu Gln Asn Ala Arg Asp Ile Gln Asp Met
    2480            2485            2490

Arg Ile Lys Lys Lys Gln Arg Gln Arg Val Phe Pro Gln Pro Gly
    2495            2500            2505

Ser Leu Tyr Leu Ala Lys Thr Ser Thr Leu Pro Arg Ile Ser Leu
    2510            2515            2520

Lys Ala Ala Val Gly Gly Gln Val Pro Ser Ala Cys Ser His Lys
    2525            2530            2535

Gln Leu Tyr Thr Tyr Gly Val Ser Lys His Cys Ile Lys Ile Asn
    2540            2545            2550

Ser Lys Asn Ala Glu Ser Phe Gln Phe His Thr Glu Asp Tyr Phe
    2555            2560            2565

Gly Lys Glu Ser Leu Trp Thr Gly Lys Gly Ile Gln Leu Ala Asp
    2570            2575            2580

Gly Gly Trp Leu Ile Pro Ser Asn Asp Gly Lys Ala Gly Lys Glu
    2585            2590            2595
```

```
Glu Phe Tyr Arg Ala Leu Cys Asp Thr Pro Gly Val Asp Pro Lys
2600                2605                2610

Leu Ile Ser Arg Ile Trp Val Tyr Asn His Tyr Arg Trp Ile Ile
2615                2620                2625

Trp Lys Leu Ala Ala Met Glu Cys Ala Phe Pro Lys Glu Phe Ala
2630                2635                2640

Asn Arg Cys Leu Ser Pro Glu Arg Val Leu Leu Gln Leu Lys Tyr
2645                2650                2655

Arg Tyr Asp Thr Glu Ile Asp Arg Ser Arg Arg Ser Ala Ile Lys
2660                2665                2670

Lys Ile Met Glu Arg Asp Asp Thr Ala Ala Lys Thr Leu Val Leu
2675                2680                2685

Cys Val Ser Asp Ile Ile Ser Leu Ser Ala Asn Ile Ser Glu Thr
2690                2695                2700

Ser Ser Asn Lys Thr Ser Ser Ala Asp Thr Gln Lys Val Ala Ile
2705                2710                2715

Ile Glu Leu Thr Asp Gly Trp Tyr Ala Val Lys Ala Gln Leu Asp
2720                2725                2730

Pro Pro Leu Leu Ala Val Leu Lys Asn Gly Arg Leu Thr Val Gly
2735                2740                2745

Gln Lys Ile Ile Leu His Gly Ala Glu Leu Val Gly Ser Pro Asp
2750                2755                2760

Ala Cys Thr Pro Leu Glu Ala Pro Glu Ser Leu Met Leu Lys Ile
2765                2770                2775

Ser Ala Asn Ser Thr Arg Pro Ala Arg Trp Tyr Thr Lys Leu Gly
2780                2785                2790

Phe Phe Pro Asp Pro Arg Pro Phe Pro Leu Pro Leu Ser Ser Leu
2795                2800                2805

Phe Ser Asp Gly Gly Asn Val Gly Cys Val Asp Val Ile Ile Gln
2810                2815                2820

Arg Ala Tyr Pro Ile Gln Trp Met Glu Lys Thr Ser Ser Gly Leu
2825                2830                2835

Tyr Ile Phe Arg Asn Glu Arg Glu Glu Glu Lys Glu Ala Ala Lys
2840                2845                2850

Tyr Val Glu Ala Gln Gln Lys Arg Leu Glu Ala Leu Phe Thr Lys
2855                2860                2865

Ile Gln Glu Glu Phe Glu Glu His Glu Glu Asn Thr Thr Lys Pro
2870                2875                2880

Tyr Leu Pro Ser Arg Ala Leu Thr Arg Gln Gln Val Arg Ala Leu
2885                2890                2895

Gln Asp Gly Ala Glu Leu Tyr Glu Ala Val Lys Asn Ala Ala Asp
2900                2905                2910

Pro Ala Tyr Leu Glu Gly Tyr Phe Ser Glu Glu Gln Leu Arg Ala
2915                2920                2925

Leu Asn Asn His Arg Gln Met Leu Asn Asp Lys Lys Gln Ala Gln
2930                2935                2940

Ile Gln Leu Glu Ile Arg Lys Ala Met Glu Ser Ala Glu Gln Lys
2945                2950                2955

Glu Gln Gly Leu Ser Arg Asp Val Thr Thr Val Trp Lys Leu Arg
2960                2965                2970

Ile Val Ser Tyr Ser Lys Lys Glu Lys Asp Ser Val Ile Leu Ser
2975                2980                2985

Ile Trp Arg Pro Ser Ser Asp Leu Tyr Ser Leu Leu Thr Glu Gly
```

2990                    2995                    3000

Lys Arg Tyr Arg Ile Tyr His Leu Ala Thr Ser Lys Ser Lys Ser
        3005                    3010                    3015

Lys Ser Glu Arg Ala Asn Ile Gln Leu Ala Ala Thr Lys Lys Thr
        3020                    3025                    3030

Gln Tyr Gln Gln Leu Pro Val Ser Asp Glu Ile Leu Phe Gln Ile
        3035                    3040                    3045

Tyr Gln Pro Arg Glu Pro Leu His Phe Ser Lys Phe Leu Asp Pro
        3050                    3055                    3060

Asp Phe Gln Pro Ser Cys Ser Glu Val Asp Leu Ile Gly Phe Val
        3065                    3070                    3075

Val Ser Val Val Lys Lys Thr Gly Leu Ala Pro Phe Val Tyr Leu
        3080                    3085                    3090

Ser Asp Glu Cys Tyr Asn Leu Leu Ala Ile Lys Phe Trp Ile Asp
        3095                    3100                    3105

Leu Asn Glu Asp Ile Ile Lys Pro His Met Leu Ile Ala Ala Ser
        3110                    3115                    3120

Asn Leu Gln Trp Arg Pro Glu Ser Lys Ser Gly Leu Leu Thr Leu
        3125                    3130                    3135

Phe Ala Gly Asp Phe Ser Val Phe Ser Ala Ser Pro Lys Glu Gly
        3140                    3145                    3150

His Phe Gln Glu Thr Phe Asn Lys Met Lys Asn Thr Val Glu Asn
        3155                    3160                    3165

Ile Asp Ile Leu Cys Asn Glu Ala Glu Asn Lys Leu Met His Ile
        3170                    3175                    3180

Leu His Ala Asn Asp Pro Lys Trp Ser Thr Pro Thr Lys Asp Cys
        3185                    3190                    3195

Thr Ser Gly Pro Tyr Thr Ala Gln Ile Ile Pro Gly Thr Gly Asn
        3200                    3205                    3210

Lys Leu Leu Met Ser Ser Pro Asn Cys Glu Ile Tyr Tyr Gln Ser
        3215                    3220                    3225

Pro Leu Ser Leu Cys Met Ala Lys Arg Lys Ser Val Ser Thr Pro
        3230                    3235                    3240

Val Ser Ala Gln Met Thr Ser Lys Ser Cys Lys Gly Glu Lys Glu
        3245                    3250                    3255

Ile Asp Asp Gln Lys Asn Cys Lys Lys Arg Arg Ala Leu Asp Phe
        3260                    3265                    3270

Leu Ser Arg Leu Pro Leu Pro Pro Pro Val Ser Pro Ile Cys Thr
        3275                    3280                    3285

Phe Val Ser Pro Ala Ala Gln Lys Ala Phe Gln Pro Pro Arg Ser
        3290                    3295                    3300

Cys Gly Thr Lys Tyr Glu Thr Pro Ile Lys Lys Lys Glu Leu Asn
        3305                    3310                    3315

Ser Pro Gln Met Thr Pro Phe Lys Lys Phe Asn Glu Ile Ser Leu
        3320                    3325                    3330

Leu Glu Ser Asn Ser Ile Ala Asp Glu Glu Leu Ala Leu Ile Asn
        3335                    3340                    3345

Thr Gln Ala Leu Leu Ser Gly Ser Thr Gly Glu Lys Gln Phe Ile
        3350                    3355                    3360

Ser Val Ser Glu Ser Thr Arg Thr Ala Pro Thr Ser Ser Glu Asp
        3365                    3370                    3375

Tyr Leu Arg Leu Lys Arg Arg Cys Thr Thr Ser Leu Ile Lys Glu
        3380                    3385                    3390

```
Gln Glu Ser Ser Gln Ala Ser Thr Glu Glu Cys Glu Lys Asn Lys
    3395            3400                3405
Gln Asp Thr Ile Thr Thr Lys Lys Tyr Ile
    3410            3415
```

<210> SEQ ID NO 4
<211> LENGTH: 11386
<212> TYPE: DNA
<213> ORGANISM: Homo sapiens

<400> SEQUENCE: 4

| | | | | | |
|---|---|---|---|---|---|
| gtggcgcgag | cttctgaaac | taggcggcag | aggcggagcc | gctgtggcac | tgctgcgcct | 60 |
| ctgctgcgcc | tcgggtgtct | tttgcggcgg | tgggtcgccg | ccgggagaag | cgtgagggga | 120 |
| cagatttgtg | accggcgcgg | ttttgtcag | cttactccgg | ccaaaaaga | actgcacctc | 180 |
| tggagcggac | ttatttacca | agcattggag | gaatatcgta | ggtaaaaatg | cctattggat | 240 |
| ccaaagagag | gccaacattt | tttgaaattt | ttaagacacg | ctgcaacaaa | gcagatttag | 300 |
| gaccaataag | tcttaattgg | tttgaagaac | tttcttcaga | agctccaccc | tataattctg | 360 |
| aacctgcaga | agaatctgaa | cataaaaaca | acaattacga | accaaaccta | tttaaaactc | 420 |
| cacaaaggaa | accatcttat | aatcagctgg | cttcaactcc | aataatattc | aaagagcaag | 480 |
| ggctgactct | gccgctgtac | caatctcctg | taaaagaatt | agataaattc | aaattagact | 540 |
| taggaaggaa | tgttcccaat | agtagacata | aaagtcttcg | cacagtgaaa | actaaaatgg | 600 |
| atcaagcaga | tgatgtttcc | tgtccacttc | taaattcttg | tcttagtgaa | agtcctgttg | 660 |
| ttctacaatg | tacacatgta | acaccacaaa | gagataagtc | agtggtatgt | gggagtttgt | 720 |
| ttcatacacc | aaagttttgtg | aagggtcgtc | agacaccaaa | acatatttct | gaaagtctag | 780 |
| gagctgaggt | ggatcctgat | atgtcttggt | caagttcttt | agctacacca | cccaccctta | 840 |
| gttctactgt | gctcatagtc | agaaatgaag | aagcatctga | aactgtattt | cctcatgata | 900 |
| ctactgctaa | tgtgaaaagc | tatttttcca | atcatgatga | aagtctgaag | aaaaatgata | 960 |
| gatttatcgc | ttctgtgaca | gacagtgaaa | acacaaatca | aagagaagct | gcaagtcatg | 1020 |
| gatttggaaa | aacatcaggg | aattcattta | agtaaaatag | ctgcaaagac | cacattggaa | 1080 |
| agtcaatgcc | aaatgtccta | gaagatgaag | tatatgaaac | agttgtagat | acctctgaag | 1140 |
| aagatagttt | tcattatgt | ttttctaaat | gtagaacaaa | aaatctacaa | aaagtaagaa | 1200 |
| ctagcaagac | taggaaaaaa | attttccatg | aagcaaacgc | tgatgaatgt | gaaaaatcta | 1260 |
| aaaaccaagt | gaaagaaaaa | tactcatttg | tatctgaagt | ggaaccaaat | gatactgatc | 1320 |
| cattagattc | aaatgtagca | aatcagaagc | cctttgagag | tggaagtgac | aaaatctcca | 1380 |
| aggaagttgt | accgtctttg | gcctgtgaat | ggtctcaact | aaccctttca | ggtctaaatg | 1440 |
| gagcccagat | ggagaaaata | cccctattgc | atatttcttc | atgtgaccaa | aatatttcag | 1500 |
| aaaaagacct | attagacaca | gagaacaaaa | gaaagaaaga | ttttcttact | tcagagaatt | 1560 |
| ctttgccacg | tatttctagc | ctaccaaaat | cagagaagcc | attaaatgag | gaaacagtgg | 1620 |
| taaataagag | agatgaagag | cagcatcttg | aatctcatac | agactgcatt | cttgcagtaa | 1680 |
| agcaggcaat | atctgaact | tctccagtgg | cttcttcatt | tcagggtatc | aaaaagtcta | 1740 |
| tattcagaat | aagagaatca | cctaaagaga | ctttcaatgc | aagttttttca | ggtcatatga | 1800 |
| ctgatccaaa | ctttaaaaaa | gaaactgaag | cctctgaaag | tggactggaa | atacatactg | 1860 |
| tttgctcaca | gaaggaggac | tccttatgtc | caaatttaat | tgataatgga | agctggccag | 1920 |

```
ccaccaccac acagaattct gtagctttga agaatgcagg tttaatatcc actttgaaaa    1980
agaaaacaaa taagtttatt tatgctatac atgatgaaac atcttataaa ggaaaaaaaa    2040
taccgaaaga ccaaaaatca gaactaatta actgttcagc ccagtttgaa gcaaatgctt    2100
ttgaagcacc acttacattt gcaaatgctg attcaggttt attgcattct tctgtgaaaa    2160
gaagctgttc acagaatgat tctgaagaac caactttgtc cttaactagc tcttttggga    2220
caattctgag gaaatgttct agaaatgaaa catgttctaa taatacagta atctctcagg    2280
atcttgatta taaagaagca aaatgtaata aggaaaaact acagttattt attaccccag    2340
aagctgattc tctgtcatgc ctgcaggaag gacagtgtga aaatgatcca aaaagcaaaa    2400
aagtttcaga tataaaagaa gaggtcttgg ctgcagcatg tcacccagta caacattcaa    2460
aagtggaata cagtgatact gactttcaat cccagaaaag tcttttatat gatcatgaaa    2520
atgccagcac tcttatttta actcctactt ccaaggatgt tctgtcaaac ctagtcatga    2580
tttctagagg caaagaatca tacaaaatgt cagacaagct caaaggtaac aattatgaat    2640
ctgatgttga attaaccaaa aatattccca tggaaaagaa tcaagatgta tgtgctttaa    2700
atgaaaatta taaaaacgtt gagctgttgc cacctgaaaa atacatgaga gtagcatcac    2760
cttcaagaaa ggtacaattc aaccaaaaca caaatctaag agtaatccaa aaaaatcaag    2820
aagaaactac ttcaatttca aaaataactg tcaatccaga ctctgaagaa cttttctcag    2880
acaatgagaa taatttttgtc ttccaagtag ctaatgaaag gaataatctt gctttaggaa    2940
atactaagga acttcatgaa acagacttga cttgtgtaaa cgaacccatt ttcaagaact    3000
ctaccatggt tttatatgga gacacaggtg ataaacaagc aacccaagtg tcaattaaaa    3060
aagatttggt ttatgttctt gcagaggaga acaaaaatag tgtaaagcag catataaaaa    3120
tgactctagg tcaagattta aaatcggaca tctccttgaa tatagataaa ataccagaaa    3180
aaaataatga ttacatgaac aaatgggcag gactcttagg tccaatttca aatcacagtt    3240
ttggaggtag cttcagaaca gcttcaaata aggaaatcaa gctctctgaa cataacatta    3300
agaagagcaa aatgttcttc aaagatattg aagaacaata tcctactagt ttagcttgtg    3360
ttgaaattgt aaataccttg gcattagata tcaaaagaa actgagcaag cctcagtcaa    3420
ttaatactgt atctgcacat ttacagagta gtgtagttgt ttctgattgt aaaaatagtc    3480
atataaccccc tcagatgtta ttttccaagc aggattttaa ttcaaaccat aatttaacac    3540
ctagccaaaa ggcagaaatt acagaacttt ctactatatt agaagaatca ggaagtcagt    3600
ttgaatttac tcagtttaga aaaccaagct acatattgca gaagagtaca tttgaagtgc    3660
ctgaaaacca gatgactatc ttaaagacca cttctgagga atgcagagat gctgatcttc    3720
atgtcataat gaatgcccca tcgattggtc aggtagacag cagcaagcaa tttgaaggta    3780
cagttgaaat taaacggaag tttgctggcc tgttgaaaaa tgactgtaac aaaagtgctt    3840
ctggttattt aacagatgaa aatgaagtgg ggtttagggg cttttattct gctcatggca    3900
caaaactgaa tgtttctact gaagctctgc aaaaagctgt gaaactgttt agtgatattg    3960
agaatattag tgaggaaact tctgcagagg tacatccaat aagtttatct tcaagtaaat    4020
gtcatgattc tgttgtttca atgtttaaga tagaaaatca taatgataaa actgtaagtg    4080
aaaaaaataa taaatgccaa ctgatattac aaaataatat tgaaatgact actggcactt    4140
ttgttgaaga aattactgaa aattacaaga gaaatactga aaatgaagat aacaaatata    4200
ctgctgccag tagaaattct cataacttag aatttgatgg cagtgattca agtaaaaatg    4260
atactgtttg tattcataaa gatgaaacgg acttgctatt tactgatcag cacaacatat    4320
```

```
gtcttaaatt atctggccag tttatgaagg agggaaacac tcagattaaa gaagatttgt    4380
cagatttaac ttttttggaa gttgcgaaag ctcaagaagc atgtcatggt aatacttcaa    4440
ataaagaaca gttaactgct actaaaacgg agcaaaatat aaaagatttt gagacttctg    4500 atacatttt tcagactgca agtgggaaaa atattagtgt cgccaaagag tcatttaata    4560
aaattgtaaa tttctttgat cagaaaccag aagaattgca taacttttcc ttaaattctg    4620
aattacattc tgacataaga aagaacaaaa tggacattct aagttatgag gaaacagaca    4680
tagttaaaca caaaatactg aaagaaagtg tcccagttgg tactggaaat caactagtga    4740
ccttccaggg acaacccgaa cgtgatgaaa agatcaaaga acctactcta ttgggttttc    4800
atacagctag cgggaaaaaa gttaaaattg caaggaatc tttggacaaa gtgaaaaacc    4860
tttttgatga aaaagagcaa ggtactagtg aaatcaccag ttttagccat caatgggcaa    4920
agaccctaaa gtacagagag gcctgtaaag accttgaatt agcatgtgag accattgaga    4980
tcacagctgc cccaaagtgt aaagaaatgc agaattctct caataatgat aaaaaccttg    5040
tttctattga gactgtggtg ccacctaagc tcttaagtga taatttatgt agacaaactg    5100
aaaatctcaa aacatcaaaa agtatctttt tgaaagttaa agtacatgaa aatgtagaaa    5160
aagaaacagc aaaaagtcct gcaacttgtt acacaaatca gtccccttat tcagtcattg    5220
aaaattcagc cttagctttt tacacaagtt gtagtgaaaa acttctgtg agtcagactt    5280 cattacttga agcaaaaaaa tggcttagag aaggaatatt tgatggtcaa ccagaaagaa    5340
taaatactgc agattatgta ggaaattatt tgtatgaaaa taattcaaac agtactatag    5400
ctgaaaatga caaaaatcat ctctccgaaa aacaagatac ttatttaagt aacagtagca    5460
tgtctaacag ctattcctac cattctgatg aggtatataa tgattcagga tatctctcaa    5520
aaaataaact tgattctggt attgagccag tattgaagaa tgttgaagat caaaaaaaca    5580 ctagttttc caaagtaata tccaatgtaa aagatgcaaa tgcataccca caaactgtaa    5640
atgaagatat ttgcgttgag gaacttgtga ctagctcttc accctgcaaa aataaaaatg    5700
cagccattaa attgtccata tctaatagta ataattttga ggtagggcca cctgcattta    5760
ggatagccag tggtaaaatc gtttgtgttt cacatgaaac aattaaaaaa gtgaaagaca    5820
tatttacaga cagtttcagt aaagtaatta aggaaaacaa cgagaataaa tcaaaaattt    5880
gccaaacgaa aattatggca ggttgttacg aggcattgga tgattcagag gatattcttc    5940
ataactctct agataatgat gaatgtagca cgcattcaca taaggttttt gctgacattc    6000
agagtgaaga aattttacaa cataaccaaa atatgtctgg attggagaaa gtttctaaaa    6060
tatcaccttg tgatgttagt ttggaaactt cagatatatg taaatgtagt atagggaagc    6120
ttcataagtc agtctcatct gcaaatactt gtgggatttt tagcacagca agtgaaaat    6180 ctgtccaggt atcagatgct tcattacaaa acgcaagaca agtgttttct gaaatagaag    6240
atagtaccaa gcaagtcttt tccaaagtat tgtttaaaag taacgaacat tcagaccagc    6300
tcacaagaga agaaaatact gctatacgta ctccagaaca tttaatatcc caaaaggct    6360 tttcatataa tgtggtaaat tcatctgctt tctctggatt tagtacagca agtgggaagc    6420
aagtttccat tttagaaagt tccttacaca agttaaggg agtgttagag gaatttgatt    6480
taatcagaac tgagcatagt cttcactatt cacctacgtc tagacaaaat gtatcaaaaa    6540
tacttcctcg tgttgataag agaaacccag agcactgtgt aaactcagaa atggaaaaaa    6600
cctgcagtaa agaatttaaa ttatcaaata acttaaatgt tgaaggtggt tcttcagaaa    6660
```

```
ataatcactc tattaaagtt tctccatatc tctctcaatt tcaacaagac aaacaacagt    6720
tggtattagg aaccaaagtg tcacttgttg agaacattca tgttttggga aaagaacagg    6780
cttcacctaa aaacgtaaaa atggaaattg gtaaaactga aacttttttct gatgttcctg   6840 tgaaaacaaa tatagaagtt tgttctactt actccaaaga ttcagaaaac tactttgaaa    6900
cagaagcagt agaaattgct aaagctttta tggaagatga tgaactgaca gattctaaac    6960
tgccaagtca tgccacacat tctcttttta catgtcccga aaatgaggaa atggttttgt    7020
caaattcaag aattggaaaa agaagaggag agccccttat cttagtggga gaaccctcaa    7080
tcaaaagaaa cttattaaat gaatttgaca ggataataga aaatcaagaa aaatccttaa    7140
aggcttcaaa aagcactcca gatggcacaa taaaagatcg aagattgttt atgcatcatg    7200
tttctttaga gccgattacc tgtgtaccct ttcgcacaac taaggaacgt caagagatac    7260
agaatccaaa ttttaccgca cctggtcaag aatttctgtc taaatctcat ttgtatgaac    7320
atctgacttt ggaaaaatct tcaagcaatt tagcagtttc aggacatcca ttttatcaag    7380
tttctgctac aagaaatgaa aaaatgagac acttgattac tacaggcaga ccaaccaaag    7440
tctttgttcc acctttttaaa actaaatcac attttcacag agttgaacag tgtgttagga    7500
atattaactt ggaggaaaac agacaaaagc aaaacattga tggacatggc tctgatgata    7560
gtaaaaataa gattaatgac aatgagaatc atcagtttaa caaaaacaac tccaatcaag    7620
cagcagctgt aactttcaca aagtgtgaag aagaaccttt agatttaatt acaagtcttc    7680
agaatgccag agatatacag gatatgcgaa ttaagaagaa acaaaggcaa cgcgtctttc    7740
cacagccagg cagtctgtat cttgcaaaaa catccactct gcctcgaatc tctctgaaag    7800
cagcagtagg aggccaagtt ccctctgcgt gttctcataa acagctgtat acgtatggcg    7860
tttctaaaca ttgcataaaa attaacagca aaaatgcaga gtcttttcag tttcacactg    7920
aagattattt tggtaaggaa agtttatgga ctggaaaagg aatacagttg gctgatggtg    7980
gatggctcat accctccaat gatggaaagg ctggaaaaga agaattttat agggctctgt    8040
gtgacactcc aggtgtggat ccaaagctta tttctagaat ttgggtttat aatcactata    8100
gatggatcat atgaaactg gcagctatgg aatgtgcctt tcctaaggaa tttgctaata    8160
gatgcctaag cccagaaagg gtgcttcttc aactaaaata cagatatgat acggaaattg    8220
atagaagcag aagatcggct ataaaaaaga taatggaaag ggatgacaca gctgcaaaaa    8280
cacttgttct ctgtgtttct gacataattt cattgagcgc aaatatatct gaaacttcta    8340
gcaataaaac tagtagtgca gatacccaaa aagtggccat tattgaactt acagatgggt    8400
ggtatgctgt taaggcccag ttagatcctc ccctcttagc tgtcttaaag aatggcagac    8460
tgacagttgg tcagaagatt attcttcatg gagcagaact ggtgggctct cctgatgcct    8520
gtacacctct tgaagcccca gaatctctta tgttaaagat ttctgctaac agtactcggc    8580
ctgctcgctg gtataccaaa cttggattct ttcctgaccc tagaccttt cctctgccct    8640 tatcatcgct tttcagtgat ggaggaaatg ttggttgtgt tgatgtaatt attcaaagag    8700 catacccta acagtggatg gagaagacat catctggatt atacatattt cgcaatgaaa    8760
gagaggaaga aaaggaagca gcaaaatatg tggaggccca acaaaagaga ctagaagcct    8820
tattcactaa aattcaggag gaatttgaag aacatgaaga aaacacaaca aaaccatatt    8880
taccatcacg tgcactaaca agacagcaag ttcgtgcttt gcaagatggt gcagagcttt    8940
atgaagcagt gaagaatgca gcagacccag cttaccttga gggttatttc agtgaagagc    9000
agttaagagc cttgaataat cacaggcaaa tgttgaatga taagaaacaa gctcagatcc    9060
```

```
agttggaaat taggaaggcc atggaatctg ctgaacaaaa ggaacaaggt ttatcaaggg    9120
atgtcacaac cgtgtggaag ttgcgtattg taagctattc aaaaaaagaa aaagattcag    9180
ttatactgag tatttggcgt ccatcatcag atttatattc tctgttaaca gaaggaaaga    9240
gatacagaat ttatcatctt gcaacttcaa aatctaaaag taaatctgaa agagctaaca    9300
tacagttagc agcgacaaaa aaaactcagt atcaacaact accggtttca gatgaaattt    9360
tatttcagat ttaccagcca cgggagcccc ttcacttcag caaattttta gatccagact    9420
ttcagccatc ttgttctgag gtggacctaa taggatttgt cgtttctgtt gtgaaaaaaa    9480
caggacttgc ccctttcgtc tatttgtcag acgaatgtta caatttactg gcaataaagt    9540
tttggataga ccttaatgag gacattatta agcctcatat gttaattgct gcaagcaacc    9600
tccagtggcg accagaatcc aaatcaggcc ttcttacttt atttgctgga gattttctg    9660 tgttttctgc tagtccaaaa gagggccact ttcaagagac attcaacaaa atgaaaaata    9720
ctgttgagaa tattgacata ctttgcaatg aagcagaaaa caagcttatg catatactgc    9780
atgcaaatga tcccaagtgg tccaccccaa ctaaagactg tacttcaggg ccgtacactg    9840
ctcaaatcat tcctggtaca ggaaacaagc ttctgatgtc ttctcctaat tgtgagatat    9900
attatcaaag tcctttatca ctttgtatgg ccaaaaggaa gtctgtttcc acacctgtct    9960
cagcccagat gacttcaaag tcttgtaaag gggagaaaga gattgatgac caaaagaact    10020
gcaaaaagag aagagccttg gatttcttga gtagactgcc tttacctcca cctgttagtc    10080
ccatttgtac atttgtttct ccggctgcac agaaggcatt tcagccacca aggagttgtg    10140
gcaccaaata cgaaacaccc ataaagaaaa aagaactgaa ttctcctcag atgactccat    10200
ttaaaaaatt caatgaaatt tctcttttgg aaagtaattc aatagctgac gaagaacttg    10260
cattgataaa tacccaagct cttttgtctg gttcaacagg agaaaaacaa tttatatctg    10320
tcagtgaatc cactaggact gctcccacca gttcagaaga ttatctcaga ctgaaacgac    10380
gttgtactac atctctgatc aaagaacagg agagttccca ggccagtacg gaagaatgtg    10440
agaaaaataa gcaggacaca attacaacta aaaaatatat ctaagcattt gcaaaggcga    10500
caataaatta ttgacgctta accttttccag tttataagac tggaatataa tttcaaacca    10560
cacattagta cttatgttgc acaatgagaa aagaaattag tttcaaattt acctcagcgt    10620
ttgtgtatcg ggcaaaaatc gttttgcccg attccgtatt ggtatacttt tgcttcagtt    10680
gcatatctta aaactaaatg taatttatta actaatcaag aaaaacatct ttggctgagc    10740
tcggtggctc atgcctgtaa tcccaacact ttgagaagct gaggtgggag gagtgcttga    10800
ggccaggagt tcaagaccag cctgggcaac atagggagac ccccatcttt acaaagaaaa    10860 aaaaagggg aaaagaaaat cttttaaatc tttggatttg atcactacaa gtattatttt    10920
acaagtgaaa taaacatacc attttctttt agattgtgtc attaaatgga atgaggtctc    10980
ttagtacagt tattttgatg cagataattc cttttagttt agctactatt ttaggggatt    11040
ttttttagag gtaactcact atgaaatagt tctccttaat gcaaatatgt tggttctgct    11100
atagttccat cctgttcaaa agtcaggatg aatatgaaga gtggtgtttc cttttgagca    11160
attcttcatc cttaagtcag catgattata agaaaaatag aaccctcagt gtaactctaa    11220 ttcctttta ctattccagt gtgatctctg aaattaaatt acttcaacta aaaattcaaa    11280
tactttaaat cagaagattt catagttaat ttatttttt tttcaacaaa atggtcatcc    11340
aaactcaaac ttgagaaaat atcttgcttt caaattggca ctgatt                  11386
```

<210> SEQ ID NO 5
<211> LENGTH: 340
<212> TYPE: PRT
<213> ORGANISM: Homo sapiens

<400> SEQUENCE: 5

Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
    50                  55                  60

Gly Ile Ser Glu Ala Lys Ala Asp Lys Ile Leu Thr Glu Ser Arg Ser
65                  70                  75                  80

Val Ala Arg Leu Glu Cys Asn Ser Val Ile Leu Val Tyr Cys Thr Leu
                85                  90                  95

Arg Leu Ser Gly Ser Ser Asp Ser Pro Ala Ser Ala Ser Arg Val Val
            100                 105                 110

Gly Thr Thr Gly Gly Ile Glu Thr Gly Ser Ile Thr Glu Met Phe Gly
        115                 120                 125

Glu Phe Arg Thr Gly Lys Thr Gln Ile Cys His Thr Leu Ala Val Thr
    130                 135                 140

Cys Gln Leu Pro Ile Asp Arg Gly Gly Gly Glu Gly Lys Ala Met Tyr
145                 150                 155                 160

Ile Asp Thr Glu Gly Thr Phe Arg Pro Glu Arg Leu Leu Ala Val Ala
                165                 170                 175

Glu Arg Tyr Gly Leu Ser Gly Ser Asp Val Leu Asp Asn Val Ala Tyr
            180                 185                 190

Ala Arg Ala Phe Asn Thr Asp His Gln Thr Gln Leu Leu Tyr Gln Ala
        195                 200                 205

Ser Ala Met Met Val Glu Ser Arg Tyr Ala Leu Leu Ile Val Asp Ser
    210                 215                 220

Ala Thr Ala Leu Tyr Arg Thr Asp Tyr Ser Gly Arg Gly Glu Leu Ser
225                 230                 235                 240

Ala Arg Gln Met His Leu Ala Arg Phe Leu Arg Met Leu Leu Arg Leu
                245                 250                 255

Ala Asp Glu Phe Gly Val Ala Val Ile Thr Asn Gln Val Val Ala
            260                 265                 270

Gln Val Asp Gly Ala Ala Met Phe Ala Ala Asp Pro Lys Lys Pro Ile
        275                 280                 285

Gly Gly Asn Ile Ile Ala His Ala Ser Thr Thr Arg Leu Tyr Leu Arg
    290                 295                 300

Lys Gly Arg Gly Glu Thr Arg Ile Cys Lys Ile Tyr Asp Ser Pro Cys
305                 310                 315                 320

Leu Pro Glu Ala Glu Ala Met Phe Ala Ile Asn Ala Asp Gly Val Gly
                325                 330                 335

Asp Ala Lys Asp
            340

<210> SEQ ID NO 6
<211> LENGTH: 2147
<212> TYPE: DNA
<213> ORGANISM: Homo sapiens

<400> SEQUENCE: 6

```
gaaagccgct ggcggaccgc gcgcagcggc cagagaccga gccctaagga gagtgcggcg      60
cttcccgagg cgtgcagctg ggaactgcaa ctcatctggg ttgtgcgcag aaggctgggg     120
caagcgagta gagaagtgga gctaatggca atgcagatgc agcttgaagc aaatgcagat     180
acttcagtgg aagaagaaag ctttggccca caacccatttt cacggttaga gcagtgtggc     240
ataaatgcca acgatgtgaa gaaattggaa gaagctggat ccatactgt ggaggctgtt     300
gcctatgcgc caagaagga gctaataaat attaagggaa ttagtgaagc caaagctgat     360
aaaattctga cggagtctcg ctctgttgcc aggctggagt gcaatagcgt gatcttggtc     420
tactgcaccc tccgcctctc aggttcaagt gattctcctg cctcagcctc ccgagtagtt     480
gggactacag gtggaattga gactggatct atcacagaaa tgtttggaga attccgaact     540
gggaagaccc agatctgtca tacgctagct gtcacctgcc agcttcccat tgaccgggt     600
ggaggtgaag gaaaggccat gtacattgac actgagggta cctttaggcc agaacggctg     660
ctggcagtgg ctgagaggta tggtctctct ggcagtgatg tcctggataa tgtagcatat     720
gctcgagcgt tcaacacaga ccaccagacc cagctccttt atcaagcatc agccatgatg     780
gtagaatcta ggtatgcact gcttattgta gacagtgcca ccgcccttta cagaacagac     840
tactcgggtc gaggtgagct ttcagccagg cagatgcact tggccaggtt tctgcggatg     900
cttctgcgac tcgctgatga gtttggtgta gcagtggtaa tcactaatca ggtggtagct     960
caagtggatg gagcagcgat gtttgctgct gatcccaaaa aacctattgg aggaaatatc    1020
atcgcccatg catcaacaac cagattgtat ctgaggaaag gaagagggga aaccagaatc    1080
tgcaaaatct acgactctcc ctgtcttcct gaagctgaag ctatgttcgc cattaatgca    1140
gatggagtgg gagatgccaa agactgaatc attgggtttt tcctctgtta aaaaccttaa    1200
gtgctgcagc ctaatgagag tgcactgctc cctggggttc tctacaggcc tcttcctgtt    1260
gtgactgcca ggataaagct tccgggaaaa cagctattat atcagctttt ctgatggtat    1320
aaacaggaga caggtcagta gtcacaaact gatctaaaat gtttattcct tctgtagtgt    1380
attaatctct gtgtgttttc tttggttttg gaggagggg atgaagtatc tttgacatgg    1440
tgccttagga atgacttggg tttaacaagc tgtctactgg acaatcttat gtttccaaga    1500
gaactaaagc tggagagacc tgaccttct ctcacttcta aattaatggt aaaataaaat    1560
gcctcagcta tgtagcaaag ggaatgggtc tgcacagatt ctttttttct gtcagtaaaa    1620
ctctcaagca ggttttaag ttgtctgtct gaatgatctt gtgtaaggtt ttggttatgg    1680
agtcttgtgc caaacctact aggccattag cccttcacca tctacctgct tggtctttca    1740
ttgctaagac taactcaaga taatcctaga gtcttaaagc atttcaggcc agtgtggtgt    1800
cttgcgcctg tactcccagc actttgggag gccgaggcag gtggatcgct tgagcccagg    1860
agttttaagt ccagcttggc caaggtggtg aaatcccatc tctacaaaaa atgcagaact    1920
taatctggac acactgttac acgtgcctgt agtcccagct actcgatagc ctgaggtggg    1980
agaatcactt aagcctggaa ggtggaagtt gcagtgagtc gagattgcac tgctgcattc    2040
cagccaggg gacagagtga gaccatgttt caaacaagaa acatttcaga gggtaagtaa    2100
acagatttga ttgtgaggct tctaataaag tagttattag tagtgaa                  2147
```

<210> SEQ ID NO 7
<211> LENGTH: 18
<212> TYPE: DNA

```
<213> ORGANISM: Unknown
<220> FEATURE:
<223> OTHER INFORMATION: Description of Unknown:
      I-SceI rare cutting endonuclease site sequence

<400> SEQUENCE: 7
tagggataac agggtaat                                                    18

<210> SEQ ID NO 8
<211> LENGTH: 15
<212> TYPE: DNA
<213> ORGANISM: Unknown
<220> FEATURE:
<223> OTHER INFORMATION: Description of Unknown:
      I-PpoI rare cutting endonuclease site sequence

<400> SEQUENCE: 8
ctctcttaag gtagc                                                       15

<210> SEQ ID NO 9
<211> LENGTH: 23
<212> TYPE: DNA
<213> ORGANISM: Escherichia coli

<400> SEQUENCE: 9
aattagtatg ttgtaactaa agt                                              23

<210> SEQ ID NO 10
<211> LENGTH: 23
<212> TYPE: DNA
<213> ORGANISM: Escherichia coli

<400> SEQUENCE: 10
aataagtatg ttgtaactaa agt                                              23

<210> SEQ ID NO 11
<211> LENGTH: 23
<212> TYPE: DNA
<213> ORGANISM: Escherichia coli

<400> SEQUENCE: 11
atataggatg ttgtaactaa tat                                              23

<210> SEQ ID NO 12
<211> LENGTH: 14
<212> TYPE: DNA
<213> ORGANISM: Escherichia coli
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 12
gnrngttgta ayka                                                        14

<210> SEQ ID NO 13
<211> LENGTH: 23
<212> TYPE: DNA
<213> ORGANISM: Escherichia coli

<400> SEQUENCE: 13
cgatcgtatg ttgtaactat ctc                                              23
```

```
<210> SEQ ID NO 14
<211> LENGTH: 23
<212> TYPE: DNA
<213> ORGANISM: Escherichia coli

<400> SEQUENCE: 14
aacatggaag ttgtaactaa ccg                                              23

<210> SEQ ID NO 15
<211> LENGTH: 23
<212> TYPE: DNA
<213> ORGANISM: Escherichia coli

<400> SEQUENCE: 15
cattagtatg ttgtaactaa atg                                              23

<210> SEQ ID NO 16
<211> LENGTH: 23
<212> TYPE: DNA
<213> ORGANISM: Escherichia coli

<400> SEQUENCE: 16
gtcaaggatg ttgtaactaa cca                                              23

<210> SEQ ID NO 17
<211> LENGTH: 23
<212> TYPE: DNA
<213> ORGANISM: Escherichia coli

<400> SEQUENCE: 17
ttaaagtatg ttgtaactaa gca                                              23

<210> SEQ ID NO 18
<211> LENGTH: 23
<212> TYPE: DNA
<213> ORGANISM: Escherichia coli

<400> SEQUENCE: 18
cgattgagag ttgtaatgaa gtc                                              23

<210> SEQ ID NO 19
<211> LENGTH: 23
<212> TYPE: DNA
<213> ORGANISM: Escherichia coli

<400> SEQUENCE: 19
ccttcgtatg ttgtaacgac gat                                              23

<210> SEQ ID NO 20
<211> LENGTH: 23
<212> TYPE: DNA
<213> ORGANISM: Escherichia coli

<400> SEQUENCE: 20
acgcagtaag ttgtaactaa tgc                                              23

<210> SEQ ID NO 21
<211> LENGTH: 23
<212> TYPE: DNA
<213> ORGANISM: Escherichia coli

<400> SEQUENCE: 21
```

```
tatgggtacg ttgtaattag gga                                              23
```

<210> SEQ ID NO 22
<211> LENGTH: 23
<212> TYPE: DNA
<213> ORGANISM: Escherichia coli

<400> SEQUENCE: 22

```
gcactgggtg ttgtaatgac gca                                              23
```

<210> SEQ ID NO 23
<211> LENGTH: 23
<212> TYPE: DNA
<213> ORGANISM: Escherichia coli

<400> SEQUENCE: 23

```
tacccgcagg ttgtaacgag agc                                              23
```

<210> SEQ ID NO 24
<211> LENGTH: 309
<212> TYPE: PRT
<213> ORGANISM: Escherichia coli

<400> SEQUENCE: 24

Met Ala Arg Tyr Asp Leu Val Asp Arg Leu Asn Thr Thr Phe Arg Gln
1               5                   10                  15

Met Glu Gln Glu Leu Ala Ile Phe Ala Ala His Leu Glu Gln His Lys
            20                  25                  30

Leu Leu Val Ala Arg Val Phe Ser Leu Pro Glu Val Lys Lys Glu Asp
        35                  40                  45

Glu His Asn Pro Leu Asn Arg Ile Glu Val Lys Gln His Leu Gly Asn
    50                  55                  60

Asp Ala Gln Ser Leu Ala Leu Arg His Phe Arg His Leu Phe Ile Gln
65                  70                  75                  80

Gln Gln Ser Glu Asn Arg Ser Ser Lys Ala Ala Val Arg Leu Pro Gly
                85                  90                  95

Val Leu Cys Tyr Gln Val Asp Asn Leu Ser Gln Ala Ala Leu Val Ser
            100                 105                 110

His Ile Gln His Ile Asn Lys Leu Lys Thr Thr Phe Glu His Ile Val
        115                 120                 125

Thr Val Glu Ser Glu Leu Pro Thr Ala Ala Arg Phe Glu Trp Val His
    130                 135                 140

Arg His Leu Pro Gly Leu Ile Thr Leu Asn Ala Tyr Arg Thr Leu Thr
145                 150                 155                 160

Val Leu His Asp Pro Ala Thr Leu Arg Phe Gly Trp Ala Asn Lys His
                165                 170                 175

Ile Ile Lys Asn Leu His Arg Asp Glu Val Leu Ala Gln Leu Glu Lys
            180                 185                 190

Ser Leu Lys Ser Pro Arg Ser Val Ala Pro Trp Thr Arg Glu Glu Trp
        195                 200                 205

Gln Arg Lys Leu Glu Arg Glu Tyr Gln Asp Ile Ala Ala Leu Pro Gln
    210                 215                 220

Asn Ala Lys Leu Lys Ile Lys Arg Pro Val Lys Val Gln Pro Ile Ala
225                 230                 235                 240

Arg Val Trp Tyr Lys Gly Asp Gln Lys Gln Val Gln His Ala Cys Pro
                245                 250                 255

Thr Pro Leu Ile Ala Leu Ile Asn Arg Asp Asn Gly Ala Gly Val Pro

```
            260                 265                 270
Asp Val Gly Glu Leu Leu Asn Tyr Asp Ala Asp Asn Val Gln His Arg
        275                 280                 285

Tyr Lys Pro Gln Ala Gln Pro Leu Arg Leu Ile Ile Pro Arg Leu His
    290                 295                 300

Leu Tyr Val Ala Asp
305
```

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
catcaaggaa accctggact actg                                          24

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctcggctag gtaggggatc                                               20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctgggtagtt tgtaagcatc c                                             21

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caataaactg ctggtctcag gc                                            22

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggaaatggca acttgcctag                                               20

<210> SEQ ID NO 30
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctgcgagcag tcttcagaaa g                                              21

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttccgtggtg aaggagctt                                                 19

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tggctgcacg atcacaac                                                  18

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcctggacag aagacagca                                                 19

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cagtcccaca tcacaagacg                                                20

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ

<400> SEQUENCE: 35
cgctcaccca tgacacaggt gc                                             22
```

```
<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' BHQ

<400> SEQUENCE: 36
tgcacagctg cccaatatct ggg                                           23

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
atgagctgga gaggatgctg                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctgggcagtt gctgtcttct                                               20

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggtgctcatc tagttgtgat cg                                            22

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctgtaccagg taggcatcca                                               20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
```

-continued agcctaggtg tccagctgtc                                          20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctgcaatcac ctggcttagt t                                        21

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tctgccactg tgaaaaatgc                                          20

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcaagctggg ctgaagatt                                           19

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtgggacgac tggaatgagg                                          20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gcaccttttg gtgtctctgg                                          20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggatggacca tgcagcaaga                                                       20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccattcaaac cgaagggcg                                                        19

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aggccagagg aatgcctgaa                                                       20

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccagtcatct ccatcctcta cc                                                    22

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tggtcagaat tcaggttggc                                                       20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tttcaggacg tcagtcagcg                                                       20

<210> SEQ ID NO 53
<211> LENGTH: 15438
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (382)..(382)
<223> OTHER INFORMATION: a, c, t, g, unknown or other

<400> SEQUENCE: 53

```
ccccgcggca ggccctccga gcgtggtgga gccgttctgt gagacagccg ggtacgagtc      60
gtgacgctgg aagggcaag cgggtggtgg gcaggaatgc ggtccgccct gcagcaaccg     120
gagggggagg gagaagggag cggaaaagtc tccaccggac gcggccatgg ctcggggggg     180
ggggggcagc ggaggascgc ttccggccga cgtctcgtcg ctgattggct tyttttcctc     240
ccgccgtgtg tgaaaacaca aatggcgtgt tttggttggc gtaaggcgcc tgtcagttaa     300
cggcagccgg agtgcgcagc cgccggcagc ctcgctctgc ccactgggtg ggcgggagg      360
taggtggggt gaggcgagct gnacgtgcgg gcgcggtcgg cctctggcgg ggcggggag      420
gggagggagg gtcagcgaaa gtagctcgcg cgcgagcggc cgcccaccct cccccttcctc    480
tgggggagtc gttttacccg ccgcggccg ggcctcgtcg tctgattggc tctcggggcc      540
cagaaaactg gcccttgcca ttggctcgtg ttcgtgcaag ttgagtccat ccgccggcca     600
gcggggcgcg cgaggaggcg ctcccaggtt ccggccctcc cctcggcccc cgccgcaga      660
gtctggccgc gcgcccctgc gcaacgtggc aggaagcgcg cgctgggggc gggacgggc      720
agtagggctg agcggctgcg gggcgggtgc aagcacgttt ccgacttgag ttgcctcaag     780
aggggcgtgc tgagccagac ctccatcgcg cactccgggg agtggaggga aggagcgagg     840
gctcagttgg gctgttttgg aggcaggaag cacttgctct cccaaagtcg ctctgagttg     900
ttatcagtaa gggagctgca gtggagtagg cggggagaag gccgcaccct tctccggagg     960
ggggagggga gtgttgcaat acctttctgg gagttctctg ctgcctcctg gcttctgagg    1020
accgccctgg gcctgggaga atcccttgcc ccctcttccc ctcgtgatct gcaactccag    1080
tctttctagc cttaattaag ggatctgtag ggcgcagtag tccagggttt ccttgatgat    1140
gtcatactta tcctgtccct ttttttttcca cagctcgcgg ttgaggacaa actcttcgcg    1200
gtctttccag tggggatcga cggtatcgta gagtcgaggc cgctctagaa ctagtggatc    1260
taccatgacc gagtacaagc ccacggtgcg cctcgccacc cgcgacgacg tccccgggc     1320
cgtacgcacc ctcgccgccg cgttcgccga ctaccccgcc acgcgccaca ccgtcgaccc    1380
ggaccgccac atcgagcggg tcaccgagct gcaagaactc ttcctcacgc gcgtcgggct    1440
cgacatcggc aaggtgtggg tcgcggacga cggcgccgcg gtggcggtct ggaccacgcc    1500
ggagagcgtc gaagcggggg cggtgttcgc cgagatcggc ccgcgcatgg ccgagttgag    1560
cggttcccgg ctggccgcgc agcaacagat ggaaggcctc ctggcgccgc accggcccaa    1620
ggagcccgcg tggttcctgg ccaccgtcgg cgtctcgccc gaccaccagg caagggtct     1680
gggcagcgcc gtcgtgctcc ccggagtgga ggcggccgag cgcgccgggg tgcccgcctt    1740
cctggagacc tccgcgcccc gcaacctccc cttctacgag cggctcggct tcaccgtcac    1800
cgccgacgtc gagtgcccga aggaccgcgc gacctggtgc atgacccgca agcccggtgc    1860
ctgactcgac cctaggggga ggctaactga aacacgaag gagacaatac cggaaggaac     1920
ccgcgctatg acggcaataa aaagacagaa taaaacgcac ggtgttgggt cgtttgttca    1980
taaacgcggg gttcggtccc agggctggca ctctgtcgat accccaccga gaccccattg    2040
gggccaatac gcccgcgttt cttcctttc cccaccccac cccccaagtt cgggtgaagg     2100
cccagggctc gcagccaacg tcggggcggc aggccctgcc atagcctcag gttactcgga    2160
tctcgacctc gagggcccc cgcggggtggg gaagatctcg gggtgccat cctggtcgag     2220
ctggacggcg acgtaaacgg ccacaagttc agcgtgtccg gcgagggcga gggcgatgcc    2280
```

-continued

```
acctacggca agctgaccct gaagttcatc tgcaccaccg gcaagctgcc cgtgccctgg    2340
cccaccctcg tgaccaccct gacctacggc gtgcagtgct tcagccgcta ccccgaccac    2400
atgaagcagc acgacttctt caagtccgcc atgcccgaag gctacgtcca ggagcgcacc    2460
atcttcttca aggacgacgg caactacaag acccgcgccg aggtgaagtt cgagggcgac    2520
accctggtga accgcatcga gctgaagggc atcgacttca aggaggacgg caacatcctg    2580
gggcacaagc tggagtacaa ctacaacagc cacaacgtct atatcatggc cgacaagcag    2640
aagaacggca tcaaggtgaa cttcaagatc cgccacaaca tcgaggacgg cagcgtgcag    2700
ctcgccgacc actaccagca gaacacccc atcggcgacg gccccgtgct gctgcccgac    2760
aaccactacc tgagcaccca gtccgccctg agcaaagacc ccaacgagaa gcgcgatcac    2820
atggtcctgc tggagttcgt gaccgccgcc gggatcactc tcggcatgga cgagctgtac    2880
aagtaaagcg gccgcgactc tagatcataa tcagccatac cacatttgta gaggttttac    2940
ttgctttaaa aaacctccca cacctccccc tgaacctgaa acataaaatg aatgcaattg    3000
ttgttgttaa cttgtttatt gcagcttata atggttacaa ataaagcaat agcatcacaa    3060
atttcacaaa taaagcattt ttttcactgc attctagttg tggtttgtcc aaactcatca    3120 atgtcggat cccgccaatt gtctagattt ctctaatcac ttttttttca aggcaatcag    3180
ggtatattat attgtacttc agcacagttt tagagaacaa ttgttataat taaatgataa    3240
ggtagaatat ttctgcatat aaattctggc tggcgtggaa atattcttat tggtagaaac    3300
aactacatcc tggtcatcat cctgcctttc tctttatggt tacaatgata tacactgttt    3360
gagatgagga taaatactc tgagtccaaa ccgggcccct ctgctaacca tgttcatgcc    3420
ttcttctttt tcctacagga ctcctccctg caggacggcg agttcatcta caaggtgaag    3480
ctgcgcggca ccaacttccc ctccgacggc ccgtaatgc agaagaagac catgggctgg    3540
gaggcctcct ccgagcggat gtaccccgag gacggcgccc tgaagggcga gatcaagatg    3600
aggctgaagc tgaaggacgg tggccactac gacgccgagg tcaagaccac ctacatggcc    3660
aagaagcccg tgcagctgcc cggcgcctac aagaccgaca tcaagctgga catcacctcc    3720
cacaacgagg actacaccat cgtggaacag tacgagcgcg ccgagggccg ccactccacc    3780
ggcggtatgg atgaactcta taataagca cgggccctat tctatagtgt cacctaaatg    3840
ctagagctcg ctgatcagcc tcgactgtgc cttctagttg ccagccatct gttgtttgcc    3900 cctccccgt gccttccttg accctggaag gtgccactcc cactgtcctt tcctaataaa    3960
atgaggaaat tgcatcgcat tgtctgagta ggtgtcattc tattctgggg ggtggggtgg    4020
ggcaggacag caaggggag gattgggaag acaatagcag gcatgctggg gaggatctgt    4080
gtggaaagtc cccaggctcc ccaggcaggc agaagtatgc aaagcatgca tctcaattag    4140
tcagcaacca ggtgtggaaa gtccccaggc tccccagcag gcagaagtat gcaaagcatg    4200
catctcaatt agtcagcaac catagtcccg cccctaactc cgcccatccc gcccctaact    4260
ccgcccagtt ccgcccattc tccgcccat ggctgactaa ttttttttat ttatgcagag    4320
gccgaggccg cctctgcctc tgagctattc cagaagtagt gaggaggctt ttttggaggc    4380
ctaggctttt gcaaaaagct cccgggagct tgtatatcca ttttcggata gcttaacta    4440 aaccatggta tcaaaggtg aagaaaacaa tatggcagtc atcaaggagt tcatgcgctt    4500
caaggtgcgc atggagggct ccgtgaacgg ccacgagttc gagatcgagg gcgagggcga    4560
gggccgcccc tacgagggca cccagaccgc caagctgaag gtgaccgagg gtggcccct    4620 gcccttcgcc tgggacatcc tgtcccctca gttcatgtac ggctccaagg cctacgtgaa    4680
```

```
gcaccccgcc gacatcccc g actacttgaa gctgtccttc cccgagggct tcaagtggga    4740
gcgcgtgatg aacttcgagg acggcggcgt ggtgaccgtg acccaggtga gtttggggac    4800
ccttgattgt tctttctttt tcgctattgt aaaattcatg ttatatggag ggggcaaagt    4860
tttcagggtg ttgtttagaa tgggaagatg tcccttgtat caccatggac cctcatgata    4920
attttgtttc tttcactttc tactctgttg acaaccattg tctcctctta ttttcttttc    4980
attttctgta acttttcgt taaactttag cttgcatttg taacgaattt ttaaattcac     5040
ttttgtttat ttgtcagatt gtaagtaccg ggacccggaa ttctaccggg taggggaggc    5100
gcttttccca aggcagtctg gagcatgcgc tttagcagcc ccgctggcac ttggcgctac    5160
acaagtggcc tctggcctcg cacacattcc acatccaccg gtagcgccaa ccggctccgt    5220
tctttggtgg ccccttcgcg ccacttctac tcctccccta gtcaggaagt ttcccccagc    5280
aagctcgcgt cgtgcaggac gtgacaaatg gaagtagcac gtctcactag tctcgtgcag    5340
atggacagca ccgctgagca atggaagcgg gtaggccttt ggggcagcgg ccaatagcag    5400
ctttgttcct tcgctttctg ggctcagagg ctgggaaggg gtgggtccgg gggcgggctc    5460
aggggcgggc tcaggggcgg gcgggcgccc gaaggtcctc ccgaggcccg gcattctgca    5520
cgcttcaaaa gcgcacgtct gccgcgctgt tctcctcttc ctcatctccg ggcctttcga    5580
cctgcagccc aagctctagc gctaccggtc gccaccatgg tgagcaaggg cgaggagctg    5640
ttcaccgggg tggtgcccat cctggtcgag ctggacggcg acgtaaacgg ccacaagttc    5700
agcgtgtccg gcgagggcga gggcgatgcc acctacggca agctgaccct gaagttcatc    5760
tgcaccaccg gcaagctgcc cgtgccctgg cccaccctcg tgaccaccct gacctacggc    5820
gtgcagtgct tcagccgcta ccccgaccac atgaagcagc acgacttctt caagtccgcc    5880
atgcccgaag gctacgtcca ggagcgcacc atcttcttca aggacgacgg caactacaag    5940
acccgcgccg aggtgaagtt cgagggcgac accctggtga accgcatcga gctgaagggc    6000
atcgtaggga taacagggta atcaaggagg acggcaacat cctggggcac aagctggagt    6060
acaactacaa cagccacaac gtctatatca tggccgacaa gcagaagaac ggcatcaagg    6120
tgaacttcaa gatccgccac aacatcgagg acggcagcgt gcagctcgcc gaccactacc    6180
agcagaacac ccccatcggc gacggccccg tgctgctgcc cgacaaccac tacctgagca    6240
cccagtccgc cctgagcaaa gaccccaacg agaagcgcga tcacatggtc ctgctggagt    6300
tcgtgaccgc cgccgggatc actctcggca tggacgagct gtacaagtaa gcggccgcg     6360 actctagatc ataatcagcc ataccacatt tgtagaggtt ttacttgctt taaaaaacct    6420
cccacacctc ccctgaaccc tgaaacataa aatgaatgca attgttgttg ttaacttgtt    6480
tattgcagct tataatggtt acaaataaag caatagcatc acaaatttca caaataaagc    6540
atttttttca ctgcattcta gttgtggttt gtccaaactc atcaatgtcg gatggccgcg    6600
ctggggatgc ggtgggctct atggcttatg aggcggaaag aaccagctgg ggctcgatcc    6660
tctagttggc gcgccggcta aagatgggc gggagtcttc tgggcaggct taaaggctaa    6720
cctggtgtgt gggcgttgtc ctgcagggga attgaacagg tgtaaaattg gagggacaag    6780
acttcccaca gattttcggt tttgtcggga agttttttaa taggggcaaa taggaaaatg    6840
gaggatagga gtcatctggg gtttatgcag caaaactaca ggtatattgc ttgtatccgc    6900
ctcggagatt tccatgagga gataaagaca tgtcacccga gtttatactc tcctgcttag    6960
atcctactac agtatgaaat acagtgtygc gaggtagact atgtaagcag atttaatcat    7020
```

```
tttaaagagc ccagtacttc atatccattt ctcccgctcc ttctgcagcc ttatcaaaag    7080
gtatttagaa cactcatttt agccccattt tcatttatta tactggctta tccaacccct    7140
agacagagca ttggcatttt cccttccctg atcttagaag tctgatgact catgaaacca    7200
gacagattag ttacatacac cacaaatcga ggctgtagct ggggcctcaa cactgcagtt    7260
cttttataac tccttagtac actttttgtt gatcctttgc cttgatcctt aattttcagt    7320
gtctatcacc tctcccgtca ggtggtgttc cacatttggg cctattctca gtccagggag    7380
ttttacaaca atagatgtat tgagaatcca acctaaagct taactttcca ctcccatgaa    7440
tgcctctctc cttttctcc attataactg agctatwacc attaatggtt tcaggtggat     7500
gtctcctccc ccaatatacc tgatgtatct acatattgcc aggctgatat tttaagacat    7560
waaaggtata tttcattatt gagccacatg gtattgatta ctgctactaa aattttgtca    7620
ttgtacacat ctgtaaaagg tggttccttt tggaatgcaa agttcaggtg tttgttgtct    7680
ttcctgacct aaggtcttgt gagcttgtat ttttctatt taagcagtgc tttctcttgg     7740
actggcttga ctcatggcat tctacacgtt attgctggtc taaatgtgat tttgccaagc    7800
ttcttcagga cctataattt tgcttgactt gtagccaaac acaagtaaaa tgattaagca    7860
acaaatgtat ttgtgaagct tggttttag gttgttgtgt tgtgtgtgct tgtgctctat     7920
aataatacta tccaggggct ggagaggtgg ctcggagttc aagagcacag actgctcttc    7980
cagaagtcct gagttcaatt cccagcaacc acatggtggc tcacaaccat ctgtaatggg    8040
atctgatgcc ctcttctggt gtgtctgaag accacaagtg tattcacatt aaataaataa    8100
tcctccttct tcttcttttt ttttttttaa agagaatwct gtctccagta gaattactga    8160
agtaatgaaa tactttgtgt ttgttccaat atggwagcca ataatcaaat actcttwagc    8220
actggaaatg taccaaggaa ctattttatt taagtgwact gtggacagag gagccataac    8280
tgcagacttg tgggatacag aagaccaatg cagacttaat gtcttttctc ttacactaag    8340
caataaagaa ataaaaattg aacttctagt atcctatttg ttaaactgct agctttacta    8400
acttttgtgc ttcatctata caaagctgaa agctaagtct gcagccatta ctaaacatga    8460
aagcaagtaa tgataatttt ggatttcaaa aatgtagggc cagagtttag ccagccagtg    8520
gtggtgcttg cctttatgcc ttaatcccag cactctggag gcagagacag gcagatctct    8580
gagtttgagc ccagcctggt ctacacatca agttctatct aggatagcca ggaatacaca    8640
cagaaaccct gttggggagg ggggctctga gatttcataa aattataatt gaagcattcc    8700
ctaatgagcc actatggatg tggctaaatc cgtctacctt tctgatgaga tttgggtatt    8760
attttttctg tctctgctgt tggttgggtc ttttgacact gtgggctttc ttaaagcctc    8820
cttccctgcc atgtggtctc ttgtttgcta ctaacttccc atggcttaaa tggcatggct    8880
ttttgccttc taagggcagc tgctgagwtt tgcagcctga tttccagggt ggggttggga    8940
aatctttcaa acactaaaat tgtcctttaa tttttttta aaaaatgggt tatataataa    9000
acctcataaa atagttatga ggagtgaggt ggactaatat taatgagtcc ctcccctata    9060
aaagagctat taaggctttt tgtcttatac taactttttt tttaaatgtg gtatctttag    9120
aaccaagggt cttagagttt tagtatacag aaactgttgc atcgcttaat cagattttct    9180
agtttcaaat ccagagaatc caaattcttc acagccaaag tcaaattaag aatttctgac    9240
tttaatgtta tttgctactg tgaatataaa atgatagctt ttcctgaggc agggtctcac    9300
tatgtatctc tgcctgatct gcaacaagat atgtagacta aagttctgcc tgcttttgtc    9360
tcctgaatac taaggttaaa atgtagtaat acttttggaa cttgcaggtc agattctttt    9420
```

```
ataggggaca cactaaggga gcttgggtga tagttggtaa atgtgtttaa gtgatgaaaa    9480
cttgaattat tatcaccgca acctactttt taaaaaaaaa agccaggcct gttagagcat    9540
gctaagggat ccctaggact tgctgagcac acaagagtag tacttggcag gctcctggtg    9600
agagcatatt tcaaaaaaca aggcagacaa ccaagaaact acagtaaggt tacctgtctt    9660
taaccatctg catatacaca gggatattaa aatattccaa ataatatttc attcaagttt    9720
tcccccatca aattgggaca tggatttctc cggtgaatag gcagagttgg aaactaaaca    9780
aatgttggtt ttgtgatttg tgaaattgtt ttcaagtgat agttaaagcc catgagatac    9840
agaacaaagc tgctatttcg aggtctcttg gttatactca gaagcacttc tttgggtttc    9900
cctgcactat cctgatcatg tgctaggcct wccttaggct gattgttgtt caaataactt    9960
aagtttcctg tcaggtgatg tcatatgatt tcatatatca aggcaaaaca tgttatatat   10020
gttaaacatt tgkacttaat gtgaaagtta ggtctttgtg ggttttgatt ttaatttcaa   10080
aacctgagct aaataagtca ttttacatgt cttacatttg gtgaattgta tattgtggtt   10140
tgcaggcaag actctctgac ctagtaaccc tcctatagag cactttgctg ggtcacaagt   10200
ctaggagtca agcatttcac cttgaagttg agacgttttg ttagtgtata ctagttatat   10260
gttggaggac atgtttatcc agaagatatt caggactatt tttgactggg ctaaggaatt   10320
gattctgatt agcactgtta gtgagcattg agtggccttt aggcttgaat tggagtcact   10380
tgtatatctc aaataatgct ggccttttt waaaagccct tgttctttat caccctgttt   10440
tctacataat ttttgttcaa agaaatactt gtttggatct ccttttgaca acaatagcat   10500
gttttcaagc catatttttt ttccttttttt tttttttttt tggttttcg agacagggtt   10560
tctctgtata gccctggctg tcctggaact cactttgtag accaggctgg cctcgaactc   10620
agaaatccgc ctgcctctgc ctcctgagtg ccgggattaa aggcgtgcac caccacgcct   10680
ggctaagttg gatattttgt atataactat aaccaatact aactccactg ggtggatttt   10740
taattcagtc agtagtctta agtggtcttt attggcccctt attaaaatct actgttcact   10800
ctaacagagg ctgttggact agtggsacta agcaacttcc tacgatata ctagcagata   10860
agggtcaggg atagaaacta gtctagcgtt ttgtatacct accagcttat actaccttgt   10920
tctgatagaa atatttagga catctagctt atcgatccgt cgacggtatc gataagcttg   10980
atatcgaatt ctaccgggta ggggaggcgc ttttccaagg cagtctgagc atgcgcttag   11040
cagccccgct ggcacttggc gctacacaag tggcctytgg cctcgcacac attccacatc   11100
caccggtagg cgccaaccgg ctccgttctt tggtggcccc ttcgcgccac cttctwctcc   11160
tcccctagtc aggaagttcc cccccgcccc gcagctcgcg tcgtsaggac gtgacaaatg   11220
gaagtagcac gtctcactag tctcgtcaga tggacagcac cgctgagcaa tggaagcggg   11280
taggcctttg gggcagcggc caatagcagc tttgctcctt cgctttctgg gctcagaggc   11340
tgggaagggg tgggtccggg ggcgggctca ggggcgggct caggggcggg gcgggcgccc   11400
gaaggtcctc cggaggcccg gcattctgca cgcttcaaaa gcgcacgtct gccgcgctgt   11460
tctcctcttc ctcatctccg ggcctttcga cctgcaggtc ctcgccatgg atcctgatga   11520
tgttgttatt cttctaatct tttgtatgga aaacttttct tcgtaccacg ggactaaacc   11580
tggttatgta gattccattc aaaaaggtat acaaaagcca aaatctggta cacaaggaaa   11640
ttatgacgat gattggaaag gggttttatag taccgacaat aaatacgacg ctgcgggata   11700
ctctgtagat aatgaaaacc cgctctctgg aaaagctgga ggcgtggtca aagtgacgta   11760
```

```
tccaggactg acgaaggttc tcgcactaaa agtggataat gccgaaacta ttaagaaaga    11820
gttaggttta agtctcactg aaccgttgat ggagcaagtc ggaacggaag agtttatcaa    11880
aaggttcggt gatggtgctt cgcgtgtagt gctcagcctt cccttcgctg aggggagttc    11940
tagcgttgaa tatattaata actgggaaca ggcgaaagcg ttaagcgtag aacttgagat    12000
taattttgaa acccgtggaa aacgtggcca agatgcgatg tatgagtata tggctcaagc    12060
ctgtgcagga aatcgtgtca ggcgatctct ttgtgaagga accttacttc tgtggtgtga    12120
cataattgga caaactacct acagagattt aaagctctaa ggtaaatata aaatttttaa    12180
gtgtataatg tgttaaacta ctgattctaa ttgtttgtgt attttagatt ccaacctatg    12240
gaactgatga atgggagcag tggtggaatg cagatcctag agctcgctga tcagcctcga    12300
ctgtgccttc tagttgccag ccatctgttg tttgccccte cccgtgcct tccttgaccc      12360
tggaaggtgc cactcccact gtcctttcct aataaaatga ggaaattgca tcgcattgtc    12420
tgagtaggtg tcattctatt ctggggggtg gggtggggca ggacagcaag ggggaggatt    12480
gggaagacaa tagcaggcat gctggggatg cggtgggctc tatggcttct gaggcggaaa    12540
gaaccagctg gggctcgacc tcgagggggg gcccggtacc cagcttttgt tccctttagt    12600
gagggttaat tgcgcgcttg gcgtaatcat ggtcatagct gtttcctgtg tgaaattgtt    12660
atccgctcac aattccacac aacatacgag ccggaagcat aaagtgtaaa gcctggggtg    12720
cctaatgagt gagctaactc acattaattg cgttgcgctc actgcccgct ttccagtcgg    12780
gaaacctgtc gtgccagctg cattaatgaa tcggccaacg cgcggggaga ggcggtttgc    12840
gtattgggcg ctcttccgct tcctcgctca ctgactcgct gcgctcggtc gttcggctgc    12900
ggcgagcggt atcagctcac tcaaaggcgg taatacggtt atccacagaa tcaggggata    12960
acgcaggaaa gaacatgtga gcaaaaggcc agcaaaaggc caggaaccgt aaaaaggccg    13020
cgttgctggc gtttttccat aggctccgcc cccctgacga gcatcacaaa aatcgacgct    13080
caagtcagag gtggcgaaac ccgacaggac tataaagata ccaggcgttt ccccctggaa    13140
gctccctcgt gcgctctcct gttccgaccc tgccgcttac cggatacctg tccgcctttc    13200
tcccttcggg aagcgtggcg ctttctcata gctcacgctg taggtatctc agttcggtgt    13260
aggtcgttcg ctccaagctg ggctgtgtgc acgaaccccc cgttcagccc gaccgctgcg    13320
ccttatccgg taactatcgt cttgagtcca acccggtaag acacgactta tcgccactgg    13380
cagcagccac tggtaacagg attagcagag cgaggtatgt aggcggtgct acagagttct    13440
tgaagtggtg gcctaactac ggctacacta aaggacagt atttggtatc tgcgctctgc    13500
tgaagccagt taccttcgga aaaagagttg gtagctcttg atccggcaaa caaaccaccg    13560
ctggtagcgg tggttttttt gtttgcaagc agcagattac gcgcagaaaa aaaggatctc    13620
aagaagatcc tttgatcttt tctacggggt ctgacgctca gtggaacgaa aactcacgtt    13680
aagggatttt ggtcatgaga ttatcaaaaa ggatcttcac ctagatcctt ttaaattaaa    13740
aatgaagttt taaatcaatc taaagtatat atgagtaaac ttggtctgac agttaccaat    13800
gcttaatcag tgaggcacct atctcagcga tctgtctatt tcgttcatcc atagttgcct    13860
gactccccgt cgtgtagata actacgatac gggagggctt accatctggc cccagtgctg    13920
caatgatacc gcgagaccca cgctcaccgg ctccagattt atcagcaata aaccagccag    13980
ccggaagggc cgagcgcaga agtggtcctg caactttatc cgcctccatc cagtctatta    14040
attgttgccg ggaagctaga gtaagtagtt cgccagttaa tagtttgcgc aacgttgttg    14100
ccattgctac aggcatcgtg gtgtcacgct cgtcgtttgg tatggcttca ttcagctccg    14160
```

```
gttcccaacg atcaaggcga gttacatgat cccccatgtt gtgcaaaaaa gcggttagct   14220
ccttcggtcc tccgatcgtt gtcagaagta agttggccgc agtgttatca ctcatggtta   14280
tggcagcact gcataattct cttactgtca tgccatccgt aagatgcttt tctgtgactg   14340
gtgagtactc aaccaagtca ttctgagaat agtgtatgcg cgaccgagt tgctcttgcc    14400 cggcgtcaat acgggataat accgcgccac atagcagaac tttaaaagtg ctcatcattg   14460
gaaaacgttc ttcggggcga aaactctcaa ggatcttacc gctgttgaga tccagttcga   14520
tgtaacccac tcgtgcaccc aactgatctt cagcatcttt tactttcacc agcgtttctg   14580
ggtgagcaaa aacaggaagg caaaatgccg caaaaaaggg aataagggcg acacggaaat   14640
gttgaatact catactcttc cttttcaat attattgaag catttatcag gttattgtc     14700 tcatgagcgg atacatattt gaatgtattt agaaaaataa acaataggg gttccgcgca    14760 catttccccg aaaagtgcca cctaaattgt aagcgttaat attttgttaa aattcgcgtt   14820
aaatttttgt taaatcagct cattttttaa ccaataggcc gaaatcggca aaatccctta   14880
taaatcaaaa gaatagaccg agatagggtt gagtgttgtt ccagtttgga caagagtcc    14940 actattaaag aacgtggact ccaacgtcaa agggcgaaaa accgtctatc agggcgatgg   15000
cccactacgt gaaccatcac cctaatcaag ttttttgggg tcgaggtgcc gtaaagcact   15060
aaatcggaac cctaaaggga gcccccgatt tagagcttga cggggaaagc cggcgaacgt   15120
ggcgagaaag gaagggaaga aagcgaaagg agcgggcgct agggcgctgg caagtgtagc   15180
ggtcacgctg cgcgtaacca ccacacccgc cgcgcttaat gcgccgctac agggcgcgtc   15240
ccattcgcca ttcaggctgc gcaactgttg ggaagggcga tcggtgcggg cctcttcgct   15300
attacgccag ctggcgaaag ggggatgtgc tgcaaggcga ttaagttggg taacgccagg   15360
gttttcccag tcacgacgtt gtaaaacgac ggccagtgag cgcgcgtaat acgactcact   15420
atagggcgaa ttggagct                                                 15438
```

<210> SEQ ID NO 54
<211> LENGTH: 7113
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
```

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctagagtcg    900
atcctgagaa cttcagggtg agtttgggga cccttgattg ttctttcttt ttcgctattg    960
taaaattcat gttatatgga gggggcaaag ttttcagggt gttgtttaga atgggaagat   1020
gtcccttgta tcaccatgga ccctcatgat aattttgttt ctttcacttt ctactctgtt   1080
gacaaccatt gtctcctctt attttctttt cattttctgt aacttttcg ttaaacttta    1140 gcttgcattt gtaacgaatt tttaaattca cttttgttta tttgtcagat tgtaagtact   1200
ttctctaatc actttttttt caaggcaatc agggtatatt atattgtact tcagcacagt   1260
tttagagaac aattgttata attaaatgat aaggtagaat atttctgcat ataaattctg   1320
gctggcgtgg aaatattctt attggtagaa acaactacat cctggtcatc atcctgcctt   1380
tctctttatg gttacaatga tatacactgt ttgagatgag gataaaatac tctgagtcca   1440
aaccgggccc ctctgctaac catgttcatg ccttcttctt tttcctacag ctcctgggca   1500
acgtgctggt tgtgctgtc gaccccaagc tggccgctcg agccaccatg gaacaaaagc    1560
tgatttctga agaagacttg gctagcgaac aaaagctgat ttctgaagaa gacttggaac   1620
aaaagctgat ttctgaagaa gacttgaccg gtatgccaaa aaagaagaga aaggtattag   1680
gatccatggc cagatacgac ctggtggaca ggctgaacac caccttcagg cagatggagc   1740
aggagctggc catcttcgcc gctcacctgg agcagcacaa gctgctggtg gcccgggtgt   1800
tctccctgcc tgaggtgaag aaggaggatg agcacaaccc actgaatcgc atcgaggtga   1860
agcagcacct gggcaacgat gctcagagcc tggctctgcg ccacttcagg cacctgttca   1920
tccagcagca gtccgagaac cgctcttcca aggccgctgt gaggctgcca ggagtgctgt   1980
gctaccaggt ggacaacctg tcccaggccg ccctggtgtc tcacatccag cacatcaaca   2040
agctgaagac cacattcgag cacatcgtga ccgtggagtc cgagctgcca accgcggccc   2100
ggttcgagtg ggtgcacaga cacctgccag gcctgatcac actgaacgct tacaggaccc   2160
tgaccgtgct gcacgatcct gctaccctga gatttggatg ggccaacaag cacatcatca   2220
agaacctgca cagagacgag gtgctggccc agctggagaa gagcctgaag agccccaggt   2280
ctgtggctcc ctggaccagg gaggagtggc agagaaagct ggagcgcgag taccaggaca   2340
tcgccgccct gcccagaaac gccaagctga agatcaagag acctgtgaag gtgcagccaa   2400
tcgccagagt gtggtacaag ggcgaccaga agcaggtgca gcacgcctgc cccacaccac   2460
tgatcgccct gatcaatcgg gacaacggcg ccggagtgcc agacgtggga gagctgctga   2520
actacgacgc cgataatgtg cagcaccgct acaagcccca ggcccagccc ctgcggctga   2580
tcatcccacg gctgcacctg tacgtggctg actgatgaga attctgcaga tatccatcac   2640
actggcggcc ctagagggcc ctattctata gtgtcaccta aatgctagag ctcgctgatc   2700
agcctcgact gtgccttcta gttgccagcc atctgttgtt tgcccctccc ccgtgccttc   2760
cttgaccctg gaaggtgcca ctcccactgt ccttttccta ataaaatgagg aaattgcatc   2820 gcattgtctg agtaggtgtc attctattct ggggggtggg gtgggcagg acagcaaggg    2880 ggaggattgg gaagacaata gcaggcatgc tggggatgcg gtgggctcta tggcttctga   2940
ggcggaaaga accagctggg gctctagggg gtatccccac gcgccctgta gcggcgcatt   3000
aagcgcggcg ggtgtggtgg ttacgcgcag cgtgaccgct acacttgcca gcgccctagc   3060
```

```
gcccgctcct ttcgctttct tcccttcctt tctcgccacg ttcgccggct ttccccgtca    3120
agctctaaat cggggcatcc ctttagggtt ccgatttagt gctttacggc acctcgaccc    3180
caaaaaactt gattagggtg atggttcacg tagtgggcca tcgccctgat agacggtttt    3240
tcgccctttg acgttggagt ccacgttctt aatagtgga ctcttgttcc aaactggaac    3300
aacactcaac cctatctcgg tctattcttt tgatttataa gggattttgg ggatttcggc    3360
ctattggtta aaaatgagc tgatttaaca aaaatttaac gcgaattaat tctgtgaat     3420 gtgtgtcagt tagggtgtgg aaagtcccca ggctcccag gcaggcagaa gtatgcaaag    3480
catgcatctc aattagtcag caaccaggtg tggaaagtcc ccaggctccc cagcaggcag   3540
aagtatgcaa agcatgcatc tcaattagtc agcaaccata gtcccgcccc taactccgcc   3600
catcccgccc ctaactccgc ccagttccgc ccattctccg ccccatggct gactaatttt   3660
ttttatttat gcagaggccg aggccgcctc tgcctctgag ctattccaga agtagtgagg   3720 aggcttttt ggaggcctag gcttttgcaa aaagctcccg ggagcttgta tatccatttt     3780
cggatctgat caagagacag gatgaggatc gtttcgcatg attgaacaag atggattgca    3840
cgcaggttct ccggccgctt gggtggagag gctattcggc tatgactggg cacaacagac    3900
aatcggctgc tctgatgccg ccgtgttccg gctgtcagcg caggggcgcc cggttctttt    3960
tgtcaagacc gacctgtccg gtgccctgaa tgaactgcag gacgaggcag cgcggctatc    4020
gtggctggcc acgacgggcg ttccttgcgc agctgtgctc gacgttgtca ctgaagcggg    4080
aagggactgg ctgctattgg gcgaagtgcc ggggcaggat ctcctgtcat ctcaccttgc    4140
tcctgccgag aaagtatcca tcatggctga tgcaatgcgg cggctgcata cgcttgatcc    4200
ggctacctgc ccattcgacc accaagcgaa acatcgcatc gagcgagcac gtactcggat    4260
ggaagccggt cttgtcgatc aggatgatct ggacgaagag catcagggc tcgcgccagc     4320 cgaactgttc gccaggctca aggcgcgcat gcccgacggc gaggatctcg tcgtgaccca    4380
tggcgatgcc tgcttgccga atatcatggt ggaaaatggc cgcttttctg gattcatcga    4440
ctgtggccgg ctgggtgtgg cggaccgcta tcaggacata gcgttggcta cccgtgatat    4500
tgctgaagag cttggcggcg aatgggctga ccgcttcctc gtgctttacg gtatcgccgc    4560
tcccgattcg cagcgcatcg ccttctatcg ccttcttgac gagttcttct gagcgggact    4620
ctggggttcg aaatgaccga ccaagcgacg cccaacctgc catcacgaga tttcgattcc    4680
accgccgcct tctatgaaag gttgggcttc ggaatcgttt tccgggacgc cggctggatg    4740
atcctccagc gcggggatct catgctggag ttcttcgccc accccaactt gtttattgca    4800
gcttataatg gttacaaata agcaatagc atcacaaatt tcacaaataa agcatttttt     4860
tcactgcatt ctagttgtgg tttgtccaaa ctcatcaatg tatcttatca tgtctgtata    4920
ccgtcgacct ctagctagag cttggcgtaa tcatggtcat agctgtttcc tgtgtgaaat    4980
tgttatccgc tcacaattcc acacaacata cgagccggaa gcataaagtg taaagcctgg    5040
ggtgcctaat gagtgagcta actcacatta attgcgttgc gctcactgcc cgctttccag    5100
tcgggaaacc tgtcgtgcca gctgcattaa tgaatcggcc aacgcgcggg gagaggcggt    5160
ttgcgtattg ggcgctcttc cgcttcctcg ctcactgact cgctgcgctc ggtcgttcgg    5220
ctgcggcgag cggtatcagc tcactcaaag gcggtaatac ggttatccac agaatcaggg    5280
gataacgcag gaaagaacat gtgagcaaaa ggccagcaaa aggccaggaa ccgtaaaaag    5340
gccgcgttgc tggcgttttt ccataggctc cgcccccctg acgagcatca caaaaatcga    5400
cgctcaagtc agaggtggcg aaacccgaca ggactataaa gataccaggc gtttccccct    5460
```

```
ggaagctccc tcgtgcgctc tcctgttccg accctgccgc ttaccggata cctgtccgcc    5520
tttctccctt cgggaagcgt ggcgctttct caatgctcac gctgtaggta tctcagttcg    5580
gtgtaggtcg ttcgctccaa gctgggctgt gtgcacgaac cccccgttca gcccgaccgc    5640
tgcgccttat ccgtaacta tcgtcttgag tccaacccgg taagacacga cttatcgcca    5700
ctggcagcag ccactggtaa caggattagc agagcgaggt atgtaggcgg tgctacagag    5760
ttcttgaagt ggtggcctaa ctacggctac actagaagga cagtatttgg tatctgcgct    5820
ctgctgaagc cagttacctt cggaaaaaga gttggtagct cttgatccgg caaacaaacc    5880
accgctggta gcggtggttt ttttgtttgc aagcagcaga ttacgcgcag aaaaaaagga    5940
tctcaagaag atcctttgat cttttctacg gggtctgacg ctcagtggaa cgaaaactca    6000
cgttaaggga ttttggtcat gagattatca aaaaggatct tcacctagat ccttttaaat    6060
taaaaatgaa gttttaaatc aatctaaagt atatatgagt aaacttggtc tgacagttac    6120
caatgcttaa tcagtgaggc acctatctca gcgatctgtc tatttcgttc atccatagtt    6180
gcctgactcc ccgtcgtgta gataactacg atacgggagg gcttaccatc tggccccagt    6240
gctgcaatga taccgcgaga cccacgctca ccggctccag atttatcagc aataaaccag    6300
ccagccggaa gggccgagcg cagaagtggt cctgcaactt tatccgcctc catccagtct    6360
attaattgtt gccgggaagc tagagtaagt agttcgccag ttaatagttt gcgcaacgtt    6420
gttgccattg ctacaggcat cgtggtgtca cgctcgtcgt ttggtatggc ttcattcagc    6480
tccggttccc aacgatcaag gcgagttaca tgatccccca tgttgtgcaa aaaagcggtt    6540
agctccttcg gtcctccgat cgttgtcaga agtaagttgg ccgcagtgtt atcactcatg    6600
gttatggcag cactgcataa ttctcttact gtcatgccat ccgtaagatg cttttctgtg    6660
actggtgagt actcaaccaa gtcattctga gaatagtgta tgcggcgacc gagttgctct    6720
tgcccggcgt caatacggga taataccgcg ccacatagca gaactttaaa agtgctcatc    6780
attggaaaac gttcttcggg gcgaaaactc tcaaggatct taccgctgtt gagatccagt    6840
tcgatgtaac ccactcgtgc acccaactga tcttcagcat cttttacttt caccagcgtt    6900
tctgggtgag caaaaacagg aaggcaaaat gccgcaaaaa agggaataag ggcgacacgg    6960
aaatgttgaa tactcatact cttcctttt caatattatt gaagcattta tcagggttat    7020
tgtctcatga gcggatacat atttgaatgt atttagaaaa ataaacaaat aggggttccg    7080
cgcacatttc cccgaaaagt gccacctgac gtc                                 7113
```

<210> SEQ ID NO 55
<211> LENGTH: 16672
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (382)..(382)
<223> OTHER INFORMATION: a, c, t, g, unknown or other

<400> SEQUENCE: 55

```
ccccgcggca ggccctccga gcgtggtgga gccgttctgt gagacagccg ggtacgagtc     60
gtgacgctgg aaggggcaag cgggtggtgg gcaggaatgc ggtccgccct gcagcaaccg    120
gagggggagg gagaagggag cggaaaaagtc tccaccggac gcggccatgg ctcggggggg    180
ggggggcagc ggaggascgc ttccggccga cgtctcgtcg ctgattggct tyttttcctc    240
```

```
ccgccgtgtg tgaaaacaca aatggcgtgt tttggttggc gtaaggcgcc tgtcagttaa    300
cggcagccgg agtgcgcagc cgccggcagc ctcgctctgc ccactgggtg gggcgggagg    360
taggtggggt gaggcgagct gnacgtgcgg gcgcggtcgg cctctggcgg ggcggggag     420 gggagggagg gtcagcgaaa gtagctcgcg cgcgagcggc cgcccaccct ccccttcctc    480
tgggggagtc gttttacccg ccgccggccg ggcctcgtcg tctgattggc tctcggggcc    540
cagaaaactg gcccttgcca ttggctcgtg ttcgtgcaag ttgagtccat ccgccggcca    600 gcggggcgg cgaggaggcg ctcccaggtt ccggccctcc cctcggcccc gcgccgcaga     660
gtctggccgc gcgcccctgc gcaacgtggc aggaagcgcg cgctggggc ggggacgggc     720 agtagggctg agcggctgcg gggcgggtgc aagcacgttt ccgacttgag ttgcctcaag    780
aggggcgtgc tgagccagac ctccatcgcg cactccgggg agtggaggga aggagcgagg    840
gctcagttgg gctgttttgg aggcaggaag cacttgctct cccaaagtcg ctctgagttg    900
ttatcagtaa gggagctgca gtggagtagg cggggagaag gccgcaccct tctccggagg    960 ggggaggga gtgttgcaat acctttctgg gagttctctg ctgcctcctg gcttctgagg    1020
accgccctgg gcctgggaga atcccttgcc ccctcttccc ctcgtgatct gcaactccag   1080
tctttctagc cttaattaag ggatctgtag ggcgcagtag tccagggttt ccttgatgat   1140
gtcatactta tcctgtccct ttttttttcca cagctcgcgg ttgaggacaa actcttcgcg  1200
gtctttccag tggggatcga cggtatcgta gagtcgaggc cgctctagaa ctagtggatc   1260
taccatgacc gagtacaagc ccacggtgcg cctcgccacc cgcgacgacg tcccccgggc   1320
cgtacgcacc ctcgccgccg cgttcgccga ctaccccgcc acgcgccaca ccgtcgaccc   1380
ggaccgccac atcgagcggg tcaccgagct gcaagaactc ttcctcacgc gcgtcgggct   1440
cgacatcggc aaggtgtggg tcgcggacga cggcgccgcg gtggcggtct ggaccacgcc   1500
ggagagcgtc gaagcggggg cggtgttcgc cgagatcggc ccgcgcatgg ccagttgag    1560 cggttcccgg ctggccgcgc agcaacagat ggaaggcctc ctggcgccgc accggcccaa   1620
ggagcccgcg tggttcctgg ccaccgtcgg cgtctcgccc gaccaccagg gcaagggtct   1680
gggcagcgcc gtcgtgctcc ccggagtgga ggcgccgag cgcgccgggg tgcccgcctt    1740
cctggagacc tccgcgcccc gcaacctccc cttctacgag cggctcggct tcaccgtcac   1800
cgccgacgtc gagtgcccga aggaccgcgc gacctggtgc atgacccgca agcccggtgc   1860
ctgactcgac cctaggggga ggctaactga aacacggaag gagacaatac cggaaggaac   1920
ccgcgctatg acggcaataa aaagacagaa taaaacgcac ggtgttgggt cgtttgttca   1980
taaacgcggg gttcggtccc agggctggca ctctgtcgat accccaccga daccccattg   2040
gggccaatac gcccgcgttt cttccttttc cccaccccac cccccaagtt cgggtgaagg   2100
cccagggctc gcagccaacg tcggggcggc aggccctgcc atagcctcag gttactcgga   2160
tctcgacctc gagacgcgtg ccccactcc acaatttcaa aaaaaagagt ggccacttgt    2220
ctttgtttat gggcccatt ggcgtggagc cccgtttaat tttcgggggt gttagagaca    2280
accagtggag tccgctgctg tcggcgtcca ctctctttcc ccttgttaca aatagagtgt   2340
aacaacatgg ttcacctgtc ttggtccctg cctgggacac atcttaataa ccccagtatc   2400
atattgcact aggattatgt gttgcccata gccataaatt cgtgtgagat ggacatccag   2460
tctttacggc ttgtccccac cccatggatt tctattgtta aagatattca gaatgtttca   2520
ttcctacact agtatttatt gcccaagggg tttgtgaggg ttatattggt gtcatagcac   2580
```

```
aatgccacca ctgaaccccc cgtccaaatt ttattctggg ggcgtcacct gaaaccttgt   2640
tttcgagcac ctcacataca ccttactgtt cacaactcag cagttattct attagctaaa   2700
cgaaggagaa tgaagaagca ggcgaagatt caggagagtt cactgcccgc tccttgatct   2760
tcagccactg cccttgtgac taaaatggtt cactaccctc gtggaatcct gaccccatgt   2820
aaataaaacc gtgacagctc atggggtggg agatatcgct gttccttagg acccttttac   2880
taaccctaat tcgatagcat atgcttcccg ttgggtaaca tatgctattg aattagggtt   2940
agtctggata gtatatacta ctacccggga agcatatgct acccgtttag ggttaacaag   3000
ggggccttat aaacactatt gctaatgccc tcttgagggt ccgcttatcg gtagctacac   3060
aggcccctct gattgacgtt ggtgtagcct cccgtagtct tcctgggccc ctgggaggta   3120
catgtccccc agcattggtg taagagcttc agccaagagt tacacataaa ggtacgtacc   3180
agtcttcgaa agatctcggg gtgcccatcc tggtcgagct ggacggcgac gtaaacggcc   3240
acaagttcag cgtgtccggc gagggcgagg gcgatgccac ctacggcaag ctgaccctga   3300
agttcatctg caccaccggc aagctgcccg tgccctggcc caccctcgtg accaccctga   3360
cctacggcgt gcagtgcttc agccgctacc ccgaccacat gaagcagcac gacttcttca   3420
agtccgccat gcccgaaggc tacgtccagg agcgcaccat cttcttcaag gacgacggca   3480
actacaagac ccgcgccgag gtgaagttcg agggcgacac cctggtgaac cgcatcgagc   3540
tgaagggcat cgacttcaag gaggacggca acatcctggg gcacaagctg gagtacaact   3600
acaacagcca caacgtctat atcatggccg acaagcagaa gaacggcatc aaggtgaact   3660
tcaagatccg ccacaacatc gaggacggca gcgtgcagct cgccgaccac taccagcaga   3720
acacccccat cggcgacggc cccgtgctgc tgcccgacaa ccactacctg agcacccagt   3780
ccgccctgag caaagacccc aacgagaagc gcgatcacat ggtcctgctg gagttcgtga   3840
ccgccgccgg gatcactctc ggcatggacg agctgtacaa gtaaagcggc cgcgactcta   3900
gatcataatc agccatacca catttgtaga ggttttactt gctttaaaaa acctcccaca   3960 cctcccctg aacctgaaac ataaaatgaa tgcaattgtt gttgttaact tgtttattgc   4020
agcttataat ggttacaaat aaagcaatag catcacaaat ttcacaaata aagcattttt   4080
ttcactgcat tctagttgtg gtttgtccaa actcatcaat gtcgggatcc cgccaattgt   4140
ctagatttct ctaatcactt tttttcaag gcaatcaggg tatattatat tgtacttcag   4200
cacagtttta gagaacaatt gttataatta aatgataagg tagaatattt ctgcatataa   4260
attctggctg gcgtggaaat attcttattg gtagaaacaa ctacatcctg gtcatcatcc   4320
tgcctttctc tttatggtta caatgatata cactgtttga gatgaggata aaatactctg   4380
agtccaaacc gggcccctct gctaaccatg ttcatgcctt cttctttttc ctacaggact   4440
cctccctgca ggacggcgag ttcatctaca aggtgaagct gcgcggcacc aacttcccct   4500
ccgacggccc cgtaatgcag aagaagacca tgggctggga ggcctcctcc gagcggatgt   4560
accccgagga cggcgccctg aagggcgaga tcaagatgag gctgaagctg aaggacggtg   4620
gccactacga cgccgaggtc aagaccacct acatggccaa gaagcccgtg cagctgcccg   4680
gcgcctacaa gaccgacatc aagctggaca tcacctccca caacgaggac tacaccatcg   4740
tggaacagta cgagcgcgcc gagggccgcc actccaccgg cggtatggat gaactctata   4800
aataagcacg ggcctattc tatagtgtca cctaaatgct agagctcgct gatcagcctc   4860
gactgtgcct tctagttgcc agccatctgt tgtttgcccc tcccccgtgc cttccttgac   4920
cctggaaggt gccactccca ctgtccttt ctaataaaat gaggaaattg catcgcattg   4980
```

```
tctgagtagg tgtcattcta ttctgggggg tggggtgggg caggacagca agggggagga    5040
ttgggaagac aatagcaggc atgctgggga ggatctgtgt ggaaagtccc caggctcccc    5100
aggcaggcag aagtatgcaa agcatgcatc tcaattagtc agcaaccagg tgtggaaagt    5160
ccccaggctc cccagcaggc agaagtatgc aaagcatgca tctcaattag tcagcaacca    5220
tagtcccgcc cctaactccg cccatcccgc ccctaactcc gcccagttcc gcccattctc    5280
cgccccatgg ctgactaatt tttttattt atgcagaggc cgaggccgcc tctgcctctg    5340
agctattcca gaagtagtga ggaggctttt ttggaggcct aggcttttgc aaaaagctcc    5400
cgggagcttg tatatccatt ttcggataag cttaactaaa ccatggtatc aaaaggtgaa    5460
gaaaacaata tggcagtcat caaggagttc atgcgcttca aggtgcgcat ggagggctcc    5520
gtgaacggcc acgagttcga gatcgagggc gagggcgagg ccgcccta cgagggcacc    5580 cagaccgcca agctgaaggt gaccgagggt ggcccctgc ccttcgcctg gacatcctg    5640 tcccctcagt tcatgtacgg ctccaaggcc tacgtgaagc accccgccga catccccgac    5700
tacttgaagc tgtccttccc cgagggcttc aagtgggagc gcgtgatgaa cttcgaggac    5760
ggcggcgtgg tgaccgtgac ccaggtgagt ttggggaccc ttgattgttc tttcttttc    5820 gctattgtaa aattcatgtt atatggaggg ggcaaagttt tcagggtgtt gtttagaatg    5880
ggaagatgtc ccttgtatca ccatggaccc tcatgataat tttgtttctt tcactttcta    5940
ctctgttgac aaccattgtc tcctcttatt ttcttttcat tttctgtaac ttttttcgtta   6000 aactttagct tgcatttgta acgaattttt aaattcactt ttgtttatt gtcagattgt    6060 aagtaccggg acccggaatt ctaccgggta ggggaggcgc ttttcccaag gcagtctgga    6120
gcatgcgctt tagcagcccc gctggcactt ggcgctacac aagtggcctc tggcctcgca    6180
cacattccac atccaccggt agcgccaacc ggctccgttc tttggtggcc ccttcgcgcc    6240
acttctactc ctcccctagt caggaagttt cccccagcaa gctcgcgtcg tgcaggacgt    6300
gacaaatgga agtagcacgt ctcactagtc tcgtgcagat ggacagcacc gctgagcaat    6360
ggaagcgggt aggcctttgg ggcagcggcc aatagcagct ttgttccttc gctttctggg    6420
ctcagaggct gggaaggggt gggtccgggg gcgggctcag gggcgggctc aggggcgggc    6480
gggcgcccga aggtcctccc gaggcccggc attctgcacg cttcaaaagc gcacgtctgc    6540
cgcgctgttc tcctcttcct catctccggg cctttcgacc tgcagcccaa gctctagcgc    6600
taccggtcgc caccatggtg agcaagggcg aggagctgtt caccggggtg gtgcccatcc    6660
tggtcgagct ggacggcgac gtaaacggcc acaagttcag cgtgtccggc gagggcgagg    6720
gcgatgccac ctacggcaag ctgaccctga agttcatctg caccaccggc aagctgcccg    6780
tgccctggcc cacccttgtg accaccctga cctacggcgt gcagtgcttc agccgctacc    6840
ccgaccacat gaagcagcac gacttcttca gtccgccat gcccgaaggc tacgtccagg    6900
agcgcaccat cttcttcaag gacgacggca actacaagac ccgcgccgag gtgaagttcg    6960
agggcgacac cctggtgaac cgcatcgagc tgaagggcat cgtagggata acgctcatat    7020
atcgataata agtatgttgt aactaaagtc gtgaaataag tatgttgtaa ctaaagtctt    7080
acaataagta tgttgtaact aaagtgtata cctttccgga tagggataac gctcatatat    7140
cgataataag tatgttgtaa ctaaagtcgt gaaataagta tgttgtaact aaagtcttac    7200
aataagtatg ttgtaactaa agtgtatacc tttccggata gggataacag ggtaatcaag    7260
gaggacggca acatcctggg gcacaagctg gagtacaact acaacagcca caacgtctat    7320
```

```
atcatggccg acaagcagaa gaacggcatc aaggtgaact tcaagatccg ccacaacatc    7380
gaggacggca gcgtgcagct cgccgaccac taccagcaga acaccccccat cggcgacggc    7440 cccgtgctgc tgcccgacaa ccactacctg agcacccagt ccgccctgag caaagacccc    7500
aacgagaagc gcgatcacat ggtcctgctg gagttcgtga ccgccgccgg gatcactctc    7560
ggcatggacg agctgtacaa gtaaagcggc cgcgactcta gatcataatc agccatacca    7620
catttgtaga ggttttactt gctttaaaaa acctcccaca cctcccctg aacctgaaac    7680 ataaaatgaa tgcaattgtt gttgttaact tgtttattgc agcttataat ggttacaaat    7740
aaagcaatag catcacaaat ttcacaaata aagcattttt ttcactgcat tctagttgtg    7800
gtttgtccaa actcatcaat gtcggatggc cgcgctgggg atgcggtggg ctctatggct    7860
tatgaggcgg aaagaaccag ctggggctcg atcctctagt tggcgcgccg gctagaagat    7920
gggcgggagt cttctgggca ggcttaaagg ctaacctggt gtgtgggcgt tgtcctgcag    7980
gggaattgaa caggtgtaaa attggaggga caagacttcc cacagatttt cggttttgtc    8040
gggaagtttt ttaatagggg caaataggaa aatggaggat aggagtcatc tggggtttat    8100
gcagcaaaac tacaggtata ttgcttgtat ccgcctcgga gatttccatg aggagataaa    8160
gacatgtcac ccgagtttat actctcctgc ttagatccta ctacagtatg aaatacagtg    8220
tygcgaggta gactatgtaa gcagatttaa tcattttaaa gagcccagta cttcatatcc    8280
atttctcccg ctccttctgc agccttatca aaggtatt agaacactca ttttagcccc    8340
attttcattt attatactgg cttatccaac ccctagacag agcattggca ttttcccttt    8400
cctgatctta gaagtctgat gactcatgaa accagacaga ttagttacat acaccacaaa    8460
tcgaggctgt agctggggcc tcaacactgc agttcttta taactcctta gtacactttt    8520
tgttgatcct ttgccttgat ccttaatttt cagtgtctat cacctctccc gtcaggtggt    8580
gttccacatt tgggcctatt ctcagtccag ggagttttac aacaatagat gtattgagaa    8640
tccaacctaa agcttaactt tccactccca tgaatgcctc tctccttttt ctccattata    8700
actgagctat waccattaat ggtttcaggt ggatgtctcc tcccccaata tacctgatgt    8760
atctacatat tgccaggctg atattttaag acatwaaagg tatatttcat tattgagcca    8820
catggtattg attactgcta ctaaaatttt gtcattgtac acatctgtaa aaggtggttc    8880
cttttggaat gcaaagttca ggtgtttgtt gtctttcctg acctaaggtc ttgtgagctt    8940
gtattttttc tatttaagca gtgctttctc ttggactggc ttgactcatg gcattctaca    9000
cgttattgct ggtctaaatg tgattttgcc aagcttcttc aggacctata attttgcttg    9060
acttgtagcc aaacacaagt aaaatgatta agcaacaaat gtatttgtga agcttggttt    9120
ttaggttgtt gtgttgtgtg tgcttgtgct ctataataat actatccagg ggctggagag    9180
gtggctcgga gttcaagagc acagactgct cttccagaag tcctgagttc aattcccagc    9240
aaccacatgg tggctcacaa ccatctgtaa tgggatctga tgccctcttc tggtgtgtct    9300
gaagaccaca agtgtattca cattaaataa ataatcctcc ttcttcttct ttttttttt    9360 ttaaagagaa twctgtctcc agtagaatta ctgaagtaat gaaatacttt gtgtttgttc    9420
caatatggwa gccaataatc aaatactctt wagcactgga aatgtaccaa ggaactattt    9480
tatttaagtg wactgtggac agaggagcca taactgcaga cttgtgggat acagaagacc    9540
aatgcagact taatgtcttt tctcttacac taagcaataa agaaataaaa attgaacttc    9600
tagtatccta tttgttaaac tgctagcttt actaactttt gtgcttcatc tatacaaagc    9660
tgaaagctaa gtctgcagcc attactaaac atgaaagcaa gtaatgataa ttttggattt    9720
```

```
caaaaatgta gggccagagt ttagccagcc agtggtggtg cttgccttta tgccttaatc   9780
ccagcactct ggaggcagag acaggcagat ctctgagttt gagcccagcc tggtctacac   9840
atcaagttct atctaggata gccaggaata cacacagaaa ccctgttggg gagggggct    9900 ctgagatttc ataaaattat aattgaagca ttccctaatg agccactatg gatgtggcta   9960
aatccgtcta cctttctgat gagatttggg tattattttt tctgtctctg ctgttggttg  10020
ggtcttttga cactgtgggc tttcttaaag cctccttccc tgccatgtgg tctcttgttt  10080
gctactaact tcccatggct taaatggcat ggcttttttgc cttctaaggg cagctgctga  10140
gwtttgcagc ctgatttcca gggtggggtt gggaaatctt tcaaacacta aaattgtcct  10200 ttaattttttt tttaaaaaat gggttatata ataaacctca taaaatagtt atgaggagtg  10260
aggtggacta atattaatga gtccctcccc tataaaagag ctattaaggc ttttttgtctt  10320 atactaactt ttttttttaaa tgtggtatct ttagaaccaa gggtcttaga gttttagtat  10380
acagaaactg ttgcatcgct taatcagatt ttctagtttc aaatccagag aatccaaatt  10440
cttcacagcc aaagtcaaat taagaatttc tgactttaat gttatttgct actgtgaata  10500
taaaatgata gcttttcctg aggcagggtc tcactatgta tctctgcctg atctgcaaca  10560
agatatgtag actaaagttc tgcctgcttt tgtctcctga atactaaggt taaaatgtag  10620
taatactttt ggaacttgca ggtcagattc ttttataggg gacacactaa gggagcttgg  10680
gtgatagttg gtaaatgtgt ttaagtgatg aaaacttgaa ttattatcac cgcaacctac  10740
tttttaaaaa aaaagccag gcctgttaga gcatgctaag ggatccctag gacttgctga  10800
gcacacaaga gtagtacttg gcaggctcct ggtgagagca tatttcaaaa aacaaggcag  10860
acaaccaaga aactcagta aggttacctg tctttaacca tctgcatata cacagggata  10920
ttaaaatatt ccaaataata tttcattcaa gttttccccc atcaaattgg gacatggatt  10980
tctccggtga ataggcagag ttggaaacta aacaaatgtt ggttttgtga tttgtgaaat  11040
tgttttcaag tgatagttaa agcccatgag atacagaaca aagctgctat ttcgaggtct  11100
cttggttata ctcagaagca cttctttggg tttccctgca ctatcctgat catgtgctag  11160
gcctwcctta ggctgattgt tgttcaaata acttaagttt cctgtcaggt gatgtcatat  11220
gatttcatat atcaaggcaa aacatgttat atatgttaaa catttgkact taatgtgaaa  11280
gttaggtctt tgtgggtttt gattttaatt tcaaaacctg agctaaataa gtcattttac  11340
atgtcttaca tttggtgaat tgtatattgt ggtttgcagg caagactctc tgacctagta  11400
accctcctat agagcacttt gctgggtcac aagtctagga gtcaagcatt tcaccttgaa  11460
gttgagacgt tttgttagtg tatactagtt atatgttgga ggacatgttt atccagaaga  11520
tattcaggac tattttgac tgggctaagg aattgattct gattagcact gttagtgagc  11580
attgagtggc ctttaggctt gaattggagt cacttgtata tctcaaataa tgctggcctt  11640
ttttwaaaag cccttgttct ttatcaccct gttttctaca taattttttgt tcaaagaaat  11700 acttgtttgg atctccttttt gacaacaata gcatgttttc aagccatatt tttttttcctt  11760 tttttttttt tttttggttt ttcgagacag ggtttctctg tatagccctg gctgtcctgg  11820
aactcacttt gtagaccagg ctggcctcga actcagaaat ccgcctgcct ctgcctcctg  11880
agtgccggga ttaaaggcgt gcaccaccac gcctggctaa gttggatatt ttgtatataa  11940
ctataaccaa tactaactcc actgggtgga tttttaattc agtcagtagt cttaagtggt  12000
ctttattggc cccttattaaa atctactgtt cactctaaca gaggctgttg gactagtggs  12060
```

```
actaagcaac ttcctacgga tatactagca gataagggtc agggatagaa actagtctag    12120
cgttttgtat acctaccagc ttatactacc ttgttctgat agaaatattt aggacatcta    12180
gcttatcgat ccgtcgacgg tatcgataag cttgatatcg aattctaccg ggtaggggag    12240
gcgcttttcc aaggcagtct gagcatgcgc ttagcagccc cgctggcact tggcgctaca    12300
caagtggcct ytggcctcgc acacattcca catccaccgg taggcgccaa ccggctccgt    12360
tctttggtgg cccccttcgcg ccaccttctw ctcctcccct agtcaggaag ttcccccccg    12420
ccccgcagct cgcgtcgtsa ggacgtgaca aatggaagta gcacgtctca ctagtctcgt    12480
cagatggaca gcaccgctga gcaatggaag cgggtaggcc tttggggcag cggccaatag    12540
cagctttgct ccttcgcttt ctgggctcag aggctgggaa ggggtgggtc cggggcggg    12600 ctcaggggcg ggctcagggg cggggcgggc gcccgaaggt cctccggagg cccggcattc    12660
tgcacgcttc aaaagcgcac gtctgccgcg ctgttctcct cttcctcatc tccgggcctt    12720
tcgacctgca ggtcctcgcc atggatcctg atgatgttgt tattcttcta atcttttgta    12780
tggaaaactt ttcttcgtac cacgggacta aacctggtta tgtagattcc attcaaaaag    12840
gtatacaaaa gccaaaatct ggtacacaag gaaattatga cgatgattgg aaagggtttt    12900
atagtaccga caataaatac gacgctgcgg gatactctgt agataatgaa aacccgctct    12960
ctggaaaagc tggaggcgtg gtcaaagtga cgtatccagg actgacgaag gttctcgcac    13020
taaaagtgga taatgccgaa actattaaga aagagttagg tttaagtctc actgaaccgt    13080
tgatggagca agtcggaacg gaagagttta tcaaaaggtt cggtgatggt gcttcgcgtg    13140
tagtgctcag ccttcccttc gctgagggga gttctagcgt tgaatatatt aataactggg    13200
aacaggcgaa agcgttaagc gtagaacttg agattaattt tgaaacccgt ggaaaacgtg    13260
gccaagatgc gatgtatgag tatatggctc aagcctgtgc aggaaatcgt gtcaggcgat    13320
ctctttgtga aggaacctta cttctgtggt gtgacataat tggacaaact acctacagag    13380
atttaaagct ctaaggtaaa tataaaattt ttaagtgtat aatgtgttaa actactgatt    13440
ctaattgttt gtgtattta gattccaacc tatggaactg atgaatggga gcagtggtgg    13500
aatgcagatc ctagagctcg ctgatcagcc tcgactgtgc cttctagttg ccagccatct    13560
gttgtttgcc cctcccccgt gccttccttg accctggaag gtgccactcc cactgtcctt    13620
tcctaataaa atgaggaaat tgcatcgcat tgtctgagta ggtgtcattc tattctgggg    13680
ggtggggtgg ggcaggacag caaggggag gattgggaag acaatagcag gcatgctggg    13740
gatgcggtgg gctctatggc ttctgaggcg gaaagaacca gctggggctc gacctcgagg    13800
gggggcccgg tacccagctt ttgttccctt tagtgagggt taattgcgcg cttggcgtaa    13860
tcatggtcat agctgtttcc tgtgtgaaat tgttatccgc tcacaattcc acacaacata    13920
cgagccggaa gcataaagtg taaagcctgg ggtgcctaat gagtgagcta actcacatta    13980
attgcgttgc gctcactgcc cgctttccag tcgggaaacc tgtcgtgcca gctgcattaa    14040
tgaatcggcc aacgcgcggg gagaggcggt ttgcgtattg ggcgctcttc cgcttcctcg    14100
ctcactgact cgctgcgctc ggtcgttcgg ctgcggcgag cggtatcagc tcactcaaag    14160
gcggtaatac ggttatccac agaatcaggg gataacgcag gaaagaacat gtgagcaaaa    14220
ggccagcaaa aggccaggaa ccgtaaaaag gccgcgttgc tggcgttttt ccataggctc    14280
cgcccccctg acgagcatca aaaaatcga cgctcaagtc agaggtggcg aaacccgaca    14340
ggactataaa gataccaggc gtttccccct ggaagctccc tcgtgcgctc tcctgttccg    14400
accctgccgc ttaccggata cctgtccgcc tttctccctt cgggaagcgt ggcgctttct    14460
```

```
catagctcac gctgtaggta tctcagttcg gtgtaggtcg ttcgctccaa gctgggctgt    14520
gtgcacgaac cccccgttca gcccgaccgc tgcgccttat ccggtaacta tcgtcttgag    14580
tccaacccgg taagacacga cttatcgcca ctggcagcag ccactggtaa caggattagc    14640
agagcgaggt atgtaggcgg tgctacagag ttcttgaagt ggtggcctaa ctacggctac    14700
actagaagga cagtatttgg tatctgcgct ctgctgaagc cagttacctt cggaaaaaga    14760
gttggtagct cttgatccgg caaacaaacc accgctggta gcggtggttt ttttgtttgc    14820
aagcagcaga ttacgcgcag aaaaaaagga tctcaagaag atcctttgat cttttctacg    14880
gggtctgacg ctcagtggaa cgaaaactca cgttaaggga ttttggtcat gagattatca    14940
aaaaggatct tcacctagat ccttttaaat taaaaatgaa gttttaaatc aatctaaagt    15000
atatatgagt aaacttggtc tgacagttac caatgcttaa tcagtgaggc acctatctca    15060
gcgatctgtc tatttcgttc atccatagtt gcctgactcc ccgtcgtgta gataactacg    15120
atacgggagg gcttaccatc tggccccagt gctgcaatga taccgcgaga cccacgctca    15180
ccggctccag atttatcagc aataaaccag ccagccggaa gggccgagcg cagaagtggt    15240
cctgcaactt tatccgcctc catccagtct attaattgtt gccgggaagc tagagtaagt    15300
agttcgccag ttaatagttt gcgcaacgtt gttgccattg ctacaggcat cgtggtgtca    15360
cgctcgtcgt ttggtatggc ttcattcagc tccggttccc aacgatcaag gcgagttaca    15420
tgatccccca tgttgtgcaa aaaagcggtt agctccttcg gtcctccgat cgttgtcaga    15480
agtaagttgg ccgcagtgtt atcactcatg gttatggcag cactgcataa ttctcttact    15540
gtcatgccat ccgtaagatg cttttctgtg actggtgagt actcaaccaa gtcattctga    15600
gaatagtgta tgcggcgacc gagttgctct tgcccggcgt caatacggga taataccgcg    15660
ccacatagca gaactttaaa agtgctcatc attggaaaac gttcttcggg gcgaaaactc    15720
tcaaggatct taccgctgtt gagatccagt tcgatgtaac ccactcgtgc acccaactga    15780
tcttcagcat cttttacttt caccagcgtt tctgggtgag caaaaacagg aaggcaaaat    15840
gccgcaaaaa agggaataag ggcgacacgg aaatgttgaa tactcatact cttccttttt    15900
caatattatt gaagcattta tcagggttat tgtctcatga gcggatacat atttgaatgt    15960
atttagaaaa ataaacaaat aggggttccg cgcacatttc cccgaaaagt gccacctaaa    16020
ttgtaagcgt taatattttg ttaaaattcg cgttaaattt ttgttaaatc agctcatttt    16080
ttaaccaata ggccgaaatc ggcaaaatcc cttataaatc aaaagaatag accgagatag    16140
ggttgagtgt tgttccagtt tggaacaaga gtccactatt aaagaacgtg gactccaacg    16200
tcaaagggcg aaaaaccgtc tatcagggcg atggcccact acgtgaacca tcaccctaat    16260
caagtttttt ggggtcgagg tgccgtaaag cactaaatcg aaccctaaa gggagccccc    16320 gatttagagc ttgacgggga agccggcgaa cgtggcgaga aaggaaggg aagaaagcga    16380 aaggagcggg cgctagggcg ctggcaagtg tagcggtcac gctgcgcgta accaccacac    16440
ccgccgcgct taatgcgccg ctacagggcg cgtcccattc gccattcagg ctgcgcaact    16500
gttgggaagg gcgatcggtg cgggcctctt cgctattacg ccagctggcg aaagggggat    16560
gtgctgcaag gcgattaagt tgggtaacgc cagggttttc ccagtcacga cgttgtaaaa    16620
cgacggccag tgagcgcgcg taatacgact cactataggg cgaattggag ct            16672
```